US011649266B2

(12) United States Patent
Izumi Willcoxon et al.

(10) Patent No.: US 11,649,266 B2
(45) Date of Patent: May 16, 2023

(54) INSECTICIDAL POLYPEPTIDES HAVING IMPROVED ACTIVITY SPECTRUM AND USES THEREOF

(71) Applicant: PIONEER HI-BRED INTERNATIONAL, INC., Johnston, IA (US)

(72) Inventors: Michi Izumi Willcoxon, Palo Alto, CA (US); Takashi Yamamoto, Dublin, CA (US)

(73) Assignee: PIONEER HI-BRED INTERNATIONAL, INC.

( * ) Notice: Subject to any disclaimer, the term of this patent is extended or adjusted under 35 U.S.C. 154(b) by 160 days.

(21) Appl. No.: 17/111,115

(22) Filed: Dec. 3, 2020

(65) Prior Publication Data

US 2021/0147492 A1 May 20, 2021

Related U.S. Application Data

(63) Continuation of application No. 15/518,677, filed as application No. PCT/US2015/055491 on Oct. 14, 2015, now abandoned.

(60) Provisional application No. 62/064,877, filed on Oct. 16, 2014.

(51) Int. Cl.
| | |
|---|---|
| *C07K 14/325* | (2006.01) |
| *C12N 15/82* | (2006.01) |
| *A01N 65/44* | (2009.01) |
| *A01N 65/22* | (2009.01) |
| *A01N 37/46* | (2006.01) |
| *A01N 63/50* | (2020.01) |
| *A01N 63/10* | (2020.01) |

(52) U.S. Cl.
CPC ............ *C07K 14/325* (2013.01); *A01N 37/46* (2013.01); *A01N 63/10* (2020.01); *A01N 63/50* (2020.01); *A01N 65/22* (2013.01); *A01N 65/44* (2013.01); *C12N 15/8286* (2013.01); *Y02A 40/146* (2018.01)

(58) Field of Classification Search
CPC ...... C07K 14/325; A01N 53/50; A01N 63/10; A01N 37/46; A01N 65/22; A01M 65/44; C12N 15/8286
See application file for complete search history.

(56) References Cited

U.S. PATENT DOCUMENTS

| | | | |
|---|---|---|---|
| 5,723,758 A | 3/1998 | Payne et al. | |
| 7,790,846 B2 | 9/2010 | Flannagan et al. | |
| 8,735,560 B1 | 5/2014 | English et al. | |
| 9,663,795 B2 | 5/2017 | Meade et al. | |
| 10,934,330 B2 | 3/2021 | Gao et al. | |
| 11,028,407 B2 | 6/2021 | Lu et al. | |
| 2006/0112447 A1 | 5/2006 | Bogdanova et al. | |
| 2009/0313722 A1 | 12/2009 | Abad et al. | |
| 2010/0192256 A1 | 7/2010 | Abad et al. | |
| 2010/0235951 A1 | 9/2010 | Van Rie et al. | |
| 2012/0311746 A1 | 12/2012 | Meade et al. | |
| 2014/0242048 A1 | 8/2014 | Ding et al. | |

FOREIGN PATENT DOCUMENTS

| | | |
|---|---|---|
| WO | 9504146 A2 | 2/1995 |
| WO | 9924581 A2 | 5/1999 |
| WO | 0114562 A2 | 3/2001 |
| WO | 0119859 A2 | 3/2001 |
| WO | 2009152023 A1 | 12/2009 |
| WO | 2010085295 A2 | 7/2010 |
| WO | 2010120452 A1 | 10/2010 |
| WO | 2013134734 A2 | 9/2013 |
| WO | 2014055881 A1 | 4/2014 |
| WO | 2015021139 A2 | 2/2015 |
| WO | 2016061391 | 4/2016 |
| WO | WO2014138339 | 6/2017 |

OTHER PUBLICATIONS

International Search Report and Written Opinion for International Application PCT/US15/55491 dated Mar. 11, 2016.
Bohorova, N. et al: Novel synthetic Bacillus thuringiensis cry1B gene and the cry1B-cry1Ab translational fusion confer resistance to southwestern corn borer, sugarcane borer and fall armyworm in transgenic tropical maize, Theor Appl Genet, 2001, vol. 103, pp. 817-826.
Wagner, L, et al: Molecular Approaches to Improve the Insecticidal Activity of Bacillus thuringiensis Cry Toxins, Toxins, 2014, vol. 6, pp. 2393-2423.
Bowie, et al; Science (1990) 257:1306-1310.
Burgess, et al; J. of Cell Bio. (1990) 111:2129-2138.
Lazar, et al.; Molecular and Cellular Biology (1988) 8:1247-1252.
Bork; Genome Research (2000) 10:398-400.

*Primary Examiner* — Robert A Zeman

(57) ABSTRACT

The disclosure provides nucleic acids, and variants and fragments thereof, derived from strains of *Bacillus thuringiensis* encoding variant polypeptides having increased pesticidal activity against insect pests, including Lepidoptera and Coleopteran. Particular embodiments of the disclosure provide isolated nucleic acids encoding pesticidal proteins, pesticidal compositions, DNA constructs, and transformed microorganisms and plants comprising a nucleic acid of the embodiments. These compositions find use in methods for controlling pests, especially plant pests.

4 Claims, 17 Drawing Sheets

Specification includes a Sequence Listing.

Fig. 1a

```
                    1                                                  50
   Cry1Bd    (1)  MTSNRKNENEIINALSIPAVSNHSAQMDLSLDARIEDSLCIAEGNNINPL
   IP1B-B1   (1)  MPSNRKNENEIIN-----AVSNHSAQMDLSLDARIEDSLCVAEVNNIDPF
     MP258   (1)  M SNRKNENEIINALSIPAVSNHSAQMDLSPDARIEDSLCIAEGNNINPL
  IP1B-B21   (1)  MPSNRKNENEIINALSIPAVSNHSAQMDLSLDARIEDSLCIAEGNNINPL
  IP1B-B22   (1)  MPSNRKNENGIINALSIPAVSNHSAQMDLSPDARIEDSLCVAEVNNIDPF
  IP1B-B23   (1)  MPSNRKNENEIIN-----AVSNHSAQMDLSPDARIEDSLCVAEVNNIDPF
  IP1B-B24   (1)  MPSNRKNENEIINALSIPAVSNHSAQMDLSLDARIEDSLCIAEGNNINPL
  IP1B-B25   (1)  MPSNRKNENEIINALSIPAVSNHSAQMDLSLDARIEDSLCIAEGNNINPL
  IP1B-B26   (1)  MPSNRKNENEIINALSIPAVSNHSAQMDLSLDARIEDSLCIAEGNNINPL
  IP1B-B27   (1)  MPSNRKNENEIINALSIPAVSNHSAQMDLSLDARIEDSLCIAEGNNINPL
  IP1B-B28   (1)  MPSNRKNENEIINALSIPAVSNHSAQMDLSLDARIEDSLCIAEGNNINPL
  IP1B-B29   (1)  MPSNRKNENEIINALSIPAVSNHSAQMDLSLDARIEDSLCIAEGNNINPL
  IP1B-B40   (1)  MPSNRKNENEIINALSIPAVSNHSAQMDLSLDARIEDSLCIAEGNNINPL
  IP1B-B41   (1)  MPSNRKNENEIINALSIPAVSNHSAQMDLSLDARIEDSLCIAEGNNINPL
  IP1B-B42   (1)  MPSNRKNENEIINALSIPAVSNHSAQMDLSLDARIEDSLCIAEGNNINPL
  IP1B-B43   (1)  MPSNRKNENEIINALSIPAVSNHSAQMDLSLDARIEDSLCIAEGNNINPL
  IP1B-B44   (1)  MPSNRKNENEIINALSIPAVSNHSAQMDLSLDARIEDSLCIAEGNNINPL
  IP1B-B45   (1)  MPSNRKNENEIINALSIPAVSNHSAQMDLSLDARIEDSLCIAEGNNINPL
  IP1B-B46   (1)  MPSNRKNENEIINALSIPAVSNHSAQMDLSLDARIEDSLCIAEGNNINPL
  IP1B-B47   (1)  MPSNRKNENEIINALSIPAVSNHSAQMDLSLDARIEDSLCIAEGNNINPL
  IP1B-B31   (1)  MPSNRKNENEIIN-----AVSNHSAQMDLSLDARIEDSLCVAEVNNIDPF
  IP1B-B32   (1)  MPSNRKNENEIIN-----AVSNHSAQMDLSLDARIEDSLCVAEVNNIDPF
  IP1B-B33   (1)  MPSNRKNENEIIN-----AVSNHSAQMDLSLDARIEDSLCVAEVNNIDPF
  IP1B-B34   (1)  MPSNRKNENEIIN-----AVSNHSAQMDLSLDARIEDSLCVAEVNNIDPF
     GS060   (1)  MPSNRKNENEIINALSIPAVSNHSAQMDLSPDARIEDSLCVAEGNNIDPF 51                                                100
   Cry1Bd   (51)  VSASTVQTGINIAGRILGVLGVPFAGQLASFYSFLVGELWPSGRDPWEIF
   IP1B-B1  (46)  VSASTVQTGISIAGRILGVLGVPFAGQLASFYSFLVGELWPSGRDPWEIF
     MP258  (51)  VSASTVQTGINIAGRILGVLGVPFAGQLASFYSFIVGELWPSGRDPWEIF
  IP1B-B21  (51)  VSASTVQTGINIAGRILGVLGVPFAGQLASFYSFIVGELWPSGRDPWEIF
  IP1B-B22  (51)  VSASTVQTGINIAGRILGVLGVPFAGQLASFYSFIVGELWPSGRDPWEIF
  IP1B-B23  (46)  VSASTVQTGINIAGRILGVLGVPFAGQLASFYSFLVGELWPSGRDPWEIF
  IP1B-B24  (51)  VSASTVQTGINIAGRILGVLGVPFAGQLASFYSFIVGELWPSGRDPWEIF
  IP1B-B25  (51)  VSASTVQTGINIAGRILGVLGVPFAGQLASFYSFIVGELWPSGRDPWEIF
  IP1B-B26  (51)  VSASTVQTGINIAGRILGVLGVPFAGQLASFYSFIVGELWPSGRDPWEIF
  IP1B-B27  (51)  VSASTVQTGINIAGRILGVLGVPFAGQLASFYSFIVGELWPSGRDPWEIF
  IP1B-B28  (51)  VSASTVQTGINIAGRILGVLGVPFAGQLASFYSFIVGELWPSGRDPWEIF
  IP1B-B29  (51)  VSASTVQTGINIAGRILGVLGVPFAGQLASFYSFIVGELWPSGRDPWEIF
  IP1B-B40  (51)  VSASTVQTGINIAGRILGVLGVPFAGQLASFYSFIVGELWPSGRDPWEIF
  IP1B-B41  (51)  VSASTVQTGINIAGRILGVLGVPFAGQLASFYSFIVGELWPSGRDPWEIF
  IP1B-B42  (51)  VSASTVQTGINIAGRILGVLGVPFAGQLASFYSFIVGELWPSGRDPWEIF
  IP1B-B43  (51)  VSASTVQTGINIAGRILGVLGVPFAGQLASFYSFIVGELWPSGRDPWEIF
  IP1B-B44  (51)  VSASTVQTGINIAGRILGVLGVPFAGQLASFYSFIVGELWPSGRDPWEIF
  IP1B-B45  (51)  VSASTVQTGINIAGRILGVLGVPFAGQLASFYSFIVGELWPSGRDPWEIF
  IP1B-B46  (51)  VSASTVQTGINIAGRILGVLGVPFAGQLASFYSFIVGELWPSGRDPWEIF
  IP1B-B47  (51)  VSASTVQTGINIAGRILGVLGVPFAGQLASFYSFIVGELWPSGRDPWEIF
  IP1B-B31  (46)  VSASTVQTGISIAGRILGVLGVPFAGQLASFYSFLVGELWPSGRDPWEIF
  IP1B-B32  (46)  VSASTVQTGISIAGRILGVLGVPFAGQLASFYSFLVGELWPSGRDPWEIF
  IP1B-B33  (46)  VSASTVQTGINIAGRILGVLGVPFAGQLASFYSFLVGELWPSGRDPWEIF
  IP1B-B34  (46)  VSASTVQTGISIAGRILGVLGVPFAGQLASFYSFLVGELWPSGRDPWEIF
     GS060  (51)  VSASTVQTGISIAGRILGVLGVPFAGQLASFYSFLVGELWPSGRDPWEIF
```

Fig. 1b

```
              101                                                150
  Cry1Bd (101) LEHVEQLIRQQVTENTRNTAIARLEGLGRGYRSYQQALETWLDNRNDARS
  IP1B-B1 (96) MEHVEQIVRQQITDSVRDTAIARLEGLGRGYRSYQQALETWLDNRNDARS
   MP258 (101) LEHVEQLVRQQITENARNTALARLQGLGASFRAYQQSLEDWLENRDDART
 IP1B-B21 (101) MEHVEQLVRQQITENARNTALARLQGLGASFRAYQQSLEDWLENRDNART
 IP1B-B22 (101) LEHVEQLVRQQITENARNTALARLQGLGASFRAYQQSLEDWLENRDDART
 IP1B-B23 (96) MEHVEQIVRQQITENARNTALARLQGLGASFRAYQQSLEDWLENRDDART
 IP1B-B24 (101) MEHVEQLVRQQITENARNTALARLQGLGASFRAYQQSLEDWLENRDNART
 IP1B-B25 (101) MEHVEQLVRQQITENARNTALARLQGLGASFRAYQQSLEDWLENRDNART
 IP1B-B26 (101) MEHVEQLVRQQITENARNTALARLQGLGASFRAYQQSLEDWLENRDNART
 IP1B-B27 (101) MEHVEQLVRQAITLNARNTALARLQGLGASFRAYQQSLEDWLENRDNART
 IP1B-B28 (101) MEHVEQLVRQAITLNARNTALARLQGLGASFRAYQQSLEDWLENRDNART
 IP1B-B29 (101) MEHVEQLVRQAITLNARNTALARLQGLGASFRAYQQSLEDWLENRDNART
 IP1B-B40 (101) MEHVEQLVRQHITENARNTALARLQGLGASFRAYQQSLEDWLENRDNART
 IP1B-B41 (101) MEHVEQLVRQHITENARNTALARLQGLGASFRAYQQSLEDWLENRDNART
 IP1B-B42 (101) MEHVEQLVRQMITLNARNTALARLQGLGASFRAYQQSLEDWLENRDNART
 IP1B-B43 (101) MEHVEQLVRQMITMNARNTALARLQGLGASFRAYQQSLEDWLENRDNART
 IP1B-B44 (101) MEHVEQLVRQMITHNARNTALARLQGLGASFRAYQQSLEDWLENRDNART
 IP1B-B45 (101) MEHVEQLVRQHITMNARNTALARLQGLGASFRAYQQSLEDWLENRDNART
 IP1B-B46 (101) MEHVEQLVRQMITHNARNTALARLQGLGASFRAYQQSLEDWLENRDNART
 IP1B-B47 (101) MEHVEQLVRQHITMNARNTALARLQGLGASFRAYQQSLEDWLENRDNART
 IP1B-B31 (96) MEHVEQIVRQQITDSVRDTAIARLEGLGRGYRSYQQALETWLDNRNDARS
 IP1B-B32 (96) MEHVEQIVRQQITDSVRDTAIARLEGLGRGYRSYQQALETWLDNRNDARS
 IP1B-B33 (96) MEHVEQIVRQQITDSVRDTAIARLEGLGRGYRSYQQALETWLDNRNDARS
 IP1B-B34 (96) LEHVEQLIRQQVTENTRNTAIARLEGLGRGYRSYQQALETWLDNRNDARS
   GS060 (101) MEHVEQIVRQQITDSVRDTAIARLEGLGRGYRSYQQALETWLDNRNDARS 151                                                200
  Cry1Bd (151) RSIILERYVALELDITTAIPLFRIRNEEVPLLMVYAQAANLHLLLLRDAS
  IP1B-B1 (146) RSIIRERYIALELDITTAIPLFSIRNQEVPLLMVYAQAANLHLLLLRDAS
   MP258 (151) RSVLYTQYIALELDFLNAMPLFAINNQQVPLLMVYAQAANLHLLLLRDAS
 IP1B-B21 (151) RSVLYTQYIALELDFLNAMPLFAINNQQVPLLMVYAQAANLHLLLLRDAS
 IP1B-B22 (151) RSVLYTQYIALELDFLNAMPLFAINNQRVPLLMVYAQAANLHLLLLRDAS
 IP1B-B23 (146) RSVLYTQYIALELDFLNAMPLFAINNQQVPLLMVYAQAANLHLLLLRDAS
 IP1B-B24 (151) RSVLYTQYIALELDFLNAMPLFAINNQQVPLLMVYAQAANLHLLLLRDAS
 IP1B-B25 (151) RSVLYTQYIALELDFLNAMPLFAINNQQVPLLMVYAQAANLHLLLLRDAS
 IP1B-B26 (151) RSVLYTQYIALELDFLNAMPLFAINNQQVPLLMVYAQAANLHLLLLRDAS
 IP1B-B27 (151) RSVLYTQYIALELDFLNAMPLFAINNQQVPLLMVYAQAANLHLLLLRDAS
 IP1B-B28 (151) RSVLYTQYIALELDFLNAMPLFAINNQQVPLLMVYAQAANLHLLLLRDAS
 IP1B-B29 (151) RSVLYTQYIALELDFLNAMPLFAINNQQVPLLMVYAQAANLHLLLLRDAS
 IP1B-B40 (151) RSVLYTQYIALELDFLNAMPLFAINNQQVPLLMVYAQAANLHLLLLRDAS
 IP1B-B41 (151) RSVLYTQYIALELDFLNAMPLFAINNQQVPLLMVYAQAANLHLLLLRDAS
 IP1B-B42 (151) RSVLYTQYIALELDFLNAMPLFAINNQQVPLLMVYAQAANLHLLLLRDAS
 IP1B-B43 (151) RSVLYTQYIALELDFLNAMPLFAINNQQVPLLMVYAQAANLHLLLLRDAS
 IP1B-B44 (151) RSVLYTQYIALELDFLNAMPLFAINNQQVPLLMVYAQAANLHLLLLRDAS
 IP1B-B45 (151) RSVLYTQYIALELDFLNAMPLFAINNQQVPLLMVYAQAANLHLLLLRDAS
 IP1B-B46 (151) RSVLYTQYIALELDFLNAMPLFAINNQQVPLLMVYAQAANLHLLLLRDAS
 IP1B-B47 (151) RSVLYTQYIALELDFLNAMPLFAINNQQVPLLMVYAQAANLHLLLLRDAS
 IP1B-B31 (146) RSIIRERYIALELDITTAIPLFSIRNQEVPLLMVYAQAANLHLLLLRDAS
 IP1B-B32 (146) RSIIRERYIALELDITTAIPLFSIRNQEVPLLMVYAQAANLHLLLLRDAS
 IP1B-B33 (146) RSIILERYIALELDITTAIPLFSIRNQEVPLLMVYAQAANLHLLLLRDAS
 IP1B-B34 (146) RSIILERYVALELDITTAIPLFSIRNQEVPLLMVYAQAANLHLLLLRDAS
   GS060 (151) RSIIRERYIALELDITTAIPLFSIRNQEVPLLMVYAQAANLHLLLLRDAS
```

Fig. 1c

```
             201                                                  250
   Cry1Bd (201) LFGSEWGMASSDVNQYYQEQIRYTEEYSNHCVQWYNTGLNNLRGTNAESW
   IP1B-B1 (196) LFGSEWGMSSSDVNQYYQEQIRYTEEYSNHCVQWYNTGLNNLRGTNAESW
    MP258 (201) LFGSEFGLTSQEIQRYYERQAEKTREYSDYCARWYNTGLNNLRGTNAESW
  IP1B-B21 (201) LFGSEFGLTSQEIQRYYERQAEKTREYSDYCARWYNTGLNNLRGTNAESW
  IP1B-B22 (201) LFGSEFGLTSQEIQRYYERQAEKTREYSDYCARWYNTGLNNLRGTNAESW
  IP1B-B23 (196) LFGSEFGLTSQEIQRYYERQAEKTREYSDYCARWYNTGLNNLRGTNAESW
  IP1B-B24 (201) LFGSEFGLTSQEIQRYYERQAEKTREYSDYCARWYNTGLNNLRGTNAESW
  IP1B-B25 (201) LFGSEFGLTSQEIQRYYERQAEKTREYSDYCARWYNTGLNNLRGTNAESW
  IP1B-B26 (201) LFGSEFGLTSQEIQRYYERQAEKTREYSDYCARWYNTGLNNLRGTNAESW
  IP1B-B27 (201) LFGSEFGLTSQEIQRYYERQAEKTREYSDYCARWYNTGLNNLRGTNAESW
  IP1B-B28 (201) LFGSEFGLTSQEIQRYYERQAEKTREYSDYCARWYNTGLNNLRGTNAESW
  IP1B-B29 (201) LFGSEFGLTSQEIQRYYERQAEKTREYSDYCARWYNTGLNNLRGTNAESW
  IP1B-B40 (201) LFGSEFGLTSQEIQRYYERQAEKTREYSDYCARWYNTGLNNLRGTNAESW
  IP1B-B41 (201) LFGSEFGLTSQEIQRYYERQAEKTREYSDYCARWYNTGLNNLRGTNAESW
  IP1B-B42 (201) LFGSEFGLTSQEIQRYYERQAEKTREYSDYCARWYNTGLNNLRGTNAESW
  IP1B-B43 (201) LFGSEFGLTSQEIQRYYERQAEKTREYSDYCARWYNTGLNNLRGTNAESW
  IP1B-B44 (201) LFGSEFGLTSQEIQRYYERQAEKTREYSDYCARWYNTGLNNLRGTNAESW
  IP1B-B45 (201) LFGSEFGLTSQEIQRYYERQAEKTREYSDYCARWYNTGLNNLRGTNAESW
  IP1B-B46 (201) LFGSEFGLTSQEIQRYYERQAEKTREYSDYCARWYNTGLNNLRGTNAESW
  IP1B-B47 (201) LFGSEFGLTSQEIQRYYERQAEKTREYSDYCARWYNTGLNNLRGTNAESW
  IP1B-B31 (196) LFGSEWGMSSSDVNQYYQEQIRYTEEYSNHCVQWYNTGLNNLRGTNAESW
  IP1B-B32 (196) LFGSEWGMSSSDVNQYYQEQIRYTEEYSNHCVQWYNTGLNNLRGTNAESW
  IP1B-B33 (196) LFGSEWGMASSDVNQYYQEQIRYTEEYSNHCVQWYNTGLNNLRGTNAESW
  IP1B-B34 (196) LFGSEWGMSSADVNQYYQEQIRYTEEYSNHCVQWYNTGLNNLRGTNAESW
    GS060 (201) LFGSEWGMSSADVNQYYQEQIRYTEEYSNHCVQWYNTGLNRLRGTTAESW 251                                                  300
   Cry1Bd (251) LRYNQFRRDLTLGVLDLVALFPSYDTRTYPINTSAQLTREIYTDPIGRTN
   IP1B-B1 (246) LRYNQFRRDLTLGVLDLVALFPSYDTRVYPMNTSAQLTREIYTDPIGRTN
    MP258 (251) LRYNQFRRDLTLGVLDLVALFPSYDTRIYPINTSAQLTREIYTDPIGRTN
  IP1B-B21 (251) LRYNQFRRDLTLGVLDLVALFPSYDTRIYPINTSAQLTREIYTDPIGRTN
  IP1B-B22 (251) LRYNQFRRDLTLGVLDLVALFPSYDTRVYPINTSAQLTREIYTDPIGRTN
  IP1B-B23 (246) LRYNQFRRDLTLGVLDLVALFPSYDTRIYPINTSAQLTREIYTDPIGRTN
  IP1B-B24 (251) LRYNQFRRDLTLGVLDLVALFPSYDTRIYPINTSAQLTREIYTDPIGRTN
  IP1B-B25 (251) LRYNQFRRDLTLGVLDLVALFPSYDTRIYPINTSAQLTREIYTDPIGRTN
  IP1B-B26 (251) LRYNQFRRDLTLGVLDLVALFPSYDTRIYPINTSAQLTREIYTDPIGRTN
  IP1B-B27 (251) LRYNQFRRDLTLGVLDLVALFPSYDTRIYPINTSAQLTREIYTDPIGRTN
  IP1B-B28 (251) LRYNQFRRDLTLGVLDLVALFPSYDTRIYPINTSAQLTREIYTDPIGRTN
  IP1B-B29 (251) LRYNQFRRDLTLGVLDLVALFPSYDTRIYPINTSAQLTREIYTDPIGRTN
  IP1B-B40 (251) LRYNQFRRDLTLGVLDLVALFPSYDTRIYPINTSAQLTREIYTDPIGRTN
  IP1B-B41 (251) LRYNQFRRDLTLGVLDLVALFPSYDTRIYPINTSAQLTREIYTDPIGRTN
  IP1B-B42 (251) LRYNQFRRDLTLGVLDLVALFPSYDTRIYPINTSAQLTREIYTDPIGRTN
  IP1B-B43 (251) LRYNQFRRDLTLGVLDLVALFPSYDTRIYPINTSAQLTREIYTDPIGRTN
  IP1B-B44 (251) LRYNQFRRDLTLGVLDLVALFPSYDTRIYPINTSAQLTREIYTDPIGRTN
  IP1B-B45 (251) LRYNQFRRDLTLGVLDLVALFPSYDTRIYPINTSAQLTREIYTDPIGRTN
  IP1B-B46 (251) LRYNQFRRDLTLGVLDLVALFPSYDTRIYPINTSAQLTREIYTDPIGRTN
  IP1B-B47 (251) LRYNQFRRDLTLGVLDLVALFPSYDTRIYPINTSAQLTREIYTDPIGRTN
  IP1B-B31 (246) LRYNQFRRDLTLGVLDLVALFPSYDTRVYPMNTSAQLTREIYTDPIGRTN
  IP1B-B32 (246) LRYNQFRRDLTLGVLDLVALFPSYDTRTYPINTSAQLTREIYTDPIGRTN
  IP1B-B33 (246) LRYNQFRRDLTLGVLDLVALFPSYDTRTYPINTSAQLTREIYTDPIGRTN
  IP1B-B34 (246) LRYNQFRRDLTLGVLDLVALFPSYDTRTYPINTSAQLTREIYTDPIGRTN
    GS060 (251) VRYNQFRRDLTLGVLDLVALFPSYDTRTYPIPTTAQLTREVYTDPNGVVA
```

Fig. 1d

```
                  301                                                350
   Cry1Bd  (301)  APSGFASTNWFNNNAPSFSAIEAAIFRPPHLLDFPEQLTIYSASSRWSST
   IP1B-B1  (296)  APSGFASTNWFNNNAPSFSAIEAAIFRPPHLLDFPEQLTIYSASSRWSST
    MP258  (301)  APSGFASTNWFNNNAPSFSAIEAAVIRPPHLLDFPEQLTIFSVLSRWSNT
  IP1B-B21  (301)  APSGFASTNWFNNNAPSFSAIEAAIFRPPHLLDFPEQLTIYSASSRWSST
  IP1B-B22  (301)  APSGFASTNWFNNNAPSFSAIEAAVIRPPHLLDFPEQLTIFSVLSRWSST
  IP1B-B23  (296)  APSGFASTNWFNNNAPSFSAIEAAVIRPPHLLDFPEQLTIYSASSRWSST
  IP1B-B24  (301)  APSGFASTNWFNNNAPSFSAIEAAIFRPPHLLDFPEQLTIYSASSRWSST
  IP1B-B25  (301)  APSGFASTNWFNNNAPSFSAIEAAIFRPPHLLDFPEQLTIYSASSRWSST
  IP1B-B26  (301)  APSGFASTNWFNNNAPSFSAIEAAIFRPPHLLDFPEQLTIYSASSRWSST
  IP1B-B27  (301)  APSGFASTNWFNNNAPSFSAIEAAIFRPPHLLDFPEQLTIYSASSRWSST
  IP1B-B28  (301)  APSGFASTNWFNNNAPSFSAIEAAIFRPPHLLDFPEQLTIYSASSRWSST
  IP1B-B29  (301)  APSGFASTNWFNNNAPSFSAIEAAIFRPPHLLDFPEQLTIYSASSRWSST
  IP1B-B40  (301)  APSGFASTNWFNNNAPSFSAIEAAIFRPPHLLDFPEQLTIYSASSRWSST
  IP1B-B41  (301)  APSGFASTNWFNNNAPSFSAIEAAIFRPPHLLDFPEQLTIYSASSRWSST
  IP1B-B42  (301)  APSGFASTNWFNNNAPSFSAIEAAIFRPPHLLDFPEQLTIYSASSRWSST
  IP1B-B43  (301)  APSGFASTNWFNNNAPSFSAIEAAIFRPPHLLDFPEQLTIYSASSRWSST
  IP1B-B44  (301)  APSGFASTNWFNNNAPSFSAIEAAIFRPPHLLDFPEQLTIYSASSRWSST
  IP1B-B45  (301)  APSGFASTNWFNNNAPSFSAIEAAIFRPPHLLDFPEQLTIYSASSRWSST
  IP1B-B46  (301)  APSGFASTNWFNNNAPSFSAIEAAIFRPPHLLDFPEQLTIYSASSRWSST
  IP1B-B47  (301)  APSGFASTNWFNNNAPSFSAIEAAIFRPPHLLDFPEQLTIYSASSRWSST
  IP1B-B31  (296)  APSGFASTNWFNNNAPSFSAIEAAIFRPPHLLDFPEQLTIYSASSRWSST
  IP1B-B32  (296)  APSGFASTNWFNNNAPSFSAIEAAIFRPPHLLDFPEQLTIYSASSRWSST
  IP1B-B33  (296)  APSGFASTNWFNNNAPSFSAIEAAIFRPPHLLDFPEQLTIYSASSRWSST
  IP1B-B34  (296)  APSGFASTNWFNNNAPSFSAIEAAIFRPPHLLDFPEQLTIYSASSRWSST
    GS060  (301)  GPN--NS--WFRN-GASFSAIENAIIRQPHLYDFLTNLTIYTRRS-QVGT 351                                                400
   Cry1Bd  (351)  QHMNYWVGHRLNFRPIGGTLNTSTQGLTNNTSINPVTLQFTSRDVYRTES
   IP1B-B1  (346)  QHMNYWVGHRLNSRPIIGSLTSTHGATN-TSINPVTLQFTSRDVYRTES
    MP258  (351)  QYMNYWVGHRLNSRPIIGSLTSTHGITN-TSINPVTLQFTSRDVYRTES
  IP1B-B21  (351)  QHMNYWVGHRLNFRPIGGTLNTSTHGATN-TSINPVTLQFTSRDVYRTES
  IP1B-B22  (351)  QHMNYWVGHRLESRTIRGSLSTSTHGNTN-TSINPVTLQFTSRDVYRTES
  IP1B-B23  (346)  QHMNYWVGHRLNFRPIGGTLNTSTHGATN-TSINPVTLQFTSRDVYRTES
  IP1B-B24  (351)  QHMNYWVGHRLNFRPIGGTLNTSTHGATN-TSINPVTLQFTSRDVYRTES
  IP1B-B25  (351)  QHMNYWVGHRLNFRPIGGTLNTSTHGATN-TSINPVTLQFTSRDVYRTES
  IP1B-B26  (351)  QHMNYWVGHRLNFRPIGGTLNTSTHGATN-TSINPVTLQFTSRDVYRTES
  IP1B-B27  (351)  QHMNYWVGHRLNFRPIGGTLNTSTHGATN-TSINPVTLQFTSRDVYRTES
  IP1B-B28  (351)  QHMNYWVGHRLYFRPINGTLNTSTHGATN-TSINPVTLQFTSRDVYRTES
  IP1B-B29  (351)  QHMNYWVGHRLYFRPIQGTLNTSTHGATN-TSINPVTLQFTSRDVYRTES
  IP1B-B40  (351)  QHMNYWVGHRLNFRPIHGTLNTSTHGATN-TSINPVTLQFTSRDVYRTES
  IP1B-B41  (351)  QHMNYWVGHRLNFRPIHGTLNTSTHGATN-TSINPVTLQFTSRDVYRTES
  IP1B-B42  (351)  QHMNYWVGHRLNFRPIGGTLNTSTHGATN-TSINPVTLQFTSRDVYRTES
  IP1B-B43  (351)  QHMNYWVGHRLNFRPIGGTLNTSTHGATN-TSINPVTLQFTSRDVYRTES
  IP1B-B44  (351)  QHMNYWVGHRLNFRPIGGTLNTSTHGATN-TSINPVTLQFTSRDVYRTES
  IP1B-B45  (351)  QHMNYWVGHRLNFRPIGGTLNTSTHGATN-TSINPVTLQFTSRDVYRTES
  IP1B-B46  (351)  QHMNYWVGHRLNFRPINGTLNTSTHGATN-TSINPVTLQFTSRDVYRTES
  IP1B-B47  (351)  QHMNYWVGHRLNFRPINGTLNTSTHGATN-TSINPVTLQFTSRDVYRTES
  IP1B-B31  (346)  QHMNYWVGHRLNFRPIGGTLNTSTQGLTNNTSINPVTLQFTSRDVYRTES
  IP1B-B32  (346)  QHMNYWVGHRLNFRPIGGTLNTSTQGLTNNTSINPVTLQFTSRDVYRTES
  IP1B-B33  (346)  QHMNYWVGHRLNFRPIGGTLNTSTQGLTNNTSINPVTLQFTSRDVYRTES
  IP1B-B34  (346)  QHMNYWVGHRLNFRPIGGTLNTSTQGLTNNTSINPVTLQFTSRDVYRTES
    GS060  (345)  TIMNLWAGHRITNRIQGGSTSEMVYGAITNPVSVSDIPFVNRDVYRTVS
```

Fig. 1e

```
              401                                                450
   Cry1Bd (401) NAGINILFTTPVNGVPWARFNFINPQNIYERGATTYSQPYQGVGIQLFDS
   IP1B-B1 (395) FAGINILFTTPVNGVPWARFNFINPQNIYERGATTYSQPYQGVGIQLFDS
    MP258 (400) YAGINILLTTPVNGVPWARFNWRNPLNSLR-GSLLYTIGYTGVGTQLFDS
  IP1B-B21 (400) YAGINILLTTPVNGVPWARFNWRNPLNSLR-GSLLYTIGYTGVGTQLFDS
  IP1B-B22 (400) YAGINILLTTPVNGVPWARFNWRNPLNSLR-GSLLYTIGYTGVGTQLFDS
  IP1B-B23 (395) YAGINILLTTPVNGVPWARFNWRNPLNSLR-GSLLYTIGYTGVGIQLFDS
  IP1B-B24 (400) YAGINILLTTPVNGVPWARFNWRNPLNSLR-GSLLYTIGYTGVGTQLFDS
  IP1B-B25 (400) YAGINILLTTPVNGVPWARFNWRNPLNSLR-GSLLYTIGYTGVGTQLFDS
  IP1B-B26 (400) YAGINILLTTPVNGVPWARFNWRNPLNSLR-GSLLYTIGYTGVGTQLFDS
  IP1B-B27 (400) YAGINILLTTPVNGVPWARFNWRNPLNSLR-GSLLYTIGYTGVGTQLFDS
  IP1B-B28 (400) YAGINILLTTPVNGVPWARFNWRNPLNSLR-GSLLYTIGYTGVGTQLFDS
  IP1B-B29 (400) YAGINILLTTPVNGVPWARFNWRNPLNSLR-GSLLYTIGYTGVGTQLFDS
  IP1B-B40 (400) YAGINILLTTPVNGVPWARFNWRNPLNSLR-GSLLYTIGYTGVGTQLFDS
  IP1B-B41 (400) YAGINILLTTPVNGVPWARFNWRNPLNSLR-GSLLYTIGYTGVGTQLFDS
  IP1B-B42 (400) YAGINILLTTPVNGVPWARFNWRNPLNSLR-GSLLYTIGYTGVGTQLFDS
  IP1B-B43 (400) YAGINILLTTPVNGVPWARFNWRNPLNSLR-GSLLYTIGYTGVGTQLFDS
  IP1B-B44 (400) YAGINILLTTPVNGVPWARFNWRNPLNSLR-GSLLYTIGYTGVGTQLFDS
  IP1B-B45 (400) YAGINILLTTPVNGVPWARFNWRNPLNSLR-GSLLYTIGYTGVGTQLFDS
  IP1B-B46 (400) YAGINILLTTPVNGVPWARFNWRNPLNSLR-GSLLYTIGYTGVGTQLFDS
  IP1B-B47 (400) YAGINILLTTPVNGVPWARFNWRNPLNSLR-GSLLYTIGYTGVGTQLFDS
  IP1B-B31 (396) NAGINILFTTPVNGVPWARFNFINPQNIYERGATTYSQPYQGVGIQLFDS
  IP1B-B32 (396) NAGINILFTTPVNGVPWARFNFINPQNIYERGATTYSQPYQGVGIQLFDS
  IP1B-B33 (396) NAGINILFTTPVNGVPWARFNFINPQNIYERGATTYSQPYQGVGIQLFDS
  IP1B-B34 (396) NAGINILFTTPVNGVPWARFNFINPQNIYERGATTYSQPYQGVGIQLFDS
    GS060 (395) LAGGLGSLSGIRYGLTRVDFDMIFRNHPDIVTGLFYHPGHAGIATQVKDS 451                                                500
   Cry1Bd (451) ETELPPETTERPNYESYSHRLSHIGLIIGNTLRAPVYSWTHRSADRTNTI
   IP1B-B1 (445) ETELPPETTERPNYESYSHRLSHIGLIIGNTLRAPVYSWTHRSADRTNTI
    MP258 (449) ETELPPETTERPNYESYSHRLSNIRLISGNTLRAPVYSWTHRSADRTNTI
  IP1B-B21 (449) ETELPPETTERPNYESYSHRLSNIRLIIGNTLRAPVYSWTHRSADRTNTI
  IP1B-B22 (449) ETELPPETTERPNYESYSHRLSHIGLIIGNTLRAPVYSWTHRSADRTNTT
  IP1B-B23 (444) ETELPPETTERPNYESYSHRLSNIRLISGNTLRAPVYSWTHRSADRTNTI
  IP1B-B24 (449) ETELPPETTERPNYESYSHRLSNIRLIIGNTLRAPVYSWTHRSADRTNTI
  IP1B-B25 (449) ETELPPETTERPNYESYSHRLSNIRLIIGNTLRAPVYSWTHRSADRTNTI
  IP1B-B26 (449) ETELPPETTERPNYESYSHRLSNIRLIISNTLRAPVYSWTHRSADRTNTI
  IP1B-B27 (449) ETELPPETTERPNYESYSHRLSNIRLIISGTLRAPVYSWTHRSADRTNTI
  IP1B-B28 (449) ETELPPETTERPNYESYSHRLSNIRLIIGNTLRAPVYSWTHRSADRTNTI
  IP1B-B29 (449) ETELPPETTERPNYESYSHRLSNIRLIIGNTLRAPVYSWTHRSADRTNTI
  IP1B-B40 (449) ETELPPETTERPNYESYSHRLSNIRLIISNTLRAPVYSWTHRSADRTNTI
  IP1B-B41 (449) ETELPPETTERPNYESYSHRLSNIRLIIGNTLRAPVYSWTHRSADRTNTI
  IP1B-B42 (449) ETELPPETTERPNYESYSHRLSNIRLIIGGTLRAPVYSWTHRSADRTNTI
  IP1B-B43 (449) ETELPPETTERPNYESYSHRLSNIRLIIGGTLRAPVYSWTHRSADRTNTI
  IP1B-B44 (449) ETELPPETTERPNYESYSHRLSNIRLIIGGTLRAPVYSWTHRSADRTNTI
  IP1B-B45 (449) ETELPPETTERPNYESYSHRLSNIRLIIGGTLRAPVYSWTHRSADRTNTI
  IP1B-B46 (449) ETELPPETTERPNYESYSHRLSNIRLIIGNTLRAPVYSWTHRSADRTNTI
  IP1B-B47 (449) ETELPPETTERPNYESYSHRLSNIRLIIGNTLRAPVYSWTHRSADRTNTI
  IP1B-B31 (446) ETELPPETTERPNYESYSHRLSHIGLIIGNTLRAPVYSWTHRSATTTNTI
  IP1B-B32 (446) ETELPPETTERPNYESYSHRLSHIGLIIGNTLRAPVYSWTHRSATTTNTI
  IP1B-B33 (446) ETELPPETTERPNYESYSHRLSHIGLIIGNTLRAPVYSWTHRSATTTNTI
  IP1B-B34 (446) ETELPPETTERPNYESYSHRLSHIGLIIGNTLRAPVYSWTHRSATTTNTI
    GS060 (445) ETELPPETTEQPNYRAFSHLLSHISMGPTTQDVPPVYSWTHQSADRTNTI
```

Fig. 1f

```
                  501                                                550
Cry1Bd    (501)   GPNRITQIPAVKGRFLFNG-SVISGPGFTGGDVVRLNRNNGNIQNRGYIE
IP1B-B1   (495)   GPNRITQIPAVKGRFLFNG-SVISGPGFTGGDVVRLNRNNGNIQNRGYIE
MP258     (499)   ATNIITQIPAVKGNFLFNG-SVISGPGFTGGDLVRLNNSGNNIQNRGYLE
IP1B-B21  (499)   ATNIITQIPAVKGNFLFNG-SVISGPGFTGGDLVRLNNSGNNIQNRGYIE
IP1B-B22  (499)   GPNRITQIPAVKGNFLFNG-SVISGPGFTGGDLVRLNNSGNNIQNRGYLE
IP1B-B23  (494)   ATNIITQIPAVKGNFLFNG-SVTSGPGFTGGDLVRLNNSGNNIQNRGYLE
IP1B-B24  (499)   ATNIITQIPAVKGNFLFNG-SVISGPGFTGGDLVRLNNSGNNIQNRGYIE
IP1B-B25  (499)   ATNIITQIPAVKGNFLFNG-SVISGPGFTGGDLVRLNNSGNNIQNRGYIE
IP1B-B26  (499)   ATNIITQIPAVKGNFLFNG-SVISGPGFTGGDLVRLNNSGNNIQNRGYIE
IP1B-B27  (499)   ATNIITQIPAVKGNFLFNG-SVISGPGFTGGDLVRLNNSGNNIQNRGYIE
IP1B-B28  (499)   ATNIITQIPAVKGNFLFNG-SVISGPGFTGGDLVRLNNSGNNIQNRGYIE
IP1B-B29  (499)   ATNIITQIPAVKGNFLFNG-SVISGPGFTGGDLVRLNNSGNNIQNRGYIE
IP1B-B40  (499)   ATNIITQIPAVKGNFLFNG-SVISGPGFTGGDLVRLNNSGNNIYNRGYIE
IP1B-B41  (499)   ATNIITQIPAVKGNFLFNG-SVISGPGFTGGDLVRLNNSGNNIYNRGYIE
IP1B-B42  (499)   ATNIITQIPAVKGNFLFNG-SVISGPGFTGGDLVRLNNSGNNIQNRGYIE
IP1B-B43  (499)   ATNIITQIPAVKGNFLFNG-SVISGPGFTGGDLVRLNNSGNNIQNRGYIE
IP1B-B44  (499)   ATNIITQIPAVKGNFLFNG-SVISGPGFTGGDLVRLNNSGNNIQNRGYIE
IP1B-B45  (499)   ATNIITQIPAVKGNFLFNG-SVISGPGFTGGDLVRLNNSGNNIQNRGYIE
IP1B-B46  (499)   ATNIITQIPAVKGNFLFNG-SVISGPGFTGGDLVRLNNSGNNIQNRGYIE
IP1B-B47  (499)   ATNIITQIPAVKGNFLFNG-SVISGPGFTGGDLVRLNNSGNNIQNRGYIE
IP1B-B31  (496)   DPERINQIPLVKGFRVWGGTSVITGPGFTGGDILRRNTFGDFVSLQVNIN
IP1B-B32  (496)   DPERINQIPLVKGFRVWGGTSVITGPGFTGGDILRRNTFGDFVSLQVNIN
IP1B-B33  (496)   DPERINQIPLVKGFRVWGGTSVITGPGFTGGDILRRNTFGDFVSLQVNIN
IP1B-B34  (496)   DPERINQIPLVKGFRVWGGTSVITGPGFTGGDILRRNTFGDFVSLQVNIN
GS060     (495)   NSDRITQIPLVKAHTLQSGTTVVKGPGFTGGDILRRTSGGPFAFSNVNLD 551                                                600
Cry1Bd    (550)   VPIQFTSTSTRYRVRVRYASVTSIELNVNLGNSS-------IFTNTLPAT
IP1B-B1   (544)   VPIQFTSTSTRYRVRVRYASVTSIELNVNLGNSS-------IFTNTLPAT
MP258     (548)   VPIQFISTSTRYRVRVRYASVTPIQLSVNWGNSN-------IFSSIVPAT
IP1B-B21  (548)   VPIQFISTSTRYRVRVRYASVTPIQLSVNWGNSN-------IFSSIVPAT
IP1B-B22  (548)   VPIQFISTSTRYRVRVRYASVTPIQLSVNWGNSN-------IFSSIVPAT
IP1B-B23  (543)   VPIQFISTSTRYRVRVRYASVTPIQLSVNWGNSN-------IFSSIVPAT
IP1B-B24  (548)   VPIQFISTSTRYRVRVRYASVTPIQLSVNWGNSN-------IFSRIVPAT
IP1B-B25  (548)   VPIQFISTSTRYRVRVRYASVTPIRLSVNWGNSN-------IFSSIVPAT
IP1B-B26  (548)   VPIQFISTSTRYRVRVRYASVTPIRLSVNWGNSN-------IFSSIVPAT
IP1B-B27  (548)   VPIQFISTSTRYRVRVRYASVTPIRLSVNWGNSN-------IFSSIVPAT
IP1B-B28  (548)   VPIQFISTSTRYRVRVRYASVTPIRLSVNWGNSN-------IFSSIVPAT
IP1B-B29  (548)   VPIQFISTSTRYRVRVRYASVTPIRLSVNWGNSN-------IFSSIVPAT
IP1B-B40  (548)   VPIQFISTSTRYRVRVRYASVTPIRLSVNWGNSN-------IFSSIVPAT
IP1B-B41  (548)   VPIQFISTSTRYRVRVRYASVTPIRLSVNWGNSN-------IFSTIVPAT
IP1B-B42  (548)   VPIQFISTSTRYRVRVRYASVTPIRLSVNWGNSN-------IFSSIVPAT
IP1B-B43  (548)   VPIQFISTSTRYRVRVRYASVTPIRLSVNWGNSN-------IFSSIVPAT
IP1B-B44  (548)   VPIQFISTSTRYRVRVRYASVTPIRLSVNWGNSN-------IFSSIVPAT
IP1B-B45  (548)   VPIQFISTSTRYRVRVRYASVTPIRLSVNWGNSN-------IFSSIVPAT
IP1B-B46  (548)   VPIQFISTSTRYRVRVRYASVTPIRLSVNWGNSN-------IFSSIVPAT
IP1B-B47  (548)   VPIQFISTSTRYRVRVRYASVTPIRLSVNWGNSN-------IFSSIVPAT
IP1B-B31  (546)   SPIT-----QRYRLRFRYASSRDARVIVLTGAASTGVGGQVSVNMPIQKT
IP1B-B32  (546)   SPIT-----QRYRLRFRYASSRDARVIVLTGAASTGVGGQVSVNMPIQKT
IP1B-B33  (546)   SPIT-----QRYRLRFRYASSRDARVIVLTGAASTGVGGQVSVNMPIQKT
IP1B-B34  (546)   SPIT-----QRYRLRFRYASSRDARVIVLTGAASTGVGGQVSVNMPIQKT
GS060     (545)   FNIS-----QRYRARIRYASTTNLRIYVTVAGER-------IFAGQFDKT
```

Fig. 1g

```
                  601                                                  650
   Cry1Bd (593)  AASLDNLQSGDFGYVEINNAFTS---ATGNIVGARN------FSANAEV
   IP1B-B1 (587) AASLDNLQSGDFGYVEINNAFTS---ATGNIVGARN------FSANAEV
    MP258 (591)  ATSLDNLQSRDFGYFESTNAFTS---ATGNVVGVRN------FSENAGV
  IP1B-B21 (591) ATSLDNLQSRNFGYFESTNAFTS---ATGNVVGVRN------FSENAGV
  IP1B-B22 (591) ATSLDNLQSRDFGYFESTNAFTS---ATGNVVGVRN------FSENAGV
  IP1B-B23 (586) ATSLDNLQSRDFGYFESTNAFTS---ATGNVVGVRN------FSENAGV
  IP1B-B24 (591) AYSLDNLQSRNFGYFESTNAFTS---ATGNVVGVRN------FSENAGV
  IP1B-B25 (591) ATSLDNLQSRNFGYFESRNAFTS---ATGNVVGVRN------FSENAGV
  IP1B-B26 (591) ATSLDNLQSRNFGYFESRNAFTS---ATGNVVGVRN------FSENAGV
  IP1B-B27 (591) ATSLDNLQSRNFGYFESRNAFTS---ATGNVVGVRN------FSENAGV
  IP1B-B28 (591) ATSLDNLQSRNFGYFESRNAFTS---ATGNVVGVRN------FSENAGV
  IP1B-B29 (591) ATSLDNLQSRNFGYFESRNAFTS---ATGNVVGVRN------FSENAGV
  IP1B-B40 (591) ATSLDNLQSRNFGYFESRNAFTS---ATGNVVGVRN------FSENAGV
  IP1B-B41 (591) ATSLDNLQSRNFGYFESRNAFTS---ATGNVVGVRN------FSENAGV
  IP1B-B42 (591) ATSLDNLQSRNFGYFESRNAFTS---ATGNVVGVRN------FSENAGV
  IP1B-B43 (591) ATSLDNLQSRNFGYFESRNAFTS---ATGNVVGVRN------FSENAGV
  IP1B-B44 (591) ATSLDNLQSRNFGYFESRNAFTS---ATGNVVGVRN------FSENAGV
  IP1B-B45 (591) ATSLDNLQSRNFGYFESRNAFTS---ATGNVVGVRN------FSENAGV
  IP1B-B46 (591) ATSLDNLQSRNFGYFESRNAFTS---ATGNVVGVRN------FSENAGV
  IP1B-B47 (591) ATSLDNLQSRNFGYFESRNAFTS---ATGNVVGVRN------FSENAGV
  IP1B-B31 (591) MEIGENLTSRTFRYTDFSNPFSFR--ANPDIIGISEQPLFGAGSISSGEL
  IP1B-B32 (591) MEIGENLTSRTFRYTDFSNPFSFR--ANPDIIGISEQPLFGAGSISSGEL
  IP1B-B33 (591) MEIGENLTSRTFRYTDFSNPFSFR--ANPDIIGISEQPLFGAGSISSGEL
  IP1B-B34 (591) MEIGENLTSRTFRYTDFSNPFSFR--ANPDIIGISEQPLFGAGSISSGEL
    GS060 (583) MDAGAPLTFQSFSYATINTAFTFPERSSSLTVGADT------FSSGNEV 651             675
   Cry1Bd (633)  IIDRFEFIPVTATFEAEYDLERAQK
   IP1B-B1 (627) IIDRFEFIPVTATFEAEYDLERAQK
    MP258 (631)  IIDRFEFIPVTATFEAEYDLERAQE
  IP1B-B21 (631) IIDRFEFIPVTATFEAEYDLERAQE
  IP1B-B22 (631) IIDRFEFIPVTATFEAEYDLERAQE
  IP1B-B23 (626) IIDRFEFIPVTATFEAEYDLERAQE
  IP1B-B24 (631) IIDRFEFIPVTATFEAEYDLERAQE
  IP1B-B25 (631) IIDRFEFIPVTATFEAEYDLERAQE
  IP1B-B26 (631) IIDRFEFIPVTATFEAEYDLERAQE
  IP1B-B27 (631) IIDRFEFIPVTATFEAEYDLERAQE
  IP1B-B28 (631) IIDRFEFIPVTATFEAEYDLERAQE
  IP1B-B29 (631) IIDRFEFIPVTATFEAEYDLERAQE
  IP1B-B40 (631) IIDRFEFIPVTATFEAEYDLERAQE
  IP1B-B41 (631) IIDRFEFIPVTATFEAEYDLERAQE
  IP1B-B42 (631) IIDRFEFIPVTATFEAEYDLERAQE
  IP1B-B43 (631) IIDRFEFIPVTATFEAEYDLERAQE
  IP1B-B44 (631) IIDRFEFIPVTATFEAEYDLERAQE
  IP1B-B45 (631) IIDRFEFIPVTATFEAEYDLERAQE
  IP1B-B46 (631) IIDRFEFIPVTATFEAEYDLERAQE
  IP1B-B47 (631) IIDRFEFIPVTATFEAEYDLERAQE
  IP1B-B31 (639) YIDKIEIILADATFEAESDLERAQK
  IP1B-B32 (639) YIDKIEIILADATFEAESDLEGARK
  IP1B-B33 (639) YIDKIEIILADATFEAESDLEKAQK
  IP1B-B34 (639) YIDKIEIILADATFEAESDLERAQK
    GS060 (626) YVDRFELIPVTATFEAESDLERARK
```

Fig. 2a

```
Met Thr Ser Asn Arg Lys Asn Glu Asn Glu Ile Ile Asn Ala Leu Ser
1               5                   10                  15
****************************************************************

Ile Pro Ala Val Ser Asn His Ser Ala Gln Met Asp Leu Ser Pro Asp
            20                  25                  30
****************************************************************

Ala Arg Ile Glu Asp Ser Leu Cys Ile Ala Glu Gly Asn Asn Ile Asn
        35                  40                  45
******##########################################################

Pro Leu Val Ser Ala Ser Thr Val Gln Thr Gly Ile Asn Ile Ala Gly
    50                  55                  60
################################################################

Arg Ile Leu Gly Val Leu Gly Val Pro Phe Ala Gly Gln Leu Ala Ser
65              70                  75                      80
################################################################

Phe Tyr Ser Phe Ile Val Gly Glu Leu Trp Pro Ser Gly Arg Asp Pro
                85                  90                  95
################################################################

Trp Glu Ile Phe Leu Glu His Val Gln Leu Val Arg Gln Gln Ile
            100                 105                 110
################################################################

Thr Glu Asn Ala Arg Asn Thr Ala Leu Ala Arg Leu Gln Gly Leu Gly
        115                 120                 125
################################################################

Ala Ser Phe Arg Ala Tyr Gln Ser Leu Glu Asp Trp Leu Glu Asn
    130                 135                 140
################################################################
```

Fig.2b

```
Arg Asp Asp Ala Arg Thr Arg Ser Val Leu Tyr Thr Gln Tyr Ile Ala
145                 150                 155                 160
################################################################

Leu Glu Leu Asp Phe Leu Asn Ala Met Pro Leu Phe Ala Ile Asn Asn
                165                 170                 175
################################################################

Gln Gln Val Pro Leu Leu Met Val Tyr Ala Gln Ala Ala Asn Leu His
            180                 185                 190
################################################################

Leu Leu Leu Leu Arg Asp Ala Ser Leu Phe Gly Ser Glu Phe Gly Leu
            195                 200                 205
################################################################

Thr Ser Gln Glu Ile Gln Arg Tyr Tyr Glu Arg Gln Ala Glu Lys Thr
        210                 215                 220
################################################################

Arg Glu Tyr Ser Asp Tyr Cys Ala Arg Trp Tyr Asn Thr Gly Leu Asn
225                 230                 235                 240
################################################################

Asn Leu Arg Gly Thr Asn Ala Glu Ser Trp Leu Arg Tyr Asn Gln Phe
                245                 250                 255
################################################################

Arg Arg Asp Leu Thr Leu Gly Val Leu Asp Leu Val Ala Leu Phe Pro
                260                 265                 270
################################################################

Ser Tyr Asp Thr Arg Ile Tyr Pro Ile Asn Thr Ser Ala Gln Leu Thr
            275                 280                 285
#################&&&&&&&&&&&&&&&&&&&&&&&&&&&&&&&&&&&&&&&&&&&&&&&
```

Fig. 2c

Arg Glu Ile Tyr Thr Asp Pro Ile Gly Arg Thr Asn Ala Pro Ser Gly
290             295             300
&&&&&&&&&&&&&&&&&&&&&&&&&&&&&&&&&&&&&&&&&&&&&&&&

Phe Ala Ser Thr Asn Trp Phe Asn Asn Ala Pro Ser Phe Ser Ala
305             310             315             320
&&&&&&&&&&&&&&&&&&&&&&&&&&&&&&&&&&&&&&&&&&&&&&&&

Ile Glu Ala Ala Val Ile Arg Pro Pro His Leu Leu Asp Phe Pro Glu
        325             330             335
&&&&&&&&&&&&&&&&&&&&&&&&&&&&&&&&&&&&&&&&&&&&&&&&

Gln Leu Thr Ile Phe Ser Val Leu Ser Arg Trp Ser Asn Thr Gln Tyr
        340             345             350
&&&&&&&&&&&&&&&&&&&&&&&&&&&&&&&&&&&&&&&&&&&&&&&&

Met Asn Tyr Trp Val Gly His Arg Leu Glu Ser Arg Thr Ile Arg Gly
        355             360             365
&&&&&&&&&&&&&&&&&&&&&&&&&&&&&&&&&&&&&&&&&&&&&&&&

Ser Leu Ser Thr Ser Thr His Gly Asn Thr Asn Thr Ser Ile Asn Pro
370             375             380
&&&&&&&&&&&&&&&&&&&&&&&&&&&&&&&&&&&&&&&&&&&&&&&&

Val Thr Leu Gln Phe Thr Ser Arg Asp Val Tyr Arg Thr Glu Ser Tyr
385             390             395             400
&&&&&&&&&&&&&&&&&&&&&&&&&&&&&&&&&&&&&&&&&&&&&&&&

Ala Gly Ile Asn Ile Leu Leu Thr Thr Pro Val Asn Gly Val Pro Trp
        405             410             415
&&&&&&&&&&&&&&&&&&&&&&&&&&&&&&&&&&&&&&&&&&&&&&&&

Ala Arg Phe Asn Trp Arg Asn Pro Leu Asn Ser Leu Arg Gly Ser Leu
        420             425             430
&&&&&&&&&&&&&&&&&&&&&&&&&&&&&&&&&&&&&&&&&&&&&&&&

Fig. 2d

Leu Tyr Thr Ile Gly Tyr Thr Gly Val Gly Thr Gln Leu Phe Asp Ser
      435                440              445
&&&&&&&&&&&&&&&&&&&&&&&&&&&&&&&&&&&&&&&&&&&&&&&&

Glu Thr Glu Leu Pro Pro Glu Thr Thr Glu Arg Pro Asn Tyr Glu Ser
   450                  455              460
&&&&&&&&&&&&&&&&&&&&&&&&&&&&&&&&&&&&&&&&&&&&&&&&

Tyr Ser His Arg Leu Ser Asn Ile Arg Leu Ile Ser Gly Asn Thr Leu
465                 470              475              480
&&&&&&&&&&&&&&&&&&&&&&&&&&&&&&&&&&&&&&&&&&&&&&&&

Arg Ala Pro Val Tyr Ser Trp Thr His Arg Ser Ala Asp Arg Thr Asn
      485                490              495
&&&&&&&&&&&&&&&&&&&&&&&&&&&&&&&&&&&&&&!!!!!!!!!!!

Thr Ile Ala Thr Asn Ile Ile Thr Gln Ile Pro Ala Val Lys Gly Asn
      500                505              510
!!!!!!!!!!!!!!!!!!!!!!!!!!!!!!!!!!!!!!!!!!!!!!!!

Phe Leu Phe Asn Gly Ser Val Ile Ser Gly Pro Gly Phe Thr Gly Gly
      515                520              525
!!!!!!!!!!!!!!!!!!!!!!!!!!!!!!!!!!!!!!!!!!!!!!!!

Asp Leu Val Arg Leu Asn Asn Ser Gly Asn Asn Ile Gln Asn Arg Gly
   530                  535              540
!!!!!!!!!!!!!!!!!!!!!!!!!!!!!!!!!!!!!!!!!!!!!!!!

Tyr Leu Glu Val Pro Ile Gln Phe Ile Ser Thr Ser Thr Arg Tyr Arg
545                 550              555              560
!!!!!!!!!!!!!!!!!!!!!!!!!!!!!!!!!!!!!!!!!!!!!!!!

Val Arg Val Arg Tyr Ala Ser Val Thr Pro Ile Gln Leu Ser Val Asn
      565                570              575
!!!!!!!!!!!!!!!!!!!!!!!!!!!!!!!!!!!!!!!!!!!!!!!!

Fig. 2e

```
Trp Gly Asn Ser Asn Ile Phe Ser Ser Ile Val Pro Ala Thr Ala Thr
            580                 585                 590
!!!!!!!!!!!!!!!!!!!!!!!!!!!!!!!!!!!!!!!!!!!!!!!!!

Ser Leu Asp Asn Leu Gln Ser Arg Asp Phe Gly Tyr Phe Glu Ser Thr
            595                 600                 605
!!!!!!!!!!!!!!!!!!!!!!!!!!!!!!!!!!!!!!!!!!!!!!!!!

Asn Ala Phe Thr Ser Ala Thr Gly Asn Val Val Gly Val Arg Asn Phe
        610                 615                 620
!!!!!!!!!!!!!!!!!!!!!!!!!!!!!!!!!!!!!!!!!!!!!!!!!

Ser Glu Asn Ala Gly Val Ile Ile Asp Arg Phe Glu Phe Ile Pro Val
625                 630                 635                 640
!!!!!!!!!!!!!!!!!!!!!!!!!!!!!!!!!!!!!!!!!!!!!!!!!

Thr Ala Thr Phe Glu Ala Glu Tyr Asp Leu Glu Arg Ala Gln Glu
                645                 650                 655
!!!!!!!!!!!!!!!!!!!!!!!!!!!!!!!!!!!!!!!!!!!!!!!!!
```

Fig. 3

```
                   1                                                    50
Cry1Be Dom I   (1) IEDSLCIAEGNNIDPFVSASTVQTGINIAGRILGVLGVPFAGQIASFYSF
MP258  Dom I   (1) IEDSLCIAEGNNINPLVSASTVQTGINIAGRILGVLGVPFAGQLASFYSF 51                                                  100
Cry1Be Dom I  (51) LVGELWPRGRDPWEIFLEHVEQLIRQQVTENTRDTALARLQGLGNSFRAY
MP258  Dom I  (51) IVGELWPSGRDPWEIFLEHVEQLVRQQITENARNTALARLQGLGASFRAY 101                                                 150
Cry1Be Dom I (101) QQSLEDWLENRDDARTRSVLYTQYIALELDFLNAMPLFAIRNQEVPLLMV
MP258  Dom I (101) QQSLEDWLENRDDARTRSVLYTQYIALELDFLNAMPLFAINNQQVPLLMV

```
              1                                                  50
Cry1Ah D3  (1) -NNIIASDSITQIPAVKGNFLFNGSVISGPGFTGGDLVRLNSSGNNIQNR
Cry1Bd D3  (1) RTNTIGPNRITQIPAVKGRFLFNGSVISGPGFTGGDVVRLNRNNGNIQNR
Cry1Bh D3  (1) RTNTIGPNRITQIPAVKGRFLFNGSVISGPGFTGGDVVRLNRNNGNIQNR
Cry1Bi D3  (1) RTNTIGPNRITQIPAVKGNLLFNGSVISGPGFTGGDLVRLNNSGNNIQNR
 MP258 D3  (1) RTNTIATNIITQIPAVKGNFLFNGSVISGPGFTGGDLVRLNNSGNNIQNR 51                                                 100
Cry1Ah D3 (50) GYIEVPIHFPSTSTRYRVRVRYASVTPIHLNVNWGNSSIFSNTVPATATS
Cry1Bd D3 (51) GYIEVPIQFTSTSTRYRVRVRYASVTSIELNVNLGNSSIFTNTLPATAAS
Cry1Bh D3 (51) GYIEVPIQFTSTSTRYRVRVRYASVTSIELNVNWGNSSIFTNTLPATAAS
Cry1Bi D3 (51) GYLEVPIQFTSTSTRYRVRVRYASVTPIHLSVNWGNSNIFSSTVPATAAS
 MP258 D3 (51) GYLEVPIQFISTSTRYRVRVRYASVTPIQLSVNWGNSNIFSSIVPATATS 101                                                150
Cry1Ah D3 (100) LDNLQSSDFGYFESANAFTSSLGNIVGVRNFSGTAGVIIDRFEFIPVTAT
Cry1Bd D3 (101) LDNLQSGDFGYVEINNAFTSATGNIVGARNFSANAEVIIDRFEFIPVTAT
Cry1Bh D3 (101) LDNLQSGDFGYVEINNAFTSATGNIVGVRNFSANAEVIIDRFEFIPVTAT
Cry1Bi D3 (101) LDNLQSRDFGYFESTNAFTSVTGNVVGVRNFSENARVIIDRFEFIPVTAT
 MP258 D3 (101) LDNLQSRDFGYFESTNAFTSATGNVVGVRNFSENAGVIIDRFEFIPVTAT 151     162
Cry1Ah D3 (150) LEAEYNLERAQK
Cry1Bd D3 (151) FEAEYDLERAQK
Cry1Bh D3 (151) FEAKYDLERAQK
Cry1Bi D3 (151) FEAEYDLERAQE
 MP258 D3 (151) FEAEYDLERAQE
```

Fig. 5a

```
                       1                                                  50
MP258  D1&2     (1)    IEDSLCIAEGNNINPLVSASTVQTGINIAGRILGVLGVPFAGQLASFYSF
Cry1Be D1&2     (1)    IEDSLCIAEGNNIDPFVSASTVQTGINIAGRILGVLGVPFAGQIASFYSF
Cry1Bi D1&2     (1)    IEDGLCIAEGEYIDPFVSASTVQTGISIAGRILGVLGVPFAGQLASFYSF
Cry1Bg D1&2     (1)    IEDGLCIAEGEYIDPFVSASTVQTGISIAGRILGVLGVPFAGQLASFYSF
Cry1Bf D1&2     (1)    IEDSLCIAEGNNINPLVSASTVQTGINIAGRILGVLGVPFAGQIASFYSF
Cry1Ba D1&2     (1)    IEDSLCIAEGNNIDPFVSASTVQTGINIAGRILGVLGVPFAGQLASFYSF
Cry1Bh D1&2     (1)    IEDSLCVAEVNNIDPFVSASTVQTGINIAGRILGVLGVPFAGQLASFYSF
Cry1Bd D1&2     (1)    IEDSLCIAEGNNINPLVSASTVQTGINIAGRILGVLGVPFAGQLASFYSF
Cry1Bb D1&2     (1)    IEDSLCVAEVNNIDPFVSASTVQTGINIAGRILGVLGVPFAGQLASFYSF
Cry1Bc D1&2     (1)    IEDSLCVAEVNNIDPFVSASTVQTGINIAGRILGVLGVPFAGQLASFYSF 51                                                 100
MP258  D1&2    (51)    IVGELWPSGRDPWEIFLEHVEQLVRQQITENARNTALARLQGLGASFRAY
Cry1Be D1&2    (51)    LVGELWPRGRDPWEIFLEHVEQLIRQQVTENTRDTALARLQGLGNSFRAY
Cry1Bi D1&2    (51)    IVGELWPKGRDQWEIFMEHVEQLVRQQITANARNTALARLQGLGDSFRAY
Cry1Bg D1&2    (51)    IVGELWPKGRDQWEIFMEHVEQLVRQQITANARNTALARLQGLGDSFRAY
Cry1Bf D1&2    (51)    LVGELWPRGRDQWEIFLEHVEQLINQQITENARNTALARLQGLGDSFRAY
Cry1Ba D1&2    (51)    LVGELWPRGRDQWEIFLEHVEQLINQQITENARNTALARLQGLGDSFRAY
Cry1Bh D1&2    (51)    LVGELWPSGRDPWEIFLEHVEQLIRQQVTENTRNTAIARLEGLGRGYRSY
Cry1Bd D1&2    (51)    LVGELWPSGRDPWEIFLEHVEQLIRQQVTENTRNTAIARLEGLGRGYRSY
Cry1Bb D1&2    (51)    LVGELWPSGRDPWEIFLEHVEQLIRQQVTENTRNTAIARLEGLGRGYRSY
Cry1Bc D1&2    (51)    LVGELWPSGRDPWEIFLEHVEQLIRQQVTENTRNTAIARLEGLGRGYRSY 101                                                150
MP258  D1&2   (101)    QQSLEDWLENRDDARTRSVLYTQYIALELDFLNAMPLFAINNQQVPLLMV
Cry1Be D1&2   (101)    QQSLEDWLENRDDARTRSVLYTQYIALELDFLNAMPLFAIRNQEVPLLMV
Cry1Bi D1&2   (101)    QQSLEDWLENRNDARTRSVLYTQYIALELDFLNAMPLFAIREQEVPLLMV
Cry1Bg D1&2   (101)    QQSLEDWLENRNDARTRSVLYTQYIALELDFLNAMPLFAIREQEVPLLMV
Cry1Bf D1&2   (101)    QQSLEDWLENRDDARTRSVLYTQYIALELDFLNAMPLFAIRNQEVPLLMV
Cry1Ba D1&2   (101)    QQSLEDWLENRDDARTRSVLYTQYIALELDFLNAMPLFAIRNQEVPLLMV
Cry1Bh D1&2   (101)    QQALETWLDNRNDARSRSIILERYVALELDITTAIPLFRIRNQEVPLLMV
Cry1Bd D1&2   (101)    QQALETWLDNRNDARSRSIILERYVALELDITTAIPLFRIRNEEVPLLMV
Cry1Bb D1&2   (101)    QQALETWLDNRNDARSRSIILERYVALELDITTAIPLFRIRNEEVPLLMV
Cry1Bc D1&2   (101)    QQALETWLDNRNDARSRSIILERYVALELDITTAIPLFRIRNEEVPLLMV 151                                                200
MP258  D1&2   (151)    YAQAANLHLLLLRDASLFGSEFGLTSQEIQRYYERQAEKTREYSDYCARW
Cry1Be D1&2   (151)    YAQAANLHLLLLRDASLFGSEFGLTSQEIQRYYERQVEKTREYSDYCARW
Cry1Bi D1&2   (151)    YAQAANLHLLLLRDASLYGREFGLTSQEIQRYYERQVERTRDYSDHCVQW
Cry1Bg D1&2   (151)    YAQAANLHLLLLRDASLYGREFGLTSQEIQRYYERQVERTRDYSDHCVQW
Cry1Bf D1&2   (151)    YAQAANLHLLLLRDASLFGSEFGLTSQEIQRYYERQVEQTRDYSDYCVEW
Cry1Ba D1&2   (151)    YAQAANLHLLLLRDASLFGSEFGLTSQEIQRYYERQVERTRDYSDYCVEW
Cry1Bh D1&2   (151)    YAQAANLHLLLLRDASLFGSEWGTASSDVNQYYQEQIRYTEEYSNHCVQW
Cry1Bd D1&2   (151)    YAQAANLHLLLLRDASLFGSEWGMASSDVNQYYQEQIRYTEEYSNHCVQW
Cry1Bb D1&2   (151)    YAQAANLHLLLLRDASLFGSEWGMASSDVNQYYQEQIRYTEEYSNHCVQW
Cry1Bc D1&2   (151)    YAQAANLHLLLLRDASLFGSEWGMASSDVNQYYQEQIRYTEEYSNHCVQW
```

Fig. 5b

```
              201                                                      250
MP258 D1&2  (201) YNTGLNNLRGTNAESWLRYNQFRRDLTLGVLDLVALFPSYDTRIYPINTS
Cry1Be D1&2 (201) YNTGLNNLRGTNAESWLRYNQFRRDLTLGVLDLVALFPSYDTRVYPMNTS
Cry1Bi D1&2 (201) YNTGLNNLRGTNAESWVRYNQFRRDLTLGVLDLVALFPSYDTRTYPINTS
Cry1Bg D1&2 (201) YNTGLNNLRGTNAESWVRYNQFRRDLTLGVLDLVALFPSYDTRTYPINTS
Cry1Bf D1&2 (201) YNTGLNSLRGTNAASWVRYNQFRRDLTLGVLDLVALFPSYDTRTYPINTS
Cry1Ba D1&2 (201) YNTGLNSLRGTNAASWVRYNQFRRDLTLGVLDLVALFPSYDTRTYPINTS
Cry1Bh D1&2 (201) YNTGLNNLRGTNAESWVRYNQFRRDLTLGVLDLVALFPSYDTRTYPINTS
Cry1Bd D1&2 (201) YNTGLNNLRGTNAESWLRYNQFRRDLTLGVLDLVALFPSYDTRTYPINTS
Cry1Bb D1&2 (201) YNTGLNNLRGTNAESWLRYNQFRRDLTLGVLDLVALFPSYDTRTYPINTS
Cry1Bc D1&2 (201) YNTGLNNLRGTNAESWLRYNQFRRDLTLGVLDLVALFPSYDTRTYPINTS 251                                                      300
MP258 D1&2  (251) AQLTREIYTDPIGRTNAPSGFASTNWFNNNAPSFSAIEAAVIRPPHLLDF
Cry1Be D1&2 (251) AQLTREIYTDPIGRTNAPSGFASTNWFNNNAPSFSAIEAAVIRPPHLLDF
Cry1Bi D1&2 (251) AQLTREVYTDAIGATGVN--MASMNWYNNNAPSFSAIETAVIRSPHLLDF
Cry1Bg D1&2 (251) AQLTREVYTDAIGATGVN--MASMNWYNNNAPSFSAIETAVIRSPHLLDF
Cry1Bf D1&2 (251) AQLTREVYTDAIGATGVN--MASMNWYNNNAPSFSAIETAVIRSPHLLDF
Cry1Ba D1&2 (251) AQLTREVYTDAIGATGVN--MASMNWYNNNAPSFSAIEAAIRSPHLLDF
Cry1Bh D1&2 (251) AQLTREVYTDAIGTVHPSQAFASTTWFNNNAPSFSAIEAAVIRPPHLLDF
Cry1Bd D1&2 (251) AQLTREIYTDPIGRTNAPSGFASTNWFNNNAPSFSAIEAAIFRPPHLLDF
Cry1Bb D1&2 (251) AQLTREIYTDPIGRTNAPSGFASTNWFNNNAPSFSAIEAAIFRPPHLLDF
Cry1Bc D1&2 (251) AQLTREIYTDPIGRTNAPSGFASTNWFNNNAPSFSAIEAAIFRPPHLLDF 301                                                      350
MP258 D1&2  (301) PEQLTIFSVLSRWSNTQYMNYWVGHRLESRTIRGSLSTSTHGNTN-TSIN
Cry1Be D1&2 (301) PEQLTIFSVLSRWSNTQYMNYWVGHRLESRTIRGSLSTSTHGNTN-TSIN
Cry1Bi D1&2 (299) LEQLKIFSASSRWSNTRHMTYWRGHTIQSRPIRGALITSTHGNTN-TSIN
Cry1Bg D1&2 (299) LEQLKIFSASSRWSNTRHMTYWRGHTIQSRPIRGALITSTHGNTN-TSIN
Cry1Bf D1&2 (299) LEQLTIFSTSSRWSATRHMTYWRGHTIQSRPIGGGLNTSTHGSTN-TSIN
Cry1Ba D1&2 (299) LEQLTIFSASSRWSNTRHMTYWRGHTIQSRPIGGGLNTSTHGATN-TSIN
Cry1Bh D1&2 (301) PEQLTIYSTLSRWSNTQFMNIWAGHRLESRPIAGSLNTSTQGSTN-TSIN
Cry1Bd D1&2 (301) PEQLTIYSASSRWSSTQHMNYWVGHRLNFRPIGGTLNTSTQGLTNNTSIN
Cry1Bb D1&2 (301) PEQLTIYSASSRWSSTQHMNYWVGHRLNFRPIGGTLNTSTQGLTNNTSIN
Cry1Bc D1&2 (301) PEQLTIYSASSRWSSTQHMNYWVGHRLNFRPIGGTLNTSTQGLTNNTSIN 351                                                      400
MP258 D1&2  (350) PVTLQFTSRDVYRTESYAGINIL--LTTPVNGVPWARFNWRNPLNSLR-G
Cry1Be D1&2 (350) PVTLQFTSRDVYRTESFAGINIL--LTTPVNGVPWARFNWRNPLNSLR-G
Cry1Bi D1&2 (348) PVTFQFPSRDVYRTESYAGVLLWGIYLEPIHGVPTVRFNFRNPQNTFERG
Cry1Bg D1&2 (348) PVTFQFPSRDVYRTESYAGVLLWGIYLEPIHGVPTVRFNFRNPQNTFERG
Cry1Bf D1&2 (348) PVRLSFFSRDVYWTESYAGVLLWGIYLEPIHGVPTVRFNFRNPQNTFERG
Cry1Ba D1&2 (348) PVTLRFASRDVYRTESYAGVLLWGIYLEPIHGVPTVRFNFTNPQNISDRG
Cry1Bh D1&2 (350) PVTLQFTSRDIYRTESLAGLNIF--ITQPVNGVPWVRFNWRNPLNSLR-G
Cry1Bd D1&2 (351) PVTLQFTSRDVYRTESNAGTNIL--FTTPVNGVPWARFNFINPQNIYERG
Cry1Bb D1&2 (351) PVTLQFTSRDVYRTESNAGTNIL--FTTPVNGVPWARFNFINPQNIYERG
Cry1Bc D1&2 (351) PVTLQFTSRDVYRTESNAGTNIL--FTTPVNGVPWARFNFINPQNIYERG
```

Fig. 5c

```
                401                                                  450
MP258  D1&2  (397) SLLYTIGYTGVGTQLFDSETELPPETTERPNYESYSHRLSNIRLISGNTL
Cry1Be D1&2  (397) SLLYTIGYTGVGTQLFDSETELPPETTERPNYESYSHRLSNIRLISGNTL
Cry1Bi D1&2  (398) TANYSQPYESPGLQLKDSETELPPETTERPNYESYSHRLSHIGIILQTRL
Cry1Bg D1&2  (398) TANYSQPYESPGLQLKDSETELPPETTERPNYESYSHRLSHIGIILQTRL
Cry1Bf D1&2  (398) TANYSQPYESPGLQLKDSETELPPETTERPNYESYSHRLSHIGLISQSRV
Cry1Ba D1&2  (398) TANYSQPYESPGLQLKDSETELPPETTERPNYESYSHRLSHIGIILQSRV
Cry1Bh D1&2  (397) SLLYTIGYTGVGTQLQDSETELPPETTERPNYESYSHRLSHIGLISSSHV
Cry1Bd D1&2  (399) ATTYSQPYQGVGIQLFDSETELPPETTERPNYESYSHRLSHIGLIIGNTL
Cry1Bb D1&2  (399) ATTYSQPYQGVGIQLFDSETELPPETTERPNYESYSHRLSHIGLIIGNTL
Cry1Bc D1&2  (399) ATTYSQPYQGVGIQLFDSETELPPETTERPNYESYSHRLSHIGLIIGNTL 451         464
MP258  D1&2  (447) RAPVYSWTHRSAD-
Cry1Be D1&2  (447) RAPVYSWTHRSADR
Cry1Bi D1&2  (448) NVPVYSWTHRSADR
Cry1Bg D1&2  (448) NVPVYSWTHRSADR
Cry1Bf D1&2  (448) HVPVYSWTHRSADR
Cry1Ba D1&2  (448) NVPVYSWTHRSADR
Cry1Bh D1&2  (447) RALVYSWTHRSADR
Cry1Bd D1&2  (449) RAPVYSWTHRSADR
Cry1Bb D1&2  (449) RAPVYSWTHRSADR
Cry1Bc D1&2  (449) RAPVYSWTHRSADR
```

INSECTICIDAL POLYPEPTIDES HAVING IMPROVED ACTIVITY SPECTRUM AND USES THEREOF

CROSS-REFERENCE TO RELATED APPLICATIONS

This application is a continuation of U.S. Ser. No. 15/518,677 filed Apr. 12, 2017, which is a national stage application filed under 35 U.S.C. 371 of PCT/US15/55491 filed Oct. 14, 2015, which claims the benefit of and priority to Provisional Patent Application No. 62/064,877 filed on Oct. 16, 2014, the disclosures of which are expressly incorporated herein by reference in their entireties.

REFERENCE TO SEQUENCE LISTING SUBMITTED ELECTRONICALLY

A sequence listing having the file name "5409WOPCT-_SequenceListing.txt" created on Sep. 24, 2015 and having a size of 267 kilobytes is filed in computer readable form concurrently with the specification. The sequence listing is part of the specification and is herein incorporated by reference in its entirety.

FIELD

The present disclosure relates to recombinant nucleic acids that encode pesticidal polypeptides having insecticidal activity against corn earworm and/or fall armyworm and/or an improved spectrum of pesticidal activity against insect pests. Compositions and methods of the disclosure utilize the disclosed nucleic acids, and their encoded pesticidal polypeptides, to control plant pests.

BACKGROUND

Insect pests are a major factor in the loss of the world's agricultural crops. For example, armyworm feeding, black cutworm damage, or European corn borer damage can be economically devastating to agricultural producers. Insect pest-related crop loss from European corn borer attacks on field and sweet corn alone has reached about one billion dollars a year in damage and control expenses.

Traditionally, the primary method for impacting insect pest populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* (Bt) and *Bacillus papilliae* are among the most successful biocontrol agents discovered to date. Insect pathogenicity has also been attributed to strains of *B. larvae, B. lentimorbus, B. sphaericus* (Harwook, ed., ((1989) *Bacillus* (Plenum Press), 306), and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants have been genetically engineered to produce pesticidal proteins isolated from strains of Bt (see, e.g., Aronson (2002) *Cell Mol. Life Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. In addition, potatoes genetically engineered to contain pesticidal Cry toxins have been sold to the American farmer. While they have proven to be very successful commercially, these genetically engineered, insect-resistant crop plants provide resistance to only a narrow range of the economically important insect pests.

Accordingly, there remains a need for new Bt toxins with an improved spectrum of insecticidal activity against insect pests, e.g., toxins which are improved active against insects from the order Lepidoptera and/or Coleoptera. In addition, there remains a need for biopesticides having activity against a variety of insect pests and for biopesticides which have improved insecticidal activity.

SUMMARY

Compositions and methods are provided for impacting insect pests. More specifically, the embodiments of the present disclosure relate to methods of impacting insects utilizing nucleotide sequences encoding insecticidal peptides to produce transformed microorganisms and plants that express an insecticidal polypeptide of the embodiments. In some embodiments, the nucleotide sequences encode polypeptides that are pesticidal for at least one insect belonging to the order Lepidoptera.

In some aspects nucleic acid molecules and fragments and variants thereof are provided, which encode polypeptides that possess pesticidal activity against insect pests (e.g. SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, and SEQ ID NO: 46, and encoding the polypeptide of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45, respectively). The wild-type (e.g., naturally occurring)

nucleotide sequence of the embodiments, which was obtained from Bt, encodes an insecticidal peptide. The embodiments further provide fragments and variants of the disclosed nucleotide sequence that encode biologically active (e.g., insecticidal) polypeptides.

In another aspect variant Cry1B polypeptides are provided, encoded by a modified (e.g., mutagenized or manipulated) nucleic acid molecule of the embodiments. In particular examples, pesticidal proteins of the embodiments include fragments of full-length proteins and polypeptides that are produced from mutagenized nucleic acids designed to introduce particular amino acid sequences into the polypeptides of the embodiments. In particular embodiments, the polypeptides have enhanced pesticidal activity relative to the activity of the naturally occurring polypeptide from which they are derived.

In another aspect the nucleic acids of the embodiments can also be used to produce transgenic (e.g., transformed) monocot or dicot plants that are characterized by genomes that comprise at least one stably incorporated nucleotide construct comprising a coding sequence of the embodiments operably linked to a promoter that drives expression of the encoded pesticidal polypeptide. Accordingly, transformed plant cells, plant tissues, plants, and seeds thereof are also provided.

In another aspect transformed plant can be produced using a nucleic acid that has been optimized for increased expression in a host plant. For example, one of the pesticidal polypeptides of the embodiments can be back-translated to produce a nucleic acid comprising codons optimized for expression in a particular host, for example a crop plant such as a corn (*Zea mays*) plant. Expression of a coding sequence by such a transformed plant (e.g., dicot or monocot) will result in the production of a pesticidal polypeptide and confer increased insect resistance to the plant. Some embodiments provide transgenic plants expressing pesticidal polypeptides that find use in methods for impacting various insect pests.

In another aspect, pesticidal or insecticidal compositions containing the variant Cry1B polypeptides of the embodiments are provided and the composition can optionally comprise further insecticidal peptides. The embodiments encompass the application of such compositions to the environment of insect pests in order to impact the insect pests.

BRIEF DESCRIPTION OF THE FIGURES

FIG. 1a-1g shows an amino acid sequence alignment, using the ALIGNX® module of the Vector NTI® suite, of Cry1Bd (SEQ ID NO: 1), IP1B-B1 (SEQ ID NO: 3), IP1B-B21 (SEQ ID NO: 5), IP1B-B22 (SEQ ID NO: 7), IP1B-B23 (SEQ ID NO: 9), IP1B-B24 (SEQ ID NO: 11), IP1B-B25 (SEQ ID NO: 13), IP1B-B26 (SEQ ID NO: 15), IP1B-B27 (SEQ ID NO: 17), IP1B-B28 (SEQ ID NO: 19), IP1B-B29 (SEQ ID NO: 21), IP1B-B31 (SEQ ID NO: 23), IP1B-B32 (SEQ ID NO: 25), IP1B-B33 (SEQ ID NO: 27), IP1B-B34 (SEQ ID NO: 29), IP1B-B40 (SEQ ID NO: 31), IP1B-B41 (SEQ ID NO: 33), IP1B-B42 (SEQ ID NO: 35), IP1B-B43 (SEQ ID NO: 37), IP1B-B44 (SEQ ID NO: 39), IP1B-B45 (SEQ ID NO: 41), IP1B-B46 (SEQ ID NO: 43), IP1B-B47 (SEQ ID NO: 45), MP258 (SEQ ID NO: 47), and GS060 (SEQ ID NO: 49). The amino acid sequence diversity between the Cry1B polypeptides is highlighted.

FIG. 2a-2e shows the amino acid sequence of MP258 (SEQ ID NO: 47) with the leader region (*), Domain I (#), Domain II (&), and Domain III (!) indicated below the sequence.

FIG. 3 shows an amino acid sequence alignment, using the ALIGNX® module of the Vector NTI® suite, of the Cry1Be type Domain I of Cry1Be (amino acids 35-276 of SEQ ID NO: 58) and the Cry1Be type Domain I of MP258 (amino acids 36-276 of SEQ ID NO: 47). The amino acid sequence diversity between Domains I of the Cry1B polypeptides is highlighted.

FIG. 4 shows an amino acid sequence alignment, using the ALIGNX® module of the Vector NTI® suite, of Domain III of Cry1Ah (SEQ ID NO: 61), Cry1Bd (SEQ ID NO: 1), Cry1Bh (SEQ ID NO: 52), Cry1Bi (SEQ ID NO: 54), and MP258 (SEQ ID NO: 47). The amino acid sequence diversity between Domain III the Cry1B polypeptides is highlighted.

FIG. 5a-5c shows an amino acid sequence alignment, using the ALIGNX® module of the Vector NTI® suite, of Domain I and Domain II of MP258 (SEQ ID NO: 47), Cry1Be (SEQ ID NO: 58), Cry1Bi (SEQ ID NO: 54), Cry1Bg (SEQ ID NO: 60), Cry1Bf (SEQ ID NO: 59), Cry1Ba (SEQ ID NO: 55), Cry1Bh (SEQ ID NO: 52), Cry1Bd (SEQ ID NO: 1), Cry1Bb (SEQ ID NO: 56), and Cry1Bc (SEQ ID NO: 57). The amino acid sequence diversity between Domain I and Domain II of the Cry1B polypeptides is highlighted.

DETAILED DESCRIPTION

The embodiments of the disclosure are drawn to compositions and methods for impacting insect pests, particularly plant pests. More specifically, the isolated nucleic acid of the embodiments, and fragments and variants thereof, comprise nucleotide sequences that encode pesticidal polypeptides (e.g., proteins). The disclosed pesticidal proteins are biologically active (e.g., pesticidal) against insect pests such as, but not limited to, insect pests of the order Lepidoptera and/or Coleoptera.

The compositions of the embodiments comprise isolated nucleic acids, and fragments and variants thereof, which encode pesticidal polypeptides, expression cassettes comprising nucleotide sequences of the embodiments, isolated pesticidal proteins, and pesticidal compositions. Some embodiments provide modified pesticidal polypeptides having improved insecticidal activity against Lepidopterans relative to the pesticidal activity of the corresponding wild-type protein. The embodiments further provide plants and microorganisms transformed with these novel nucleic acids, and methods involving the use of such nucleic acids, pesticidal compositions, transformed organisms, and products thereof in impacting insect pests.

The nucleic acids and nucleotide sequences of the embodiments may be used to transform any organism to produce the encoded pesticidal proteins. Methods are provided that involve the use of such transformed organisms to impact or control plant pests. The nucleic acids and nucleotide sequences of the embodiments may also be used to transform organelles such as chloroplasts (McBride et al. (1995) *Biotechnology* 13: 362-365; and Kota et al. (1999) *Proc. Natl. Acad. Sci. USA* 96: 1840-1845).

The embodiments further relate to the identification of fragments and variants of the naturally-occurring coding sequence that encode biologically active pesticidal proteins. The nucleotide sequences of the embodiments find direct use in methods for impacting pests, particularly insect pests such as pests of the order Lepidoptera. Accordingly, the embodiments provide new approaches for impacting insect pests that do not depend on the use of traditional, synthetic chemical insecticides. The embodiments involve the discovery of naturally-occurring, biodegradable pesticides and the genes that encode them.

The embodiments further provide fragments and variants of the naturally occurring coding sequence that also encode biologically active (e.g., pesticidal) polypeptides. The nucleic acids of the embodiments encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The embodiments further provide mutations which confer improved or altered properties on the polypeptides of the embodiments. See, e.g. U.S. Pat. No. 7,462,760.

In the description that follows, a number of terms are used extensively. The following definitions are provided to facilitate understanding of the embodiments.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is generally free of sequences (such as, for example, protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the embodiments means that the isolated protein is substantially free of cellular material and includes preparations of protein having less than about 30%, 20%, 10%, or 5% (by dry weight) of contaminating protein. When the protein of the embodiments or biologically active portion thereof is recombinantly produced, culture medium represents less than about 30%, 20%, 10%, or 5% (by dry weight) of chemical precursors or non-protein-of-interest chemicals.

A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes.

As used herein a "non-genomic nucleic acid sequence" or "non-genomic nucleic acid molecule" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

As used herein, the term "impacting insect pests" refers to effecting changes in insect feeding, growth, and/or behavior at any stage of development, including but not limited to: killing the insect; retarding growth; preventing reproductive capability; antifeedant activity; and the like.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins.

As used herein, the term "pesticidally effective amount" means a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

As used herein, the term "recombinantly engineered" or "engineered" means the utilization of recombinant DNA technology to introduce (e.g., engineer) a change in the protein structure based on an understanding of the protein's mechanism of action and a consideration of the amino acids being introduced, deleted, or substituted.

As used herein, the term "mutant nucleotide sequence" or "mutation" or "mutagenized nucleotide sequence" means a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a mutant insecticidal toxin showing improved or decreased insecticidal activity, or an amino acid sequence which confers improved or decreased insecticidal activity on a polypeptide containing it. As used herein, the term “mutant” or “mutation” in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A mutant polypeptide shows improved or decreased insecticidal activity, or represents an amino acid sequence which confers improved insecticidal activity on a polypeptide containing it. Thus, the term “mutant” or “mutation” refers to either or both of the mutant nucleotide sequence and the encoded amino acids. Mutants may be used alone or in any compatible combination with other mutants of the embodiments or with other mutants. A “mutant polypeptide” may conversely show a decrease in insecticidal activity. Where more than one mutation is added to a particular nucleic acid or protein, the mutations may be added at the same time or sequentially; if sequentially, mutations may be added in any suitable order.

As used herein, the term “improved insecticidal activity” or “improved pesticidal activity” refers to an insecticidal polypeptide of the embodiments that has enhanced insecticidal activity relative to the activity of its corresponding wild-type protein, and/or an insecticidal polypeptide that is effective against a broader range of insects, and/or an insecticidal polypeptide having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type insecticidal polypeptide determined against the same insect.

For example, an improved pesticidal or insecticidal activity is provided where a wider or narrower range of insects is impacted by the polypeptide relative to the range of insects that is affected by a wild-type Bt toxin. A wider range of impact may be desirable where versatility is desired, while a narrower range of impact may be desirable where, for example, beneficial insects might otherwise be impacted by use or presence of the toxin. While the embodiments are not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

The term “toxin” as used herein refers to a polypeptide showing pesticidal activity or insecticidal activity or improved pesticidal activity or improved insecticidal activity. “Bt” or “*Bacillus thuringiensis*” toxin is intended to include the broader class of Cry toxins found in various strains of Bt, which includes such toxins as, for example, Cry1s, Cry2s, or Cry3s.

The terms “proteolytic site” or “cleavage site” refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

Research has shown that the insect gut proteases of Lepidopterans include trypsins, chymotrypsins, and elastases. See, e.g., Lenz et al. (1991) *Arch. Insect Biochem. Physiol.* 16: 201-212; and Hedegus et al. (2003) *Arch. Insect Biochem. Physiol.* 53: 30-47. For example, about 18 different trypsins have been found in the midgut of *Helicoverpa armigera* larvae (see Gatehouse et al. (1997) *Insect Biochem. Mol. Biol.* 27: 929-944). The preferred proteolytic substrate sites of these proteases have been investigated. See, e.g., Peterson et al. (1995) *Insect Biochem. Mol. Biol.* 25: 765-774.

Efforts have been made to understand the mechanism of action of Bt toxins and to engineer toxins with improved properties. It has been shown that insect gut proteases can affect the impact of Bt Cry proteins on the insect. Some proteases activate the Cry proteins by processing them from a "protoxin" form into a toxic form, or "toxin." See, Oppert (1999) *Arch. Insect Biochem. Phys.* 42: 1-12; and Carroll et al. (1997) *J. Invertebrate Pathology* 70: 41-49. This activation of the toxin can include the removal of the N- and C-terminal peptides from the protein and can also include internal cleavage of the protein. Other proteases can degrade the Cry proteins. See Oppert, ibid.

A comparison of the amino acid sequences of Cry toxins of different specificities reveals five highly-conserved sequence blocks. Structurally, the toxins comprise three distinct Domains which are, from the N- to C-terminus: a cluster of seven alpha-helices implicated in pore formation (referred to as "Domain I"), three anti-parallel beta sheets implicated in cell binding (referred to as "Domain 2"), and a beta sandwich (referred to as "Domain 3"). The location and properties of these Domains are known to those of skill in the art. See, for example, Li et al. (1991) *Nature,* 305:815-821 and Morse et al. (2001) *Structure,* 9:409-417. When reference is made to a particular domain, such as Domain I, it is understood that the exact endpoints of the domain with regard to a particular sequence are not critical so long as the sequence or portion thereof includes sequence that provides at least some function attributed to the particular domain. Thus, for example, when referring to "Domain I," it is intended that a particular sequence includes a cluster of seven alpha-helices, but the exact endpoints of the sequence used or referred to with regard to that cluster are not critical. One of skill in the art is familiar with the determination of such endpoints and the evaluation of such functions.

In an effort to improve Cry2B toxins, an effort was undertaken to identify the nucleotide sequences encoding the crystal proteins from the selected strains, which had improved activity compared to the native toxin. Depending upon the characteristics of a given preparation, it was recognized that the demonstration of pesticidal activity sometimes required trypsin pretreatment to activate the pesticidal proteins. Thus, it is understood that some pesticidal proteins require protease digestion (e.g., by trypsin, chymotrypsin, and the like) for activation, while other proteins are biologically active (e.g., pesticidal) in the absence of activation.

Such molecules may be altered by means described, for example, U.S. Pat. No. 7,462,760. In addition, nucleic acid sequences may be engineered to encode polypeptides that contain additional mutations that confer improved or altered pesticidal activity relative to the pesticidal activity of the naturally occurring polypeptide. The nucleotide sequences of such engineered nucleic acids comprise mutations not found in the wild type sequences.

The mutant polypeptides of the embodiments are generally prepared by a process that involves the steps of: obtaining a nucleic acid sequence encoding a Cry family polypeptide; analyzing the structure of the polypeptide to identify particular "target" sites for mutagenesis of the underlying gene sequence based on a consideration of the proposed function of the target domain in the mode of action of the toxin; introducing one or more mutations into the nucleic acid sequence to produce a desired change in one or more amino acid residues of the encoded polypeptide sequence; and assaying the polypeptide produced for pesticidal activity.

Many of the Bt insecticidal toxins are related to various degrees by similarities in their amino acid sequences and tertiary structure and means for obtaining the crystal structures of Bt toxins are well known. Exemplary high-resolution crystal structure solution of both the Cry3A and Cry3B polypeptides are available in the literature. The solved structure of Cry3A (Li et al. (1991) *Nature* 353:815-821) provides insight into the relationship between structure and function of the toxin. A combined consideration of the published structural analyses of Bt toxins and the reported function associated with particular structures, motifs, and the like indicates that specific regions of the toxin are correlated with particular functions and discrete steps of the mode of action of the protein. For example, many toxins isolated from Bt are generally described as comprising three domains: a seven-helix bundle that is involved in pore formation, a three-sheet domain that has been implicated in receptor binding, and a beta-sandwich motif (Li et al. (1991) *Nature* 305: 815-821).

As reported in U.S. Pat. Nos. 7,105,332, and 7,462,760, the toxicity of Cry proteins can be improved by targeting the region located between alpha helices 3 and 4 of Domain I of the toxin. This theory was premised on a body of knowledge concerning insecticidal toxins, including: 1) that alpha helices 4 and 5 of Domain I of Cry3A toxins had been reported to insert into the lipid bilayer of cells lining the midgut of susceptible insects (Gazit et al. (1998) *Proc. Natl. Acad. Sci. USA* 95: 12289-12294); 2) the inventors' knowledge of the location of trypsin and chymotrypsin cleavage sites within the amino acid sequence of the wild-type protein; 3) the observation that the wild-type protein was more active against certain insects following in vitro activation by trypsin or chymotrypsin treatment; and 4) reports that digestion of toxins from the 3' end resulted in decreased toxicity to insects.

A series of mutations may be created and placed in a variety of background sequences to create novel polypeptides having enhanced or altered pesticidal activity. See, e.g., U.S. Pat. No. 7,462,760. These mutants include, but are not limited to: the addition of at least one more protease-sensitive site (e.g., trypsin cleavage site) in the region located between helices 3 and 4 of Domain I; the replacement of an original protease-sensitive site in the wild-type sequence with a different protease-sensitive site; the addition of multiple protease-sensitive sites in a particular location; the addition of amino acid residues near protease-sensitive site(s) to alter folding of the polypeptide and thus enhance digestion of the polypeptide at the protease-sensitive site(s); and adding mutations to protect the polypeptide from degradative digestion that reduces toxicity (e.g., making a series of mutations wherein the wild-type amino acid is replaced by valine to protect the polypeptide from digestion). Mutations may be used singly or in any combination to provide polypeptides of the embodiments.

Homologous sequences were identified by similarity search on the non-redundant database (nr) of National Center for Bioinformatics Information (NCBI) using BLAST and PSI-BLAST. The homologous proteins were made up of Cry toxins primarily from *Bacillus thuringiensis*.

A mutation which is an additional or alternative protease-sensitive site may be sensitive to several classes of proteases such as serine proteases, which include trypsin and chymotrypsin, or enzymes such as elastase. Thus, a mutation which is an additional or alternative protease-sensitive site may be designed so that the site is readily recognized and/or cleaved by a category of proteases, such as mammalian proteases or insect proteases. A protease-sensitive site may also be designed to be cleaved by a particular class of enzymes or a particular enzyme known to be produced in an organism, such as, for example, a chymotrypsin produced by the corn earworm *Heliothis zea* (Lenz et al. (1991) *Arch. Insect Biochem. Physiol.* 16: 201-212). Mutations may also confer resistance to proteolytic digestion, for example, to digestion by chymotrypsin at the C-terminus of the peptide.

The presence of an additional and/or alternative protease-sensitive site in the amino acid sequence of the encoded polypeptide can improve the pesticidal activity and/or specificity of the polypeptide encoded by the nucleic acids of the embodiments. Accordingly, the nucleotide sequences of the embodiments can be recombinantly engineered or manipulated to produce polypeptides having improved or altered insecticidal activity and/or specificity compared to that of an unmodified wild-type toxin. In addition, the mutations disclosed herein may be placed in or used in conjunction with other nucleotide sequences to provide improved properties. For example, a protease-sensitive site that is readily cleaved by insect chymotrypsin, e.g., a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be placed in a Cry background sequence to provide improved toxicity to that sequence. In this manner, the embodiments provide toxic polypeptides with improved properties.

For example, a mutagenized Cry nucleotide sequence can comprise additional mutants that comprise additional codons that introduce a second trypsin-sensitive amino acid sequence (in addition to the naturally occurring trypsin site) into the encoded polypeptide. An alternative addition mutant of the embodiments comprises additional codons designed to introduce at least one additional different protease-sensitive site into the polypeptide, for example, a chymotrypsin-sensitive site located immediately 5' or 3' of the naturally occurring trypsin site. Alternatively, substitution mutants may be created in which at least one codon of the nucleic acid that encodes the naturally occurring protease-sensitive site is destroyed and alternative codons are introduced into the nucleic acid sequence in order to provide a different (e.g., substitute) protease-sensitive site. A replacement mutant may also be added to a Cry sequence in which the naturally-occurring trypsin cleavage site present in the encoded polypeptide is destroyed and a chymotrypsin or elastase cleavage site is introduced in its place.

It is recognized that any nucleotide sequence encoding the amino acid sequences that are proteolytic sites or putative proteolytic sites (for example, sequences such as RR, or LKM) can be used and that the exact identity of the codons used to introduce any of these cleavage sites into a variant polypeptide may vary depending on the use, i.e., expression in a particular plant species. It is also recognized that any of the disclosed mutations can be introduced into any polynucleotide sequence of the embodiments that comprises the codons for amino acid residues that provide the native trypsin cleavage site that is targeted for modification. Accordingly, variants of either full-length toxins or fragments thereof can be modified to contain additional or alternative cleavage sites, and these embodiments are intended to be encompassed by the scope of the embodiments disclosed herein.

It will be appreciated by those of skill in the art that any useful mutation may be added to the sequences of the embodiments so long as the encoded polypeptides retain pesticidal activity. Thus, sequences may also be mutated so that the encoded polypeptides are resistant to proteolytic digestion by chymotrypsin. More than one recognition site can be added in a particular location in any combination, and multiple recognition sites can be added to or removed from the toxin. Thus, additional mutations can comprise three, four, or more recognition sites. It is to be recognized that multiple mutations can be engineered in any suitable polynucleotide sequence; accordingly, either full-length sequences or fragments thereof can be modified to contain additional or alternative cleavage sites as well as to be resistant to proteolytic digestion. In this manner, the embodiments provide Cry toxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with wild-type toxins or by comparing mutant toxins which differ in their amino acid sequence. Putative proteolytic sites and proteolytic sites include, but are not limited to, the following sequences: RR, a trypsin cleavage site; LKM, a chymotrypsin site; and a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Compositions of the embodiments include nucleic acids, and fragments and variants thereof that encode pesticidal polypeptides. In particular, the embodiments provide for isolated nucleic acid molecules comprising nucleotide sequences encoding the amino acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 and SEQ ID NO: 45, or the nucleotide sequences encoding said amino acid sequence, for example the nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 or SEQ ID NO: 46, and fragments and variants thereof.

In particular, the embodiments provide for isolated nucleic acid molecules encoding the amino acid sequence shown in SEQ ID NO: 4 or SEQ ID NO: 8, or the nucleotide sequences encoding said amino acid sequence, for example the nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, and SEQ ID NO: 46, and fragments and variants thereof.

Also of interest are optimized nucleotide sequences encoding the pesticidal proteins of the embodiments. As used herein, the phrase "optimized nucleotide sequences" refers to nucleic acids that are optimized for expression in a particular organism, for example a plant. Optimized nucleotide sequences may be prepared for any organism of interest using methods known in the art. See, for example, U.S. Pat. No. 7,462,760, which describes an optimized nucleotide sequence encoding a disclosed pesticidal protein. In this example, the nucleotide sequence was prepared by reverse-translating the amino acid sequence of the protein and changing the nucleotide sequence so as to comprise maize-preferred codons while still encoding the same amino acid sequence. This procedure is described in more detail by Murray et al. (1989) *Nucleic Acids Res.* 17:477-498. Optimized nucleotide sequences find use in increasing expression of a pesticidal protein in a plant, for example monocot plants of the Gramineae (Poaceae) family such as, for example, a maize or corn plant.

In some embodiments polypeptides are provided comprising an amino acid sequence set forth in SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 and fragments and variants thereof.

In some embodiments polypeptides are provided comprising an amino acid sequence set forth in SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 and fragments and variants thereof.

In some embodiments polypeptides are provided comprising an amino acid sequence set forth in SEQ ID NO: 23, SEQ ID NO: 25, SEQ ID NO: 27 or SEQ ID NO: 29, and fragments and variants thereof.

In some embodiments variant Cry1B polypeptides having an amino acid substitution compared to the corresponding reference Cry1B polypeptide are provides that have increased insecticidal activity against corn earworm and/or fall armyworm compared to the "corresponding reference Cry1B polypeptide". By "corresponding reference Cry1B polypeptide" is meant a wild type or native Cry1B polypeptide or variant Cry1B polypeptide of the present embodiments, which can serve as the amino acid sequence that is mutagenized to create variant Cry1B polypeptide. In some embodiments the corresponding reference Cry1B polypeptide comprises a Cry1Be type Domain I and a Cry1Ah type Domain III. By "Cry1Be type Domain I" is meant an amino acid sequence comprising a Domain I, which comprises a cluster of seven alpha-helices, of a three domain Cry1 polypeptide, having at least 90%, at least 91%, at least 92% at least 93% at least 94%, at least 95% at least 96%, at least 97%, at least 98%, at least 99% or greater sequence identity to amino acids 36-276 of SEQ ID NO: 58 (Cry1Be) or amino acids 35-276 of SEQ ID NO: 47. An amino acid sequence alignment of Domain I of Cry1Be (SEQ ID NO: 58) and MP258 (SEQ ID NO: 47) is shown in FIG. 3. Similarly, other native Cry1B polypeptides can be aligned with Cry1Be (SEQ ID NO: 58) and MP258 (SEQ ID NO: 47) to identify other Cry1Be type Domain I regions. By "Cry1Ah type Domain III" is meant an amino acid sequence comprising a Domain III, of a three domain Cry1 polypeptide having at least 80%, at least 81%, at least 82%, at least 83%, at least 84%, at least 85%, at least 86%, at least 87%, at least 88%, at least 89%, at least 90%, at least 91%, at least 92% at least 93% at least 94%, at least 95% at least 96%, at least 97%, at least 98%, at least 99% or greater sequence identity to amino acids 483-643 of SEQ ID NO: 61 (Cry1Ah) or 494-655 of SEQ ID NO: 47. An amino acid sequence alignment of Domain III of Cry1Ah (SEQ ID NO: 61), Cry1Bd (SEQ ID NO: 1), Cry1Bh (SEQ ID NO: 52), Cry1Bi (SEQ ID NO: 54), and MP258 (SEQ ID NO: 47) is shown in FIG. 4. Similarly, other native Cry1B polypeptides can be aligned with Cry1Ah (SEQ ID NO: 61), Cry1Bd, Cry1Bh (SEQ ID NO: 52), Cry1Bi (SEQ ID NO: 54), and/or MP258 (SEQ ID NO: 47) to identify other Cry1Ah type Domain III regions. In some embodiments the corresponding reference Cry1B polypeptide comprises a Cry1Ba type Domain I and Domain II. By "Cry1Ba type Domain I and Domain II" is meant an amino acid sequence comprising a Domain I and Domain II, of a three domain Cry1B polypeptide, having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92% at least 93% at least 94%, at least 95% at least 96%, at least 97%, at least 98%, at least 99% or greater sequence identity to amino acids 30-489 of SEQ ID NO: 55 (Cry1Ba). An amino acid sequence alignment of Domain I and Domain II of MP258 (SEQ ID NO: 47), Cry1Be (SEQ ID NO: 58), Cry1Bi (SEQ ID NO: 54), Cry1Bg (SEQ ID NO: 60), Cry1Bf (SEQ ID NO: 59), Cry1Ba (SEQ ID NO: 55), Cry1Bh (SEQ ID NO: 52), Cry1Bd (SEQ ID NO: 1), Cry1Bb (SEQ ID NO: 56), and Cry1Bc (SEQ ID NO: 57) is shown in FIG. 5. Similarly, other native Cry1B polypeptides can be aligned with Cry1Ba (SEQ ID NO: 55) and MP258 (SEQ ID NO: 47) to identify other Cry1Ba type Domain I and Domain II regions.

In some embodiments the corresponding reference Cry1B polypeptide comprises a Cry1Be type Domain I and Domain II. By "Cry1Be type Domain I and Domain II" is meant an amino acid sequence comprising a Domain I and Domain II, of a three domain Cry1B polypeptide, having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92% at least 93% at least 94%, at least 95% at least 96%, at least 97%, at least 98%, at least 99% or greater sequence identity to amino acids 35-494 of SEQ ID NO: 58 (Cry1Be) or amino acids 35-493 of SEQ ID NO: 47. An amino acid sequence alignment of Domain I and Domain II of MP258 (SEQ ID NO: 47), Cry1Be (SEQ ID NO: 58), Cry1Bi (SEQ ID NO: 54), Cry1Bg (SEQ ID NO: 60), Cry1Bf (SEQ ID NO: 59), Cry1Ba (SEQ ID NO: 55), Cry1Bh (SEQ ID NO: 52), Cry1Bd (SEQ ID NO: 1), Cry1Bb (SEQ ID NO: 56), and Cry1Bc (SEQ ID NO: 57) is shown in FIG. 5. Similarly, other native Cry1B polypeptides can be aligned with Cry1Be (SEQ ID NO: 58) and MP258 (SEQ ID NO: 47) to identify other Cry1Be type Domain I and Domain II regions.

By "improved activity" or "increased activity" is intended an increase of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or higher increase in the pesticidal activity of the variant protein compared to the activity of the corresponding reference Cry1B polypeptide.

In some embodiments, the improvement consists of a decrease in the EC50 of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or greater reduction in the EC50 of the variant Cry1B polypeptide relative to the pesticidal activity of the corresponding reference Cry1B polypeptide.

In some embodiments the EC50 of the variant Cry1B polypeptide is <100 ppm, <90 ppm, <80 ppm, <70 ppm, <60 ppm, <50 ppm, <45 ppm, <40 ppm, <35 ppm, <30 ppm, <25 ppm, <20 ppm, <19 ppm, <18 ppm, <17 ppm, <16 ppm, <15 ppm, <14 ppm, <13 ppm, <12 ppm, <11 ppm, <10 ppm, <9 ppm, <8 ppm, <7 ppm, <6 ppm, <5 ppm, <4 ppm, <3 ppm, <2 ppm, <1 ppm, <0.9 ppm, <0.8 ppm, <0.7 ppm, <0.6 ppm, <0.5 ppm, <0.4 ppm, <0.3 ppm, <0.2 ppm or <0.1 ppm.

In some embodiments, the improvement consists of an increase in the Mean FAE Index of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or higher increase in the Mean FAE Index of the variant Cry1B polypeptide relative to the pesticidal activity of the corresponding reference Cry1B polypeptide.

"Mean FAE Index" (MFI) refers to the mean of multiple FAEGN an arithmetic mean of FAEGN. As used herein, the "Mean Deviation Score" refers to the arithmetic mean of multiple Deviation Scores.

In some embodiments, the improvement consists of an increase in the Mean Deviation Score of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or higher increase in the Mean Deviation Score of the variant Cry1B polypeptide relative to the pesticidal activity of the corresponding reference Cry1B polypeptide.

In some embodiments the improved activity of the variant Cry1B polypeptide is relative to the pesticidal activity of SEQ ID NO: 1 (Cry1Bd), SEQ ID NO: 47 (MP258), SEQ ID NO: 52 (Cry1Bh), SEQ ID NO: 54 (Cry1B0, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45.

In particular embodiments, pesticidal proteins of the embodiments provide full-length insecticidal polypeptides, fragments of full-length insecticidal polypeptides, and variant polypeptides that are produced from mutagenized nucleic acids designed to introduce particular amino acid sequences into polypeptides of the embodiments. In particular embodiments, the amino acid sequences that are introduced into the polypeptides comprise a sequence that provides a cleavage site for an enzyme such as a protease.

It is known in the art that the pesticidal activity of Bt toxins is typically activated by cleavage of the peptide in the insect gut by various proteases. Because peptides may not always be cleaved with complete efficiency in the insect gut, fragments of a full-length toxin may have enhanced pesticidal activity in comparison to the full-length toxin itself. Thus, some of the polypeptides of the embodiments include fragments of a full-length insecticidal polypeptide, and some of the polypeptide fragments, variants, and mutations will have enhanced pesticidal activity relative to the activity of the naturally occurring insecticidal polypeptide from which they are derived, particularly if the naturally occurring insecticidal polypeptide is not activated in vitro with a protease prior to screening for activity. Thus, the present application encompasses truncated versions or fragments of the sequences.

Mutations may be placed into any background sequence, including such truncated polypeptides, so long as the polypeptide retains pesticidal activity. One of skill in the art can readily compare two or more proteins with regard to pesticidal activity using assays known in the art or described elsewhere herein. It is to be understood that the polypeptides of the embodiments can be produced either by expression of a nucleic acid disclosed herein, or by the use of standard molecular biology techniques.

It is recognized that the pesticidal proteins may be oligomeric and will vary in molecular weight, number of residues, component peptides, activity against particular pests, and other characteristics. However, by the methods set forth herein, proteins active against a variety of pests may be isolated and characterized. The pesticidal proteins of the embodiments can be used in combination with other Bt toxins or other insecticidal proteins to increase insect target range. Furthermore, the use of the pesticidal proteins of the embodiments in combination with other Bt toxins or other insecticidal principles of a distinct nature has particular utility for the prevention and/or management of insect resistance. Other insecticidal agents include protease inhibitors (both serine and cysteine types), α-amylase, and peroxidase.

Fragments and variants of the nucleotide and amino acid sequences and the polypeptides encoded thereby are also encompassed by the embodiments. As used herein the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. Thus, it is acknowledged that some of the polynucleotide and amino acid sequences of the embodiments can correctly be referred to as both fragments and mutants.

It is to be understood that the term "fragment," as it is used to refer to nucleic acid sequences of the embodiments, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a nucleotide sequence of the embodiments that encodes a biologically active portion of a pesticidal protein of the embodiments will encode at least 15, 25, 30, 50, 100, 200, 250 or 300 contiguous amino acids, or up to the total number of amino acids present in a pesticidal polypeptide of the embodiments (for example, 651 amino acids for SEQ ID NO: 3). Thus, it is understood that the embodiments also encompass polypeptides that are fragments of the exemplary pesticidal proteins of the embodiments and having lengths of at least 15, 25, 30, 50, 100, 200, 250 or 300 contiguous amino acids, or up to the total number of amino acids present in a pesticidal polypeptide of the embodiments (for example, 651 amino acids for SEQ ID NO: 3). Fragments of a nucleotide sequence of the embodiments that are useful as hybridization probes or PCR primers generally need not encode a biologically active portion of a pesticidal protein. Thus, a fragment of a nucleic acid of the embodiments may encode a biologically active portion of a pesticidal protein, or it may be a fragment that can be used as a hybridization probe or PCR primer using methods disclosed herein. A biologically active portion of a pesticidal protein can be prepared by isolating a portion of one of the nucleotide sequences of the embodiments, expressing the encoded portion of the pesticidal protein (e.g., by recombinant expression in vitro), and assessing the activity of the encoded portion of the pesticidal protein.

Nucleic acids that are fragments of a nucleotide sequence of the embodiments comprise at least 16, 20, 50, 75, 100, 150, 200, 250, 300, 350, 400, 450, 500, 600, 700, 800, 850, 900 or 950 nucleotides, or up to the number of nucleotides present in a nucleotide sequence disclosed herein (for example, 1953 nucleotides for SEQ ID NO: 4). Particular embodiments envision fragments derived from (e.g., produced from) a first nucleic acid of the embodiments, wherein the fragment encodes a truncated toxin having pesticidal activity. Truncated polypeptides encoded by the polynucleotide fragments of the embodiments are having pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' end of the native or corresponding full-length coding sequence.

The term "variants" is used herein to refer to substantially similar sequences. For nucleotide sequences, conservative variants include those sequences that, because of the degeneracy of the genetic code, encode the amino acid sequence of one of the pesticidal polypeptides of the embodiments. Those having ordinary skill in the art will readily appreciate that due to the degeneracy of the genetic code, a multitude of nucleotide sequences encoding of the present disclosure exist.

In some embodiments the nucleic acid molecule encoding the polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, and Liu H et al. *Mol Bio Rep* 37:677-684, 2010, herein incorporated by reference. A *Zea* maize codon usage table can be also found at kazusa.or.jp/codon/cgi-bin/showcodon.cgi?species=4577, which can be accessed using the www prefix.

A *Glycine max* codon usage table is shown in Table 3 and can also be found at kazusa.or.jp/codon/cgi-bin/showcodon.cgi?species=3847&aa=1&style=N, which can be accessed using the www prefix.

The skilled artisan will further appreciate that changes can be introduced by mutation of the nucleic acid sequences thereby leading to changes in the amino acid sequence of the encoded polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Naturally occurring allelic variants such as these can be identified with the use of well-known molecular biology techniques, such as, for example, polymerase chain reaction (PCR) and hybridization techniques as outlined herein.

In some embodiments the polynucleotide encoding the polypeptide of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 is a non-genomic nucleic acid sequence.

Variant nucleotide sequences also include synthetically derived nucleotide sequences, such as those generated, for example, by using site-directed mutagenesis but which still encode a pesticidal protein of the embodiments, such as a mutant toxin. Generally, variants of a particular nucleotide sequence of the embodiments will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the embodiments may differ from that sequence by as few as 1-15 nucleotides, as few as 1-10, such as 6-10, as few as 5, as few as 4, 3, 2, or even 1 nucleotide.

Variants of a particular nucleotide sequence of the embodiments (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptides of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 are disclosed. Percent sequence identity between any two polypeptides can be calculated using sequence alignment programs described elsewhere herein using default parameters. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

As used herein, the term "variant protein" encompasses polypeptides that are derived from a native protein by: deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term "variant protein" encompasses biologically active fragments of a native protein that comprise a sufficient number of contiguous amino acid residues to retain the biological activity of the native protein, i.e., to have pesticidal activity. Such pesticidal activity may be different or improved relative to the native protein or it may be unchanged, so long as pesticidal activity is retained.

Variant proteins encompassed by the embodiments are biologically active, that is they continue to possess the desired biological activity of the native protein, that is, pesticidal activity as described herein. Such variants may result from, for example, genetic polymorphism or from human manipulation. Biologically active variants of a native pesticidal protein of the embodiments will have at least about 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the embodiments may differ from that protein by as few as 1-15 amino acid residues, as few as 1-10, such as 6-10, as few as 5, as few as 4, 3, 2, or even 1 amino acid residue.

In some embodiment the insecticidal polypeptide has at least 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45.

In some embodiments the polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the polypeptide has increased digestibility of proteolytic fragments in an insect gut. In some embodiments the polypeptide has increased stability in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

The embodiments further encompass a microorganism that is transformed with at least one nucleic acid of the embodiments, with an expression cassette comprising the nucleic acid, or with a vector comprising the expression cassette. In some embodiments, the microorganism is one that multiplies on plants. An embodiment of the disclosure relates to an encapsulated pesticidal protein which comprises a transformed microorganism capable of expressing at least one pesticidal protein of the embodiments.

The embodiments provide pesticidal compositions comprising a transformed microorganism of the embodiments. In such embodiments, the transformed microorganism is generally present in the pesticidal composition in a pesticidally effective amount, together with a suitable carrier. The embodiments also encompass pesticidal compositions comprising an isolated protein of the embodiments, alone or in combination with a transformed organism of the embodiments and/or an encapsulated pesticidal protein of the embodiments, in an insecticidally effective amount, together with a suitable carrier.

The embodiments further provide a method of increasing insect target range by using a pesticidal protein of the embodiments in combination with at least one other or "second" pesticidal protein. Any pesticidal protein known in the art can be employed in the methods of the embodiments. Such pesticidal proteins include, but are not limited to, Bt toxins, protease inhibitors, α-amylases, and peroxidases.

The embodiments also encompass transformed or transgenic plants comprising at least one nucleotide sequence of the embodiments. In some embodiments, the plant is stably transformed with a nucleotide construct comprising at least one nucleotide sequence of the embodiments operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes whole plants, plant organs (e.g., leaves, stems, roots, etc.), seeds, plant cells, and progeny of same. Parts of transgenic plants are within the scope of the embodiments and comprise, for example, plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, originating in transgenic plants or their progeny previously transformed with a DNA molecule of the embodiments and therefore consisting at least in part of transgenic cells. The class of plants that can be used in the methods of the embodiments is generally as broad as the class of higher plants amenable to transformation techniques, including both monocotyledonous and dicotyledonous plants.

While the embodiments do not depend on a particular biological mechanism for increasing the resistance of a plant to a plant pest, expression of the nucleotide sequences of the embodiments in a plant can result in the production of the pesticidal proteins of the embodiments and in an increase in the resistance of the plant to a plant pest. The plants of the embodiments find use in agriculture in methods for impacting insect pests. Certain embodiments provide transformed crop plants, such as, for example, maize plants, which find use in methods for impacting insect pests of the plant, such as, for example, Lepidopteran pests.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences of proteins of agricultural interest.

Thus, the proteins of the embodiments may be altered in various ways including amino acid substitutions, deletions, truncations, and insertions. Methods for such manipulations are generally known in the art. For example, amino acid sequence variants of the pesticidal proteins can be prepared by introducing mutations into a synthetic nucleic acid (e.g., DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein.

The mutagenized nucleotide sequences of the embodiments may be modified so as to change about 1, 2, 3, 4, 5, 6, 8, 10, 12 or more of the amino acids present in the primary sequence of the encoded polypeptide. Alternatively, even more changes from the native sequence may be introduced such that the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more of the codons altered, or otherwise modified compared to the corresponding wild-type protein. In the same manner, the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more additional codons compared to the corresponding wild-type protein. It should be understood that the mutagenized nucleotide sequences of the embodiments are intended to encompass biologically functional, equivalent peptides which have pesticidal activity, such as an improved pesticidal activity as determined by antifeedant properties against European corn borer larvae. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary amino acid substitution groups that take several of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the embodiments include both the naturally occurring sequences and mutant forms. Likewise, the proteins of the embodiments encompass both naturally occurring proteins and variations (e.g., truncated polypeptides) and modified (e.g., mutant) forms thereof. Such variants will continue to possess the desired pesticidal activity. Obviously, the mutations that will be made in the nucleotide sequence encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al. (1985) *J. Econ. Entomol.* 78: 290-293 and Czapla and Lang (1990) *J. Econ. Entomol.* 83: 2480-2485, herein incorporated by reference.

Variant nucleotide sequences and proteins also encompass sequences and proteins derived from a mutagenic and recombinogenic procedure such as DNA shuffling. With such a procedure, one or more different coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence of the embodiments may be shuffled between the nucleotide sequences of the embodiments and corresponding portions of other known Cry nucleotide sequences to obtain a new gene coding for a protein with an improved property of interest.

Properties of interest include, but are not limited to, pesticidal activity per unit of pesticidal protein, protein stability, and toxicity to non-target species particularly humans, livestock, and plants and microbes that express the pesticidal polypeptides of the embodiments. The embodiments are not bound by a particular shuffling strategy, only that at least one nucleotide sequence of the embodiments, or part thereof, is involved in such a shuffling strategy. Shuffling may involve only nucleotide sequences disclosed herein or may additionally involve shuffling of other nucleotide sequences known in the art. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook". See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cry sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37 C, and a wash in 0.5× to 1×SSC at 55 to 60° C.

Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Center for Biotechnology Information website on the world wide web at ncbi.hlm.nih.gov. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%. 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$ depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures, and the like.

A further embodiment relates to a transformed organism such as an organism selected from the group consisting of plant and insect cells, bacteria, yeast, baculovirus, protozoa, nematodes, and algae. The transformed organism comprises: a DNA molecule of the embodiments, an expression cassette comprising the said DNA molecule, or a vector comprising the said expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the Cry toxin sequence to be under the transcriptional regulation of the regulatory regions. The DNA construct may additionally contain selectable marker genes.

The DNA construct will include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about $1/1000$ transcripts to about $1/100,000$ transcripts to about $1/500,000$ transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481;

and U.S. Pat. Nos. 7,709,702; and 7,462,481); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the embodiments.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Bio/technology* 6: 923-926); and Lec1 transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues, ed.* Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the Cry toxin protein or variants and fragments thereof directly into the plant or the introduction of the Cry toxin transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cry toxin polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants, including, but not limited to: corn, alfalfa, sunflower, *Brassica* spp., soybean, cotton, safflower, peanut, sorghum, wheat, millet, tobacco, sugarcane, etc.

Turfgrasses include, but are not limited to: annual bluegrass (*Poa annus*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (Dactyls *glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithi*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mung bean, lima bean, fava bean, lentils, chickpea, etc.

In certain embodiments the nucleic acid sequences of the embodiments can be stacked with any combination of polynucleotide sequences of interest in order to create plants with a desired phenotype. For example, the polynucleotides of the embodiments may be stacked with any other polynucleotides encoding polypeptides having pesticidal and/or insecticidal activity, such as other Bt toxic proteins (described in U.S. Pat. Nos. 5,366,892; 5,747,450; 5,736,514; 5,723,756; 5,593,881; and Geiser et al. (1986) *Gene* 48:109), pentin (described in U.S. Pat. No. 5,981,722) and the like. The combinations generated can also include multiple copies of any one of the polynucleotides of interest. The polynucleotides of the embodiments can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,049); barley high lysine (Williamson et al. (1987) Eur. J. Biochem. 165: 99-106; and WO 98/20122) and high methionine proteins (Pedersen et al. (1986) J. Biol. Chem. 261: 6279; Kirihara et al. (1988) Gene 71: 359; and Musumura et al. (1989) Plant Mol. Biol. 12: 123)); increased digestibility (e.g., modified storage proteins (U.S. Pat. No. 6,858,778); and thioredoxins (U.S. Pat. No. 7,009,087), the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) Science 266:789; Martin et al. (1993) Science 262: 1432; and Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene as disclosed in U.S. Pat. Nos. 7,709,702; and 7,462,481; and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170: 5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

In some embodiment the stacked trait may be a trait or event that has received regulatory approval which are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications isaaa.org/gmapprovaldatabase/default.asp, which can be accessed using the www prefix).

These stacked combinations can be created by any method including but not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a nucleotide sequence encoding a pesticidal protein of the embodiments may be treated with a seed protectant coating comprising a seed treatment compound, such as, for example, captan, carboxin, thiram, methalaxyl, pirimiphos-methyl, and others that are commonly used in seed treatment. In one embodiment, a seed protectant coating comprising a pesticidal composition of the embodiments is used alone or in combination with one of the seed protectant coatings customarily used in seed treatment.

It is recognized that the genes encoding the pesticidal proteins can be used to transform insect pathogenic organisms. Such organisms include baculovirus, fungi, protozoa, bacteria, and nematodes.

A gene encoding a pesticidal protein of the embodiments may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium* pollulans. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook; Maniatis et al. (Cold Spring Harbor Laboratory Press, Cold Spring Harbor, N.Y.); Davis et al., eds. (1980) *Advanced Bacterial Genetics* (Cold Spring Harbor Laboratory Press, Cold Spring Harbor, N.Y.) and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa, P. fluorescens*), *Erwinia* spp., and *Flavobacterium* spp., and other such organisms, including Bt, *E. coli, Bacillus subtilis*, and the like.

Genes encoding the pesticidal proteins of the embodiments can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the embodiments can be introduced into a root-colonizing *Bacillus cereus* by standard methods known in the art.

Genes encoding pesticidal proteins can be introduced, for example, into the root-colonizing *Bacillus* by means of electro transformation. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria, such as *E. coli*, for example. Advantages of having pesticidal proteins secreted are: (1) avoidance of potential cytotoxic effects of the pesticidal protein expressed; and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J,* 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Pesticidal proteins of the embodiments can be fermented in a bacterial host and the resulting bacteria processed and used as a microbial spray in the same manner that Bt strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express Bt toxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EP0192319, and the references cited therein.

In the embodiments, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal composition(s) that is, for example, a suspension, a solution, an emulsion, a dusting powder, a dispersible granule or pellet, a wettable powder, and an emulsifiable concentrate, an aerosol or spray, an impregnated granule, an adjuvant, a coatable paste, a colloid, and also encapsulations in, for example, polymer substances. Such formulated compositions may be prepared by such conventional means as desiccation, lyophilization, homogenization, extraction, filtration, centrifugation, sedimentation, or concentration of a culture of cells comprising the polypeptide.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the pesticidal proteins produced by the bacterial strains of the embodiments include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4, 7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the embodiments can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins of the embodiments, can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) Animal Tissue Techniques (W.H. Freeman and Co.).

In other embodiments, it may be advantageous to treat the Cry toxin polypeptides with a protease, for example trypsin, to activate the protein prior to application of a pesticidal protein composition of the embodiments to the environment of the target pest. Methods for the activation of protoxin by a serine protease are well known in the art. See, for example, Cooksey (1968) *Biochem. J.* 6:445-454 and Carroll and Ellar (1989) *Biochem. J.* 261:99-105, the teachings of which are herein incorporated by reference. For example, a suitable activation protocol includes, but is not limited to, combining a polypeptide to be activated, for example a purified novel Cry polypeptide (e.g., having the amino acid sequence set forth in SEQ ID NO: 4 or SEQ ID NO: 8, and trypsin at a 1/100 weight ratio of protein/trypsin in 20 nM $NaHCO_3$, pH 8 and digesting the sample at 36° C. for 3 hours.

The compositions (including the transformed microorganisms and pesticidal proteins of the embodiments) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the pesticidal protein and/or transformed microorganisms of the embodiments may be mixed with grain to protect the grain during storage. It is generally important to obtain good control of pests in the early stages of plant growth, as this is the time when the plant can be most severely damaged. The compositions of the embodiments can conveniently contain another insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, an herbicide, an insecticide, a fertilizer, an inert carrier, and dead cells of a *Bacillus* strain or transformed microorganism of the embodiments.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae: *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hubner (cotton leaf worm); *Anticarsia gemmatalis* Hubner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira (Xylomyges)curialis* Grote (citrus cutworm); *Euxoa messoria* Harris (darksided cutworm); *Helicoverpa armigera* Hubner (American bollworm); *H. zea* Boddie (corn earworm or cotton bollworm); *Heliothis virescens* Fabricius (tobacco budworm); *Hypena scabra* Fabricius (green cloverworm); *Mamestra configurata* Walker (bertha armyworm); *M. brassicae* Linnaeus (cabbage moth); *Melanchra picta* Harris (zebra caterpillar); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hubner (beet armyworm); *S. litura* Fabricius (tobacco cutworm, cluster caterpillar); *Trichoplusia ni* Hubner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hubner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); Orthaga thyrisalis Walker (tea tree web moth); *Ostrinia nubilalis* Hubner (European corn borer); *Plodia interpunctella* Hubner (Indian meal moth); *Scirpophaga incertulas* Walker (yellow stem borer); *Udea rubigalis* Guenee (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit *tortrix* moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hubner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenee; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (*Diaprepes* root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, lssidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci*

Gennadius (tobacco whitefly, sweetpotato whitefly); *B. argentifolii* Bellows & Perring (silverleaf whitefly); *Blissus leucopterus leucopterus* Say (chinch bug); Blostomatidae spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); Cimicidae spp.; Coreidae spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schaffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); L. *Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *Melanaphis sacchari* Zehntner (sugarcane aphid); Melanaspis *glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; Pemphigus spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicolfis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); Pyrrhocoridae spp.; *Quadraspidiotus perniciosus* Comstock (San Jose scale); Reduviidae spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); Tinidae spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus* grypus Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cylindrotermes nordenskioeldi* Holmgren and *Pseudacanthotermes militaris* Hagen (sugarcane termite). Insects of the order Thysanoptera are also of interest, including but not limited to thrips, such as *Stenchaetothrips minutus* van Deventer (sugarcane thrips).

Insect pests may be tested for pesticidal activity of compositions of the embodiments in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83(6): 2480-2485. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXPERIMENTALS

Example 1—Generation of Cry1B Variants with Improved Spectrum of Insecticidal Activity The Cry1Bd insecticidal protein having an amino acid of SEQ ID NO: 1 (U.S. Pat. No. 8,692,065) has high insecticidal activity (ILC50=1 ppm) against European corn borer (*Ostrinia nubilalis*) larvae but low insecticidal activity (ILC50>1000 ppm and ~400 ppm respectively) against corn earworm (*Helicoverpa zea*) and fall armyworm (*Spodoptera frugiperda*). The Cry1B insecticidal protein, referred to as MP258 (Serial No. PCT/US14/49923) having an amino acid of SEQ ID NO: 47 has high insecticidal activity (ILC50=4 ppm) against European corn borer (*Ostrinia nubilalis*) larvae but lower insecticidal activity (ILC50 24 ppm and 62 ppm respectively) against corn earworm (*Helicoverpa zea*) and fall armyworm (*Spodoptera frugiperda*). A series of variant Cry1B polypeptides derived from Cry1Bd (SEQ ID NO: 1) and MP258 were designed to improve the insecticidal activity against corn earworm (CEVV) and/or fall armyworm (FAVV) compared to Cry1Bd (SEQ ID NO: 1) and/or MP258 (SEQ ID NO: 47) while maintaining the ECB insecticidal activity. Variant Cry1B polypeptides having improved insecticidal activity that were generated include those indicated in Table 1. The insecticidal activity of the Cry1B variants was determined as described in Example 4 and the insecticidal activity results are shown in Table 3. An amino acid sequence alignment of the variant Cry1B polypeptides is shown in FIG. 1.

TABLE 1

| Clone ID | Polypeptide | Polynucleotide |
|---|---|---|
| Cry1Bd | SEQ ID NO: 1 | SEQ ID NO: 2 |
| IP1B-B1 | SEQ ID NO: 3 | SEQ ID NO: 4 |
| IP1B-B21 | SEQ ID NO: 5 | SEQ ID NO: 6 |
| IP1B-B22 | SEQ ID NO: 7 | SEQ ID NO: 8 |
| IP1B-B23 | SEQ ID NO: 9 | SEQ ID NO: 10 |
| IP1B-B24 | SEQ ID NO: 11 | SEQ ID NO: 12 |
| IP1B-B25 | SEQ ID NO: 13 | SEQ ID NO: 14 |
| IP1B-B26 | SEQ ID NO: 15 | SEQ ID NO: 16 |
| IP1B-B27 | SEQ ID NO: 17 | SEQ ID NO: 18 |
| IP1B-B28 | SEQ ID NO: 19 | SEQ ID NO: 20 |
| IP1B-B29 | SEQ ID NO: 21 | SEQ ID NO: 22 |
| IP1B-B31 | SEQ ID NO: 23 | SEQ ID NO: 24 |
| IP1B-B32 | SEQ ID NO: 25 | SEQ ID NO: 26 |
| IP1B-B33 | SEQ ID NO: 27 | SEQ ID NO: 28 |
| IP1B-B34 | SEQ ID NO: 29 | SEQ ID NO: 30 |
| IP1B-B40 | SEQ ID NO: 31 | SEQ ID NO: 32 |
| IP1B-B41 | SEQ ID NO: 33 | SEQ ID NO: 34 |
| IP1B-B42 | SEQ ID NO: 35 | SEQ ID NO: 36 |
| IP1B-B43 | SEQ ID NO: 37 | SEQ ID NO: 38 |
| IP1B-B44 | SEQ ID NO: 39 | SEQ ID NO: 40 |
| IP1B-B45 | SEQ ID NO: 41 | SEQ ID NO: 42 |
| IP1B-B46 | SEQ ID NO: 43 | SEQ ID NO: 44 |
| IP1B-B47 | SEQ ID NO: 45 | SEQ ID NO: 46 |
| MP258 | SEQ ID NO: 47 | SEQ ID NO: 48 |
| GS060 | SEQ ID NO: 49 | SEQ ID NO: 50 |

The percent amino acid sequence identity of the Cry1B variant polypeptides calculated using the Needleman-Wunsch algorithm, as implemented in the Needle program (EMBOSS tool suite), are shown as a matrix table in Table 2a-2b. The void part of the matrix table is not shown.

TABLE 2b

| | IP1B-B31 | IP1B-B32 | IP1B-B33 | IP1B-B34 | IP1B-B40 | IP1B-B41 | IP1B-B42 | IP1B-B43 | IP1B-B44 | IP1B-B45 | IP1B-B46 | IP1B-B47 | MP258 |
|---|---|---|---|---|---|---|---|---|---|---|---|---|---|
| Cry1Bd | 80.4 | 80.4 | 81.0 | 82.0 | 83.7 | 83.9 | 83.9 | 83.9 | 83.9 | 83.9 | 83.9 | 83.9 | 82.3 |
| GS060 | 66.6 | 66.9 | 66.3 | 65.5 | 59.8 | 59.9 | 60.1 | 60.1 | 60.1 | 60.1 | 59.9 | 59.9 | 59.9 |
| IP1B-B1 | 83.6 | 83.0 | 82.7 | 81.6 | 82.8 | 82.9 | 83.1 | 83.1 | 83.1 | 83.1 | 83.1 | 83.1 | 80.9 |
| IP1B-B21 | 71.6 | 71.5 | 71.8 | 71.8 | 99.1 | 99.1 | 99.2 | 99.2 | 99.2 | 99.2 | 99.2 | 99.2 | 96.9 |
| IP1B-B22 | 70.7 | 70.4 | 70.7 | 71.0 | 94.7 | 94.7 | 94.7 | 94.7 | 94.7 | 94.7 | 94.8 | 94.8 | 97.6 |
| IP1B-B23 | 72.5 | 72.3 | 72.6 | 72.3 | 96.0 | 96.0 | 96.2 | 96.2 | 96.2 | 96.2 | 96.2 | 96.2 | 96.0 |
| IP1B-B24 | 71.6 | 71.5 | 71.8 | 71.8 | 98.8 | 98.9 | 98.9 | 98.9 | 98.9 | 98.9 | 98.9 | 98.9 | 96.6 |
| IP1B-B25 | 71.8 | 71.6 | 71.9 | 71.9 | 99.4 | 99.4 | 99.5 | 99.5 | 99.5 | 99.5 | 99.5 | 99.5 | 96.6 |
| IP1B-B26 | 71.6 | 71.5 | 71.8 | 71.8 | 99.5 | 99.2 | 99.4 | 99.4 | 99.4 | 99.4 | 99.4 | 99.4 | 96.5 |
| IP1B-B27 | 71.3 | 71.2 | 71.5 | 71.3 | 99.2 | 98.9 | 99.7 | 99.5 | 99.5 | 99.5 | 99.2 | 99.2 | 96.0 |
| IP1B-B28 | 71.3 | 71.2 | 71.5 | 71.3 | 99.1 | 99.1 | 99.4 | 99.2 | 99.2 | 99.2 | 99.5 | 99.5 | 96.3 |
| IP1B-B29 | 71.3 | 71.2 | 71.5 | 71.3 | 99.1 | 99.1 | 99.4 | 99.2 | 99.2 | 99.2 | 99.4 | 99.4 | 96.3 |
| IP1B-B31 | — | 99.4 | 99.1 | 98.0 | 71.3 | 71.6 | 71.5 | 71.5 | 71.5 | 71.5 | 71.5 | 71.5 | 69.2 |
| IP1B-B32 | — | — | 99.2 | 98.0 | 71.2 | 71.5 | 71.3 | 71.3 | 71.3 | 71.3 | 71.3 | 71.3 | 69.1 |
| IP1B-B33 | — | — | — | 98.0 | 71.5 | 71.8 | 71.6 | 71.6 | 71.6 | 71.6 | 71.6 | 71.6 | 69.4 |
| IP1B-B34 | — | — | — | — | 71.5 | 71.8 | 71.5 | 71.5 | 71.5 | 71.5 | 71.5 | 71.5 | 69.7 |
| IP1B-B40 | — | — | — | — | — | 99.7 | 99.1 | 99.1 | 99.1 | 99.2 | 99.2 | 99.4 | 96.2 |
| IP1B-B41 | — | — | — | — | — | — | 99.1 | 99.1 | 99.1 | 99.2 | 99.2 | 99.4 | 96.2 |
| IP1B-B42 | — | — | — | — | — | — | — | 99.8 | 99.8 | 99.7 | 99.5 | 99.4 | 96.2 |
| IP1B-B43 | — | — | — | — | — | — | — | — | 99.8 | 99.8 | 99.5 | 99.5 | 96.2 |
| IP1B-B44 | — | — | — | — | — | — | — | — | — | 99.7 | 99.7 | 99.4 | 96.2 |
| IP1B-B45 | — | — | — | — | — | — | — | — | — | — | 99.4 | 99.7 | 96.2 |
| IP1B-B46 | — | — | — | — | — | — | — | — | — | — | — | 99.7 | 96.3 |
| IP1B-B47 | — | — | — | — | — | — | — | — | — | — | — | — | 96.3 |

TABLE 2a

|  | GS060 | IP1B-B1 | IP1B-B21 | IP1B-B22 | IP1B-B23 | IP1B-B24 | IP1B-B25 | IP1B-B26 | IP1B-B27 | IP1B-B28 | IP1B-B29 |
|---|---|---|---|---|---|---|---|---|---|---|---|
| Cry1Bd | 65.6 | 95.4 | 84.3 | 82.6 | 82.5 | 84.3 | 84.3 | 84.2 | 83.7 | 83.7 | 83.7 |
| GS060 | — | 67.0 | 60.1 | 60.2 | 60.1 | 60.1 | 60.2 | 60.1 | 60.0 | 59.9 | 60.1 |
| IP1B-B1 | — | — | 83.4 | 82.6 | 84.5 | 83.4 | 83.4 | 83.2 | 82.9 | 82.9 | 82.9 |
| IP1B-B21 | — | — | — | 95.4 | 96.9 | 99.7 | 99.7 | 99.5 | 99.1 | 99.1 | 99.1 |
| IP1B-B22 | — | — | — | — | 95.4 | 95.1 | 95.1 | 95.0 | 94.5 | 94.8 | 94.8 |
| IP1B-B23 | — | — | — | — | — | 96.6 | 96.6 | 96.5 | 96.0 | 96.0 | 96.0 |
| IP1B-B24 | — | — | — | — | — | — | 99.4 | 99.2 | 98.8 | 98.8 | 98.8 |
| IP1B-B25 | — | — | — | — | — | — | — | 99.8 | 99.4 | 99.4 | 99.4 |
| IP1B-B26 | — | — | — | — | — | — | — | — | 99.5 | 99.2 | 99.2 |
| IP1B-B27 | — | — | — | — | — | — | — | — | — | 99.4 | 99.4 |
| IP1B-B28 | — | — | — | — | — | — | — | — | — | — | 99.8 |

Example 2—Saturation Mutagenesis at Selected Positions of MP258 and IP-1B Variant Cry1B Polypeptides The polynucleotides of SEQ ID NO: 48, SEQ ID NO: 6, SEQ ID NO: 14, and SEQ ID NO: 42 encoding MP258, IP1B-B21, IP1B-B25 and IP1B-B45 (SEQ ID NO: 47, SEQ ID NO: 5, SEQ ID NO: 13, and SEQ ID NO: 41 respectively) were used as the templates for saturation mutagenesis at selected amino acid positions. A reverse mutagenesis primer and a complementary forward mutagenesis primer were designed to create the desired amino acid substitution(s) at the site(s) of interest. Typically the mutagenesis primer was between 30 to 45 bases in length with two or more bases, usually 10 to 15, on both sides of the site of interest. In order to make saturation mutagenesis, degenerated primers that cover all possible amino acid residues were used. The mutagenic reactions were carried out using Agilent's QuikChange™ Lightening Site-Directed Mutagenesis kit. Materials provided in the kit are QuikChange™ Lightening Enzyme, 10× QuikChange™ Lightning Buffer, dNTP mix, QuikSolution™ reagent and Don restriction enzyme according to the manufactures directions.

PCR amplifications were typically carried out with Expand™ High Fidelity PCR system (Roche, Switzerland) in 50 ul containing 50-100 ng templates, 0.4-2 µM primer pair, 200 µM dNTPs and 2 Units of DNA polymerase. The mutagenesis reaction was initiated by pre-heating the reaction mixture to 94° C. for 3 min, followed by 16 cycles of the following cycling program: 94° C. for 1 min, 52° C. for 1 min and 68° C. for 8, 12, 16 or 24 min according to the length of template. The mutagenesis reaction was completed by incubation at 68° C. for 1 h. The PCR-amplification products were evaluated by agarose gel electrophoresis. The PCR products were purified by QIAquick™ PCR purification kit (Qiagen, Germany) and further treated with the restriction enzyme DpnI. An aliquot of 1 µl of the PCR product was typically transformed into BL21(DE3) cells and inoculated on Luria-Bertani (LB) plate containing 100 µg/ml ampicillin. About 48 or more colonies for saturation mutagenesis were selected and plasmid DNA was isolated for sequencing. Two step sequencing was used, first for specific mutation site(s) with one sequencing primer followed by full length sequence confirmation with multiple sequencing primers. After all 19 amino acid mutations were confirmed by sequencing, those mutant genes were advanced for expression and protein purification.

In the case of mutations made to cover the entire IP1B-B25 Domain III spanning from T495 to E655, 48 mutant clones were picked from each site and screened for the CEW activity, as described in Example 4. In order to sequence those mutant clones to determine mutated amino acids, among 151 amino acid residues subjected to mutagenesis, 103 sites were sequenced based on the number of up-mutations and down-mutations. Those sites containing mutants showing no significant activity changes were not sequenced.

Example 3—Purification of Variant Cry1B Insecticidal Proteins

Variant cry1B insecticidal protein genes were expressed in a modified pMAL vector (Cat #E8000S from New England Biolabs) as a fusion with MBP (maltose binding protein). The pMAL vector was modified to attach a 6× His tag to the N-terminal end of MBP after methionine at position 1. The plasmid containing the insecticidal protein gene was cloned in E. coli BL21 (DE3). The BL21 cells were grown in MagicMedia™ (Life Technologies) in either 96 deep well plates or flasks in a shaker running at 250 rpm at 37° C. for 8 hrs followed by 16° C. for 64 hrs. During the 16° C. incubation, the MBP-toxin fusion protein was accumulated in the BL21 cell as a soluble protein.

In order to purify the fusion protein, the E. coli cells were harvested by centrifugation and treated in a lysozyme solution consisting of 2 mg/ml lysozyme in 50 ml sodium phosphate buffer at pH8 containing 300 mM NaCl, 2 U/ml endonuclease (Epicentre) and 5 mM MaCl2 for 3 hrs at 37° C. with gentle shaking. The lysozyme treated E. coli cells were then disrupted with 1% Triton X100 and clear lysate containing the IP-1B proteins were prepared by centrifugation at 4000 rpm, 30 min (96 well plates) or 9000 rpm (flask produced samples). His tagged MBP-toxin proteins were purified from the clear lysate by affinity chromatography using NiNTA agarose from Qiagen™ following the manufacturer's standard procedure. For those clear lysate samples made in 96 well plates, Pall Corporation™ (25 Harbor Park Drive Port Washington, N.Y. 11050) 96 deep well filter plates were used as affinity chromatography columns. The purified toxin proteins eluted from NiNTA agarose was passed through Sephadex G25 to change the phosphate buffer to 25 mM HEPES-NaOH, pH8 and used in insect bioassay for determining the insecticidal. MBP was digested with $\frac{1}{100}$ (w/w) Factor Xa (New England Biolabs) at 25° C. for overnight and removed from the IP-1B proteins by Superdex 200 column chromatography utilizing the size difference and a weak affinity of MBP to Superdex.

Protein concentrations were determined by capillary electrophoresis with the LabChip™ GXII device (Caliper Life-Sciences). The protein analysis was repeated at least 3 times until the final concentrations were considered to be reliable within the predetermined deviation, less than 10%.

Example 4—Determination of the Insecticidal Activity of Variant IP-1B Proteins The activity of Cry1B polypeptide variants against major corn pests, European Corn Borer (ECB, *Ostrinia nubilalis*), Corn Earworm (ECW, *Helicoverpa zea*) and Fall Armyworm (FAW, *Spodoptera frugiperda*), was determined by feeding assay as described by Cong, R., et al. Proceedings of the 4th Pacific Rim Conferences on Biotechnology of *Bacillus thuringiensis* and its environmental impact, pp. 118-123, ed. by R. J. Akhurst, C. E. Beard and P. Hughes, published in 2002, Canberra, Australia. Briefly, the assays were conducted on an artificial diet containing the insecticidal proteins. The insecticidal proteins were prepared as described in Example 1, and 10 μL of protein samples were mixed with 40 μL of molten (40-50° C.) artificial insect diet prepared based on Southland Premix formulated for Lepidopteran insects (Southland Products, Lake Village, Ark.) with low temperature melting agarose. The diet-insecticidal protein mixture was placed in each well of a 96 well micro-titer plate. One or more neonate insect larvae were placed in each well to feed for 4 days for CEW and FAW and 5 days for ECB at 28° C.

Alternatively, insect eggs or larvae were sorted by Large Particle Flow Cytometry using COPAS™ (Complex Object Parametric Analyzer and Sorter) obtained from Union Biometrica (Holliston, Mass.) to place one egg or larva per well in a 96-well micro-titer plate that contains solidified artificial insect diet. When eggs were used to place in the assay plates, only those wells containing hatched larvae after 16 hours were used for assay data collection. Usually 90 to 95% hatch rates were obtained due to efficient COPAS sorting. After certain feeding periods, the response of insects towards the proteins was scored using a 0-3 numerical scoring system based on the size and mortality of the larvae in each well. If no response (or normal growth) was seen, a score of 0 was given. When the growth was slightly retarded, a score of 1 was given. A score of 2 meant that the larvae were severely retarded in growth (close to neonate size). A score of 3 meant death to all the larvae in the well. The percent response (Response) for each treatment was calculated by dividing the total score, a sum of scores from replicating wells for each treatment by the total highest possible scores. For example, if one treatment (one sample, one dose) had 6 replicating wells, the total highest possible score would be 3×6=18.

In order to identify variant Cry1B polypeptides that have increased levels of the activity toward those corn pests, significantly higher than the activity reference such as the wild type, non-mutated reference protein (e.g. MP258 SEQ ID NO: 47). Variant polypeptides at certain concentrations were assayed along with 4 doses of the reference protein within one 96-well assay plate. The concentrations of the insecticidal proteins were within the 4 doses of the reference protein concentrations, preferably around the middle point of the 4 dose concentrations. Each sample plate contained the reference protein in a significant number of wells such as 16 wells in 4 separate doses. Also in each plate, up to 80 mutants proteins for activity comparison with the reference protein were included. From a sample plate, 10 ul of samples from each well were picked by multi-channel pipette and dispensed in one assay plate containing 40 ul molten diet in each well and mixed on a shaker. This process of producing the assay plate was repeated as many as 6 times or more to produce a desired number of assay plates. After the diet was solidified and cooled to 4 C, neonate insect larvae were placed in each well, sealed with perforated Mylar film and incubated in a constant temperature incubator at 28° C. After certain feeding period, the insect responses were scored under a magnifying glass. The sigmoid dose-response values (Responses) were converted to liner probit dose-response values using SAS-JMP®, Generalized Linear Model, Binomial Response, Probit). The response for each protein in replicates was summed and compared with the probit dose-response line of the activity reference protein, creating a new number called the FAE guide number (Fast Activity Evaluation). For example, if a mutant protein showed a certain probit value at 40 ppm and the actual dose with the same probit value for the reference protein was 100 ppm; then the FAE value is 2.5 (100/40). This means the mutant protein is 2.5 times more potent than the reference protein. This assay was done with 2 different doses of mutant proteins at a time and repeated 3 times generating 6 FAE guide number data points for each mutant. The mean FAE guide number was called the FAE Index. For each protein, a two sided t-test was done comparing the 6 FAE guide numbers. The Bonferroni correction was used to evaluate p-values (number of novel proteins/alpha) to determine if the FAE Index was statistically significant.

The other screening method used in this patent application is High Dose Assay (HDA). In this method, test proteins at high concentrations (above EC50) were placed on the insect assay plates as described above, along with a similar concentration of one or more reference proteins with a known activity level. This HDA was often used in a tiered screening to eliminate low or no activity proteins quickly.

Yet another screening method used was High throughput Functional Assay (HFA). This assay was similar to FAE but used only one dose instead of 2 doses. Otherwise HFA, especially the way it calculates the index was identical to FAE. Therefor the HFA index has the same significance as the FAE index.

The predicted point with 50% response in the scoring scheme is called ILC50 as it is a combination of growth or feeding Inhibition and Lethal responses. In order to determine ILC50 values, each treatment (one dose) was repeated 6 or more, usually 24, times. The insecticidal activity of the Cry1B variants is shown in Table 3.

Table 4 shows the insecticidal activity against corn earworm for the amino acid substitutions having increased activity (FAE score 1.2) compared to the reference polypeptide MP258 (SEQ ID NO: 47), IP1B-B21 (SEQ ID NO: 5), IP1B-B25 (SEQ ID NO: 13), or IP1B-B45 (SEQ ID NO: 41). Table 4 indicates the position number and amino acid corresponding to positions 50-651 of MP258 (SEQ ID NO: 47); the predicted secondary structure and assignment; solvent exposure score; an alignment of the amino acid sequence of MP258 (SEQ ID NO: 47); IP1B-B21 (SEQ ID NO: 5), IP1B-B25 (SEQ ID NO: 13), IP1B-B45 (SEQ ID NO: 41), IP1B-B21 (SEQ ID NO: 5), Cry1Bd (SEQ ID NO: 1), Cry1Bh (SEQ ID NO: 52), and Cry1Bi (SEQ ID NO: 54); the polypeptide backbone the variant was made in; the amino acid substitution variant (e.g. L50R); and the FAE insecticidal score against corn earworm compared to the corresponding polypeptide backbone (MP258—SEQ ID NO: 47, IP1B-B21—SEQ ID NO: 5, IP1B-B25—SEQ ID NO: 13, or IP1B-B45—SEQ ID NO: 41).

TABLE 3

| Clone ID | Polypeptide SEQ ID NO | ECB | CEW | FAW |
|---|---|---|---|---|
| Cry1 Bd | SEQ ID NO: 1 | ILC50 = 1 ppm | ILC50 = >1000 ppm | ILC50 = ~400 ppm |
| IP1B-B1 | SEQ ID NO: 3 | ILC50 = 1.3 ppm | ILC50 = 21 ppm | ILC50 = 34.3 ppm |
| IP1B-B21 | SEQ ID NO: 5 | | ILC50 = 22.4 ppm | |
| IP1B-B22 | SEQ ID NO: 7 | | ILC50 = 27.1 ppm | |
| IP1B-B23 | SEQ ID NO: 9 | | ILC50 = 29.2 ppm | |
| IP1B-B24 | SEQ ID NO: 11 | | ILC50 = 12.6 ppm | |
| IP1B-B25 | SEQ ID NO: 13 | | ILC50 = 11.91 ppm | |
| IP1B-B26 | SEQ ID NO: 15 | | ILC50 = 8.36 ppm | |
| IP1B-B27 | SEQ ID NO: 17 | | ILC50 = 7.99 ppm | |
| IP1B-B28 | SEQ ID NO: 19 | | ILC50 = 7.74 ppm | |
| IP1B-B29 | SEQ ID NO: 21 | | ILC50 = 8.45 ppm | |
| IP1B-B31 | SEQ ID NO: 23 | | | ILC50 = 2.8 ppm |
| IP1B-B32 | SEQ ID NO: 25 | | | ILC50 = 2.9 ppm |
| IP1B-B33 | SEQ ID NO: 27 | | | ILC50 = 3.0 ppm |
| IP1B-B34 | SEQ ID NO: 29 | | | ILC50 = 2.9 ppm |
| IP1B-B40 | SEQ ID NO: 31 | | ILC50 = 5.78 ppm | |
| IP1B-B41 | SEQ ID NO: 33 | | ILC50 = 4.54 ppm | |
| IP1B-B42 | SEQ ID NO: 35 | | ILC50 = 6.2 ppm | |
| IP1B-B43 | SEQ ID NO: 37 | | ILC50 = 6.7 ppm | |
| IP1B-B44 | SEQ ID NO: 39 | | ILC50 = 6.9 ppm | |
| IP1B-B45 | SEQ ID NO: 41 | | ILC50 = 5.7 ppm | |
| IP1B-B46 | SEQ ID NO: 43 | | ILC50 = 8 ppm | |
| IP1B-B47 | SEQ ID NO: 45 | | ILC50 = 6.1 ppm | |
| MP258 | SEQ ID NO: 47 | ILC50 = 4 ppm | ILC50 = 24 ppm | ILC50 = 62 ppm |

Table 5 shows the insecticidal activity against corn earworm for the amino acid substitutions having a FAE score 1.2 compared to the polypeptide backbone MP258 (SEQ ID NO: 47), IP1B-B21 (SEQ ID NO: 5), IP1B-B25 (SEQ ID NO: 13), or IP1B-B45 (SEQ ID NO: 41). Table 5 indicates the position number and amino acid corresponding to positions 50-651 of MP258 (SEQ ID NO: 47); the polypeptide backbone the variant was made in; the amino acid substitution variant (e.g. L50R); and the FAE insecticidal score against corn earworm compared to the corresponding polypeptide backbone (MP258—SEQ ID NO: 47, IP1B-B21—SEQ ID NO: 5, IP1B-B25—SEQ ID NO: 13, or IP1B-B45—SEQ ID NO: 41.

TABLE 4

| MP258 position | a.a. | 2D Struc | 2D Assign | Sol. Exp. | MP258 | B21 | B25 | B45 | Bd | Bh | Bi | backbone |
|---|---|---|---|---|---|---|---|---|---|---|---|---|
| 50 | L | Coil | | 90 | L | L | L | L | L | F | F | B45 |
| 51 | V | Helix | a1 | 37 | V | V | V | V | V | V | V | |
| 52 | S | Helix | | 20 | S | S | S | S | S | S | S | |
| 53 | A | Helix | | 67 | A | A | A | A | A | A | A | B45 |
| 54 | S | Helix | | 47 | S | S | S | S | S | S | S | B45 |
| 55 | T | Helix | | 0 | T | T | T | T | T | T | T | |
| 56 | V | Helix | | 5 | V | V | V | V | V | V | V | |
| 57 | Q | Helix | | 75 | Q | Q | Q | Q | Q | Q | Q | B45 |
| 58 | T | Helix | | 33 | T | T | T | T | T | T | T | |
| 59 | G | Helix | | 4 | G | G | G | G | G | G | G | |
| 60 | I | Helix | | 3 | I | I | I | I | I | I | I | |
| 61 | N | Helix | | 27 | N | N | N | N | N | N | S | |
| 62 | I | Helix | | 3 | I | I | I | I | I | I | I | |
| 63 | A | Helix | | 19 | A | A | A | A | A | A | A | |
| 64 | G | Helix | | 4 | G | G | G | G | G | G | G | |
| 65 | R | Helix | | 42 | R | R | R | R | R | R | R | B45 |
| 66 | I | Helix | | 4 | I | I | I | I | I | I | I | |
| 67 | L | Helix | | 27 | L | L | L | L | L | L | L | B45 |
| 68 | G | Helix | | 113 | G | G | G | G | G | G | G | B45 |
| 69 | V | Helix | | 6 | V | V | V | V | V | V | V | |
| 70 | L | Turn | | 1 | L | L | L | L | L | L | L | B45 |
| 71 | G | Turn | | 8 | G | G | G | G | G | G | G | B45 |
| 72 | V | Coil | | 22 | V | V | V | V | V | V | V | B45 |
| 73 | P | Coil | | 46 | P | P | P | P | P | P | P | B45 |
| 74 | F | Coil | | 94 | F | F | F | F | F | F | F | B45 |
| 75 | A | Helix | a2 | 33 | A | A | A | A | A | A | A | B45 |
| 76 | G | Helix | | 115 | G | G | G | G | G | G | G | B45 |
| 77 | Q | Helix | | 53 | Q | Q | Q | Q | Q | Q | Q | B45 |
| 78 | L | Helix | | 8 | L | L | L | L | L | L | L | |
| 79 | A | Helix | | 36 | A | A | A | A | A | A | A | B45 |
| 80 | S | Helix | | 61 | S | S | S | S | S | S | S | B45 |
| 81 | F | Helix | | 4 | F | F | F | F | F | F | F | |
| 82 | Y | Helix | | 4 | Y | Y | Y | Y | Y | Y | Y | B45 |
| 83 | S | Helix | | 85 | S | S | S | S | S | S | S | |
| 84 | F | Helix | | 54 | F | F | F | F | F | F | F | |

TABLE 4-continued

| | | | | | | | | | | | |
|---|---|---|---|---|---|---|---|---|---|---|---|
| 85 | I | Helix | | 5 | I | I | I | I | L | L | I | |
| 86 | V | Helix | | 22 | V | V | V | V | V | V | V | |
| 87 | G | Helix | | 101 | G | G | G | G | G | G | G | B45 |
| 88 | E | Helix | | 19 | E | E | E | E | E | E | E | |
| 89 | L | Helix | | 2 | L | L | L | L | L | L | L | |
| 90 | W | Coil | | 11 | W | W | W | W | W | W | W | |
| 91 | P | Coil | | 44 | P | P | P | P | P | P | P | B45 |
| 92 | S | Coil | | 93 | S | S | S | S | S | S | K | B45 |
| 93 | G | Coil | | 140 | G | G | G | G | G | G | G | B45 |
| 94 | R | Coil | | 97 | R | R | R | R | R | R | R | B45 |
| 95 | D | Coil | | 35 | D | D | D | D | D | D | D | B45 |
| 96 | P | Helix | a2 | 18 | P | P | P | P | P | P | Q | |
| 97 | W | Helix | | 2 | W | W | W | W | W | W | W | |
| 98 | E | Helix | | 35 | E | E | E | E | E | E | E | |
| 99 | I | Helix | | 29 | I | I | I | I | I | I | I | |
| 100 | F | Helix | | 1 | F | F | F | F | F | F | F | |
| 101 | L | Helix | | 4 | L | M | M | M | L | L | M | |
| 102 | E | Helix | | 40 | E | E | E | E | E | E | E | |
| 103 | H | Helix | | 0 | H | H | H | H | H | H | H | |
| 104 | V | Helix | | 0 | V | V | V | V | V | V | V | |
| 105 | E | Helix | | 16 | E | E | E | E | E | E | E | |
| 106 | Q | Helix | | 75 | Q | Q | Q | Q | Q | Q | Q | B45 |
| 107 | L | Helix | | 0 | L | L | L | L | L | L | L | |
| 108 | V | Helix | | 5 | V | V | V | V | I | I | V | B45 |
| 109 | R | Turn | | 94 | R | R | R | R | R | R | R | 258 |
| 110 | Q | Coil | | 54 | Q | Q | Q | Q | Q | Q | Q | 258 |
| 111 | Q | Coil | | 87 | Q | Q | Q | H | Q | Q | Q | 258 |
| 112 | I | Coil | | 0 | I | I | I | I | V | V | I | B45 |
| 113 | T | Coil | | 80 | T | T | T | T | T | T | T | B45 |
| 114 | E | Helix | a3 | 73 | E | E | E | M | E | E | A | 258 |
| 115 | N | Helix | | 116 | N | N | N | N | N | N | N | B45 |
| 116 | A | Helix | | 11 | A | A | A | A | T | T | A | |
| 117 | R | Helix | | 18 | R | R | R | R | R | R | R | |
| 118 | N | Helix | | 79 | N | N | N | N | N | N | N | B45 |
| 119 | T | Helix | | 55 | T | T | T | T | T | T | T | B45 |
| 120 | A | Helix | | 5 | A | A | A | A | A | A | A | |
| 121 | L | Helix | | 20 | L | L | L | L | I | I | L | |
| 122 | A | Helix | | 87 | A | A | A | A | A | A | A | B45 |
| 123 | R | Helix | | 55 | R | R | R | R | R | R | R | B45 |
| 124 | L | Helix | | 6 | L | L | L | L | L | L | L | |
| 125 | Q | Helix | | 58 | Q | Q | Q | Q | E | E | Q | B45 |
| 126 | G | Helix | | 103 | G | G | G | G | G | G | G | |
| 127 | L | Helix | | 9 | L | L | L | L | L | L | L | |
| 128 | G | Helix | | 0 | G | G | G | G | G | G | G | |
| 129 | A | Helix | | 96 | A | A | A | A | R | R | D | B45 |
| 130 | S | Helix | | 37 | S | S | S | S | G | G | S | |
| 131 | F | Helix | | 2 | F | F | F | F | Y | Y | F | |
| 132 | R | Helix | | 95 | R | R | R | R | R | R | R | |
| 133 | A | Helix | | 49 | A | A | A | A | S | S | A | |
| 134 | Y | Helix | | 1 | Y | Y | Y | Y | Y | Y | Y | |
| 135 | Q | Helix | | 24 | Q | Q | Q | Q | Q | Q | Q | |
| 136 | Q | Helix | | 77 | Q | Q | Q | Q | Q | Q | Q | B45 |
| 137 | S | Helix | | 5 | S | S | S | S | A | A | S | |
| 138 | L | Helix | | 10 | L | L | L | L | L | L | L | |
| 139 | E | Helix | | 55 | E | E | E | E | E | E | E | |
| 140 | D | Helix | | 77 | D | D | D | D | T | T | D | B45 |
| 141 | W | Helix | | 6 | W | W | W | W | W | W | W | |
| 142 | L | Helix | | 67 | L | L | L | L | L | L | L | |
| 143 | E | Helix | | 76 | E | E | E | E | D | D | E | B45 |
| 144 | N | Coil | | 62 | N | N | N | N | N | N | N | B45 |
| 145 | R | Coil | | 67 | R | R | R | R | R | R | R | B45 |
| 146 | D | Coil | | 85 | D | D | D | D | N | N | N | B45 |
| 147 | D | Coil | | 31 | D | N | N | N | D | D | D | B45 |
| 148 | A | Helix | a4 | 64 | A | A | A | A | A | A | A | B45 |
| 149 | R | Helix | | 80 | R | R | R | R | R | R | R | B45 |
| 150 | T | Helix | | 22 | T | T | T | T | S | S | T | |
| 151 | R | Helix | | 57 | R | R | R | R | R | R | R | |
| 152 | S | Helix | | 93 | S | S | S | S | S | S | S | |
| 153 | V | Helix | | 65 | V | V | V | V | I | I | V | |
| 154 | L | Helix | | 0 | L | L | L | L | I | I | L | |
| 155 | Y | Helix | | 42 | Y | Y | Y | Y | L | L | Y | |
| 156 | T | Helix | | 77 | T | T | T | T | E | E | T | |
| 157 | Q | Helix | | 31 | Q | Q | Q | Q | R | R | Q | |
| 158 | Y | Helix | | 3 | Y | Y | Y | Y | Y | Y | Y | B45 |
| 159 | I | Helix | | 31 | I | I | I | I | V | V | I | B45 |
| 160 | A | Helix | | 72 | A | A | A | A | A | A | A | B45 |
| 161 | L | Helix | | 0 | L | L | L | L | L | L | L | |
| 162 | E | Helix | | 13 | E | E | E | E | E | E | E | |
| 163 | L | Helix | | 87 | L | L | L | L | L | L | L | |
| 164 | D | Helix | | 29 | D | D | D | D | D | D | D | |

TABLE 4-continued

| 165 | F | Helix | 2 | F | F | F | F | I | I | F | |
|---|---|---|---|---|---|---|---|---|---|---|---|
| 166 | L | Helix | 89 | L | L | L | L | T | T | L | B45 |
| 167 | N | Helix | 56 | N | N | N | N | T | T | N | B45 |
| 168 | A | Helix | 16 | A | A | A | A | A | A | A | |
| 169 | M | Helix | 10 | M | M | M | M | I | I | M | |
| 170 | P | Helix | 70 | P | P | P | P | P | P | P | |
| 171 | L | Helix | 30 | L | L | L | L | L | L | L | |
| 172 | F | Turn | 4 | F | F | F | F | F | F | F | |
| 173 | A | Coil | 48 | A | A | A | A | R | R | A | B45 |
| 174 | I | Coil | 45 | I | I | I | I | I | I | I | |
| 175 | N | Turn | 118 | N | N | N | N | R | R | R | |
| 176 | N | Turn | 112 | N | N | N | N | N | N | E | |
| 177 | Q | Coil | 12 | Q | Q | Q | Q | E | Q | Q | B45 |
| 178 | Q | Turn | 16 | Q | Q | Q | Q | E | E | E | B45 |
| 179 | V | Turn | 21 | V | V | V | V | V | V | V | B45 |
| 180 | P | Turn | 2 | P | P | P | P | P | P | P | B45 |
| 181 | L | Turn | 3 | L | L | L | L | L | L | L | |
| 182 | L | Helix a5 | 0 | L | L | L | L | L | L | L | |
| 183 | M | Helix | 1 | M | M | M | M | M | M | M | |
| 184 | V | Helix | 1 | V | V | V | V | V | V | V | |
| 185 | Y | Helix | 6 | Y | Y | Y | Y | Y | Y | Y | |
| 186 | A | Helix | 0 | A | A | A | A | A | A | A | |
| 187 | Q | Helix | 2 | Q | Q | Q | Q | Q | Q | Q | |
| 188 | A | Helix | 1 | A | A | A | A | A | A | A | |
| 189 | A | Helix | 0 | A | A | A | A | A | A | A | |
| 190 | N | Helix | 1 | N | N | N | N | N | N | N | |
| 191 | L | Helix | 5 | L | L | L | L | L | L | L | |
| 192 | H | Helix | 0 | H | H | H | H | H | H | H | |
| 193 | L | Helix | 1 | L | L | L | L | L | L | L | |
| 194 | L | Helix | 5 | L | L | L | L | L | L | L | |
| 195 | L | Helix | 0 | L | L | L | L | L | L | L | |
| 196 | L | Helix | 0 | L | L | L | L | L | L | L | |
| 197 | R | Helix | 7 | R | R | R | R | R | R | R | |
| 198 | D | Helix | 0 | D | D | D | D | D | D | D | |
| 199 | A | Helix | 2 | A | A | A | A | A | A | A | |
| 200 | S | Helix | 10 | S | S | S | S | S | S | S | |
| 201 | L | Helix | 16 | L | L | L | L | L | L | L | B45 |
| 202 | F | Helix | 9 | F | F | F | F | F | F | Y | |
| 203 | G | Turn | 0 | G | G | G | G | G | G | G | |
| 204 | S | Turn | 101 | S | S | S | S | S | S | R | |
| 205 | E | Turn | 66 | E | E | E | E | E | E | E | |
| 206 | F | Turn | 3 | F | F | F | F | W | W | F | B45 |
| 207 | G | Turn | 88 | G | G | G | G | G | G | G | |
| 208 | L | Coil | 12 | L | L | L | L | M | T | L | |
| 209 | T | Coil | 87 | T | T | T | T | A | A | T | B45 |
| 210 | S | Helix a6 | 126 | S | S | S | S | S | S | S | B45 |
| 211 | Q | Helix | 95 | Q | Q | Q | Q | S | S | Q | B45 |
| 212 | E | Helix | 40 | E | E | E | E | D | D | E | |
| 213 | I | Helix | 35 | I | I | I | I | V | V | I | B45 |
| 214 | Q | Helix | 58 | Q | Q | Q | Q | N | N | Q | B21 |
| 215 | R | Helix | 82 | R | R | R | R | Q | Q | R | |
| 216 | Y | Helix | 1 | Y | Y | Y | Y | Y | Y | Y | |
| 217 | Y | Helix | 17 | Y | Y | Y | Y | Y | Y | Y | |
| 218 | E | Helix | 86 | E | E | E | E | Q | Q | E | B45 |
| 219 | R | Helix | 28 | R | R | R | R | E | E | R | B21 |
| 220 | Q | Helix | 6 | Q | Q | Q | Q | Q | Q | Q | |
| 221 | A | Helix | 66 | A | A | A | A | I | I | V | B45 |
| 222 | E | Helix | 70 | E | E | E | E | R | R | E | B45 |
| 223 | K | Helix | 16 | K | K | K | K | Y | Y | R | |
| 224 | T | Helix | 33 | T | T | T | T | T | T | T | |
| 225 | R | Helix | 67 | R | R | R | R | E | E | R | B45 |
| 226 | E | Helix | 66 | E | E | E | E | E | E | D | B45 |
| 227 | Y | Helix | 3 | Y | Y | Y | Y | Y | Y | Y | |
| 228 | S | Helix | 11 | S | S | S | S | S | S | S | |
| 229 | D | Helix | 31 | D | D | D | D | N | N | D | |
| 230 | Y | Helix | 17 | Y | Y | Y | Y | H | H | H | B45 |
| 231 | C | Helix | 1 | C | C | C | C | C | C | C | |
| 232 | A | Helix | 27 | A | A | A | A | V | V | V | |
| 233 | R | Helix | 87 | R | R | R | R | Q | Q | Q | B45 |
| 234 | W | Helix | 31 | W | W | W | W | W | W | W | B45 |
| 235 | Y | Helix | 12 | Y | Y | Y | Y | Y | Y | Y | |
| 236 | N | Helix | 71 | N | N | N | N | N | N | N | B45 |
| 237 | T | Helix | 50 | T | T | T | T | T | T | T | |
| 238 | G | Helix | 8 | G | G | G | G | G | G | G | |
| 239 | L | Helix | 19 | L | L | L | L | L | L | L | |
| 240 | N | Helix | 100 | N | N | N | N | N | N | N | B45 |
| 241 | N | Helix | 92 | N | N | N | N | N | N | N | B45 |
| 242 | L | Helix | 13 | L | L | L | L | L | L | L | B45 |
| 243 | R | Coil | 76 | R | R | R | R | R | R | R | B45 |
| 244 | G | Coil | 46 | G | G | G | G | G | G | G | |

TABLE 4-continued

| | | | | | | | | | | | |
|---|---|---|---|---|---|---|---|---|---|---|---|
| 245 | T | Coil | | 107 | T | T | T | T | T | T | T | B45 |
| 246 | N | Coil | | 57 | N | N | N | N | N | N | N | B45 |
| 247 | A | Helix | a7 | 0 | A | A | A | A | A | A | A | B45 |
| 248 | E | Helix | | 60 | E | E | E | E | E | E | E | B45 |
| 249 | S | Helix | | 58 | S | S | S | S | S | S | S | |
| 250 | W | Helix | | 1 | W | W | W | W | W | W | W | |
| 251 | L | Helix | | 31 | L | L | L | L | L | V | V | |
| 252 | R | Helix | | 67 | R | R | R | R | R | R | R | B45 |
| 253 | Y | Helix | | 20 | Y | Y | Y | Y | Y | Y | Y | |
| 254 | N | Helix | | 0 | N | N | N | N | N | N | N | |
| 255 | Q | Helix | | 37 | Q | Q | Q | Q | Q | Q | Q | |
| 256 | F | Helix | | 0 | F | F | F | F | F | F | F | |
| 257 | R | Helix | | 23 | R | R | R | R | R | R | R | |
| 258 | R | Helix | | 2 | R | R | R | R | R | R | R | |
| 259 | D | Helix | | 7 | D | D | D | D | D | D | D | |
| 260 | L | Helix | | 0 | L | L | L | L | L | L | L | |
| 261 | T | Helix | | 20 | T | T | T | T | T | T | T | |
| 262 | L | Helix | | 2 | L | L | L | L | L | L | L | |
| 263 | G | Helix | | 13 | G | G | G | G | G | G | G | |
| 264 | V | Turn | | 0 | V | V | V | V | V | V | V | |
| 265 | L | Helix | | 15 | L | L | L | L | L | L | L | |
| 266 | D | Helix | | 6 | D | D | D | D | D | D | D | |
| 267 | L | Helix | | 6 | L | L | L | L | L | L | L | |
| 268 | V | Helix | | 3 | V | V | V | V | V | V | V | |
| 269 | A | Helix | | 7 | A | A | A | A | A | A | A | |
| 270 | L | Turn | | 9 | L | L | L | L | L | L | L | |
| 271 | F | Turn | | 0 | F | F | F | F | F | F | F | |
| 272 | P | Helix | | 29 | P | P | P | P | P | P | P | |
| 273 | S | Helix | | 2 | S | S | S | S | S | S | S | |
| 274 | Y | Helix | | 0 | Y | Y | Y | Y | Y | Y | Y | |
| 275 | D | Coil | | 22 | D | D | D | D | D | D | D | |
| 276 | T | Turn | | 30 | T | T | T | T | T | T | T | |
| 277 | R | Turn | | 58 | R | R | R | R | R | R | R | B45 |
| 278 | I | Turn | | 44 | I | I | I | I | T | T | T | |
| 279 | Y | Coil | | 4 | Y | Y | Y | Y | Y | Y | Y | |
| 280 | P | Coil | | 30 | P | P | P | P | P | P | P | B45 |
| 281 | I | Coil | | 39 | I | I | I | I | I | I | I | B45 |
| 282 | N | Coil | | 42 | N | N | N | N | N | N | N | |
| 283 | T | Sheet | | 0 | T | T | T | T | T | T | T | |
| 284 | S | Sheet | | 72 | S | S | S | S | S | S | S | |
| 285 | A | Coil | | 8 | A | A | A | A | A | A | A | |
| 286 | Q | Coil | | 6 | Q | Q | Q | Q | Q | Q | Q | |
| 287 | L | Coil | | 9 | L | L | L | L | L | L | L | |
| 288 | T | Coil | | 2 | T | T | T | T | T | T | T | |
| 289 | R | Coil | | 8 | R | R | R | R | R | R | R | |
| 290 | E | Sheet | b1 | 11 | E | E | E | E | E | E | E | |
| 291 | I | Sheet | | 1 | I | I | I | I | I | V | V | |
| 292 | Y | Sheet | | 7 | Y | Y | Y | Y | Y | Y | Y | |
| 293 | T | Coil | | 8 | T | T | T | T | T | T | T | |
| 294 | D | Coil | | 24 | D | D | D | D | D | D | D | |
| 295 | P | Coil | | 4 | P | P | P | P | P | A | A | |
| 296 | I | Coil | | 3 | I | I | I | I | I | I | I | |
| 297 | G | Coil | | 15 | G | G | G | G | G | G | G | |
| 298 | R | Coil | | 16 | R | R | R | R | R | T | A | |
| 299 | T | Coil | | 48 | T | T | T | T | T | V | T | |
| 300 | N | Coil | | 59 | N | N | N | N | N | H | G | |
| 301 | A | Coil | | 109 | A | A | A | A | A | P | V | |
| 302 | P | Coil | | 63 | P | P | P | P | P | S | N | |
| 303 | S | Coil | | 0 | S | S | S | S | S | Q | — | 258 |
| 304 | G | Coil | | 67 | G | G | G | G | G | A | — | |
| 305 | F | Coil | | 78 | F | F | F | F | F | F | M | |
| 306 | A | Coil | | 31 | A | A | A | A | A | A | A | 258 |
| 307 | S | Coil | | 11 | S | S | S | S | S | S | S | |
| 308 | T | Coil | | 29 | T | T | T | T | T | T | M | |
| 309 | N | Coil | | 20 | N | N | N | N | N | T | N | |
| 310 | W | Helix | | 5 | W | W | W | W | W | W | W | |
| 311 | F | Helix | | 8 | F | F | F | F | F | F | Y | |
| 312 | N | Helix | | 48 | N | N | N | N | N | N | N | |
| 313 | N | Coil | | 60 | N | N | N | N | N | N | N | |
| 314 | N | Coil | | 96 | N | N | N | N | N | N | N | |
| 315 | A | Coil | | 0 | A | A | A | A | A | A | A | |
| 316 | P | Coil | | 33 | P | P | P | P | P | P | P | |
| 317 | S | Coil | | 65 | S | S | S | S | S | S | S | |
| 318 | F | Helix | a8 | 6 | F | F | F | F | F | F | F | |
| 319 | S | Helix | | 96 | S | S | S | S | S | S | S | |
| 320 | A | Helix | | 58 | A | A | A | A | A | A | A | |
| 321 | I | Helix | | 4 | I | I | I | I | I | I | I | |
| 322 | E | Helix | | 39 | E | E | E | E | E | E | E | |
| 323 | A | Helix | | 98 | A | A | A | A | A | A | T | |
| 324 | A | Helix | | 52 | A | A | A | A | A | A | A | |

TABLE 4-continued

| | | | | | | | | | | | |
|---|---|---|---|---|---|---|---|---|---|---|---|
| 325 | V | Helix | | 18 | V | I | I | I | I | V | V |
| 326 | I | Coil | | 24 | I | F | F | F | F | I | I |
| 327 | R | Coil | | 11 | R | R | R | R | R | R | R |
| 328 | P | Coil | | 77 | P | P | P | P | P | P | S |
| 329 | P | Coil | | 53 | P | P | P | P | P | P | P |
| 330 | H | Coil | | 21 | H | H | H | H | H | H | H |
| 331 | L | Coil | | 17 | L | L | L | L | L | L | L |
| 332 | L | Coil | | 3 | L | L | L | L | L | L | L |
| 333 | D | Sheet | | 21 | D | D | D | D | D | D | D |
| 334 | F | Sheet | | 6 | F | F | F | F | F | F | F |
| 335 | P | Sheet | | 13 | P | P | P | P | P | P | L |
| 336 | E | Coil | | 19 | E | E | E | E | E | E | E |
| 337 | Q | Sheet | b2 | 48 | Q | Q | Q | Q | Q | Q | Q |
| 338 | L | Sheet | | 11 | L | L | L | L | L | L | L |
| 339 | T | Sheet | | 13 | T | T | T | T | T | T | K |
| 340 | I | Sheet | | 0 | I | I | I | I | I | I | I |
| 341 | F | Sheet | | 30 | F | Y | Y | Y | Y | Y | F |
| 342 | S | Sheet | | 5 | S | S | S | S | S | S | S |
| 343 | V | Sheet | | 29 | V | A | A | A | A | T | A |
| 344 | L | Sheet | | 88 | L | S | S | S | S | L | S |
| 345 | S | Sheet | | 39 | S | S | S | S | S | S | S |
| 346 | R | Sheet | | 67 | R | R | R | R | R | R | R |
| 347 | W | Sheet | | 41 | W | W | W | W | W | W | W |
| 348 | S | Turn | L1 | 51 | S | S | S | S | S | S | S |
| 349 | N | Turn | | 113 | N | S | S | S | S | S | N |
| 350 | T | Turn | | 78 | T | T | T | T | T | T | T |
| 351 | Q | Sheet | b3 | 36 | Q | Q | Q | Q | Q | Q | R |
| 352 | Y | Sheet | | 45 | Y | H | H | H | H | F | H |
| 353 | M | Sheet | | 0 | M | M | M | M | M | M | M |
| 354 | N | Sheet | | 19 | N | N | N | N | N | N | T |
| 355 | Y | Sheet | | 4 | Y | Y | Y | Y | Y | I | Y |
| 356 | W | Sheet | | 1 | W | W | W | W | W | W | W |
| 357 | V | Coil | | 9 | V | V | V | V | V | A | R |
| 358 | G | Sheet | | 0 | G | G | G | G | G | G | R |
| 359 | H | Sheet | | 0 | H | H | H | H | H | H | H |
| 360 | R | Sheet | | 61 | R | R | R | R | R | R | T | B21 |
| 361 | L | Sheet | | 13 | L | L | L | L | L | L | I |
| 362 | E | Sheet | | 20 | E | N | N | N | N | E | Q | B21 |
| 363 | S | Sheet | | 8 | S | F | F | F | F | S | S |
| 364 | R | Sheet | | 40 | R | R | R | R | R | R | R |
| 365 | T | Sheet | | 10 | T | P | P | P | P | P | P |
| 366 | I | Turn | | 1 | I | I | I | I | I | I | I |
| 367 | R | Turn | | 70 | R | G | G | G | G | A | R | B21 |
| 368 | G | Coil | | 21 | G | G | G | G | G | G | G |
| 369 | S | Coil | | 116 | S | T | T | T | T | S | A |
| 370 | L | Sheet | b4 | 37 | L | L | L | L | L | L | L |
| 371 | S | Sheet | | 117 | S | N | N | N | N | N | I |
| 372 | T | Sheet | | 29 | T | T | T | T | T | T | T |
| 373 | S | Sheet | | 45 | S | S | S | S | S | S | S |
| 374 | T | Sheet | | 63 | T | T | T | T | T | T | T |
| 375 | H | Sheet | | 29 | H | H | H | H | Q | Q | H |
| 376 | G | Sheet | | 23 | G | G | G | G | G | G | G |
| 377 | N | Coil | | 80 | N | A | A | A | L | S | N |
| 378 | T | Coil | | 24 | T | T | T | T | T | T | T |
| 379 | N | Coil | | 106 | N | N | N | N | N | N | N |
| — | — | | | — | — | — | — | — | N | — | — |
| 380 | T | Coil | | 74 | T | T | T | T | T | T | T |
| 381 | S | Coil | | 124 | S | S | S | S | S | S | S |
| 382 | I | Coil | | 20 | I | I | I | I | I | I | I |
| 383 | N | Sheet | b5 | 76 | N | N | N | N | N | N | N |
| 384 | P | Sheet | | 66 | P | P | P | P | P | P | P |
| 385 | V | Sheet | | 42 | V | V | V | V | V | V | V |
| 386 | T | Sheet | | 99 | T | T | T | T | T | T | T |
| 387 | L | Sheet | | 5 | L | L | L | L | L | L | F |
| 388 | Q | Sheet | | 109 | Q | Q | Q | Q | Q | Q | Q |
| 389 | F | Coil | | 3 | F | F | F | F | F | F | F |
| 390 | T | Turn | | 66 | T | T | T | T | T | T | P |
| 391 | S | Turn | | 56 | S | S | S | S | S | S | S |
| 392 | R | Coil | | 28 | R | R | R | R | R | R | R |
| 393 | D | Sheet | | 3 | D | D | D | D | D | D | D |
| 394 | V | Sheet | | 1 | V | V | V | V | I | V | V |
| 395 | Y | Coil | | 8 | Y | Y | Y | Y | Y | Y | Y |
| 396 | R | Sheet | b6 | 31 | R | R | R | R | R | R | R |
| 397 | T | Sheet | | 6 | T | T | T | T | T | T | T |
| 398 | E | Sheet | | 35 | E | E | E | E | E | E | E |
| 399 | S | Sheet | | 3 | S | S | S | S | S | S | S |
| 400 | Y | Sheet | | 35 | Y | Y | Y | Y | N | L | Y |
| 401 | A | Sheet | | 1 | A | A | A | A | A | A | A |
| 402 | G | Sheet | | 0 | G | G | G | G | G | G | G |
| 403 | I | Sheet | | 0 | I | I | I | I | T | L | V |

TABLE 4-continued

| | | | | | | | | | | | |
|---|---|---|---|---|---|---|---|---|---|---|---|
| 404 | N | Sheet | | 0 | N | N | N | N | N | L | |
| 405 | I | Sheet | | 53 | I | I | I | I | I | L | |
| 406 | L | Coil | L2 | 38 | L | L | L | L | F | W | 258 |
| — | — | | | | — | — | — | — | — | G | |
| — | — | | | | — | — | — | — | — | I | |
| 407 | L | Coil | | 114 | L | L | L | F | I | Y | 258 |
| 408 | T | Coil | | 107 | T | T | T | T | T | L | |
| 409 | T | Coil | | 50 | T | T | T | T | Q | E | |
| 410 | P | Sheet | | 1 | P | P | P | P | P | P | |
| 411 | V | Sheet | | 12 | V | V | V | V | V | I | |
| 412 | N | Sheet | | 3 | N | N | N | N | N | H | |
| 413 | G | Sheet | | 0 | G | G | G | G | G | G | |
| 414 | V | Coil | | 0 | V | V | V | V | V | V | |
| 415 | P | Coil | | 6 | P | P | P | P | P | P | |
| 416 | W | Sheet | b7 | 21 | W | W | W | W | W | T | |
| 417 | A | Sheet | | 1 | A | A | A | A | A | V | V |
| 418 | R | Sheet | | 42 | R | R | R | R | R | R | B21 |
| 419 | F | Sheet | | 2 | F | F | F | F | F | F | |
| 420 | N | Sheet | | 17 | N | N | N | N | N | N | |
| 421 | W | Sheet | | 4 | W | W | W | W | F | W | F |
| 422 | R | Sheet | | 17 | R | R | R | R | I | R | R |
| 423 | N | Sheet | | 18 | N | N | N | N | N | N | |
| 424 | P | Turn | | 23 | P | P | P | P | P | P | |
| 425 | L | Turn | | 96 | L | L | L | L | Q | L | Q B21 |
| 426 | N | Turn | | 50 | N | N | N | N | N | N | |
| 427 | S | Turn | | 71 | S | S | S | S | I | S | T B21 |
| 428 | L | Sheet | b8 | 104 | L | L | L | L | Y | L | F |
| 429 | R | Sheet | | 57 | R | R | R | R | E | R | E B21 |
| — | — | | | | — | — | — | — | R | — | R |
| 430 | G | Sheet | | 71 | G | G | G | G | G | G | G |
| 431 | S | Sheet | | 56 | S | S | S | S | A | S | T B21 |
| 432 | L | Sheet | | 42 | L | L | L | L | T | L | A |
| 433 | L | Sheet | | 39 | L | L | L | L | T | L | N |
| 434 | Y | Sheet | | 4 | Y | Y | Y | Y | Y | Y | Y |
| 435 | T | Sheet | | 54 | T | T | T | T | S | T | S B21 |
| 436 | I | Coil | | 21 | I | I | I | I | Q | I | Q |
| 437 | G | Coil | | 75 | G | G | G | G | P | G | P B21 |
| 438 | Y | Coil | | 5 | Y | Y | Y | Y | Y | Y | Y |
| 439 | T | Coil | | 60 | T | T | T | T | Q | T | E B21 |
| 440 | G | Coil | | 77 | G | G | G | G | G | G | S |
| 441 | V | Coil | | 13 | V | V | V | V | V | V | P |
| 442 | G | Sheet | b9 | 67 | G | G | G | G | G | G | G |
| 443 | T | Sheet | | 37 | T | T | T | T | I | T | L |
| 444 | Q | Sheet | | 39 | Q | Q | Q | Q | Q | Q | Q |
| 445 | L | Sheet | | 87 | L | L | L | L | L | L | L |
| 446 | F | Sheet | | 31 | F | F | F | F | F | Q | K |
| 447 | D | Sheet | | 41 | D | D | D | D | D | D | D B21 |
| 448 | S | Helix | | 2 | S | S | S | S | S | S | S |
| 449 | E | Helix | | 31 | E | E | E | E | E | E | E |
| 450 | T | Helix | | 76 | T | T | T | T | T | T | T |
| 451 | E | Helix | | 15 | E | E | E | E | E | E | E |
| 452 | L | Coil | | 2 | L | L | L | L | L | L | L |
| 453 | P | Coil | | 14 | P | P | P | P | P | P | P |
| 454 | P | Coil | | 21 | P | P | P | P | P | P | P |
| 455 | E | Coil | | 38 | E | E | E | E | E | E | E |
| 456 | T | Coil | | 45 | T | T | T | T | T | T | T |
| 457 | T | Coil | | 119 | T | T | T | T | T | T | T |
| 458 | E | Coil | | 95 | E | E | E | E | E | E | E |
| 459 | R | Coil | | 75 | R | R | R | R | R | R | R |
| 460 | P | Coil | | 32 | P | P | P | P | P | P | P |
| 461 | N | Helix | | 34 | N | N | N | N | N | N | N |
| 462 | Y | Helix | | 41 | Y | Y | Y | Y | Y | Y | Y |
| 463 | E | Helix | | 57 | E | E | E | E | E | E | E |
| 464 | S | Helix | | 2 | S | S | S | S | S | S | S |
| 465 | Y | Coil | | 3 | Y | Y | Y | Y | Y | Y | Y |
| 466 | S | Coil | | 0 | S | S | S | S | S | S | S |
| 467 | H | Sheet | b10 | 1 | H | H | H | H | H | H | H |
| 468 | R | Sheet | | 3 | R | R | R | R | R | R | R |
| 469 | L | Sheet | | 13 | L | L | L | L | L | L | L |
| 470 | S | Coil | | 1 | S | S | S | S | S | S | S |
| 471 | N | Sheet | | 2 | N | N | N | N | H | H | H |
| 472 | I | Sheet | | 7 | I | I | I | I | I | I | I |
| 473 | R | Sheet | | 15 | R | R | R | R | G | G | G B21 |
| 474 | L | Sheet | | 1 | L | L | L | L | L | L | I |
| 475 | I | Sheet | | 20 | I | I | I | I | I | I | I |
| 476 | S | Coil | L3 | 2 | S | I | I | I | I | S | L B21 |
| 477 | G | Turn | | 126 | G | G | G | G | G | S | Q B21 |
| 478 | N | Turn | | 105 | N | N | N | G | N | S | T B21 |
| 479 | T | Coil | | 31 | T | T | T | T | T | H | R B21 |
| 480 | L | Coil | | 16 | L | L | L | L | L | V | L |

TABLE 4-continued

| | | | | | | | | | | | |
|---|---|---|---|---|---|---|---|---|---|---|---|
| 481 | R | Coil | | 22 | R | R | R | R | R | R | N | |
| 482 | A | Sheet | b11 | 4 | A | A | A | A | A | A | V | |
| 483 | P | Sheet | | 0 | P | P | P | P | P | L | P | |
| 484 | V | Sheet | | 3 | V | V | V | V | V | V | V | |
| 485 | Y | Sheet | | 1 | Y | Y | Y | Y | Y | Y | Y | |
| 486 | S | Sheet | | 0 | S | S | S | S | S | S | S | |
| 487 | W | Sheet | | 1 | W | W | W | W | W | W | W | |
| 488 | T | Sheet | | 1 | T | T | T | T | T | T | T | |
| 489 | H | Sheet | | 8 | H | H | H | H | H | H | H | |
| 490 | R | Turn | | 39 | R | R | R | R | R | R | R | 258 |
| 491 | S | Turn | | 2 | S | S | S | S | S | S | S | |
| 492 | A | Coil | | 0 | A | A | A | A | A | A | A | |
| 493 | D | Coil | | 30 | D | D | D | D | D | D | D | |
| 494 | R | Coil | | 20 | R | R | R | R | R | R | R | |
| 495 | T | Coil | | 49 | T | T | T | T | T | T | T | B25 |
| 496 | N | Coil | | 5 | N | N | N | N | N | N | N | |
| 497 | T | Sheet | | 60 | T | T | T | T | T | T | T | |
| 498 | I | Sheet | | 9 | I | I | I | I | I | I | I | |
| 499 | A | Coil | | 68 | A | A | A | A | G | G | G | B25 |
| 500 | T | Coil | | 41 | T | T | T | T | P | P | P | |
| 501 | N | Coil | | 103 | N | N | N | N | N | N | N | |
| 502 | I | Coil | | 16 | I | I | I | I | R | R | R | B25 |
| 503 | I | Sheet | b13 | 0 | I | I | I | I | I | I | I | |
| 504 | T | Sheet | | 5 | T | T | T | T | T | T | T | |
| 505 | Q | Sheet | | 8 | Q | Q | Q | Q | Q | Q | Q | |
| 506 | I | Sheet | | 12 | I | I | I | I | I | I | I | |
| 507 | P | Sheet | | 3 | P | P | P | P | P | P | P | |
| 508 | A | Helix | | 0 | A | A | A | A | A | A | A | |
| 509 | V | Helix | | 8 | V | V | V | V | V | V | V | B25 |
| 510 | K | Helix | | 0 | K | K | K | K | K | K | K | |
| 511 | G | Coil | | 0 | G | G | G | G | G | G | G | |
| 512 | N | Coil | | 13 | N | N | N | N | R | R | N | 258 |
| 513 | F | Sheet | b14 | 47 | F | F | F | F | F | F | L | B25 |
| 514 | L | Sheet | | 23 | L | L | L | L | L | L | L | |
| 515 | F | Coil | | 29 | F | F | F | F | F | F | F | B25 |
| 516 | N | Coil | | 125 | N | N | N | N | N | N | N | |
| 517 | G | Coil | | 13 | G | G | G | G | G | G | G | B25 |
| 518 | S | Coil | | 37 | S | S | S | S | S | S | S | B25 |
| 519 | V | Sheet | | 7 | V | V | V | V | V | V | V | |
| 520 | I | Sheet | | 34 | I | I | I | I | I | I | I | B25 |
| 521 | S | Coil | | 110 | S | S | S | S | S | S | S | B25 |
| 522 | G | Coil | | 2 | G | G | G | G | G | G | G | |
| 523 | P | Coil | | 4 | P | P | P | P | P | P | P | |
| 524 | G | Coil | | 46 | G | G | G | G | G | G | G | |
| 525 | F | Coil | | 11 | F | F | F | F | F | F | F | |
| 526 | T | Coil | | 0 | T | T | T | T | T | T | T | B25 |
| 527 | G | Coil | | 13 | G | G | G | G | G | G | G | |
| 528 | G | Coil | | 2 | G | G | G | G | G | G | G | |
| 529 | D | Coil | | 47 | D | D | D | D | D | D | D | |
| 530 | L | Sheet | b15 | 8 | L | L | L | L | V | V | L | |
| 531 | V | Sheet | | 2 | V | V | V | V | V | V | V | |
| 532 | R | Sheet | | 50 | R | R | R | R | R | R | R | B25 |
| 533 | L | Sheet | | 6 | L | L | L | L | L | L | L | |
| 534 | N | Coil | | 52 | N | N | N | N | N | N | N | B25 |
| 535 | N | Coil | | 62 | N | N | N | N | R | R | N | B25 |
| 536 | S | Coil | | 50 | S | S | S | S | N | N | S | |
| 537 | G | Sheet | | 92 | G | G | G | G | N | N | G | 258 |
| 538 | N | Sheet | | 72 | N | N | N | N | G | G | N | 258 |
| 539 | N | Coil | | 4 | N | N | N | N | N | N | N | |
| 540 | I | Sheet | b16 | 2 | I | I | I | I | I | I | I | |
| 541 | Q | Sheet | | 50 | Q | Q | Q | Q | Q | Q | Q | 258 |
| 542 | N | Sheet | | 23 | N | N | N | N | N | N | N | |
| 543 | R | Sheet | | 35 | R | R | R | R | R | R | R | |
| 544 | G | Sheet | | 38 | G | G | G | G | G | G | G | |
| 545 | Y | Sheet | | 37 | Y | Y | Y | Y | Y | Y | Y | 258 |
| 546 | L | Sheet | | 8 | L | I | I | I | I | I | L | |
| 547 | E | Coil | | 101 | E | E | E | E | E | E | E | 258 |
| 548 | V | Coil | | 4 | V | V | V | V | V | V | V | |
| 549 | P | Coil | | 50 | P | P | P | P | P | P | P | |
| 550 | I | Coil | | 7 | I | I | I | I | I | I | I | |
| 551 | Q | Coil | | 90 | Q | Q | Q | Q | Q | Q | Q | B25 |
| 552 | F | Coil | | 103 | F | F | F | F | F | F | F | B25 |
| 553 | I | Coil | | 75 | I | I | I | I | T | T | T | B25 |
| 554 | S | Coil | | 120 | S | S | S | S | S | S | S | |
| 555 | T | Coil | | 79 | T | T | T | T | T | T | T | B25 |
| 556 | S | Coil | | 24 | S | S | S | S | S | S | S | B25 |
| 557 | T | Coil | | 21 | T | T | T | T | T | T | T | B25 |
| 558 | R | Sheet | b17 | 65 | R | R | R | R | R | R | R | B25 |
| 559 | Y | Sheet | | 1 | Y | Y | Y | Y | Y | Y | Y | B25 |
| 560 | R | Sheet | | 38 | R | R | R | R | R | R | R | |

TABLE 4-continued

| | | | | | | | | | | | | |
|---|---|---|---|---|---|---|---|---|---|---|---|---|
| 561 | V | Sheet | | 7 | V | V | V | V | V | V | V | |
| 562 | R | Sheet | | 21 | R | R | R | R | R | R | R | |
| 563 | V | Sheet | | 5 | V | V | V | V | V | V | V | B25 |
| 564 | R | Sheet | | 7 | R | R | R | R | R | R | R | B25 |
| 565 | Y | Sheet | | 5 | Y | Y | Y | Y | Y | Y | Y | B25 |
| 566 | A | Sheet | | 55 | A | A | A | A | A | A | A | |
| 567 | S | Sheet | | 2 | S | S | S | S | S | S | S | |
| 568 | V | Coil | | 29 | V | V | V | V | V | V | V | B25 |
| 569 | T | Coil | | 33 | T | T | T | T | T | T | T | B25 |
| 570 | P | Coil | | 69 | P | P | P | P | S | S | P | 258 |
| 571 | I | Sheet | b18 | 4 | I | I | I | I | I | I | I | B25 |
| 572 | Q | Sheet | | 32 | Q | Q | R | R | E | E | H | 258 |
| 573 | L | Sheet | | 7 | L | L | L | L | L | L | L | B25 |
| 574 | S | Sheet | | 21 | S | S | S | S | N | N | S | 258 |
| 575 | V | Sheet | | 11 | V | V | V | V | V | V | V | |
| 576 | N | Sheet | | 26 | N | N | N | N | N | N | N | |
| 577 | W | Sheet | | 6 | W | W | W | L | W | W | W | 258 |
| 578 | G | Turn | | 109 | G | G | G | G | G | G | G | |
| 579 | N | Turn | | 120 | N | N | N | N | N | N | N | |
| 580 | S | Coil | | 66 | S | S | S | S | S | S | S | |
| 581 | N | Coil | | 85 | N | N | N | N | S | S | N | 258 |
| 582 | I | Coil | | 14 | I | I | I | I | I | I | I | B25 |
| 583 | F | Sheet | b19 | 3 | F | F | F | F | F | F | F | B25 |
| 584 | S | Sheet | | 71 | S | S | S | S | T | T | S | B21 |
| 585 | S | Sheet | | 33 | S | S | S | S | N | N | S | 258 |
| 586 | I | Sheet | | 73 | I | I | I | I | T | T | T | 258 |
| 587 | V | Sheet | | 17 | V | V | V | V | L | L | V | 258 |
| 588 | P | Coil | | 77 | P | P | P | P | P | P | P | |
| 589 | A | Coil | | 38 | A | A | A | A | A | A | A | |
| 590 | T | Coil | | 6 | T | T | T | T | T | T | T | B25 |
| 591 | A | Coil | | 42 | A | A | A | A | A | A | A | 258 |
| 592 | T | Coil | | 87 | T | T | T | T | A | A | A | 258 |
| 593 | S | Turn | | 102 | S | S | S | S | S | S | S | B21 |
| 594 | L | Turn | | 130 | L | L | L | L | L | L | L | |
| 595 | D | Coil | | 63 | D | D | D | D | D | D | D | B21 |
| 596 | N | Coil | | 100 | N | N | N | N | N | N | N | B21 |
| 597 | L | Coil | | 64 | L | L | L | L | L | L | L | |
| 598 | Q | Coil | | 57 | Q | Q | Q | Q | Q | Q | Q | B21 |
| 599 | S | Coil | | 35 | S | S | S | S | S | S | S | B25 |
| 600 | R | Coil | | 58 | R | R | R | R | G | G | R | |
| 601 | D | Sheet | b20 | 20 | D | N | N | N | D | D | D | B21 |
| 602 | F | Sheet | | 55 | F | F | F | F | F | F | F | B25 |
| 603 | G | Sheet | | 27 | G | G | G | G | G | G | G | B25 |
| 604 | Y | Coil | | 4 | Y | Y | Y | Y | Y | Y | Y | |
| 605 | F | Coil | | 108 | F | F | F | F | V | V | F | 258 |
| 606 | E | Coil | | 86 | E | E | E | E | E | E | E | B21 |
| 607 | S | Coil | | 9 | S | S | S | S | I | I | S | 258 |
| 608 | T | Sheet | | 14 | T | T | R | R | N | N | T | 258 |
| 609 | N | Sheet | | 40 | N | N | N | N | N | N | N | B25 |
| 610 | A | Coil | | 0 | A | A | A | A | A | A | A | B25 |
| 611 | F | Coil | | 90 | F | F | F | F | F | F | F | B25 |
| 612 | T | Coil | | 73 | T | T | T | T | T | T | T | B25 |
| 613 | S | Coil | | 89 | S | S | S | S | S | S | S | B25 |
| 614 | A | Sheet | b22 | 51 | A | A | A | A | A | A | V | B25 |
| 615 | T | Sheet | | 14 | T | T | T | T | T | T | T | |
| 616 | G | Sheet | | 50 | G | G | G | G | G | G | G | |
| 617 | N | Sheet | | 31 | N | N | N | N | N | N | N | B25 |
| 618 | V | Sheet | | 17 | V | V | V | V | I | I | V | 258 |
| 619 | V | Sheet | | 10 | V | V | V | V | V | V | V | |
| 620 | G | Sheet | | 2 | G | G | G | G | G | G | G | |
| 621 | V | Sheet | | 4 | V | V | V | V | A | V | V | |
| 622 | R | Sheet | | 61 | R | R | R | R | R | R | R | |
| 623 | N | Coil | | 89 | N | N | N | N | N | N | N | |
| 624 | F | Coil | | 0 | F | F | F | F | F | F | F | B25 |
| 625 | S | Coil | | 123 | S | S | S | S | S | S | S | |
| 626 | E | Coil | | 83 | E | E | E | E | A | A | E | 258 |
| 627 | N | Coil | | 98 | N | N | N | N | N | N | N | |
| 628 | A | Coil | | 19 | A | A | A | A | A | A | A | B25 |
| 629 | G | Coil | | 42 | G | G | G | G | E | E | R | 258 |
| 630 | V | Sheet | b23 | 2 | V | V | V | V | V | V | V | B25 |
| 631 | I | Sheet | | 12 | I | I | I | I | I | I | I | |
| 632 | I | Sheet | | 8 | I | I | I | I | I | I | I | |
| 633 | D | Coil | | 4 | D | D | D | D | D | D | D | |
| 634 | R | Sheet | | 7 | R | R | R | R | R | R | R | |
| 635 | F | Sheet | | 23 | F | F | F | F | F | F | F | |
| 636 | E | Sheet | | 0 | E | E | E | E | E | E | E | |
| 637 | F | Sheet | | 15 | F | F | F | F | F | F | F | |
| 638 | I | Sheet | | 12 | I | I | I | I | I | I | I | |
| 639 | P | Sheet | | 6 | P | P | P | P | P | P | P | |
| 640 | V | Turn | | 33 | V | V | V | V | V | V | V | |

TABLE 4-continued

| 641 | T | Turn |   | 113 | T | T | T | T | T | T | T B25 |
| 642 | A | Coil |   | 3   | A | A | A | A | A | A | A |
| 643 | T | Coil |   | 117 | T | T | T | T | T | T | T B25 |
| 644 | F |      |   |     | F | F | F | F | F | F | F |
| 645 | E |      |   |     | E | E | E | E | E | E | E B25 |
| 646 | A |      |   |     | A | A | A | A | A | A | A B25 |
| 647 | E |      |   |     | E | E | E | E | E | K | E |
| 648 | Y |      |   |     | Y | Y | Y | Y | Y | Y | Y |
| 649 | D |      |   |     | D | D | D | D | D | D | D |
| 650 | L |      |   |     | L | L | L | L | L | L | L |
| 651 | E |      |   |     | E | E | E | E | E | E | E |

| MP258 position | Variant | FAE | Variant | FAE | Variant | FAE | Variant | FAE | Variant | FAE |
| --- | --- | --- | --- | --- | --- | --- | --- | --- | --- | --- |
| 50 | L50R | 1.72 | L50I | 1.52 | L50D | 1.5 | L50A | 1.43 | L50H | 1.42 |
|    | L50Y | 1.42 | L50S | 1.38 | L50F | 1.38 | L50V | 1.37 | L50K | 1.34 |
|    | L50N | 1.26 |      |      |      |      |      |      |      |      |
| 51 |      |      |      |      |      |      |      |      |      |      |
| 52 |      |      |      |      |      |      |      |      |      |      |
| 53 | A53R | 1.79 | A53Y | 1.72 | A53K | 1.7  | A53H | 1.45 | A53P | 1.42 |
|    | A53V | 1.35 | A53Q | 1.31 | A53D | 1.25 | A53E | 1.23 | A53G | 1.22 |
|    | A53T | 1.21 |      |      |      |      |      |      |      |      |
| 54 | S54P | 1.6  | S54K | 1.4  | S54G | 1.39 | S54A | 1.36 | S54I | 1.25 |
|    | S54R | 1.21 |      |      |      |      |      |      |      |      |
| 55 |      |      |      |      |      |      |      |      |      |      |
| 56 |      |      |      |      |      |      |      |      |      |      |
| 57 | Q57V | 1.76 | Q57R | 1.71 | Q57L | 1.54 | Q57N | 1.53 | Q57G | 1.38 |
|    | Q57D | 1.3  |      |      |      |      |      |      |      |      |
| 58 |      |      |      |      |      |      |      |      |      |      |
| 59 |      |      |      |      |      |      |      |      |      |      |
| 60 |      |      |      |      |      |      |      |      |      |      |
| 61 |      |      |      |      |      |      |      |      |      |      |
| 62 |      |      |      |      |      |      |      |      |      |      |
| 63 |      |      |      |      |      |      |      |      |      |      |
| 64 |      |      |      |      |      |      |      |      |      |      |
| 65 | R65Q | 1.54 | R65A | 1.53 | R65S | 1.48 | R65G | 1.36 |      |      |
| 66 |      |      |      |      |      |      |      |      |      |      |
| 67 | L67M | 2.03 | L67F | 1.41 | L67I | 1.27 |      |      |      |      |
| 68 | G68A | 1.83 | G68R | 1.3  | G68F | 1.27 |      |      |      |      |
| 69 |      |      |      |      |      |      |      |      |      |      |
| 70 | L70E | 1.51 | L70W | 1.3  | L70H | 1.23 |      |      |      |      |
| 71 | G71S | 1.33 |      |      |      |      |      |      |      |      |
| 72 | V72G | 1.87 |      |      |      |      |      |      |      |      |
| 73 | P73S | 1.27 | P73G | 1.35 |      |      |      |      |      |      |
| 74 | F74I | 1.92 | F74E | 1.91 | F74S | 1.64 | F74R | 1.33 | F74V | 1.25 |
|    | F74D | 1.24 |      |      |      |      |      |      |      |      |
| 75 | A75S | 2.23 | A75P | 1.67 | A75E | 1.28 |      |      |      |      |
| 76 | G76T | 2.01 | G76S | 1.76 | G76Y | 1.6  | G76V | 1.6  | G76D | 1.41 |
|    | G76R | 1.4  |      |      |      |      |      |      |      |      |
| 77 | Q77N | 1.86 | Q77D | 1.82 | Q77G | 1.78 | Q77L | 1.76 | Q77I | 1.69 |
|    | Q77H | 1.64 | Q77P | 1.63 | Q77A | 1.59 | Q77T | 1.58 | Q77M | 1.39 |
|    | Q77C | 1.38 | Q77S | 1.22 |      |      |      |      |      |      |
| 78 |      |      |      |      |      |      |      |      |      |      |
| 79 | A79S | 1.83 | A79V | 1.78 | A79T | 1.71 | A79L | 1.69 | A79R | 1.65 |
|    | A79I | 1.55 | A79P | 1.5  | A79N | 1.32 | A79Q | 1.31 | A79K | 1.23 |
| 80 | S80Q | 2.06 | S80K | 1.97 | S80G | 1.93 | S80E | 1.86 | S80R | 1.84 |
|    | S80M | 1.77 | S80N | 1.66 | S80C | 1.56 | S80W | 1.45 | S80Y | 1.44 |
|    | S80D | 1.29 |      |      |      |      |      |      |      |      |
| 81 |      |      |      |      |      |      |      |      |      |      |
| 82 | Y82F | 1.41 |      |      |      |      |      |      |      |      |
| 83 | S83E | 1.97 | S83D | 1.91 | S83G | 1.89 | S83A | 1.87 | S83K | 1.8  |
|    | S83H | 1.7  | S83R | 1.51 | S83Y | 1.39 | S83L | 1.32 |      |      |
| 84 |      |      |      |      |      |      |      |      |      |      |
| 85 |      |      |      |      |      |      |      |      |      |      |
| 86 |      |      |      |      |      |      |      |      |      |      |
| 87 | G87D | 1.95 | G87K | 1.65 | G87N | 1.44 | G87C | 1.42 | G87W | 1.28 |
|    | G87H | 1.24 |      |      |      |      |      |      |      |      |
| 88 |      |      |      |      |      |      |      |      |      |      |
| 89 |      |      |      |      |      |      |      |      |      |      |
| 90 |      |      |      |      |      |      |      |      |      |      |
| 91 | P91S | 1.64 | P91Y | 1.49 | P91T | 1.46 | P91D | 1.28 |      |      |
| 92 | S92E | 2.54 | S92G | 1.88 | S92F | 1.72 | S92V | 1.72 | S92L | 1.71 |
|    | S92T | 1.47 |      |      |      |      |      |      |      |      |
| 93 | G93H | 1.68 | G93D | 1.53 | G93I | 1.28 |      |      |      |      |
| 94 | R94L | 2.27 | R94H | 2.19 | R94T | 1.7  | R94S | 1.35 |      |      |
| 95 | D95G | 1.86 | D95Q | 1.67 | D95V | 1.55 | D95F | 1.2  |      |      |
| 96 |      |      |      |      |      |      |      |      |      |      |
| 97 |      |      |      |      |      |      |      |      |      |      |
| 98 |      |      |      |      |      |      |      |      |      |      |

TABLE 4-continued

| | | | | | | | | | |
|---|---|---|---|---|---|---|---|---|---|
| 99 | | | | | | | | | |
| 100 | | | | | | | | | |
| 101 | | | | | | | | | |
| 102 | | | | | | | | | |
| 103 | | | | | | | | | |
| 104 | | | | | | | | | |
| 105 | | | | | | | | | |
| 106 | Q106I | 2.16 | Q106A | 1.77 | Q106F | 1.74 | Q106G | 1.71 | |
| | Q106H | 1.67 | Q106C | 1.52 | Q106K | 1.43 | Q106V | 1.32 | Q106R | 1.29 |
| | Q106S | 1.25 | | | | | | | |
| 107 | | | | | | | | | |
| 108 | V108L | 1.92 | V108M | 1.55 | V108T | 1.29 | | | |
| 109 | R109S | 1.35 | R109V | 1.28 | R109N | 1.23 | | | |
| 110 | Q110T | 1.93 | Q110R | 1.51 | Q110V | 1.32 | Q110F | 1.26 | Q110H | 1.24 |
| 111 | Q111H | 4.5 | Q111L | 2.97 | Q111S | 2.37 | Q111M | 2.16 | Q111R | 2.14 |
| | Q111A | 1.99 | Q111K | 1.8 | Q111E | 1.54 | | | |
| 112 | I112L | 2.03 | | | | | | | |
| 113 | T113L | 1.44 | T113V | 1.4 | T113S | 1.34 | T113N | 1.29 | T113K | 1.25 |
| 114 | E114L | 2.67 | E114T | 2.29 | E114M | 2.11 | E114H | 2.03 | E114Y | 1.94 |
| | E114A | 1.73 | E114S | 1.67 | E114V | 1.54 | E114F | 1.39 | | |
| 115 | N115P | 1.39 | | | | | | | |
| 116 | | | | | | | | | |
| 117 | | | | | | | | | |
| 118 | N118V | 2.16 | N118T | 1.84 | N118E | 1.72 | N118D | 1.4 | N118F | 1.37 |
| | N118G | 1.22 | | | | | | | |
| 119 | T119A | 2.3 | T119M | 2.08 | T119S | 1.89 | T119K | 1.76 | T119H | 1.69 |
| | T119E | 1.66 | T119R | 1.65 | T119V | 1.44 | | | |
| 120 | | | | | | | | | |
| 121 | | | | | | | | | |
| 122 | A122R | 1.38 | A122I | 1.32 | A122F | 1.27 | A122N | 1.26 | A122G | 1.23 |
| | A122T | 1.23 | | | | | | | |
| 123 | R123K | 1.81 | | | | | | | |
| 124 | | | | | | | | | |
| 125 | Q125N | 1.83 | Q125R | 1.58 | Q125E | 1.48 | | | |
| 126 | | | | | | | | | |
| 127 | | | | | | | | | |
| 128 | | | | | | | | | |
| 129 | A129K | 1.69 | A129W | 1.56 | A129L | 1.38 | A129P | 1.32 | A129V | 1.23 |
| 130 | | | | | | | | | |
| 131 | | | | | | | | | |
| 132 | | | | | | | | | |
| 133 | | | | | | | | | |
| 134 | | | | | | | | | |
| 135 | | | | | | | | | |
| 136 | Q136I | 1.52 | Q136F | 1.34 | Q136I | 1.31 | | | |
| 137 | | | | | | | | | |
| 138 | | | | | | | | | |
| 139 | | | | | | | | | |
| 140 | D140E | 1.65 | | | | | | | |
| 141 | | | | | | | | | |
| 142 | | | | | | | | | |
| 143 | E143S | 2.18 | E143R | 1.78 | E143G | 1.64 | E143Y | 1.62 | E143M | 1.62 |
| | E143Q | 1.58 | E143L | 1.55 | E143W | 1.55 | E143T | 1.5 | E143A | 1.48 |
| | E143N | 1.37 | E143P | 1.34 | | | | | |
| 144 | N144M | 1.81 | N144A | 1.56 | N144T | 1.21 | | | |
| 145 | R145N | 1.81 | R145P | 1.55 | R145A | 1.45 | R145L | 1.44 | R145S | 1.23 |
| 146 | D146W | 1.53 | D146T | 1.3 | D146H | 1.22 | D146V | 1.21 | | |
| 147 | N147V | 1.77 | N147R | 1.65 | N147D | 1.42 | N147S | 1.37 | | |
| 148 | A148F | 2.22 | A148W | 1.83 | A148P | 1.75 | A148N | 1.74 | A148L | 1.73 |
| 149 | R149V | 2.2 | R149A | 1.89 | R149S | 1.88 | R149L | 1.49 | | |
| 150 | | | | | | | | | |
| 151 | | | | | | | | | |
| 152 | | | | | | | | | |
| 153 | | | | | | | | | |
| 154 | | | | | | | | | |
| 155 | | | | | | | | | |
| 156 | | | | | | | | | |
| 157 | | | | | | | | | |
| 158 | Y158F | 1.7 | | | | | | | |
| 159 | I159V | 1.37 | | | | | | | |
| 160 | A160V | 1.65 | | | | | | | |
| 161 | | | | | | | | | |
| 162 | | | | | | | | | |
| 163 | | | | | | | | | |
| 164 | | | | | | | | | |
| 165 | | | | | | | | | |
| 166 | L166V | 1.67 | L166E | 1.62 | L166C | 1.34 | L166I | 1.28 | L166T | 1.25 |
| 167 | N167T | 1.43 | N167M | 1.37 | N167Q | 1.3 | N167L | 1.29 | N167A | 1.22 |
| 168 | | | | | | | | | |
| 169 | | | | | | | | | |

TABLE 4-continued

| | | | | | | | | | |
|---|---|---|---|---|---|---|---|---|---|
| 170 | | | | | | | | | |
| 171 | | | | | | | | | |
| 172 | | | | | | | | | |
| 173 | A173F | 1.56 | A173T | 1.56 | | | | | |
| 174 | | | | | | | | | |
| 175 | | | | | | | | | |
| 176 | | | | | | | | | |
| 177 | Q177C | 1.78 | Q177S | 1.48 | Q177T | 1.3 | Q177P | 1.21 | |
| 178 | Q178K | 1.69 | | | | | | | |
| 179 | V179I | 2.06 | V179L | 1.67 | | | | | |
| 180 | P180A | 1.7 | P180S | 1.51 | P180L | 1.51 | P180M | 1.38 | |
| 181 | | | | | | | | | |
| 182 | | | | | | | | | |
| 183 | | | | | | | | | |
| 184 | | | | | | | | | |
| 185 | | | | | | | | | |
| 186 | | | | | | | | | |
| 187 | | | | | | | | | |
| 188 | | | | | | | | | |
| 189 | | | | | | | | | |
| 190 | | | | | | | | | |
| 191 | | | | | | | | | |
| 192 | | | | | | | | | |
| 193 | | | | | | | | | |
| 194 | | | | | | | | | |
| 195 | | | | | | | | | |
| 196 | | | | | | | | | |
| 197 | | | | | | | | | |
| 198 | | | | | | | | | |
| 199 | | | | | | | | | |
| 200 | | | | | | | | | |
| 201 | L201V | 1.27 | | | | | | | |
| 202 | | | | | | | | | |
| 203 | | | | | | | | | |
| 204 | | | | | | | | | |
| 205 | | | | | | | | | |
| 206 | F206L | 2.37 | F206I | 1.47 | F206T | 1.46 | F206W | 1.45 | |
| 207 | | | | | | | | | |
| 208 | | | | | | | | | |
| 209 | T209E | 1.86 | T209R | 1.7 | T209D | 1.66 | T209L | 1.59 | T209V | 1.3 |
| | T209C | 1.22 | | | | | | | |
| 210 | S210P | 2.15 | S210T | 1.78 | S210I | 1.46 | S210R | 1.25 | |
| 211 | Q211I | 1.9 | Q211R | 1.74 | Q211G | 1.55 | Q211T | 1.44 | Q211P | 1.33 |
| | Q211L | 1.22 | | | | | | | |
| 212 | | | | | | | | | |
| 213 | I213V | 1.71 | I213T | 1.66 | I213L | 1.64 | I213M | 1.53 | I213Q | 1.5 |
| | I213N | 1.28 | I213G | 1.21 | | | | | |
| 214 | Q214W | 3.46 | | | | | | | |
| 215 | | | | | | | | | |
| 216 | | | | | | | | | |
| 217 | | | | | | | | | |
| 218 | E218T | 1.76 | E218A | 1.65 | E218H | 1.62 | E218S | 1.55 | E218I | 1.51 |
| | E218V | 1.33 | E218Y | 1.29 | E218W | 1.21 | E218D | 1.21 | |
| 219 | R219N | 1.63 | | | | | | | |
| 220 | | | | | | | | | |
| 221 | A221L | 2.21 | A221Y | 1.86 | A221V | 1.84 | A221K | 1.81 | A221I | 1.62 |
| | A221D | 1.48 | A221G | 1.43 | A221H | 1.42 | A221W | 1.3 | A221R | 1.28 |
| | A221T | 1.25 | | | | | | | |
| 222 | E222G | 1.89 | E222M | 1.75 | E222K | 1.72 | E222T | 1.67 | E222D | 1.39 |
| | E222I | 1.36 | | | | | | | |
| 223 | | | | | | | | | |
| 224 | | | | | | | | | |
| 225 | R225V | 4.65 | R225Q | 2.37 | R225M | 2.32 | R225F | 2.07 | R225L | 2.04 |
| | R225G | 1.58 | R225I | 1.58 | R225Y | 1.55 | R225C | 1.54 | R225N | 1.46 |
| 226 | E226D | 2.17 | E226S | 2.13 | E226V | 1.68 | E226C | 1.52 | E226Y | 1.46 |
| | E226R | 1.33 | E226A | 1.24 | | | | | |
| 227 | | | | | | | | | |
| 228 | | | | | | | | | |
| 229 | | | | | | | | | |
| 230 | Y230A | 2.65 | Y230L | 1.83 | Y230S | 1.22 | | | |
| 231 | | | | | | | | | |
| 232 | | | | | | | | | |
| 233 | R233K | 2.13 | R233D | 1.96 | R233Q | 1.91 | R233G | 1.56 | R233I | 1.41 |
| | R233A | 1.26 | R233Y | 1.2 | | | | | |
| 234 | W234V | 2.15 | W234M | 2.15 | W234L | 2.06 | W234I | 1.87 | W234A | 1.55 |
| | W234R | 1.55 | W234F | 1.52 | W234Y | 1.48 | W234S | 1.22 | |
| 235 | | | | | | | | | |
| 236 | N236E | 2.2 | N236K | 1.87 | N236S | 1.43 | N236T | 1.41 | N236L | 1.41 |
| 237 | | | | | | | | | |
| 238 | | | | | | | | | |

TABLE 4-continued

| | | | | | | | | | |
|---|---|---|---|---|---|---|---|---|---|
| 239 | | | | | | | | | |
| 240 | N240Y | 1.77 | N240A | 1.56 | N240M | 1.53 | N240S | 1.5 | N240T | 1.49 |
| | N240G | 1.46 | N240K | 1.46 | N240F | 1.36 | N240L | 1.28 | N240R | 1.26 |
| | N240W | 1.22 | N240C | 1.22 | | | | | | |
| 241 | N241S | 1.7 | N241I | 1.68 | N241W | 1.62 | N241M | 1.57 | N241K | 1.48 |
| | N241Y | 1.47 | N241V | 1.33 | N241L | 1.27 | N241C | 1.21 | | |
| 242 | L242P | 2.07 | L242V | 1.44 | | | | | | |
| 243 | R243M | 2.3 | R243V | 2 | R243T | 1.84 | R243C | 1.75 | R243K | 1.72 |
| | R243I | 1.68 | R243S | 1.59 | R243Q | 1.54 | | | | |
| 244 | | | | | | | | | | |
| 245 | T245Q | 2.71 | T245Y | 2.46 | T245K | 2.4 | T245G | 2.13 | T245A | 2.03 |
| | T245I | 1.96 | T245W | 1.95 | T245H | 1.91 | T245S | 1.89 | T245M | 1.82 |
| | T245D | 1.82 | T245N | 1.77 | T245V | 1.66 | T245R | 1.64 | T245F | 1.34 |
| 246 | N246T | 1.73 | N246S | 1.69 | N246G | 1.66 | N246Q | 1.63 | | |
| 247 | A247E | 1.73 | A247S | 1.73 | A247G | 1.57 | A247P | 1.53 | | |
| 248 | E248S | 2.17 | E248N | 1.55 | E248T | 1.53 | E248L | 1.49 | E248Y | 1.49 |
| | E248V | 1.42 | E248R | 1.42 | E248F | 1.24 | | | | |
| 249 | | | | | | | | | | |
| 250 | | | | | | | | | | |
| 251 | | | | | | | | | | |
| 252 | R252N | 1.47 | R252A | 1.4 | R252F | 1.24 | | | | |
| 253 | | | | | | | | | | |
| 254 | | | | | | | | | | |
| 255 | | | | | | | | | | |
| 256 | | | | | | | | | | |
| 257 | | | | | | | | | | |
| 258 | | | | | | | | | | |
| 259 | | | | | | | | | | |
| 260 | | | | | | | | | | |
| 261 | | | | | | | | | | |
| 262 | | | | | | | | | | |
| 263 | | | | | | | | | | |
| 264 | | | | | | | | | | |
| 265 | | | | | | | | | | |
| 266 | | | | | | | | | | |
| 267 | | | | | | | | | | |
| 268 | | | | | | | | | | |
| 269 | | | | | | | | | | |
| 270 | | | | | | | | | | |
| 271 | | | | | | | | | | |
| 272 | | | | | | | | | | |
| 273 | | | | | | | | | | |
| 274 | | | | | | | | | | |
| 275 | | | | | | | | | | |
| 276 | | | | | | | | | | |
| 277 | R277Q | 1.35 | R277G | 1.27 | R277V | 1.23 | | | | |
| 278 | | | | | | | | | | |
| 279 | | | | | | | | | | |
| 280 | P280H | 1.54 | P280C | 1.32 | P280T | 1.29 | | | | |
| 281 | I281Q | 2.16 | I281M | 1.93 | I281R | 1.46 | I281K | 1.35 | I281S | 1.31 |
| | I281H | 1.29 | I281A | 1.23 | | | | | | |
| 282 | | | | | | | | | | |
| 283 | | | | | | | | | | |
| 284 | | | | | | | | | | |
| 285 | | | | | | | | | | |
| 286 | | | | | | | | | | |
| 287 | | | | | | | | | | |
| 288 | | | | | | | | | | |
| 289 | | | | | | | | | | |
| 290 | | | | | | | | | | |
| 291 | | | | | | | | | | |
| 292 | | | | | | | | | | |
| 293 | | | | | | | | | | |
| 294 | | | | | | | | | | |
| 295 | | | | | | | | | | |
| 296 | | | | | | | | | | |
| 297 | | | | | | | | | | |
| 298 | | | | | | | | | | |
| 299 | | | | | | | | | | |
| 300 | | | | | | | | | | |
| 301 | | | | | | | | | | |
| 302 | | | | | | | | | | |
| 303 | S303N | 1.28 | S303P | 1.24 | | | | | | |
| 304 | | | | | | | | | | |
| 305 | | | | | | | | | | |
| 306 | A306G | 1.47 | | | | | | | | |
| 307 | | | | | | | | | | |
| 308 | | | | | | | | | | |
| 309 | | | | | | | | | | |
| 310 | | | | | | | | | | |

TABLE 4-continued

| | | | | | | | | | |
|---|---|---|---|---|---|---|---|---|---|
| 311 | | | | | | | | | |
| 312 | | | | | | | | | |
| 313 | | | | | | | | | |
| 314 | | | | | | | | | |
| 315 | | | | | | | | | |
| 316 | | | | | | | | | |
| 317 | | | | | | | | | |
| 318 | | | | | | | | | |
| 319 | | | | | | | | | |
| 320 | | | | | | | | | |
| 321 | | | | | | | | | |
| 322 | | | | | | | | | |
| 323 | | | | | | | | | |
| 324 | | | | | | | | | |
| 325 | | | | | | | | | |
| 326 | | | | | | | | | |
| 327 | | | | | | | | | |
| 328 | | | | | | | | | |
| 329 | | | | | | | | | |
| 330 | | | | | | | | | |
| 331 | | | | | | | | | |
| 332 | | | | | | | | | |
| 333 | | | | | | | | | |
| 334 | | | | | | | | | |
| 335 | | | | | | | | | |
| 336 | | | | | | | | | |
| 337 | | | | | | | | | |
| 338 | | | | | | | | | |
| 339 | | | | | | | | | |
| 340 | | | | | | | | | |
| 341 | | | | | | | | | |
| 342 | | | | | | | | | |
| 343 | | | | | | | | | |
| 344 | | | | | | | | | |
| 345 | | | | | | | | | |
| 346 | | | | | | | | | |
| 347 | | | | | | | | | |
| 348 | | | | | | | | | |
| 349 | | | | | | | | | |
| 350 | | | | | | | | | |
| 351 | | | | | | | | | |
| 352 | | | | | | | | | |
| 353 | | | | | | | | | |
| 354 | | | | | | | | | |
| 355 | | | | | | | | | |
| 356 | | | | | | | | | |
| 357 | | | | | | | | | |
| 358 | | | | | | | | | |
| 359 | | | | | | | | | |
| 360 | R360S | 1.68 | R360N | 1.57 | R360T | 1.38 | R360Y | 1.29 | R360M | 1.23 |
| 361 | | | | | | | | | |
| 362 | N362Y | 2.25 | N362H | 1.79 | N362W | 1.64 | N362K | 1.57 | N362I | 1.57 |
| | N362D | 1.45 | N362V | 1.45 | N362A | 1.32 | N362L | 1.3 | N362G | 1.26 |
| | N362E | 1.26 | | | | | | | |
| 363 | | | | | | | | | |
| 364 | | | | | | | | | |
| 365 | | | | | | | | | |
| 366 | | | | | | | | | |
| 367 | G367H | 3.17 | G367Q | 2.72 | G367N | 1.97 | G367W | 1.84 | G367T | 1.62 |
| | G367L | 1.58 | G367Y | 1.45 | G367I | 1.37 | G367A | 1.36 | | |
| 368 | | | | | | | | | |
| 369 | | | | | | | | | |
| 370 | | | | | | | | | |
| 371 | | | | | | | | | |
| 372 | | | | | | | | | |
| 373 | | | | | | | | | |
| 374 | | | | | | | | | |
| 375 | | | | | | | | | |
| 376 | | | | | | | | | |
| 377 | | | | | | | | | |
| 378 | | | | | | | | | |
| 379 | | | | | | | | | |
| — | | | | | | | | | |
| 380 | | | | | | | | | |
| 381 | | | | | | | | | |
| 382 | | | | | | | | | |
| 383 | | | | | | | | | |
| 384 | | | | | | | | | |
| 385 | | | | | | | | | |
| 386 | | | | | | | | | |

TABLE 4-continued

| | | | | | | | | | |
|---|---|---|---|---|---|---|---|---|---|
| 387 | | | | | | | | | |
| 388 | | | | | | | | | |
| 389 | | | | | | | | | |
| 390 | | | | | | | | | |
| 391 | | | | | | | | | |
| 392 | | | | | | | | | |
| 393 | | | | | | | | | |
| 394 | | | | | | | | | |
| 395 | | | | | | | | | |
| 396 | | | | | | | | | |
| 397 | | | | | | | | | |
| 398 | | | | | | | | | |
| 399 | | | | | | | | | |
| 400 | | | | | | | | | |
| 401 | | | | | | | | | |
| 402 | | | | | | | | | |
| 403 | | | | | | | | | |
| 404 | | | | | | | | | |
| 405 | | | | | | | | | |
| 406 | L406M | 1.65 | | | | | | | |
| — | | | | | | | | | |
| — | | | | | | | | | |
| 407 | L407W | 1.99 | | | | | | | |
| 408 | | | | | | | | | |
| 409 | | | | | | | | | |
| 410 | | | | | | | | | |
| 411 | | | | | | | | | |
| 412 | | | | | | | | | |
| 413 | | | | | | | | | |
| 414 | | | | | | | | | |
| 415 | | | | | | | | | |
| 416 | | | | | | | | | |
| 417 | | | | | | | | | |
| 418 | R418K | 1.26 | R418T | 1.24 | | | | | |
| 419 | | | | | | | | | |
| 420 | | | | | | | | | |
| 421 | | | | | | | | | |
| 422 | | | | | | | | | |
| 423 | | | | | | | | | |
| 424 | | | | | | | | | |
| 425 | L425P | 1.94 | L425G | 1.31 | | | | | |
| 426 | | | | | | | | | |
| 427 | S427Y | 1.44 | | | | | | | |
| 428 | | | | | | | | | |
| 429 | R429I | 1.36 | | | | | | | |
| — | | | | | | | | | |
| 430 | | | | | | | | | |
| 431 | S431L | 1.63 | S431H | 1.63 | S431G | 1.42 | S431A | 1.3 | |
| 432 | | | | | | | | | |
| 433 | | | | | | | | | |
| 434 | | | | | | | | | |
| 435 | T435Y | 2.14 | T435H | 1.43 | T435L | 1.21 | | | |
| 436 | | | | | | | | | |
| 437 | G437S | 1.57 | G437N | 1.57 | G437A | 1.43 | G437K | 1.34 | G437R | 1.34 |
| 438 | G437Q | 1.33 | | | | | | | |
| 439 | T439M | 1.22 | T439Q | 1.21 | | | | | |
| 440 | | | | | | | | | |
| 441 | | | | | | | | | |
| 442 | | | | | | | | | |
| 443 | | | | | | | | | |
| 444 | | | | | | | | | |
| 445 | | | | | | | | | |
| 446 | | | | | | | | | |
| 447 | D447N | 1.55 | D447V | 1.52 | D447I | 1.47 | D447S | 1.34 | D447L | 1.33 |
| | D447A | 1.31 | D447E | 1.3 | D447M | 1.21 | | | |
| 448 | | | | | | | | | |
| 449 | | | | | | | | | |
| 450 | | | | | | | | | |
| 451 | | | | | | | | | |
| 452 | | | | | | | | | |
| 453 | | | | | | | | | |
| 454 | | | | | | | | | |
| 455 | | | | | | | | | |
| 456 | | | | | | | | | |
| 457 | | | | | | | | | |
| 458 | | | | | | | | | |
| 459 | | | | | | | | | |
| 460 | | | | | | | | | |
| 461 | | | | | | | | | |
| 462 | | | | | | | | | |

TABLE 4-continued

| | | | | | | | | | |
|---|---|---|---|---|---|---|---|---|---|
| 463 | | | | | | | | | |
| 464 | | | | | | | | | |
| 465 | | | | | | | | | |
| 466 | | | | | | | | | |
| 467 | | | | | | | | | |
| 468 | | | | | | | | | |
| 469 | | | | | | | | | |
| 470 | | | | | | | | | |
| 471 | | | | | | | | | |
| 472 | | | | | | | | | |
| 473 | R473T | 12.6 | R473G | 5.48 | R473A | 4.94 | R473S | 3.04 | R473M | 1.94 |
| | R473N | 1.43 | R473K | 1.42 | R473D | 1.39 | R473Y | 1.22 | R473N | 1.43 |
| 474 | | | | | | | | | |
| 475 | | | | | | | | | |
| 476 | I476Y | 1.71 | I476H | 1.55 | I476G | 1.48 | I476L | 1.32 | I476S | 1.28 |
| | I476F | 1.25 | I476M | 1.23 | | | | | | |
| 477 | G477S | 2.35 | G477A | 1.29 | | | | | | |
| 478 | N478G | 2.96 | N478K | 1.23 | | | | | | |
| 479 | T479V | 2.16 | | | | | | | | |
| 480 | | | | | | | | | |
| 481 | | | | | | | | | |
| 482 | | | | | | | | | |
| 483 | | | | | | | | | |
| 484 | | | | | | | | | |
| 485 | | | | | | | | | |
| 486 | | | | | | | | | |
| 487 | | | | | | | | | |
| 488 | | | | | | | | | |
| 489 | | | | | | | | | |
| 490 | R490Q | 3.53 | | | | | | | | |
| 491 | | | | | | | | | |
| 492 | | | | | | | | | |
| 493 | | | | | | | | | |
| 494 | | | | | | | | | |
| 495 | T495N | 1.54 | | | | | | | | |
| 496 | | | | | | | | | |
| 497 | | | | | | | | | |
| 498 | | | | | | | | | |
| 499 | A499R | 1.69 | A499S | 1.56 | A499G | 1.52 | A499M | 1.5 | A499C | 1.49 |
| | A499V | 1.42 | A499P | 1.28 | A499W | 1.26 | | | | |
| 500 | | | | | | | | | |
| 501 | | | | | | | | | |
| 502 | I502K | 2.45 | I502V | 2.26 | I502A | 1.97 | I502T | 1.96 | I502N | 1.83 |
| | I502E | 1.83 | I502L | 1.71 | I502Q | 1.61 | I502P | 1.58 | I502H | 1.57 |
| | I502R | 1.54 | I502F | 1.48 | I502S | 1.42 | I502Y | 1.37 | | |
| 503 | | | | | | | | | |
| 504 | | | | | | | | | |
| 505 | | | | | | | | | |
| 506 | | | | | | | | | |
| 507 | | | | | | | | | |
| 508 | | | | | | | | | |
| 509 | V509T | 1.26 | | | | | | | | |
| 510 | | | | | | | | | |
| 511 | | | | | | | | | |
| 512 | N512Y | 1.75 | N512P | 1.71 | N512M | 1.42 | N512R | 1.41 | N512K | 1.34 |
| | N512G | 1.31 | N512Q | 1.26 | N512I | 1.21 | N512W | 1.21 | | |
| 513 | F513G | 1.84 | F513V | 1.71 | F513P | 1.67 | F513L | 1.56 | F513H | 1.44 |
| 514 | | | | | | | | | |
| 515 | F515H | 2.24 | | | | | | | | |
| 516 | | | | | | | | | |
| 517 | G517A | 2.22 | G517H | 1.58 | G517S | 1.44 | | | | |
| 518 | S518D | 3.21 | S518A | 2.55 | S518Y | 2.53 | S518K | 2.39 | S518V | 2.37 |
| | S518L | 2.36 | S518G | 2.26 | S518H | 2.25 | S518E | 2.24 | S518R | 2.18 |
| | S518T | 2.08 | S518C | 1.76 | | | | | | |
| 519 | | | | | | | | | |
| 520 | I520V | 3.39 | I520R | 2.18 | I520Y | 2.08 | I520C | 2.05 | I520K | 1.93 |
| | I520M | 1.74 | I520E | 1.67 | I520L | 1.49 | I520F | 1.34 | I520S | 1.31 |
| | I520A | 1.25 | | | | | | | | |
| 521 | S521G | 2.71 | S521L | 2.52 | S521V | 2.47 | S521A | 2.34 | S521D | 2.09 |
| | S521I | 1.73 | S521Q | 1.56 | S521F | 1.54 | S521P | 1.52 | S521N | 1.44 |
| | S521M | 1.4 | | | | | | | | |
| 522 | | | | | | | | | |
| 523 | | | | | | | | | |
| 524 | | | | | | | | | |
| 525 | | | | | | | | | |
| 526 | T526L | 1.23 | | | | | | | | |
| 527 | | | | | | | | | |
| 528 | | | | | | | | | |
| 529 | | | | | | | | | |
| 530 | | | | | | | | | |

TABLE 4-continued

| | | | | | | | | | |
|---|---|---|---|---|---|---|---|---|---|
| 531 | | | | | | | | | |
| 532 | R532K | 2.58 | R532C | 1.98 | R532W | 1.63 | R532S | 1.59 | R532L | 1.53 |
| | R532V | 1.49 | R532H | 1.37 | R532G | 1.24 | | | | |
| 533 | | | | | | | | | | |
| 534 | N534S | 2.2 | N534Y | 1.95 | N534Q | 1.9 | N534W | 1.78 | N534E | 1.58 |
| | N534H | 1.51 | N534D | 1.49 | N534L | 1.48 | | | | |
| 535 | N535M | 2.96 | N535Q | 2.26 | N535E | 1.88 | N535F | 1.68 | N535K | 1.68 |
| | N535L | 1.48 | N535R | 1.48 | N535A | 1.43 | N535S | 1.29 | N535I | 1.23 |
| | N535D | 1.21 | | | | | | | | |
| 536 | | | | | | | | | | |
| 537 | G537W | 2.23 | G537E | 2.02 | G537F | 1.9 | G537A | 1.77 | G537K | 1.69 |
| | G537S | 1.48 | G537Q | 1.48 | G537Y | 1.43 | G537R | 1.4 | G537D | 1.33 |
| | G537V | 1.33 | G537N | 1.3 | G537H | 1.3 | G537T | 1.25 | | |
| 538 | N538G | 2.22 | N538T | 2 | N538S | 1.95 | N538V | 1.57 | N538W | 1.5 |
| | N538L | 1.47 | N538H | 1.43 | N538Q | 1.42 | N538I | 1.41 | N538D | 1.32 |
| | N538V | 1.57 | N538W | 1.5 | N538L | 1.47 | N538Q | 1.42 | N538I | 1.4 |
| | N538E | 1.3 | N538P | 1.25 | N538A | 1.23 | N538M | 1.2 | | |
| 539 | | | | | | | | | | |
| 540 | | | | | | | | | | |
| 541 | Q541Y | 2.48 | Q541W | 1.35 | Q541F | 1.27 | | | | |
| 542 | | | | | | | | | | |
| 543 | | | | | | | | | | |
| 544 | | | | | | | | | | |
| 545 | Y545F | 1.3 | | | | | | | | |
| 546 | | | | | | | | | | |
| 547 | E547A | 1.88 | E547S | 1.82 | E547G | 1.72 | E547I | 1.25 | E547M | 1.24 |
| | E547Q | 1.21 | | | | | | | | |
| 548 | | | | | | | | | | |
| 549 | | | | | | | | | | |
| 550 | | | | | | | | | | |
| 551 | Q551C | 2.51 | Q551R | 2.17 | Q551A | 1.98 | Q551S | 1.76 | Q551D | 1.54 |
| | Q551Y | 1.34 | | | | | | | | |
| 552 | F552T | 1.72 | F552V | 1.69 | F552W | 1.57 | | | | |
| 553 | I553Q | 2.41 | I553D | 2.15 | I553R | 1.96 | I553E | 1.83 | I553A | 1.78 |
| | I553F | 1.71 | I553L | 1.69 | I553P | 1.65 | I553G | 1.5 | I553W | 1.49 |
| | I553S | 1.49 | I553T | 1.47 | | | | | | |
| 554 | S554K | 1.87 | S554R | 1.56 | S554D | 1.45 | S554H | 1.43 | S554N | 1.25 |
| | S554G | 1.22 | | | | | | | | |
| 555 | T555V | 2.13 | T555M | 1.64 | T555I | 1.32 | T555W | 1.3 | | |
| 556 | S556A | 2.65 | S556W | 2.25 | S556G | 2.05 | S556D | 1.6 | S556C | 1.41 |
| | S556P | 1.27 | | | | | | | | |
| 557 | T557I | 1.75 | T557R | 1.61 | T557G | 1.55 | T557S | 1.39 | T557Q | 1.38 |
| | T557M | 1.31 | T557V | 1.28 | T557A | 1.27 | T557C | 1.26 | | |
| 558 | R558Y | 2.16 | R558K | 2.01 | R558T | 1.95 | R558L | 1.83 | R558N | 1.79 |
| | R558G | 1.75 | R558S | 1.59 | R558E | 1.53 | R558I | 1.43 | R558D | 1.4 |
| | R558F | 1.37 | R558P | 1.27 | R558V | 1.26 | R558M | 1.23 | R558H | 1.22 |
| 559 | Y559W | 1.26 | | | | | | | | |
| 560 | | | | | | | | | | |
| 561 | | | | | | | | | | |
| 562 | | | | | | | | | | |
| 563 | V563N | 4.65 | V563L | 2.56 | V563I | 2.1 | V563A | 1.39 | | |
| 564 | R564H | 4.11 | R564V | 3.28 | R564W | 3.03 | R564I | 3.02 | R564K | 2.71 |
| | R564C | 1.79 | R564S | 1.42 | R564A | 1.36 | | | | |
| 565 | Y565F | 3.4 | | | | | | | | |
| 566 | | | | | | | | | | |
| 567 | | | | | | | | | | |
| 568 | V568C | 2.44 | V568A | 2.31 | V568E | 1.81 | V568F | 1.8 | V568R | 1.65 |
| | V568G | 1.54 | V568L | 1.52 | V568S | 1.5 | V568W | 1.39 | V568N | 1.31 |
| 569 | T569I | 1.75 | T569M | 1.67 | T569G | 1.29 | T569S | 1.2 | | |
| 570 | P570M | 2.08 | P570F | 1.6 | P570W | 1.45 | P570T | 1.38 | | |
| 571 | I571G | 4.18 | I571V | 3.13 | I571T | 3.07 | I571C | 2.72 | I571L | 2.2 |
| 572 | Q572H | 2.51 | Q572P | 2.29 | Q572R | 2.03 | Q572I | 1.96 | Q572K | 1.69 |
| | Q572F | 1.65 | Q572S | 1.54 | Q572A | 1.38 | Q572V | 1.35 | Q572W | 1.3 |
| | Q572M | 1.28 | | | | | | | | |
| 573 | L573A | 3.14 | L573T | 3.09 | L573G | 2.12 | | | | |
| 574 | S574R | 1.22 | | | | | | | | |
| 575 | | | | | | | | | | |
| 576 | | | | | | | | | | |
| 577 | W577R | 3.24 | W577F | 2.01 | W577K | 1.74 | W577M | 1.72 | W577V | 1.63 |
| | W577A | 1.56 | W577T | 1.47 | W577H | 1.33 | W577G | 1.28 | W577I | 1.24 |
| 578 | | | | | | | | | | |
| 579 | | | | | | | | | | |
| 580 | | | | | | | | | | |
| 581 | N581S | 1.83 | N581K | 1.57 | | | | | | |
| 582 | I582V | 1.69 | | | | | | | | |
| 583 | F583S | 2.8 | | | | | | | | |
| 584 | S584R | 1.21 | | | | | | | | |
| 585 | S585R | 3.33 | S585T | 2.53 | S585K | 2.17 | S585H | 2.14 | S585Q | 2.04 |
| | S585L | 1.86 | S585W | 1.69 | S585N | 1.59 | S585M | 1.3 | S585F | 1.3 |
| | S585I | 1.27 | | | | | | | | |

TABLE 4-continued

| | | | | | | | | | |
|---|---|---|---|---|---|---|---|---|---|
| 586 | I586M | 4.11 | I586Y | 2.77 | I586P | 2.19 | I586A | 1.97 | I586S | 1.84 |
| | I586K | 1.83 | I586R | 1.77 | I586F | 1.73 | I586G | 1.65 | I586V | 1.6 |
| | I586Q | 1.48 | I586N | 1.41 | I586L | 1.35 | I586W | 1.32 | I586T | 1.26 |
| 587 | V587H | 2.82 | V587C | 2.28 | V587N | 1.97 | V587S | 1.85 | V587D | 1.76 |
| | V587R | 1.7 | V587A | 1.7 | V587T | 1.65 | V587K | 1.57 | V587E | 1.43 |
| | V587W | 1.4 | V587L | 1.4 | V587Y | 1.4 | V587F | 1.37 | | |
| 588 | | | | | | | | | | |
| 589 | | | | | | | | | | |
| 590 | T590A | 1.8 | T590D | 1.56 | T590F | 1.54 | T590S | 1.3 | T590G | 1.26 |
| 591 | A591H | 2.82 | A591V | 2.28 | A591N | 1.97 | A591T | 1.85 | A591D | 1.76 |
| | A591R | 1.7 | A591S | 1.7 | A591K | 1.65 | A591C | 1.65 | A591E | 1.43 |
| | A591W | 1.4 | A591L | 1.4 | A591Y | 1.4 | A591F | 1.37 | A591P | 1.26 |
| | A591Q | 1.2 | | | | | | | | |
| 592 | T592Q | 2.9 | T592M | 2.39 | T592A | 2.02 | T592Y | 1.82 | T592N | 1.8 |
| | T592K | 1.78 | T592P | 1.7 | T592S | 1.63 | T592D | 1.57 | T592I | 1.41 |
| | T592G | 1.33 | T592F | 1.23 | T592V | 1.21 | T592W | 1.21 | | |
| 593 | S593Y | 1.66 | S593G | 1.44 | S593R | 1.24 | S593V | 1.24 | | |
| 594 | | | | | | | | | | |
| 595 | D595R | 1.83 | D595S | 1.77 | D595G | 1.74 | D595H | 1.72 | D595N | 1.57 |
| | D595V | 1.55 | D595F | 1.54 | D595K | 1.52 | D595T | 1.5 | D595Y | 1.4 |
| | D595I | 1.36 | D595A | 1.3 | D595M | 1.25 | D595P | 1.21 | | |
| 596 | N596V | 2.7 | N596T | 2.45 | N596I | 2.15 | N596S | 2.14 | N596G | 1.97 |
| | N596L | 1.7 | N596W | 1.54 | N596Y | 1.33 | N596H | 1.3 | N596P | 1.3 |
| | N596D | 1.29 | | | | | | | | |
| 597 | | | | | | | | | | |
| 598 | Q598V | 1.5 | Q598G | 1.27 | Q598D | 1.22 | Q598I | 1.21 | | |
| 599 | S599C | 1.72 | S599Q | 1.72 | S599L | 1.6 | S599Y | 1.48 | S599T | 1.47 |
| | S599V | 1.44 | S599A | 1.27 | S599P | 1.24 | | | | |
| 600 | | | | | | | | | | |
| 601 | N601Y | 1.47 | N601F | 1.33 | N601V | 1.33 | N601G | 1.25 | N601M | 1.24 |
| | N601E | 1.22 | | | | | | | | |
| 602 | F602M | 2.53 | | | | | | | | |
| 603 | G603M | 2.12 | G603A | 2.04 | G603Y | 2.04 | G603R | 1.88 | G603S | 1.75 |
| | G603L | 1.57 | G603W | 1.46 | G603D | 1.3 | G603T | 1.23 | | |
| 604 | | | | | | | | | | |
| 605 | F605S | 2.2 | F605W | 1.91 | F605R | 1.89 | F605M | 1.85 | F605A | 1.63 |
| | F605I | 1.56 | F605C | 1.52 | F605V | 1.49 | F605K | 1.45 | F605I | 1.56 |
| | F605D | 1.39 | F605Y | 1.38 | F605N | 1.38 | F605Q | 1.35 | F605G | 1.34 |
| | F605E | 1.27 | F605P | 1.25 | | | | | | |
| 606 | E606R | 3.03 | E606H | 2.38 | E606K | 2.27 | E606F | 2.19 | E606Q | 2.12 |
| | E606W | 1.83 | E606G | 1.78 | E606Y | 1.76 | E606M | 1.74 | E606T | 1.64 |
| | E606A | 1.51 | E606I | 1.37 | E606L | 1.34 | E606N | 1.28 | | |
| 607 | S607R | 2.59 | S607C | 1.58 | S607T | 1.58 | S607I | 1.55 | S607Q | 1.48 |
| | S607G | 1.34 | S607D | 1.31 | S607E | 1.27 | S607V | 1.26 | | |
| 608 | T608R | 2.35 | T608S | 2.24 | T608V | 2.2 | T608L | 1.88 | T608F | 1.7 |
| | T608G | 1.5 | T608Y | 1.47 | T608A | 1.33 | T608K | 1.32 | T608W | 1.23 |
| | T608Q | 1.22 | | | | | | | | |
| 609 | N609G | 2.52 | N609P | 2.4 | N609L | 2.23 | N609R | 2.2 | N609S | 1.93 |
| | N609V | 1.91 | N609F | 1.46 | N609I | 1.31 | | | | |
| 610 | A610G | 2.13 | A610F | 1.45 | A610P | 1.29 | A610L | 1.28 | | |
| 611 | F611L | 2.19 | F611K | 1.58 | F611G | 1.48 | F611W | 1.44 | F611V | 1.38 |
| 612 | T612F | 2.32 | T612H | 2.07 | T612G | 1.36 | T612E | 1.35 | T612N | 1.31 |
| | T612D | 1.23 | T612P | 1.21 | | | | | | |
| 613 | S613M | 2.85 | S613T | 1.98 | S613W | 1.58 | S613V | 1.54 | S613N | 1.5 |
| | S613R | 1.47 | S613Y | 1.33 | S613G | 1.25 | | | | |
| 614 | A614M | 2.07 | A614S | 2.01 | A614L | 1.73 | A614H | 1.66 | A614V | 1.66 |
| | A614R | 1.64 | A614G | 1.55 | A614Y | 1.35 | A614D | 1.2 | A614R | 1.64 |
| 615 | | | | | | | | | | |
| 616 | | | | | | | | | | |
| 617 | N617V | 2.25 | N617Q | 1.96 | N617G | 1.96 | N617K | 1.76 | N617M | 1.57 |
| | N617R | 1.56 | N617C | 1.25 | N617L | 1.23 | | | | |
| 618 | V618N | 1.82 | V618H | 1.51 | V618W | 1.44 | V618R | 1.4 | V618G | 1.31 |
| | V618L | 1.3 | V618D | 1.29 | V618T | 1.24 | | | | |
| 619 | | | | | | | | | | |
| 620 | | | | | | | | | | |
| 621 | | | | | | | | | | |
| 622 | | | | | | | | | | |
| 623 | | | | | | | | | | |
| 624 | F624A | 1.27 | F624M | | | | | | | |
| 625 | | | | | | | | | | |
| 626 | E626K | 3.16 | E626G | 2.62 | E626R | 2.01 | E626T | 1.84 | E626H | 1.81 |
| | E626A | 1.71 | E626N | 1.45 | E626I | 1.44 | E626Y | 1.43 | E626Q | 1.37 |
| | E626P | 1.31 | E626S | 1.29 | | | | | | |
| 627 | | | | | | | | | | |
| 628 | A628V | 2.38 | A628F | 2.05 | A628K | 1.86 | A628Q | 1.81 | A628W | 1.62 |
| | A628S | 1.59 | A628R | 1.49 | A628G | 1.49 | A628L | 1.42 | A628I | 1.21 |
| | A628D | 1.21 | | | | | | | | |

TABLE 4-continued

| | | | | | | | | | |
|---|---|---|---|---|---|---|---|---|---|
| 629 | G629M | 1.57 | G629Q | 1.42 | G629R | 1.4 | G629P | 1.36 | G629A | 1.32 |
| | G629S | 1.28 | G629T | 1.28 | G629E | 1.23 | | | | |
| 630 | V630A | 1.9 | V630C | 1.62 | | | | | | |
| 631 | | | | | | | | | | |
| 632 | | | | | | | | | | |
| 633 | | | | | | | | | | |
| 634 | | | | | | | | | | |
| 635 | | | | | | | | | | |
| 636 | | | | | | | | | | |
| 637 | | | | | | | | | | |
| 638 | | | | | | | | | | |
| 639 | | | | | | | | | | |
| 640 | | | | | | | | | | |
| 641 | T641P | 3.01 | T641H | 2.65 | T641A | 2.45 | T641L | 2.43 | T641Q | 2.31 |
| | T641Y | 2.21 | T641E | 2.1 | T641I | 1.96 | T641S | 1.91 | T641V | 1.82 |
| | T641D | 1.57 | T641G | 1.21 | | | | | | |
| 642 | | | | | | | | | | |
| 643 | T643L | 2.72 | T643A | 2.09 | T643Q | 2.04 | T643H | 1.94 | T643S | 1.58 |
| | T643D | 1.53 | T643M | 1.51 | T643C | 1.38 | T643R | 1.26 | | |
| 644 | | | | | | | | | | |
| 645 | E645T | 2.28 | E645M | 2.26 | E645L | 1.8 | E645Y | 1.77 | E645A | 1.73 |
| | E645N | 1.71 | E645V | 1.67 | E645P | 1.65 | E645I | 1.61 | E645W | 1.48 |
| | E645C | 1.28 | E645S | 1.21 | | | | | | |
| 646 | A646S | 1.96 | A646Y | 1.95 | A646D | 1.78 | A646E | 1.65 | A646M | 1.57 |
| | A646F | 1.51 | A646H | 1.46 | A646V | 1.41 | A646W | 1.37 | A646I | 1.37 |
| | A646C | 1.27 | A646G | 1.27 | | | | | | |
| 647 | | | | | | | | | | |
| 648 | | | | | | | | | | |
| 649 | | | | | | | | | | |
| 650 | | | | | | | | | | |
| 651 | | | | | | | | | | |

TABLE 5

| MP258 position | MP258 a.a. | Backbone | Variant | FAE | Variant | FAE | Variant | FAE | Variant | FAE |
|---|---|---|---|---|---|---|---|---|---|---|
| 50 | L | B45 | L50W | 1.06 | L50M | 1.05 | L50E | 0.98 | L50T | 0.89 |
| 53 | A | B45 | A53N | 1.19 | A53I | 1.15 | A53W | 1.13 | A53L | 1.08 |
| 54 | S | B45 | S54M | 1.16 | S54Y | 1.13 | S54H | 1.11 | S54L | 1.08 |
| | | | S54D | 0.87 | S54W | 0.57 | | | | |
| 57 | Q | B45 | Q57C | 1.19 | Q57E | 1.14 | Q57S | 1.13 | Q57W | 1.13 |
| 65 | R | B45 | R65M | 1.19 | R65T | 1.15 | R65K | 1.04 | R65L | 0.99 |
| | | | R65W | 0.50 | | | | | | |
| 67 | L | B45 | L67P | 1.12 | L67Q | 1.11 | L67W | 0.54 | L67A | 0.52 |
| | | | L67S | 0.49 | L67C | 0.48 | L67D | 0.48 | L67V | 0.46 |
| 68 | G | B45 | G68D | 1.16 | G68K | 1.08 | G68M | 0.75 | G68L | 0.62 |
| | | | G68P | 0.48 | G68W | 0.37 | | | | |
| 70 | L | B45 | L70S | 1.16 | L70T | 1.11 | L70Q | 1.10 | L70A | 0.98 |
| | | | L70Y | 0.92 | L70V | 0.92 | L70P | 0.90 | L70R | 0.87 |
| 71 | G | B45 | G71D | 1.12 | G71E | 1.11 | G71F | 1.10 | G71N | 1.00 |
| | | | G71Q | 0.79 | G71C | 0.75 | G71V | 0.72 | G71L | 0.61 |
| 72 | V | B45 | V72S | 0.85 | V72R | 0.84 | V72L | 0.81 | V72F | 0.79 |
| | | | V72A | 0.66 | V72W | 0.64 | V72C | 0.64 | V72K | 0.55 |
| 73 | P | B45 | P73F | 1.14 | P73R | 1.11 | P73V | 0.80 | P73A | 0.33 |
| 74 | F | B45 | F74N | 1.19 | F74T | 1.15 | F74W | 1.04 | F74L | 1.00 |
| | | | F74C | 0.78 | F74M | 0.37 | | | | |
| 75 | A | B45 | A75D | 1.03 | A75F | 0.94 | A75R | 0.90 | A75V | 0.83 |
| 76 | G | B45 | G76K | 1.15 | G76W | 0.94 | G76Q | 0.91 | G76H | 0.54 |
| 77 | Q | B45 | Q77V | 1.15 | Q77F | 1.13 | Q77Y | 1.08 | Q77R | 0.96 |
| 79 | A | B45 | A79E | 0.98 | A79G | 0.71 | A79F | 0.57 | | |
| 80 | S | B45 | S80I | 1.20 | S80T | 0.54 | | | | |
| 83 | S | B45 | S83T | 1.19 | S83V | 0.60 | S83I | 0.60 | S83P | 0.58 |
| 87 | G | B45 | G87Y | 1.10 | G87S | 1.05 | G87F | 1.01 | G87L | 0.97 |
| 91 | P | B45 | P91I | 1.17 | P91Q | 1.14 | P91W | 1.13 | P91G | 1.05 |
| | | | P91K | 0.54 | P91C | 0.53 | P91H | 0.53 | P91A | 0.50 |
| 92 | S | B45 | S92K | 1.03 | S92W | 0.85 | S92R | 0.76 | S92M | 0.70 |
| 93 | G | B45 | G93E | 0.93 | G93N | 0.90 | G93V | 0.86 | G93L | 0.86 |
| | | | G93W | 0.74 | G93C | 0.72 | G93R | 0.69 | G93Y | 0.53 |
| 94 | R | B45 | R94E | 0.99 | R94K | 0.95 | R94V | 0.95 | R94G | 0.92 |
| | | | R94M | 0.70 | | | | | | |
| 95 | D | B45 | D95W | 1.10 | D95T | 0.94 | D95L | 0.87 | D95R | 0.83 |
| 106 | Q | B45 | Q106P | 1.08 | Q106L | 1.08 | Q106N | 0.98 | Q106Y | 0.96 |
| 108 | V | B45 | V108G | 1.14 | V108K | 1.14 | V108S | 1.06 | V108C | 1.04 |
| 109 | R | 258 | R109K | 1.07 | R109A | 1.05 | R109Q | 1.02 | R109W | 0.97 |
| | | | R109T | 0.85 | R109I | 0.84 | R109D | 0.83 | R109F | 0.79 |

TABLE 5-continued

| | | | | | | | | | |
|---|---|---|---|---|---|---|---|---|---|
| 110 | Q | 258 | Q110K | 1.19 | Q110D | 1.18 | Q110I | 1.18 | Q110M | 1.14 |
| | | | Q110C | 0.84 | Q110A | 0.77 | Q110W | 0.73 | Q110G | 0.70 |
| 111 | Q | 258 | Q111V | 1.14 | Q111W | 1.08 | Q111N | 1.01 | Q111F | 1.01 |
| | | | Q111D | 0.25 | | | | | | |
| 112 | I | B45 | I112K | 0.93 | I112G | 0.84 | I112M | 0.64 | I112C | 0.57 |
| | | | I112S | 0.27 | I112F | 0.27 | I112D | 0.26 | I112R | 0.24 |
| 113 | T | B45 | T113W | 0.98 | T113F | 0.82 | T113C | 0.75 | T113P | 0.73 |
| 114 | E | 258 | E114Q | 1.15 | E114W | 1.13 | E114C | 0.79 | E114R | 0.41 |
| 115 | N | B45 | N115I | 0.96 | N115Y | 0.93 | N115M | 0.91 | N115S | 0.88 |
| | | | N115W | 0.57 | N115K | 0.51 | N115R | 0.35 | N115H | 0.24 |
| 118 | N | B45 | N118W | 1.05 | N118K | 0.99 | N118Y | 0.92 | N118R | 0.84 |
| 119 | T | B45 | T119Y | 1.00 | T119F | 0.95 | T119P | 0.94 | T119W | 0.84 |
| 122 | A | B45 | A122E | 1.11 | A122L | 1.06 | A122S | 1.06 | A122W | 1.04 |
| 123 | R | B45 | R123H | 0.73 | R123A | 0.73 | R123Y | 0.72 | R123P | 0.63 |
| | | | R123G | 0.55 | R123N | 0.49 | R123S | 0.49 | R123M | 0.46 |
| | | | R123I | 0.24 | | | | | | |
| 125 | Q | B45 | Q125V | 1.14 | Q125I | 0.96 | Q125K | 0.63 | | |
| 129 | A | B45 | A129E | 1.08 | A129Y | 1.08 | A129R | 1.07 | A129Q | 1.06 |
| | | | A129F | 0.83 | A129I | 0.83 | | | | |
| 132 | R | B45 | R132Y | 0.98 | R132A | 0.96 | R132V | 0.96 | R132M | 0.89 |
| | | | R132F | 0.68 | R132D | 0.66 | R132G | 0.65 | R132N | 0.59 |
| 133 | A | B45 | A133D | 0.87 | A133V | 0.85 | A133S | 0.63 | A133T | 0.54 |
| | | | A133Q | 0.32 | A133F | 0.32 | A133E | 0.29 | A133L | 0.26 |
| 136 | Q | B45 | Q136G | 1.06 | Q136W | 1.03 | Q136D | 0.96 | Q136S | 0.92 |
| 140 | D | B45 | D140Q | 0.92 | D140Y | 0.73 | D140S | 0.46 | D140T | 0.40 |
| | | | D140R | 0.24 | D140A | 0.22 | D140L | 0.22 | | |
| 142 | L | B45 | L142H | 1.03 | L142Q | 0.86 | L142S | 0.78 | L142R | 0.73 |
| | | | L142W | 0.58 | L142D | 0.52 | L142C | 0.47 | L142E | 0.43 |
| 143 | E | B45 | E143K | 0.98 | E143D | 0.98 | E143V | 0.95 | | |
| 144 | N | B45 | N144F | 1.13 | N144P | 1.09 | N144S | 1.07 | N144Y | 0.94 |
| 145 | R | B45 | R145F | 1.16 | R145Q | 1.02 | R145V | 0.99 | R145T | 0.94 |
| 146 | D | B45 | D146E | 1.16 | D146A | 1.15 | D146P | 1.14 | D146S | 1.11 |
| | | | D146F | 0.95 | D146G | 0.83 | D146M | 0.80 | | |
| 147 | D | B45 | N147T | 1.02 | N147L | 1.01 | N147Y | 0.63 | N147K | 0.62 |
| | | | N147Q | 0.49 | N147G | 0.45 | | | | |
| 148 | A | B45 | A148G | 1.18 | A148Q | 1.00 | A148M | 0.95 | A148R | 0.90 |
| | | | A148E | 0.76 | | | | | | |
| 149 | R | B45 | R149F | 1.00 | R149Q | 0.99 | R149H | 0.94 | R149W | 0.94 |
| 151 | R | B45 | R151S | 1.06 | R151V | 0.90 | R151K | 0.72 | R151M | 0.69 |
| | | | B151A | 0.50 | B151I | 0.42 | B151N | 0.42 | B151Y | 0.39 |
| | | | B151F | 0.27 | | | | | | |
| 152 | S | B45 | S152K | 1.07 | S152M | 0.98 | S152C | 0.95 | S152Q | 0.89 |
| | | | S152P | 0.47 | S152Y | 0.44 | S152F | 0.41 | S152W | 0.37 |
| 159 | I | B45 | I159G | 0.92 | I159D | 0.78 | I159S | 0.59 | I159T | 0.32 |
| | | | I159P | 0.27 | I159F | 0.26 | I159W | 0.26 | I159E | 0.26 |
| 160 | A | B45 | A160F | 1.12 | A160E | 0.92 | A160P | 0.89 | A160G | 0.85 |
| 163 | L | B45 | L163F | 0.80 | L163Q | 0.72 | L163V | 0.60 | L163M | 0.56 |
| | | | L163E | 0.24 | L163G | 0.24 | L163S | 0.24 | L163B | 0.24 |
| 164 | D | B45 | D164A | 0.90 | D164S | 0.88 | D164G | 0.81 | D164M | 0.81 |
| | | | D164V | 0.54 | D164F | 0.51 | D164T | 0.49 | D164C | 0.49 |
| 166 | L | B45 | L166Q | 1.07 | L166D | 1.01 | L166M | 0.98 | L166P | 0.98 |
| | | | L166S | 0.95 | L166N | 0.92 | L166Y | 0.73 | L166F | 0.62 |
| 167 | N | B45 | N167B | 1.15 | N167G | 1.13 | N167S | 1.04 | N167C | 0.98 |
| | | | N167I | 0.67 | | | | | | |
| 173 | A | B45 | A173N | 1.12 | A173P | 0.97 | A173G | 0.92 | A173V | 0.88 |
| 174 | I | B45 | I174V | 0.91 | I174Q | 0.89 | I174H | 0.77 | I174K | 0.73 |
| | | | I174S | 0.56 | I174B | 0.33 | I174D | 0.32 | | |
| 177 | Q | B45 | Q177F | 1.10 | Q177N | 1.06 | Q177H | 1.05 | Q177Y | 1.01 |
| | | | Q177L | 0.89 | Q177D | 0.78 | Q177G | 0.74 | Q177K | 0.40 |
| 178 | Q | B45 | Q178E | 0.98 | Q178H | 0.92 | Q178W | 0.83 | Q178G | 0.78 |
| | | | Q178F | 0.53 | Q178Y | 0.50 | Q178L | 0.37 | Q178D | 0.31 |
| 179 | V | B45 | V179C | 1.01 | V179A | 0.86 | V179N | 0.80 | V179M | 0.80 |
| | | | V179B | 0.61 | V179F | 0.44 | V179W | 0.41 | V179D | 0.37 |
| 180 | P | B45 | P180C | 1.05 | P180K | 1.00 | P180T | 0.94 | P180V | 0.88 |
| | | | P180Y | 0.53 | P180W | 0.38 | P180D | 0.28 | | |
| 201 | L | B45 | L201C | 0.79 | L201N | 0.67 | L201A | 0.64 | L201P | 0.64 |
| | | | L201H | 0.55 | L201B | 0.54 | L201D | 0.52 | | |
| 206 | F | B45 | F206V | 1.00 | F206C | 0.86 | F206E | 0.76 | F206A | 0.75 |
| | | | F206S | 0.53 | F206D | 0.51 | F206K | 0.49 | F206N | 0.47 |
| 208 | L | B45 | L208F | 0.91 | L208I | 0.79 | L208Y | 0.71 | L208S | 0.71 |
| | | | L208Q | 0.44 | L208W | 0.44 | L208C | 0.39 | L208G | 0.37 |
| | | | L208D | 0.29 | | | | | | |
| 209 | T | B45 | T209S | 0.94 | T209Q | 0.88 | T209I | 0.75 | T209G | 0.68 |
| 210 | S | B45 | S210G | 1.13 | | | | | | |
| 211 | Q | B45 | Q211V | 1.17 | Q211K | 1.15 | Q211H | 1.10 | Q211E | 1.08 |
| | | | Q211S | 0.94 | Q211D | 0.54 | | | | |
| 212 | E | B45 | E212F | 1.05 | E212A | 0.86 | E212V | 0.79 | E212N | 0.78 |
| | | | E212L | 0.64 | E212Q | 0.63 | E212K | 0.61 | E212S | 0.59 |
| 213 | I | B45 | I213C | 1.11 | I213S | 0.98 | I213B | 0.94 | I213E | 0.91 |
| | | | I213P | 0.59 | I213H | 0.58 | I213A | 0.49 | | |

TABLE 5-continued

| | | | | | | | | | |
|---|---|---|---|---|---|---|---|---|---|
| 214 | Q | B21 | Q214S | 1.12 | Q214F | 1.05 | Q214Y | 1.01 | Q214D | 0.76 |
| | | | Q214T | 0.53 | Q214H | 0.52 | Q214L | 0.43 | Q214G | 0.40 |
| 215 | R | B45 | R215V | 0.95 | R215A | 0.94 | R215I | 0.85 | R215N | 0.83 |
| | | | R215S | 0.67 | R215G | 0.66 | R215T | 0.66 | R215P | 0.59 |
| 218 | E | B45 | E218G | 1.18 | E218L | 1.10 | E218C | 1.10 | E218K | 1.08 |
| 219 | R | B21 | R219Y | 1.15 | R219E | 1.13 | R219W | 1.08 | R219Q | 0.71 |
| | | | R219T | 0.05 | R219M | 0.03 | R219L | 0.01 | R219A | 0.01 |
| 221 | A | B45 | A221S | 1.16 | A221C | 1.03 | A221E | 0.91 | A221M | 0.83 |
| 222 | E | B45 | E222C | 1.13 | E222S | 1.11 | E222L | 1.10 | E222F | 1.10 |
| | | | E222R | 0.84 | E222P | 0.59 | | | | |
| 225 | R | B45 | R225W | 1.19 | R225S | 1.17 | R225E | 1.14 | R225A | 1.02 |
| 226 | E | B45 | E226T | 1.18 | E226F | 1.17 | E226G | 1.15 | E226W | 1.13 |
| | | | E226H | 0.96 | E226Q | 0.96 | | | | |
| 230 | Y | B45 | Y230F | 1.19 | Y230M | 1.15 | Y230R | 1.01 | Y230C | 0.93 |
| | | | Y230I | 0.63 | Y230V | 0.57 | Y230P | 0.53 | | |
| 233 | R | B45 | R233E | 1.19 | R233V | 1.10 | R233F | 1.09 | R233N | 1.05 |
| | | | R233H | 0.50 | | | | | | |
| 234 | W | B45 | W234G | 1.06 | W234K | 0.93 | W234T | 0.63 | W234E | 0.60 |
| 236 | N | B45 | N236Q | 1.18 | N236D | 1.16 | N236R | 1.08 | N236A | 1.04 |
| | | | N236M | 0.54 | N236C | 0.53 | N236W | 0.42 | | |
| 240 | N | B45 | N240I | 1.18 | N240D | 1.17 | N240V | 1.16 | N240E | 0.57 |
| 241 | N | B45 | N241G | 1.17 | N241F | 1.16 | N241Q | 1.15 | N241E | 1.13 |
| | | | N241R | 0.49 | | | | | | |
| 242 | L | B45 | L242M | 0.95 | L242I | 0.93 | L242C | 0.83 | L242R | 0.75 |
| | | | L242F | 0.49 | L242H | 0.46 | L242W | 0.40 | L242G | 0.39 |
| 243 | R | B45 | R243L | 0.98 | R243A | 0.86 | R243Y | 0.82 | R243F | 0.76 |
| | | | R243P | 0.46 | | | | | | |
| 244 | G | B45 | G244C | 0.94 | G244L | 0.72 | G244A | 0.71 | G244Q | 0.60 |
| | | | G244Y | 0.53 | G244E | 0.53 | G244H | 0.47 | G244M | 0.47 |
| | | | G244I | 0.26 | | | | | | |
| 245 | T | B45 | T245P | 0.96 | T245L | 0.82 | T245C | 0.71 | | |
| 246 | N | B45 | N246A | 0.85 | N246K | 0.84 | N246P | 0.79 | N246E | 0.78 |
| | | | N246Y | 0.60 | N246V | 0.60 | N246I | 0.58 | | |
| 247 | A | B45 | A247C | 0.52 | A247N | 0.52 | A247L | 0.41 | A247D | 0.41 |
| | | | A247Y | 0.30 | A247M | 0.28 | A247K | 0.28 | A247H | 0.25 |
| 248 | E | B45 | E248I | 1.11 | E248W | 1.06 | E248H | 1.01 | E248C | 0.82 |
| 252 | R | B45 | R252L | 1.09 | R252Y | 1.06 | R252K | 1.06 | R252G | 1.05 |
| | | | R252V | 0.92 | R252D | 0.90 | R252E | 0.79 | R252L | 0.76 |
| 277 | R | B45 | R277H | 1.13 | R277N | 1.07 | R277C | 0.95 | R277E | 0.88 |
| | | | R277Y | 0.82 | R277D | 0.70 | R277A | 0.69 | R277I | 0.55 |
| 280 | P | B45 | P280Q | 1.18 | P280Y | 1.08 | P280V | 0.98 | P280R | 0.90 |
| | | | P280G | 0.62 | P280A | 0.58 | P280S | 0.54 | P280D | 0.50 |
| 281 | I | B45 | I281T | 1.15 | I281N | 1.14 | I281Y | 1.14 | I281C | 1.07 |
| 303 | S | 258 | S303A | 1.09 | S303M | 0.95 | S303L | 0.70 | S303Y | 0.66 |
| | | | S303F | 0.56 | S303C | 0.43 | S303Q | 0.39 | S303V | 0.37 |
| | | | S303R | 0.03 | | | | | | |
| 304 | G | 258 | G304N | 0.22 | G304C | 0.02 | G304S | 0.01 | G304A | 0.01 |
| | | | G304E | 0.01 | G304Q | 0.01 | G304K | 0.01 | G304P | 0.01 |
| | | | G304D | 0.01 | G304M | 0.00 | G304Y | 0.00 | | |
| 305 | F | 258 | F305A | 0.07 | F305Q | 0.03 | F305N | 0.03 | F305M | 0.02 |
| | | | F305V | 0.01 | F305K | 0.01 | F305E | 0.00 | F305D | 0.00 |
| | | | F305H | 0.00 | F305P | 0.00 | F305Y | 0.00 | | |
| 306 | A | 258 | A306Q | 1.14 | A306K | 0.96 | A306N | 0.93 | A306S | 0.87 |
| | | | A306W | 0.44 | A306L | 0.33 | A306F | 0.30 | A306I | 0.30 |
| | | | A306E | 0.02 | A306Y | 0.00 | | | | |
| 308 | T | 258 | T308S | 0.63 | T308A | 0.03 | T308G | 0.02 | T308K | 0.02 |
| | | | T308N | 0.01 | T308E | 0.01 | T308R | 0.01 | T308D | 0.01 |
| | | | T308Y | 0.01 | T308W | 0.01 | T308H | 0.00 | | |
| 360 | R | B21 | R360K | 0.97 | R360A | 0.94 | R360G | 0.66 | R360H | 0.63 |
| 362 | E | B21 | N362Q | 1.20 | N362M | 1.16 | N362C | 0.95 | N362T | 0.88 |
| 364 | R | B21 | R364G | 1.02 | R364S | 0.89 | R364A | 0.39 | R364K | 0.38 |
| 367 | R | B21 | G367S | 1.09 | G367M | 0.97 | G367C | 0.53 | G367F | 0.38 |
| 406 | L | 258 | L406I | 0.76 | L406W | 0.53 | L406A | 0.39 | L406F | 0.31 |
| | | | L406N | 0.23 | L406K | 0.13 | L406T | 0.05 | L406S | 0.03 |
| | | | L406E | 0.01 | | | | | | |
| 407 | L | 258 | L407E | 1.13 | L407D | 1.00 | L407V | 0.66 | L407C | 0.56 |
| | | | L407N | 0.20 | L407M | 0.17 | L407H | 0.11 | L407S | 0.10 |
| 408 | T | 258 | T408A | 0.96 | T408Y | 0.54 | T408S | 0.48 | T408V | 0.47 |
| | | | T408R | 0.26 | T408H | 0.25 | T408K | 0.25 | T408F | 0.24 |
| | | | T408G | 0.08 | T408E | 0.02 | | | | |
| 409 | T | 258 | T409Q | 0.53 | T409M | 0.30 | T409A | 0.26 | T409I | 0.21 |
| | | | T409H | 0.11 | T409W | 0.11 | T409E | 0.10 | T409R | 0.10 |
| | | | T409D | 0.01 | T409P | 0.01 | T409G | 0.01 | | |
| 411 | V | 258 | V411I | 0.82 | V411M | 0.52 | V411L | 0.51 | V411C | 0.32 |
| | | | V411H | 0.12 | V411W | 0.11 | V411A | 0.10 | V411F | 0.09 |
| | | | V411Y | 0.02 | V411D | 0.01 | V411P | 0.01 | | |
| 418 | R | B21 | R418S | 1.13 | R418A | 1.11 | R418L | 1.09 | R418H | 0.91 |
| | | | R418Y | 0.76 | R418M | 0.69 | R418E | 0.63 | R418G | 0.58 |
| | | | R418P | 0.14 | | | | | | |

TABLE 5-continued

| | | | | | | | | | |
|---|---|---|---|---|---|---|---|---|---|
| 420 | N | B21 | N420D | 1.11 | N420Y | 1.10 | N420E | 1.04 | N420P | 1.00 |
| | | | N420V | 0.81 | N420M | 0.74 | N420K | 0.71 | N420T | 0.68 |
| | | | N420I | 0.60 | N420C | 0.50 | N420A | 0.47 | | |
| 422 | R | B21 | R422Q | 1.13 | R422S | 1.13 | R422Y | 1.06 | R422A | 1.01 |
| | | | R422N | 0.79 | R422D | 0.77 | R422W | 0.74 | R422M | 0.72 |
| | | | R422F | 0.59 | R422I | 0.51 | R422P | 0.03 | | |
| 425 | L | B21 | L425V | 1.19 | L425A | 1.16 | L425Y | 1.15 | L425M | 1.15 |
| | | | L425Q | 0.93 | L425I | 0.93 | L425W | 0.93 | L425N | 0.92 |
| | | | L425D | 0.54 | | | | | | |
| 426 | N | B21 | N426M | 1.17 | N426S | 1.09 | N426D | 1.05 | N426Y | 1.01 |
| | | | N426Q | 0.83 | N426R | 0.80 | N426T | 0.77 | N426G | 0.68 |
| | | | N426C | 0.34 | N426W | 0.31 | N426P | 0.29 | | |
| 427 | S | B21 | S427H | 1.20 | S427P | 1.14 | S427Q | 1.13 | S427N | 1.12 |
| | | | S427F | 0.87 | S427I | 0.84 | S427E | 0.83 | S427M | 0.78 |
| | | | S427V | 0.53 | S427R | 0.48 | | | | |
| 428 | L | B21 | L428N | 1.15 | L428Q | 1.08 | L428G | 1.07 | L428P | 0.96 |
| | | | L428S | 0.82 | L428W | 0.76 | L428A | 0.74 | L428V | 0.73 |
| | | | L428K | 0.52 | L428F | 0.42 | L428C | 0.28 | | |
| 429 | R | B21 | R429L | 1.13 | R429H | 1.09 | R429W | 1.09 | R429N | 1.08 |
| | | | R429Y | 0.88 | R429Q | 0.86 | R429T | 0.83 | R429G | 0.79 |
| | | | R429S | 0.54 | R429C | 0.36 | | | | |
| 431 | S | B21 | S431K | 1.15 | S431M | 1.00 | S431V | 0.90 | S431T | 0.87 |
| | | | S431R | 0.81 | S431N | 0.81 | S431I | 0.73 | S431W | 0.71 |
| 435 | T | B21 | T435M | 1.13 | T435W | 1.01 | T435F | 1.00 | T435I | 0.90 |
| | | | T435N | 0.57 | T435D | 0.55 | T435E | 0.52 | T435A | 0.52 |
| 437 | G | B21 | G437M | 1.15 | G437T | 1.13 | G437Y | 1.00 | G437F | 0.95 |
| | | | G437I | 0.75 | G437E | 0.67 | G437D | 0.62 | G437P | 0.36 |
| 439 | T | B21 | T439S | 1.20 | T439F | 1.16 | T439V | 1.16 | T439A | 1.15 |
| | | | T439K | 0.83 | T439R | 0.80 | T439L | 0.79 | T439G | 0.67 |
| | | | T439P | 0.02 | | | | | | |
| 444 | Q | B21 | Q444E | 0.91 | Q444M | 0.89 | Q444A | 0.62 | Q444H | 0.58 |
| | | | Q444F | 0.34 | Q444D | 0.31 | Q444N | 0.28 | Q444K | 0.28 |
| | | | Q444C | 0.10 | Q444R | 0.05 | Q444P | 0.01 | | |
| 447 | D | B21 | D447Q | 1.17 | D447Y | 1.16 | D447K | 1.01 | D447G | 0.94 |
| | | | D447R | 0.63 | D447P | 0.52 | D447C | 0.52 | | |
| 473 | R | B21 | R473H | 1.07 | R473C | 1.07 | R473L | 1.02 | R473Q | 1.02 |
| 476 | S | B21 | I476K | 1.13 | I476T | 1.12 | I476N | 1.07 | I476C | 0.84 |
| 477 | G | B21 | G477R | 1.04 | G477T | 1.01 | G477Q | 0.90 | G477K | 0.53 |
| | | | G477Y | 0.24 | G477C | 0.13 | G477W | 0.04 | | |
| 478 | N | B21 | N478Q | 1.14 | N478R | 1.12 | N478H | 1.06 | N478T | 1.04 |
| | | | N478D | 0.31 | N478F | 0.26 | N478C | 0.13 | | |
| 479 | T | B21 | T479G | 1.00 | T479I | 0.93 | T479L | 0.81 | T479S | 0.75 |
| | | | T479P | 0.40 | T479R | 0.30 | T479M | 0.23 | T479F | 0.19 |
| 481 | R | B21 | R481K | 0.65 | R481L | 0.48 | R481W | 0.30 | R481Y | 0.23 |
| | | | R481A | 0.13 | R481S | 0.13 | R481G | 0.07 | R481E | 0.04 |
| 492 | A | B25 | A492S | 0.93 | A492C | 0.70 | A492V | 0.69 | A492G | 0.38 |
| 498 | I | B25 | I498V | 1.02 | I498E | 0.93 | I498L | 0.90 | I498C | 0.65 |
| | | | I498R | 0.27 | | | | | | |
| 499 | A | B25 | A499D | 1.09 | | | | | | |
| 503 | I | B25 | I503C | 0.63 | I503L | 0.59 | I503V | 0.44 | | |
| 504 | T | B25 | T504S | 0.78 | T504G | 0.66 | T504A | 0.63 | T504C | 0.60 |
| 505 | Q | B25 | Q505C | 0.34 | Q505L | 0.28 | Q505E | 0.26 | Q505S | 0.20 |
| 506 | I | B25 | I506L | 0.96 | I506V | 0.94 | I506W | 0.19 | I506A | 0.11 |
| 507 | P | B25 | P507A | 0.44 | P507G | 0.34 | P507S | 0.29 | | |
| 508 | A | B25 | A508V | 0.91 | A508M | 0.64 | A508S | 0.48 | A508I | 0.23 |
| 509 | V | B25 | V509I | 0.95 | V509C | 0.86 | V509N | 0.86 | V509G | 0.83 |
| | | | V509D | 0.31 | V509E | 0.24 | | | | |
| 511 | G | B25 | G511A | 0.88 | G511S | 0.62 | | | | |
| 512 | N | 258 | N512S | 1.13 | N512C | 1.10 | N512H | 1.08 | N512L | 1.05 |
| 513 | F | B25 | F513R | 1.18 | F513A | 1.02 | F513Y | 0.91 | F513M | 0.75 |
| 514 | L | | | | | | | | | |
| 515 | F | B25 | F515W | 1.04 | F515G | 0.60 | F515R | 0.56 | F515V | 0.53 |
| | | | F515S | 0.43 | F515E | 0.22 | F515D | 0.19 | | |
| 517 | G | B25 | G517V | 0.39 | | | | | | |
| 520 | I | B25 | I520G | 1.02 | I520N | 0.93 | | | | |
| 525 | F | B25 | F525T | 0.82 | F525S | 0.79 | F525V | 0.77 | F525W | 0.72 |
| 526 | T | B25 | T526A | 0.79 | T526S | 0.70 | T526V | 0.69 | T526G | 0.24 |
| 527 | G | B25 | G527T | 0.45 | G527S | 0.23 | | | | |
| 530 | L | B25 | L530I | 0.86 | L530V | 0.80 | L530C | 0.56 | L530Y | 0.52 |
| | | | L530K | 0.22 | | | | | | |
| 531 | V | B25 | V531I | 0.96 | V531C | 0.75 | V531A | 0.21 | | |
| 533 | L | B25 | L533I | 0.86 | L533N | 0.62 | L533V | 0.54 | V531A | 0.21 |
| 534 | N | B25 | N534R | 1.17 | N534V | 1.12 | N534M | 1.04 | N534A | 0.86 |
| 535 | N | B25 | N535G | 1.10 | N535C | 0.92 | N535V | 0.91 | | |
| 536 | S | 258 | S536Y | 1.03 | S536T | 1.02 | S536A | 0.85 | S536N | 0.83 |
| | | | S536F | 0.55 | S536G | 0.49 | S536W | 0.47 | S536D | 0.35 |
| | | | S536R | 0.18 | S536L | 0.11 | S536I | 0.09 | | |
| 537 | G | 258 | G537L | 1.18 | G537M | 1.17 | G537I | 1.06 | G537C | 0.95 |
| 538 | N | 258 | N538K | 1.17 | N538Y | 0.98 | N538R | 0.80 | | |

TABLE 5-continued

| | | | | | | | | | |
|---|---|---|---|---|---|---|---|---|---|
| 539 | N | B25 | N539D | 0.95 | N539A | 0.92 | N539S | 0.88 | N539H | 0.79 |
| | | | N539T | 0.57 | N539V | 0.56 | N539G | 0.51 | N539C | 0.49 |
| 540 | I | B25 | I540V | 0.90 | I540H | 0.86 | I540S | 0.84 | I540P | 0.84 |
| 541 | Q | 258 | Q541H | 0.92 | Q541G | 0.71 | Q541A | 0.62 | Q541S | 0.54 |
| | | | Q541K | 0.20 | Q541R | 0.12 | | | | |
| 542 | N | B25 | N542R | 0.87 | N542M | 0.86 | N542A | 0.65 | N542L | 0.64 |
| | | | N542S | 0.50 | N542G | 0.41 | N542V | 0.31 | N542I | 0.24 |
| 543 | R | 258 | R543Y | 0.1104 | R543H | 0.0972 | R543G | 0.068 | R543W | 0.06 |
| | | | R543A | 0.0329 | R543V | 0.0262 | R543C | 0.0171 | R543Q | 0.0079 |
| 545 | Y | 258 | Y545A | 0.39 | Y545L | 0.34 | Y545C | 0.28 | Y545V | 0.26 |
| | | | Y545K | 0.19 | Y545R | 0.11 | Y545D | 0.10 | Y545G | 0.08 |
| 546 | L | B25 | I546V | 1.04 | I546L | 1.02 | I546M | 1.01 | I546F | 0.80 |
| 547 | E | 258 | E547K | 1.11 | E547V | 1.04 | E547R | 1.01 | E547Y | 0.94 |
| | | | E547C | 0.53 | E547W | 0.28 | E547D | 0.28 | E547F | 0.27 |
| 548 | V | B25 | V548L | 1.02 | V548S | 0.58 | V548A | 0.57 | V548G | 0.45 |
| 549 | P | B25 | P549Y | 0.52 | P549V | 0.38 | P549T | 0.50 | P549S | 0.75 |
| | | | P549D | 0.78 | P549C | 0.89 | | | | |
| 550 | I | B25 | I550V | 0.96 | I550L | 0.95 | I550A | 0.61 | I550F | 0.45 |
| 551 | Q | B25 | Q551V | 1.12 | Q551F | 1.09 | Q551M | 1.05 | Q551G | 1.01 |
| 552 | F | B25 | F552C | 1.10 | F552D | 1.06 | F552G | 1.00 | F552A | 0.98 |
| 553 | I | B25 | I553N | 1.12 | | | | | | |
| 554 | S | B25 | S554M | 0.93 | | | | | | |
| 555 | T | B25 | T555R | 1.13 | T555C | 1.13 | T555S | 0.85 | T555G | 0.78 |
| 557 | T | B25 | T557L | 1.16 | T557W | 1.05 | | | | |
| 558 | R | B25 | R558A | 1.11 | | | | | | |
| 559 | Y | B25 | Y559L | 0.67 | Y559M | 0.63 | Y559V | 0.61 | Y559A | 0.47 |
| | | | Y559R | 0.10 | Y559P | 0.07 | Y559G | 0.05 | | |
| 563 | V | B25 | V563G | 1.05 | V563S | 0.69 | V563C | 0.68 | V563T | 0.54 |
| 564 | R | B25 | R564M | 1.04 | R564G | 0.78 | R564L | 0.24 | R564P | 0.20 |
| 568 | V | B25 | V568P | 1.17 | | | | | | |
| 569 | T | B25 | T569V | 1.19 | T569E | 1.15 | T569L | 1.12 | T569R | 1.10 |
| 570 | P | 258 | P570A | 1.15 | P570K | 1.07 | P570G | 1.07 | P570Y | 1.07 |
| | | | P570S | 0.89 | P570Q | 0.79 | P570N | 0.79 | P570C | 0.70 |
| 571 | I | B25 | I571E | 1.09 | I571A | 0.90 | | | | |
| 572 | Q | 258 | Q572G | 1.16 | Q572T | 1.07 | Q572Y | 1.07 | Q572N | 0.87 |
| 574 | S | 258 | S574V | 0.82 | S574I | 0.76 | S574M | 0.69 | S574W | 0.64 |
| | | | S574N | 0.48 | S574L | 0.38 | S574E | 0.32 | S574P | 0.29 |
| 577 | W | 258 | W577L | 1.18 | W577N | 1.16 | W577C | 1.08 | W577S | 1.04 |
| 581 | N | 258 | N581I | 1.02 | N581G | 1.02 | N581F | 1.00 | N581T | 0.90 |
| | | | N581P | 0.63 | N581W | 0.58 | N581E | 0.57 | N581Q | 0.46 |
| | | | N581R | 0.00 | | | | | | |
| 584 | S | B21 | S584K | 1.14 | S584G | 1.11 | S584A | 1.00 | S584Q | 0.90 |
| | | | S584L | 0.66 | S584H | 0.65 | S584T | 0.64 | S584F | 0.59 |
| | | | S584E | 0.21 | S584P | 0.12 | | | | |
| 585 | S | 258 | S585E | 1.11 | S585Y | 1.09 | S585G | 0.93 | S585P | 0.79 |
| 590 | T | B25 | T590K | 1.00 | T590V | 0.98 | T590M | 0.73 | T590W | 0.72 |
| 591 | A | 258 | A591I | 1.17 | A591G | 1.17 | A591M | 0.94 | | |
| 592 | T | 258 | T592E | 1.04 | T592C | 0.66 | | | | |
| 593 | S | B21 | S593A | 1.10 | S593F | 1.07 | S593L | 1.06 | S593Q | 1.06 |
| | | | S593I | 0.87 | S593W | 0.84 | S593E | 0.80 | S593K | 0.79 |
| 595 | D | B21 | D595L | 1.19 | D595W | 1.18 | D595Q | 1.13 | D595C | 0.91 |
| 596 | N | B21 | N596F | 1.14 | N596C | 1.10 | N596Q | 1.06 | N596M | 0.98 |
| 598 | Q | B21 | Q598H | 1.03 | Q598F | 1.03 | Q598Y | 1.02 | Q598R | 0.95 |
| | | | Q598P | 0.82 | Q598M | 0.80 | Q598A | 0.76 | Q598T | 0.60 |
| 599 | S | B25 | S599G | 1.09 | S599D | 1.07 | S599I | 0.85 | S599W | 0.81 |
| 600 | R | B21 | R600G | 0.88 | R600S | 0.85 | R600M | 0.77 | R600A | 0.74 |
| | | | R600V | 0.65 | R600Q | 0.60 | R600I | 0.57 | R600H | 0.56 |
| | | | R600Y | 0.36 | R600D | 0.34 | R600W | 0.31 | | |
| 601 | D | B21 | N601Q | 1.14 | N601W | 1.07 | N601T | 1.00 | N601A | 0.96 |
| | | | N601R | 0.73 | N601C | 0.73 | N601I | 0.64 | N601D | 0.58 |
| 602 | F | B25 | F602L | 1.15 | F602V | 0.75 | F602Y | 0.70 | F602K | 0.59 |
| 605 | F | 258 | F605H | 1.12 | F605T | 0.96 | F605L | 0.83 | | |
| 606 | E | B21 | E606C | 1.15 | E606V | 1.03 | E606S | 0.97 | E606D | 0.85 |
| 607 | S | 258 | S607N | 1.14 | S607H | 1.08 | S607K | 1.01 | S607M | 1.01 |
| | | | S607L | 0.75 | | | | | | |
| 608 | T | 258 | T608M | 1.19 | T608H | 1.16 | T608E | 1.05 | T608D | 0.98 |
| 609 | N | B25 | N609D | 0.74 | | | | | | |
| 612 | T | B25 | T612A | 1.17 | T612L | 1.09 | T612K | 0.97 | T612Y | 0.86 |
| 613 | S | B25 | S613E | 1.01 | S613L | 0.98 | S613A | 0.97 | | |
| 614 | A | B25 | A614W | 1.15 | A614P | 1.14 | A614Q | 0.98 | | |
| 617 | N | B25 | N617E | 1.19 | N617S | 1.14 | N617F | 0.96 | | |
| 618 | V | 258 | V618F | 1.17 | V618Y | 1.11 | V618M | 1.10 | V618A | 1.10 |
| | | | V618S | 0.70 | V618C | 0.69 | V618Q | 0.67 | | |
| 620 | G | B25 | G620S | 0.38 | G620A | 0.35 | G620E | 0.27 | G620L | 0.25 |
| | | | G620W | 0.21 | G620R | 0.20 | G620M | 0.15 | | |
| 622 | R | B25 | R622H | 0.28 | R622W | 0.20 | R622C | 0.19 | R622E | 0.09 |
| 623 | N | B25 | N623S | 1.19 | N623A | 1.14 | N623D | 0.88 | N623H | 0.85 |
| | | | N623I | 0.57 | | | | | | |
| 624 | F | B25 | F624M | 1.14 | F624E | 0.86 | F624V | 0.76 | F624S | 0.73 |
| | | | F624T | 0.33 | | | | | | |

TABLE 5-continued

| | | | | | | | | | |
|---|---|---|---|---|---|---|---|---|---|
| 626 | E | 258 | E626D | 1.18 | E626L | 1.10 | E626F | 1.09 | E626C | 0.66 |
| 628 | A | B25 | A628E | 1.15 | A628T | 1.14 | | | | |
| 629 | G | 258 | G629C | 1.18 | G629L | 1.15 | G629H | 1.08 | G629I | 1.07 |
| | | | G629F | 0.85 | G629Y | 0.81 | | | | |
| 630 | V | B25 | V630I | 1.12 | V630T | 1.08 | V630L | 0.82 | V630G | 0.76 |
| 641 | T | B25 | T641M | 1.18 | T641C | 0.98 | T641K | 0.97 | | |
| 643 | T | B25 | T643V | 1.14 | T643P | 0.98 | T643E | 0.93 | T643F | 0.70 |
| 645 | E | B25 | E645R | 1.16 | E645F | 1.13 | E645D | 0.75 | | |
| 646 | A | B25 | A646N | 1.08 | A646Q | 1.06 | | | | |

| MP258 position | Variant | FAE | Variant | FAE | Variant | FAE | Variant | FAE |
|---|---|---|---|---|---|---|---|---|
| 50 | L50G | 0.73 | | | | | | |
| 53 | A53M | 1.06 | A53S | 0.55 | | | | |
| 54 | S54V | 1.03 | S54N | 0.99 | S54E | 0.95 | S54T | 0.89 |
| 57 | Q57F | 0.91 | | | | | | |
| 65 | R65V | 0.94 | R65F | 0.87 | R65E | 0.74 | R65P | 0.53 |
| 67 | L67E | 0.52 | L67Y | 0.51 | L67T | 0.51 | L67R | 0.50 |
| 68 | G68V | 0.60 | G68S | 0.54 | G68I | 0.50 | G68N | 0.50 |
| 70 | L70F | 0.97 | L70C | 0.97 | L70N | 0.96 | L70G | 0.92 |
| | L70D | 0.85 | | | | | | |
| 71 | G71R | 1.00 | G71K | 0.96 | G71A | 0.88 | G71I | 0.87 |
| | G71Y | 0.26 | G71W | 0.25 | G71T | 0.22 | | |
| 72 | V72Y | 0.75 | V72I | 0.74 | V72N | 0.72 | V72H | 0.66 |
| | V72E | 0.35 | V72P | 0.28 | | | | |
| 73 | | | | | | | | |
| 74 | F74H | 0.91 | F74K | 0.88 | F74A | 0.82 | F74Y | 0.80 |
| 75 | A75L | 0.59 | A75T | 0.59 | A75G | 0.57 | A75I | 0.29 |
| 76 | G76C | 0.52 | G76N | 0.51 | G76L | 0.50 | G76F | 0.48 |
| 77 | | | | | | | | |
| 79 | | | | | | | | |
| 80 | | | | | | | | |
| 83 | S83W | 0.53 | | | | | | |
| 87 | G87V | 0.92 | G87T | 0.69 | G87Q | 0.50 | G87I | 0.46 |
| 91 | P91F | 1.01 | P91M | 0.67 | P91L | 0.55 | P91V | 0.55 |
| 92 | S92A | 0.39 | S92P | 0.32 | | | | |
| 93 | G93A | 0.83 | G93T | 0.82 | G93S | 0.80 | G93K | 0.75 |
| 94 | R94A | 0.88 | R94W | 0.88 | R94N | 0.77 | R94I | 0.71 |
| 95 | D95K | 0.80 | D95S | 0.64 | D95E | 0.50 | D95A | 0.28 |
| 106 | Q106T | 0.52 | | | | | | |
| 108 | V108E | 0.95 | V108W | 0.83 | | | | |
| 109 | R109H | 0.92 | R109L | 0.91 | R109E | 0.91 | R109G | 0.86 |
| | R109M | 0.74 | R109C | 0.73 | R109Y | 0.49 | R109P | 0.07 |
| 110 | Q110N | 1.13 | Q110E | 1.09 | Q110S | 1.09 | Q110L | 0.89 |
| | Q110P | 0.15 | | | | | | |
| 111 | Q111P | 0.85 | Q111T | 0.79 | Q111C | 0.77 | Q111Y | 0.50 |
| 112 | I112T | 0.57 | I112E | 0.39 | I112Y | 0.28 | I112N | 0.28 |
| | I112W | 0.24 | | | | | | |
| 113 | T113I | 0.61 | | | | | | |
| 114 | E114P | 0.09 | | | | | | |
| 115 | N115V | 0.87 | N115D | 0.82 | N115L | 0.69 | N115C | 0.61 |
| 118 | N118M | 0.60 | | | | | | |
| 119 | T119L | 0.78 | T119C | 0.62 | T119G | 0.50 | T119N | 0.42 |
| 122 | A122D | 1.01 | A122V | 1.00 | A122K | 0.96 | A122C | 0.96 |
| 123 | R123T | 0.61 | R123V | 0.61 | R123L | 0.61 | R123F | 0.57 |
| | R123C | 0.43 | R123W | 0.42 | R123D | 0.32 | R123E | 0.28 |
| 125 | | | | | | | | |
| 129 | A129C | 1.05 | A129M | 0.91 | A129G | 0.90 | A129N | 0.87 |
| 132 | R132L | 0.86 | R132Q | 0.80 | R132S | 0.72 | R132E | 0.70 |
| | R132C | 0.59 | R132P | 0.36 | | | | |
| 133 | A133G | 0.47 | A133P | 0.36 | A133H | 0.33 | A133M | 0.32 |
| | A133R | 0.23 | A133Q | | | | | |
| 136 | Q136V | 0.59 | | | | | | |
| 140 | D140Q | 0.40 | D140M | 0.36 | D140C | 0.36 | D140K | 0.30 |
| 142 | L142A | 0.67 | L142G | 0.67 | L142Y | 0.66 | L142M | 0.62 |
| 143 | | | | | | | | |
| 144 | N144E | 0.86 | N144G | 0.84 | N144D | 0.52 | | |
| 145 | R145C | 0.69 | | | | | | |
| 146 | D146R | 1.05 | D146N | 1.05 | D146L | 1.01 | D146Q | 0.95 |
| 147 | N147F | 0.61 | N147I | 0.59 | N147P | 0.57 | N147M | 0.55 |
| 148 | A148Y | 0.87 | A148T | 0.85 | A148S | 0.84 | A148D | 0.83 |
| 149 | R149Y | 0.87 | R149P | 0.84 | R149G | 0.82 | R149C | 0.24 |
| 151 | R151L | 0.68 | R151G | 0.63 | R151T | 0.56 | R151Q | 0.52 |
| | B151W | 0.39 | B151E | 0.38 | B151P | 0.32 | R151D | 0.32 |
| 152 | S152L | 0.83 | S152I | 0.76 | S152B | 0.61 | S152G | 0.60 |
| | S152D | 0.32 | S152V | 0.25 | | | | |
| 159 | I159B | 0.32 | I159Y | 0.29 | I159N | 0.28 | I159M | 0.28 |
| | I159Q | 0.25 | I159L | 0.25 | | | | |

TABLE 5-continued

| | | | | | | | | |
|---|---|---|---|---|---|---|---|---|
| 160 | A160K | 0.82 | A160T | 0.81 | A160I | 0.75 | | |
| 163 | L163C | 0.28 | L163A | 0.28 | L163K | 0.27 | L163P | 0.26 |
| | L163D | 0.23 | L163N | 0.23 | | | | |
| 164 | D164B | 0.72 | D164N | 0.71 | D164L | 0.63 | D164Y | 0.56 |
| | D164I | 0.42 | D164E | 0.30 | D164P | 0.25 | | |
| 166 | L166H | 0.98 | L166G | 0.97 | L166B | 0.96 | L166K | 0.96 |
| | L166S | 0.95 | | | | | | |
| 167 | N167F | 0.92 | N167E | 0.90 | N167D | 0.87 | N167P | 0.83 |
| 173 | A173S | 0.77 | A173E | 0.56 | | | | |
| 174 | I174G | 0.72 | I174M | 0.72 | I174E | 0.63 | I174N | 0.59 |
| 177 | Q177I | 1.00 | Q177B | 0.96 | Q177M | 0.95 | Q177V | 0.93 |
| 178 | Q178S | 0.75 | Q178V | 0.74 | Q178P | 0.67 | Q178I | 0.54 |
| 179 | V179E | 0.77 | V179S | 0.75 | V179P | 0.67 | V179G | 0.61 |
| 180 | P180G | 0.83 | P180F | 0.62 | P180B | 0.60 | P180N | 0.56 |
| 201 | L201Q | 0.62 | L201G | 0.61 | L201W | 0.60 | L201Y | 0.60 |
| 206 | F206Y | 0.74 | F206Q | 0.69 | F206G | 0.58 | F206R | 0.53 |
| | F206P | 0.37 | | | | | | |
| 208 | L208E | 0.67 | L208V | 0.66 | L208M | 0.56 | L208H | 0.50 |
| | L208T | 0.35 | L208A | 0.35 | L208P | 0.34 | L208R | 0.30 |
| 209 | T209W | 0.67 | T209F | 0.64 | T209Y | 0.62 | T209P | 0.28 |
| 210 | | | | | | | | |
| 211 | Q211W | 1.03 | Q211F | 1.01 | Q211Y | 1.01 | Q211C | 1.00 |
| 212 | E212P | 0.77 | E212C | 0.72 | E212T | 0.68 | E212G | 0.64 |
| | E212B | 0.56 | | | | | | |
| 213 | I213W | 0.74 | I213D | 0.67 | I213Y | 0.63 | I213F | 0.62 |
| 214 | Q214V | 0.68 | Q214C | 0.67 | Q214E | 0.58 | Q214I | 0.53 |
| | Q214K | 0.28 | Q214R | 0.27 | | | | |
| 215 | R215Y | 0.77 | R215F | 0.75 | R215Q | 0.73 | R215K | 0.72 |
| | R215D | 0.56 | R215E | 0.54 | | | | |
| 218 | E218R | 0.93 | E218F | 0.92 | E218P | 0.55 | | |
| 219 | R219K | 0.63 | R219D | 0.53 | R219P | 0.23 | R219H | 0.07 |
| | R219V | 0.01 | R219I | 0.01 | R219C | 0.00 | | |
| 221 | A221P | 0.62 | A221Q | 0.50 | | | | |
| 222 | E222A | 0.98 | E222N | 0.98 | E222V | 0.94 | E222W | 0.90 |
| 225 | R225P | 0.87 | R225K | 0.85 | R225T | 0.77 | | |
| 226 | E226N | 1.11 | E226M | 1.05 | E226I | 1.00 | E226L | 0.98 |
| 230 | Y230T | 0.93 | Y230D | 0.88 | Y230N | 0.85 | Y230G | 0.81 |
| 233 | R233L | 1.03 | R233M | 1.01 | R233S | 0.87 | R233C | 0.78 |
| 234 | W234D | 0.59 | W234P | 0.46 | W234Q | 0.45 | | |
| 236 | N236I | 0.93 | N236Y | 0.89 | N236V | 0.89 | N236G | 0.58 |
| 240 | N240P | 0.44 | | | | | | |
| 241 | N241T | 1.12 | N241D | 1.07 | N241H | 0.90 | N241P | 0.50 |
| 242 | L242S | 0.70 | L242Q | 0.68 | L242A | 0.66 | L242N | 0.58 |
| | L242Y | 0.33 | L242K | 0.32 | | | | |
| 243 | R243H | 0.73 | R243W | 0.71 | R243G | 0.67 | R243D | 0.57 |
| 244 | G244S | 0.58 | G244D | 0.56 | G244K | 0.54 | G244R | 0.54 |
| | G244N | 0.46 | G244T | 0.37 | G244V | 0.28 | G244P | 0.28 |
| 245 | | | | | | | | |
| 246 | N246M | 0.77 | N246R | 0.76 | N246F | 0.66 | N246L | 0.61 |
| 247 | A247V | 0.39 | A247W | 0.39 | A247R | 0.31 | A247F | 0.30 |
| 248 | E248G | 0.76 | E248M | 0.74 | E248K | 0.50 | | |
| 252 | R252M | 1.05 | R252S | 0.99 | R252Q | 0.98 | R252H | 0.96 |
| | R252P | 0.66 | R252T | 0.48 | | | | |
| 277 | R277W | 0.87 | R277S | 0.87 | R277F | 0.86 | R277T | 0.85 |
| | R277P | 0.47 | | | | | | |
| 280 | P280F | 0.90 | P280W | 0.87 | P280E | 0.86 | P280K | 0.64 |
| | P280I | 0.47 | P280L | 0.46 | | | | |
| 281 | I281G | 1.00 | I281F | 0.94 | I281W | 0.82 | I281D | 0.72 |
| 303 | S303G | 0.64 | S303I | 0.61 | S303T | 0.57 | S303H | 0.57 |
| | S303W | 0.29 | S303D | 0.15 | S303K | 0.13 | S303E | 0.07 |
| 304 | G304I | 0.01 | G304L | 0.01 | G304T | 0.01 | G304F | 0.01 |
| | G304R | 0.01 | G304H | 0.01 | G304W | 0.01 | G304V | 0.01 |
| 305 | F305I | 0.01 | F305L | 0.01 | F305R | 0.01 | F305G | 0.01 |
| | F305C | 0.00 | F305W | 0.00 | F305T | 0.00 | F305S | 0.00 |
| 306 | A306M | 0.78 | A306T | 0.52 | A306H | 0.50 | A306R | 0.48 |
| | A306V | 0.26 | A306P | 0.22 | A306D | 0.09 | A306C | 0.07 |
| 308 | T308F | 0.02 | T308Q | 0.01 | T308V | 0.01 | T308C | 0.01 |
| | T308L | 0.01 | T308I | 0.01 | T308P | 0.01 | T308M | 0.01 |
| 360 | R360Q | 0.44 | R360E | 0.41 | R360L | 0.28 | | |
| 362 | | | | | | | | |
| 364 | R364M | 0.25 | | | | | | |
| 367 | | | | | | | | |
| 406 | L406C | 0.29 | L406V | 0.27 | L406Q | 0.27 | L406H | 0.24 |
| | L406Y | 0.03 | L406G | 0.02 | L406D | 0.01 | L406P | 0.01 |
| 407 | L407F | 0.46 | L407A | 0.41 | L407R | 0.34 | L407T | 0.34 |
| | L407G | 0.06 | L407K | 0.04 | L407Q | 0.02 | L407P | 0.01 |
| 408 | T408L | 0.36 | T408M | 0.32 | T408Q | 0.30 | T408N | 0.27 |
| | T408P | 0.22 | T408W | 0.20 | T408I | 0.17 | T408C | 0.11 |
| 409 | T409V | 0.20 | T409L | 0.17 | T409S | 0.16 | T409K | 0.13 |
| | T409Y | 0.08 | T409N | 0.08 | T409F | 0.05 | T409C | 0.02 |

TABLE 5-continued

| | | | | | | | | |
|---|---|---|---|---|---|---|---|---|
| 411 | V411R | 0.27 | V411N | 0.21 | V411Q | 0.19 | V411T | 0.14 |
| | V411S | 0.08 | V411G | 0.06 | V411K | 0.03 | V411E | 0.02 |
| 418 | R418D | 0.89 | R418I | 0.83 | R418V | 0.78 | R418N | 0.76 |
| | R418Q | 0.58 | R418W | 0.54 | R418F | 0.43 | R418C | 0.36 |
| 420 | N420G | 0.98 | N420L | 0.91 | N420F | 0.90 | N420W | 0.89 |
| | N420H | 0.68 | N420R | 0.68 | N420Q | 0.65 | N420S | 0.63 |
| 422 | R422T | 0.92 | R422K | 0.91 | R422L | 0.87 | R422V | 0.84 |
| | R422G | 0.67 | R422H | 0.66 | R422C | 0.63 | R422E | 0.60 |
| 425 | L425F | 1.08 | L425R | 1.04 | L425S | 1.00 | L425K | 0.96 |
| | L425H | 0.89 | L425T | 0.84 | L425E | 0.83 | L425C | 0.67 |
| 426 | N426A | 0.99 | N426V | 0.91 | N426E | 0.83 | N426L | 0.83 |
| | N426F | 0.59 | N426K | 0.59 | N426I | 0.53 | N426H | 0.51 |
| 427 | S427W | 1.10 | S427T | 1.10 | S427G | 1.03 | S427L | 0.97 |
| | S427K | 0.74 | S427A | 0.73 | S427C | 0.68 | S427D | 0.55 |
| 428 | L428T | 0.92 | L428M | 0.85 | L428H | 0.83 | L428R | 0.82 |
| | L428E | 0.72 | L428D | 0.65 | L428Y | 0.63 | L428I | 0.60 |
| 429 | R429K | 1.00 | R429M | 0.99 | R429F | 0.91 | R429A | 0.89 |
| | R429V | 0.73 | R429P | 0.72 | R429E | 0.65 | R429D | 0.63 |
| 431 | S431E | 0.87 | S431Y | 0.86 | S431Q | 0.86 | S431F | 0.82 |
| | S431P | 0.61 | S431D | 0.60 | S431C | 0.32 | | |
| 435 | T435K | 0.88 | T435Q | 0.82 | T435V | 0.79 | T435S | 0.58 |
| | T435R | 0.47 | T435C | 0.24 | T435G | 0.20 | T435P | 0.04 |
| 437 | G437H | 0.94 | G437V | 0.88 | G437W | 0.88 | G437L | 0.84 |
| | G437C | 0.26 | | | | | | |
| 439 | T439H | 1.08 | T439N | 0.99 | T439Y | 0.92 | T439I | 0.89 |
| | T439D | 0.64 | T439E | 0.58 | T439W | 0.54 | T439C | 0.17 |
| 444 | Q444T | 0.53 | Q444L | 0.48 | Q444S | 0.48 | Q444V | 0.47 |
| | Q444Y | 0.26 | Q444W | 0.24 | Q444I | 0.18 | Q444G | 0.12 |
| 447 | D447F | 0.94 | D447H | 0.94 | D447T | 0.88 | D447W | 0.78 |
| 473 | | | | | | | | |
| 476 | I476R | 0.59 | I476D | 0.40 | I476A | 0.29 | | |
| 477 | G477H | 0.42 | G477M | 0.41 | G477E | 0.33 | G477F | 0.25 |
| 478 | N478L | 0.88 | N478V | 0.82 | N478M | 0.68 | N478I | 0.59 |
| 479 | T479A | 0.66 | T479N | 0.50 | T479Q | 0.44 | T479Y | 0.40 |
| | T479W | 0.18 | | | | | | |
| 481 | R481N | 0.18 | R481T | 0.18 | R481D | 0.15 | R481F | 0.14 |
| 492 | | | | | | | | |
| 498 | I498W | 0.47 | I498M | 0.43 | I498Y | 0.37 | I498A | 0.28 |
| 499 | | | | | | | | |
| 503 | | | | | | | | |
| 504 | T504Q | 0.52 | | | | | | |
| 505 | | | | | | | | |
| 506 | | | | | | | | |
| 507 | | | | | | | | |
| 508 | | | | | | | | |
| 509 | V509S | 0.72 | V509A | 0.67 | V509W | 0.57 | V509M | 0.55 |
| 511 | | | | | | | | |
| 512 | N512T | 1.04 | N512F | 0.96 | N512A | 0.82 | | |
| 513 | | | | | | | | |
| 514 | | | | | | | | |
| 515 | F515Q | 0.51 | F515K | 0.50 | F515T | 0.45 | F515A | 0.44 |
| 517 | | | | | | | | |
| 520 | | | | | | | | |
| 525 | F525C | 0.60 | F525A | 0.40 | F525G | 0.39 | | |
| 526 | | | | | | | | |
| 527 | | | | | | | | |
| 530 | S536N | 0.41 | L530G | 0.31 | L530S | 0.27 | L530E | 0.22 |
| 531 | | | | | | | | |
| 533 | | | | | | | | |
| 534 | N534T | 0.81 | | | | | | |
| 535 | | | | | | | | |
| 536 | S536Q | 0.66 | S536C | 0.62 | S536M | 0.60 | S536H | 0.56 |
| | S536E | 0.30 | S536P | 0.27 | S536K | 0.21 | S536V | 0.20 |
| 537 | G537P | 0.57 | | | | | | |
| 538 | | | | | | | | |
| 539 | N539E | 0.77 | N539L | 0.72 | N539A | 0.60 | N539F | 0.57 |
| | N539W | 0.43 | N539Y | 0.39 | N539R | 0.18 | N539K | 0.17 |
| 540 | I540L | 0.82 | I540G | 0.51 | I540C | 0.50 | I540R | 0.17 |
| 541 | Q541E | 0.39 | Q541C | 0.37 | Q541T | 0.30 | Q541L | 0.30 |
| 542 | N542Y | 0.63 | N542H | 0.61 | N542T | 0.53 | N542C | 0.52 |
| | N542P | 0.05 | | | | | | |
| 543 | R543M | 0.0587 | R543L | 0.0419 | R543K | 0.0394 | R543S | 0.033 |
| | R543P | 0.0079 | R543D | 0.002 | R543T | 0.0011 | R543E | 0.0002 |

TABLE 5-continued

| | | | | | | | | |
|---|---|---|---|---|---|---|---|---|
| 545 | Y545H | 0.26 | Y545N | 0.25 | Y545W | 0.24 | Y545T | 0.21 |
| | Y545I | 0.07 | Y545Q | 0.07 | Y545E | 0.06 | Y545P | 0.04 |
| 546 | I546S | 0.32 | I546G | 0.23 | | | | |
| 547 | E547T | 0.85 | E547H | 0.78 | E547P | 0.75 | E547L | 0.58 |
| 548 | V548W | 0.26 | | | | | | |
| 549 | P549R | 1.03 | P549M | 0.55 | P549L | 0.86 | P549G | 1.73 |
| 550 | | | | | | | | |
| 551 | Q551E | 0.93 | Q551N | 0.87 | Q551L | 0.85 | | |
| 552 | F552Q | 0.80 | F552R | 0.51 | | | | |
| 553 | | | | | | | | |
| 554 | | | | | | | | |
| 555 | T555L | 0.27 | | | | | | |
| 557 | | | | | | | | |
| 558 | | | | | | | | |
| 559 | Y559E | 0.43 | Y559T | 0.27 | Y559S | 0.17 | Y559D | 0.10 |
| 563 | V563E | 0.05 | | | | | | |
| 564 | | | | | | | | |
| 568 | | | | | | | | |
| 569 | T569W | 1.02 | T569K | 0.82 | T569A | 0.58 | T569Y | 0.35 |
| 570 | P570V | 1.06 | P570H | 1.05 | P570R | 1.03 | P570I | 1.03 |
| | P570D | 0.52 | P570L | 0.47 | | | | |
| 571 | | | | | | | | |
| 572 | Q572E | 0.75 | Q572D | 0.75 | Q572C | 0.57 | | |
| 574 | S574Q | 0.64 | S574F | 0.56 | S574Y | 0.56 | S574A | 0.53 |
| | S574C | 0.29 | S574D | 0.26 | | | | |
| 577 | W577P | 0.97 | W577D | 0.92 | W577E | 0.81 | | |
| 581 | N581V | 0.86 | N581H | 0.70 | N581Y | 0.64 | N581M | 0.63 |
| | N581A | 0.42 | N581L | 0.32 | N581D | 0.29 | N581C | 0.13 |
| 584 | S584V | 0.81 | S584C | 0.78 | S584N | 0.67 | S584Y | 0.66 |
| | S584I | 0.54 | S584M | 0.41 | S584W | 0.38 | S584D | 0.31 |
| 585 | S585A | 0.74 | S585D | 0.67 | S585C | 0.60 | S585V | 0.47 |
| 590 | T590L | 0.54 | T590R | 0.53 | T590E | 0.52 | T590P | 0.15 |
| 591 | | | | | | | | |
| 592 | | | | | | | | |
| 593 | S593T | 1.00 | S593M | 0.96 | S593H | 0.92 | S593D | 0.89 |
| | S593N | 0.75 | S593P | 0.75 | S593C | 0.59 | | |
| 595 | D595E | 0.09 | | | | | | |
| 596 | N596E | 0.93 | N596R | 0.92 | N596K | 0.92 | | |
| 598 | Q598L | 0.92 | Q598E | 0.89 | Q598W | 0.88 | Q598N | 0.83 |
| | Q598K | 0.58 | Q598S | 0.58 | Q598C | 0.55 | | |
| 599 | S599E | 0.61 | | | | | | |
| 600 | R600E | 0.70 | R600T | 0.69 | R600K | 0.69 | R600F | 0.66 |
| | R600C | 0.54 | R600L | 0.54 | R600P | 0.47 | R600N | 0.45 |
| 601 | N601S | 0.81 | N601H | 0.79 | N601L | 0.78 | N601K | 0.76 |
| 602 | | | | | | | | |
| 605 | | | | | | | | |
| 606 | E606P | 0.39 | | | | | | |
| 607 | S607W | 1.01 | S607Y | 0.90 | S607P | 0.86 | S607F | 0.83 |
| 608 | T608P | 0.68 | T608I | 0.53 | T608C | 0.53 | T608N | 0.50 |
| 609 | | | | | | | | |
| 612 | T612W | 0.84 | T612I | 0.53 | | | | |
| 613 | | | | | | | | |
| 614 | | | | | | | | |
| 617 | | | | | | | | |
| 618 | V618P | 1.07 | V618E | 1.05 | V618K | 1.03 | V618I | 0.94 |
| 620 | G620F | 0.23 | G620K | 0.23 | G620V | 0.23 | G620Q | 0.22 |
| 622 | | | | | | | | |
| 623 | N623C | 0.70 | N623V | 0.68 | N623T | 0.65 | N623Q | 0.61 |
| 624 | F624D | 0.68 | F624C | 0.59 | F624H | 0.56 | F624R | 0.44 |
| 626 | E626M | 0.08 | | | | | | |
| 628 | | | | | | | | |
| 629 | G629V | 1.05 | G629K | 1.03 | G629D | 0.87 | G629W | 0.86 |
| 630 | V630R | 0.66 | V630D | 0.64 | V630S | 0.55 | | |
| 641 | | | | | | | | |
| 643 | | | | | | | | |
| 645 | | | | | | | | |
| 646 | | | | | | | | |

Example 5—Transient Expression in Maize Leaves and Insect Bioassay

Polynucleotides encoding the variant Cry1B polypeptides were cloned into transient expression vectors under control of the maize ubiquitin promoter (Christensen and Quail, (1996) Transgenic Research 5:213-218) and a duplicated version of the promoter from the mirabilis mosaic virus (DMMV PRO; Dey and Maiti, (1999) Plant Mol. Biol., 40:771-82). The agro-infiltration method of introducing an *Agrobacterium* cell suspension to plant cells of intact tissues so that reproducible infection and subsequent plant derived transgene expression may be measured or studied is well known in the art (Kapila, et. al., (1997) Plant Science 122:101-108). Briefly, young plantlets of maize were agro-infiltrated with normalized bacterial cell cultures of test and control strains. Leaf discs were generated from each plantlet and infested with WCRW (*Diabrotica virgifera*) along with appropriate controls. The degree of consumption of green leaf tissues was scored after 2 days of infestation.

Example 6—Transient Expression in Bush Bean Leaves and Insect Bioassay

For soybean expression optimized coding sequences can be designed. The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, excised leaf disks of bush bean, are agro-infiltrated with normalized bacterial cell cultures of test and control strains. After 4 days leaf disks are infested with 2 neonates of Soybean Looper (SBL) (*Chrysodeixis includens*), Corn Earworm, (CEW) (*Helicoverpa zea*), Velvetbean Caterpillar (VBC) (*Anticarsia gemmatalis*), or Fall Armyworm (*Spodoptera frugiperda*) alone. Control leaf discs are generated with *Agrobacterium* containing only a DsRed2 fluorescence marker (Clontech™, 1290 Terra *Bella* Ave. Mountain View, Calif. 94043) expression vector. Leaf discs from non-infiltrated plants are included as a second control. The consumption of green leaf tissue is scored three days after infestation and given scores of 0 to 9.

Example 7—*Agrobacterium*-Mediated Transformation of Maize and Regeneration of Transgenic Plants For *Agrobacterium*-mediated transformation of maize with a polynucleotide sequence of the disclosure, the method of Zhao can be used (U.S. Pat. No. 5,981,840 and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the toxin nucleotide sequence to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 8—Transformation of Soybean Embryos

Soybean embryos are bombarded with a plasmid containing the toxin nucleotide sequence operably linked to a suitable promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation includes, but is not limited to: the 35S promoter from Cauliflower Mosaic Virus (Odell, et al., (1985) Nature 313:810-812), the hygromycin phosphotransferase gene from plasmid pJR225 (from *E. coli*; Gritz, et al., (1983) Gene 25:179-188), and the 3' region of the nopaline synthase gene from the T DNA of the Ti plasmid of *Agrobacterium tumefaciens*. The expression cassette comprising a toxin nucleotide sequence (e.g., SEQ ID NO: 1, SEQ ID NO: 3 or a maize optimized sequence) operably linked to a suitable promoter can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1M), and 50 µL $CaCl_2$) (2.5M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the embodiments.

SEQUENCE LISTING

```
<160> NUMBER OF SEQ ID NOS: 61

<210> SEQ ID NO 1
<211> LENGTH: 657
<212> TYPE: PRT
<213> ORGANISM: Bacillus thuringiensis

<400> SEQUENCE: 1

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300
```

```
Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
            325                 330                 335

Gln Leu Thr Ile Tyr Ser Ala Ser Ser Arg Trp Ser Thr Gln His
            340                 345                 350

Met Asn Tyr Trp Val Gly His Arg Leu Asn Phe Arg Pro Ile Gly Gly
                355                 360                 365

Thr Leu Asn Thr Ser Thr Gln Gly Leu Thr Asn Asn Thr Ser Ile Asn
            370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
            435                 440                 445

Asp Ser Glu Thr Glu Leu Pro Pro Glu Thr Thr Glu Arg Pro Asn Tyr
450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Ala Val Lys
            500                 505                 510

Gly Arg Phe Leu Phe Asn Gly Ser Val Ile Ser Gly Pro Gly Phe Thr
            515                 520                 525

Gly Gly Asp Val Val Arg Leu Asn Arg Asn Asn Gly Asn Ile Gln Asn
            530                 535                 540

Arg Gly Tyr Ile Glu Val Pro Ile Gln Phe Thr Ser Thr Ser Thr Arg
545                 550                 555                 560

Tyr Arg Val Arg Val Arg Tyr Ala Ser Val Thr Ser Ile Glu Leu Asn
                565                 570                 575

Val Asn Leu Gly Asn Ser Ser Ile Phe Thr Asn Thr Leu Pro Ala Thr
            580                 585                 590

Ala Ala Ser Leu Asp Asn Leu Gln Ser Gly Asp Phe Gly Tyr Val Glu
            595                 600                 605

Ile Asn Asn Ala Phe Thr Ser Ala Thr Gly Asn Ile Val Gly Ala Arg
            610                 615                 620

Asn Phe Ser Ala Asn Ala Glu Val Ile Ile Asp Arg Phe Glu Phe Ile
625                 630                 635                 640

Pro Val Thr Ala Thr Phe Glu Ala Glu Tyr Asp Leu Glu Arg Ala Gln
                645                 650                 655

Lys

<210> SEQ ID NO 2
<211> LENGTH: 1971
<212> TYPE: DNA
<213> ORGANISM: Bacillus thuringiensis

<400> SEQUENCE: 2
atgccttcaa ataggaaaaa tgagaatgaa attataaatg ccttatcgat tccagctgta      60
```

-continued

```
tcgaatcatt ccgcacaaat ggatctatcg ctagatgctc gtattgagga ttctttgtgt    120
atagccgagg ggaataatat caatccactt gttagcgcat caacagtcca aacgggtata    180
aacatagctg gtagaatatt gggcgtatta ggtgtgccgt ttgctggaca actagctagt    240
ttttatagtt ttcttgttgg ggaattatgg cctagtggca gagatccatg ggaaattttc    300
ctggaacatg tagaacaact tataagacaa caagtaacag aaaatactag gaatacggct    360
attgctcgat tagaaggtct aggaagaggc tatagatctt accagcaggc tcttgaaact    420
tggttagata accgaaatga tgcaagatca agaagcatta ttcttgagcg ctatgttgct    480
ttagaacttg acattactac tgctataccg cttttcagaa tacgaaatga agaagttcca    540
ttattaatgg tatatgctca agctgcaaat ttacacctat tattattgag agacgcatcc    600
ctttttggta gtgaatgggg gatggcatct tccgatgtta accaatatta ccaagaacaa    660
atcagatata cagaggaata ttctaaccat tgcgtacaat ggtataatac agggctaaat    720
aacttaagag ggacaaatgc tgaaagttgg ttgcggtata atcaattccg tagagaccta    780
acgttagggg tattagattt agtagcccta ttcccaagct atgatactcg cacttatcca    840
atcaatacga gtgctcagtt aacaagagaa atttatacag atccaattgg gagaacaaat    900
gcaccttcag gatttgcaag tacgaattgg tttaataata atgcaccatc gttttctgcc    960
atagaggctg ccattttcag gcctccgcat ctacttgatt ttccagaaca acttacaatt   1020
tacagtgcat caagccgttg gagtagcact caacatatga attattgggt gggacatagg   1080
cttaacttcc gcccaatagg agggacatta aatacctcaa cacaaggact tactaataat   1140
acttcaatta atcctgtaac attacagttt acgtctcgtg acgtttatag aacagaatca   1200
aatgcaggga caaatatact atttactact cctgtgaatg gagtaccttg ggctagattt   1260
aattttataa accctcagaa tatttatgaa agaggcgcca ctacctacag tcaaccgtat   1320
cagggagttg ggattcaatt atttgattca gaaactgaat taccaccaga aacaacagaa   1380
cgaccaaatt atgaatcata tagtcataga ttatctcata taggactaat catagggaaac  1440
actttgagag caccagtcta ttcttggacg catcgtagtg cagatcgtac gaatacgatt   1500
ggaccaaata gaattactca aattcctgca gtgaagggaa gatttctttt taatggttct   1560
gtaatttcag gaccaggatt tactggtgga gacgtagtta gattgaatag gaataatggt   1620
aatattcaaa atagagggta tattgaagtt ccaattcaat tcacgtcgac atctaccaga   1680
tatcgagttc gagtacgtta tgcttctgta acctcgattg agctcaatgt taatttgggc   1740
aattcatcaa tttttacgaa cacattacca gcaacagctg catcattaga taatctacaa   1800
tcaggggatt ttggttatgt tgaaatcaac aatgctttta catccgcaac aggtaatata   1860
gtaggtgcta gaaattttag tgcaaatgca gaagtaataa tagacagatt tgaatttatc   1920
ccagttactg caaccttcga ggcagaatat gatttagaaa gagcacaaaa g             1971
```

<210> SEQ ID NO 3
<211> LENGTH: 651
<212> TYPE: PRT
<213> ORGANISM: Artificial Sequence
<220> FEATURE:
<223> OTHER INFORMATION: Cry1B variant

<400> SEQUENCE: 3

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30
```

```
Ser Leu Cys Val Ala Glu Val Asn Asn Ile Asp Pro Phe Val Ser Ala
         35                  40                  45

Ser Thr Val Gln Thr Gly Ile Ser Ile Ala Gly Arg Ile Leu Gly Val
 50                  55                  60

Leu Gly Val Pro Phe Ala Gly Gln Leu Ala Ser Phe Tyr Ser Phe Leu
 65                  70                  75                  80

Val Gly Glu Leu Trp Pro Ser Gly Arg Asp Pro Trp Glu Ile Phe Met
                     85                  90                  95

Glu His Val Glu Gln Ile Val Arg Gln Ile Thr Asp Ser Val Arg
                 100                 105                 110

Asp Thr Ala Ile Ala Arg Leu Glu Gly Leu Gly Arg Gly Tyr Arg Ser
                 115                 120                 125

Tyr Gln Gln Ala Leu Glu Thr Trp Leu Asp Asn Arg Asn Asp Ala Arg
 130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                 165                 170                 175

Leu Met Val Tyr Ala Gln Ala Ala Asn Leu His Leu Leu Leu Arg
                 180                 185                 190

Asp Ala Ser Leu Phe Gly Ser Glu Trp Gly Met Ser Ser Ser Asp Val
                 195                 200                 205

Asn Gln Tyr Tyr Gln Glu Gln Ile Arg Tyr Thr Glu Glu Tyr Ser Asn
 210                 215                 220

His Cys Val Gln Trp Tyr Asn Thr Gly Leu Asn Leu Arg Gly Thr
225                 230                 235                 240

Asn Ala Glu Ser Trp Leu Arg Tyr Asn Gln Phe Arg Arg Asp Leu Thr
                 245                 250                 255

Leu Gly Val Leu Asp Leu Val Ala Leu Phe Pro Ser Tyr Asp Thr Arg
                 260                 265                 270

Val Tyr Pro Met Asn Thr Ser Ala Gln Leu Thr Arg Glu Ile Tyr Thr
                 275                 280                 285

Asp Pro Ile Gly Arg Thr Asn Ala Pro Ser Gly Phe Ala Ser Thr Asn
 290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                 325                 330                 335

Ser Ala Ser Ser Arg Trp Ser Ser Thr Gln His Met Asn Tyr Trp Val
                 340                 345                 350

Gly His Arg Leu Asn Phe Arg Pro Ile Gly Gly Thr Leu Asn Thr Ser
                 355                 360                 365

Thr His Gly Ala Thr Asn Thr Ser Ile Asn Pro Val Thr Leu Gln Phe
 370                 375                 380

Thr Ser Arg Asp Val Tyr Arg Thr Glu Ser Phe Ala Gly Thr Asn Ile
385                 390                 395                 400

Leu Phe Thr Thr Pro Val Asn Gly Val Pro Trp Ala Arg Phe Asn Phe
                 405                 410                 415

Ile Asn Pro Gln Asn Ile Tyr Glu Arg Gly Ala Thr Thr Tyr Ser Gln
                 420                 425                 430

Pro Tyr Gln Gly Val Gly Ile Gln Leu Phe Asp Ser Gly Thr Glu Leu
                 435                 440                 445
```

```
Pro Pro Glu Thr Thr Glu Arg Pro Asn Tyr Glu Ser Tyr Ser His Arg
    450                 455                 460
Leu Ser His Ile Gly Leu Ile Ile Gly Asn Thr Leu Arg Ala Pro Val
465                 470                 475                 480
Tyr Ser Trp Thr His Arg Ser Ala Asp Arg Thr Asn Thr Ile Gly Pro
                485                 490                 495
Asn Arg Ile Thr Gln Ile Pro Ala Val Lys Gly Arg Phe Leu Phe Asn
            500                 505                 510
Gly Ser Val Ile Ser Gly Pro Gly Phe Thr Gly Asp Val Val Arg
        515                 520                 525
Leu Asn Arg Asn Asn Gly Asn Ile Gln Asn Arg Gly Tyr Ile Glu Val
530                 535                 540
Pro Ile Gln Phe Thr Ser Thr Ser Thr Arg Tyr Arg Val Arg Val Arg
545                 550                 555                 560
Tyr Ala Ser Val Thr Ser Ile Glu Leu Asn Val Asn Leu Gly Asn Ser
                565                 570                 575
Ser Ile Phe Thr Asn Thr Leu Pro Ala Thr Ala Ser Leu Asp Asn
            580                 585                 590
Leu Gln Ser Gly Asp Phe Gly Tyr Val Glu Ile Asn Asn Ala Phe Thr
        595                 600                 605
Ser Ala Thr Gly Asn Ile Val Gly Ala Arg Asn Phe Ser Ala Asn Ala
    610                 615                 620
Glu Val Ile Ile Asp Arg Phe Glu Phe Ile Pro Val Thr Ala Thr Phe
625                 630                 635                 640
Glu Ala Glu Tyr Asp Leu Glu Arg Ala Gln Lys
                645                 650

<210> SEQ ID NO 4
<211> LENGTH: 1953
<212> TYPE: DNA
<213> ORGANISM: Artificial Sequence
<220> FEATURE:
<223> OTHER INFORMATION: coding sequence of Cry1B variant

<400> SEQUENCE: 4
atgccttcaa ataggaaaaa tgagaatgaa attataaatg ctgtatcgaa tcattccgca      60
caaatggatc tatcgctaga tgctcgtatt gaagatagct tgtgtgtagc cgaggtgaac     120
aatattgatc catttgttag cgcatcaaca gtccaaacag gtattagtat agctggtaga     180
atattgggcg tattaggtgt gccgtttgct ggacaactag ctagttttta tagttttctt     240
gttggggaat tatggcctag cggcagagat ccatgggaaa tttttatgga acatgtcgag     300
caaattgtaa dacaacaaat aacggacagt gttagggata ccgctattgc tcgtttagaa     360
ggtctaggaa gagggtatag atcttaccag caggctcttg aaactggtt agataaccga      420 aatgatgcaa gatcaagaag cattattcgt gagagatata ttgctttaga acttgacatt     480
actactgcta taccgctttt cagcatacga aatcaagagg ttccattatt aatggtatat     540
gctcaagctg caaatttaca cctattatta ttgagagacg catcccttt tggtagtgaa      600 tgggggatgt catcttccga tgttaaccaa tattaccaag aacaaatcag atatacagag     660
gaatattcta accattgcgt acaatggtat aatacagggc taaataactt aagagggaca     720
aatgctgaaa gttggttgcg gtataatcaa ttccgtagag atctaacgtt aggagtatta     780
gatctagtgg cactattccc aagctatgac acgcgtgttt atccaatgaa taccagtgct     840
caattaacaa gagaaattta tacagatcca attgggagaa caaatgcacc ttcaggattt     900
```

-continued

```
gcaagtacga attggtttaa taataatgca ccatcgtttt ctgccataga ggctgccatt    960
ttcaggcctc cgcatctact tgattttcca gaacaactta caatttacag tgcatcaagc   1020
cgttggagta gcactcaaca tatgaattat tgggtgggac ataggcttaa cttccgccca   1080
ataggaggga cattaaatac ctcaacgcat ggggctacca atacttctat taatcctgta   1140
acattacagt tcacatctcg agacgtttat aggactgaat catttgcagg gacaaatata   1200
ctatttacta ctcctgtgaa tggagtacct tgggctagat ttaattttat aaaccctcag   1260
aatatttatg aaagaggcgc cactacctac agtcaaccgt atcagggagt tgggattcaa   1320
ttatttgatt cagaaactga attaccacca gaaacaacag aacgaccaaa ttatgaatca   1380
tatagtcata gattatctca tataggacta atcataggaa acactttgag agcaccagtc   1440
tattcttgga cgcaccgtag tgcagatcgt acgaatacga ttggaccaaa tagaattact   1500
caaattcctg cagtgaaggg aagatttctt tttaatggtt ctgtaatttc aggaccagga   1560
tttactggtg gagacgtagt tagattgaat aggaataatg gtaatattca aaatagaggg   1620
tatattgaag ttccaattca attcacgtcg acatctacca gatatcgagt tcgagtacgt   1680
tatgcttctg taacctcgat tgagctcaat gttaatttgg gcaattcatc aatttttacg   1740
aacacattac cagcaacagc tgcatcatta gataatctac aatcagggga ttttggttat   1800
gttgaaatca acaatgcttt tacatccgca acaggtaata tagtaggtgc tagaaatttt   1860
agtgcaaatg cagaagtaat aatagacaga tttgaattta tcccagttac tgcaaccttc   1920
gaggcagaat atgatttaga aagagcacaa aag                               1953
```

```

<210> SEQ ID NO 5
<211> LENGTH: 655
<212> TYPE: PRT
<213> ORGANISM: Artificial Sequence
<220> FEATURE:
<223> OTHER INFORMATION: Cry1B variant

<400> SEQUENCE: 5

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175
```

```
Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Thr Gln His
            340                 345                 350

Met Asn Tyr Trp Val Gly His Arg Leu Asn Phe Arg Pro Ile Gly Gly
                355                 360                 365

Thr Leu Asn Thr Ser Thr His Gly Ala Thr Asn Thr Ser Ile Asn Pro
            370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Thr
```

```
          595                 600                 605
Asn Ala Phe Thr Ser Ala Thr Gly Asn Val Val Gly Val Arg Asn Phe
    610                 615                 620
Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                645                 650                 655

<210> SEQ ID NO 6
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 6
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg gcaacaacat caatccgttg gtcagcgcga gcaccgtgca aaccggcatt     180
aacattgccg tcgtatcct gggtgtcctg ggcgttccgt ttgcgggtca gctggcgagc     240
ttttacagct ttatcgttgg tgagttgtgg ccgtcgggtc gtgacccttg ggagattttc     300
atggagcacg tcgagcaact ggtgcgccaa cagattacgg agaatgcgcg caacaccgct     360
ctggcgcgtc tgcaaggtct gggtgcaagc ttccgcgctt accagcagtc cctggaagat     420
tggttggaaa accgtgataa tgcgcgcact cgctccgtcc tgtacacgca gtacatcgcg     480
ctggagctgg acttcttgaa cgcgatgccg ctgtttgcaa tcaacaacca gcaagtgccg     540
ctgctgatgg tctacgccca agccgcgaat ctgcacttgc tgctgctgcg cgacgcatct     600
ctgttcggta gcgaatttgg cctgaccagc caggagatcc agcgctacta tgagcgtcag     660
gccgagaaaa cgcgtgaata ctccgactac tgcgctcgtt ggtacaacac gggtctgaac     720
aatctgcgtg gcaccaacgc ggagtcctgg ctgcgttaca accagtttcg tcgcgatctg     780
accctgggtg ttttggattt ggttgcgctg tttccgagct atgacacccg catctatccg     840
atcaacacca gcgcgcaact gactcgtgaa atctatacgg accgattgg ccgcactaat     900 gcaccgtccg gtttcgcaag caccaactgg ttcaataaca atgcaccgag cttcagcgcg     960
atcgaggccg cgatctttcg tccgccgcac ctgttggact ccccgagca gctgaccatc    1020 tactctgcat ctagccgttg gagcagcacg cagcacatga attactgggt tggccatcgt    1080
ctgaacttcc gcccgattgg tggtacgctg aacactagca cgcacggtgc cactaacacg    1140
agcatcaacc cggtgacgct gcaattcacc agccgtgatg tttaccgtac cgagtcctac    1200
gccggcatca acattctgct gaccaccccg gttaacggcg tcccttgggc tgtttcaat    1260 tggcgtaacc cactgaatag cctgcgtggt tctttgctgt acaccattgg ttataccggc    1320
gtcggtacgc aactgtttga tcggaaact gagctgccac cggaaactac cgagcgtccg    1380
aactacgaat cttatagcca ccgtctgtcc aatatccgtc tgatcatcgg caacaccctg    1440
cgtgcgccgg tgtacagctg gacccatcgt agcgccgatc gcacgaacac gattgccacc    1500
aacattatca cccagatccc ggcagtgaaa ggcaactttc tgtttaacgg cagcgtgatc    1560
agcggtccag gttttaccgg cggtgacctg gtgcgcctga acaacagcgg caacaatatc    1620
caaaaccgtg gttatatcga agtcccgatt caattcatca gcacgagcac ccgttaccgc    1680
gtccgtgttc gctacgcatc cgttacgccg atccaactga gcgttaactg gggcaattcc    1740
```

```
aacattttca gcagcattgt ccctgctacg gcgacctctc tggacaattt gcagagccgt   1800
aacttcggct atttcgaaag caccaacgct ttcaccagcg ctacgggcaa tgtggttggt   1860
gttcgcaatt tcagcgagaa tgcgggcgtc atcattgacc gttttgagtt tatcccggtg   1920
accgcgacct tcgaagcgga gtacgatctg gagcgtgcgc aggaa                   1965
```

<210> SEQ ID NO 7
<211> LENGTH: 655
<212> TYPE: PRT
<213> ORGANISM: Artificial Sequence
<220> FEATURE:
<223> OTHER INFORMATION: Cry1B variant

<400> SEQUENCE: 7

```
Met Pro Ser Asn Arg Lys Asn Glu Asn Gly Ile Ile Asn Ala Leu Ser
1               5                   10

```
             325                 330                 335
Gln Leu Thr Ile Phe Ser Val Leu Ser Arg Trp Ser Ser Thr Gln His
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser His Ile Gly Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Thr Gly Pro Asn Arg Ile Thr Gln Ile Pro Ala Val Lys Gly Asn
                500                 505                 510

Phe Leu Phe Asn Gly Ser Val Ile Ser Gly Pro Gly Phe Thr Gly Gly
            515                 520                 525

Asp Leu Val Arg Leu Asn Asn Ser Gly Asn Asn Ile Gln Asn Arg Gly
    530                 535                 540

Tyr Leu Glu Val Pro Ile Gln Phe Ile Ser Thr Ser Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
                580                 585                 590

Ser Leu Asp Asn Leu Gln Ser Arg Asp Phe Gly Tyr Phe Glu Ser Thr
            595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 8
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 8
atgccgagca atcgtaagaa tgaaaatgga atcattaacg cgctgtccat ccctgcagtg    60
agcaatcaca gcgcgcagat ggatttgagc ccggatgcgc gtatcgagga cagcctgtgt   120
gtcgccgagg taaacaatat tgatccgttc gtcagcgcga gcaccgtgca aaccggcatt   180
aacattgccg gtcgtatcct gggtgtcctg ggcgttccgt ttgcgggtca gctggcgagc   240

```
ttttacagct ttatcgttgg tgagttgtgg ccgtcgggtc gtgacccttg ggagattttc      300
ttggagcacg tcgagcaact ggtgcgccaa cagattacgg agaatgcgcg caacaccgct      360
ctggcgcgtc tgcaaggtct gggtgcaagc ttccgcgctt accagcagtc cctggaagat      420
tggttggaaa accgtgatga tgcgcgcact cgctccgtcc tgtacacgca gtacatcgcg      480
ctggagctgg acttcttgaa cgcgatgccg ctgtttgcaa tcaacaacca gcgagtgccg      540
ctgctgatgt ctacgcccca agccgcgaat ctgcacttgc tgctgctgcg cgacgcatct      600
ctgttcggta gcgaatttgg cctgaccagc caggagatcc agcgctacta tgagcgtcag      660
gccgagaaaa cgcgtgaata ctccgactac tgcgctcgtt ggtacaacac gggtctgaac      720
aatctgcgtg gcaccaacgc ggagtcctgg ctgcgttata accagtttcg tcgcgatctg      780
accctgggtg tattggattt ggttgcgctg tttccgagct atgacacccg cgtgtatccg      840
atcaacacca gcgcgcaact gactcgtgaa atctatacgg acccgattgg ccgcactaat      900
gcaccgtccg gtttcgcaag caccaactgg ttcaataaca atgcaccgag cttcagcgcg      960
atcgaggcgg ctgtcatccg tccgccgcac ctgttggact cccggagca gctgaccatc     1020 ttttctgtgt tgtctcgttg gagcagcacg cagcacatga attactgggt tggccatcgt     1080
ctggaaagcc gcaccattcg cggtagcctg agcactagca cgcacggtaa tactaacacg     1140
agcatcaacc cggtgacgct gcaattcacc agccgtgatg tttaccgtac cgagtcctac     1200
gccggcatca acattctgct gaccaccccg gttaacggcg tcccttgggc tcgtttcaat     1260
tggcgtaacc cactgaatag cctgcgtggt tctttgctgt acaccattgg ttataccggc     1320
gtcggtacgc aactgtttga ctcggaaact gagctgccac cggaaactac cgagcgtccg     1380
aactacgaat cttatagcca ccgtctgtcc catattggtc tgatcatcgg caacaccctg     1440
cgtgcaccgg tgtacagctg gacccatcgt agcgccgatc gcacgaacac gactggtccg     1500
aaccgtatca cccagatccc ggcagtgaaa ggcaactttc tgtttaacgg cagcgtgatc     1560
agcggtccag gttttaccgg cggtgacctg gtgcgcctga caacagcgg caacaatatc     1620 caaaaccgtg ttatctggaa gtcccgatt caattcatca gcacgagcac ccgttaccgc     1680
gtccgtgttc gctacgcatc cgttacgccg atccaactga gcgttaactg gggcaattcc     1740
aacattttca gcagcattgt ccctgctacg gcgacctctc tggacaattt gcagagccgt     1800
gacttcggct atttcgaaag caccaacgct ttcaccagcg ctacgggcaa tgtggttggt     1860
gttcgcaatt tcagcgagaa tgcgggcgtc atcattgacc gttttgagtt tatcccggtg     1920
accgcgacct tcgaagcgga gtacgatctg gagcgtgcgc aggaa                    1965
```

<210> SEQ ID NO 9
<211> LENGTH: 650
<212> TYPE: PRT
<213> ORGANISM: Artificial Sequence
<220> FEATURE:
<223> OTHER INFORMATION: Cry1B variant

<400> SEQUENCE: 9

```
Met Pro Ser Asn Arg Lys Asn Glu Asn Glu Ile Ile Asn Ala Val Ser
1               5                   10                  15

Asn His Ser Ala Gln Met Asp Leu Ser Pro Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Asn Ile Ala Gly Arg Ile Leu Gly Val
```

```
              50                  55                  60
Leu Gly Val Pro Phe Ala Gly Gln Leu Ala Ser Phe Tyr Ser Phe Leu
 65                  70                  75                  80

Val Gly Glu Leu Trp Pro Ser Gly Arg Asp Pro Trp Glu Ile Phe Met
                 85                  90                  95

Glu His Val Glu Gln Ile Val Arg Gln Gln Ile Thr Glu Asn Ala Arg
                100                 105                 110

Asn Thr Ala Leu Ala Arg Leu Gln Gly Leu Gly Ala Ser Phe Arg Ala
                115                 120                 125

Tyr Gln Gln Ser Leu Glu Asp Trp Leu Glu Asn Arg Asp Asp Ala Arg
            130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Asn Asn Gln Gln Val Pro Leu
                165                 170                 175

Leu Met Val Tyr Ala Gln Ala Ala Asn Leu His Leu Leu Leu Leu Arg
                180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Ala Glu Lys Thr Arg Glu Tyr Ser Asp
            210                 215                 220

Tyr Cys Ala Arg Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
                260                 265                 270

Ile Tyr Pro Ile Asn Thr Ser Ala Gln Leu Thr Arg Glu Ile Tyr Thr
            275                 280                 285

Asp Pro Ile Gly Arg Thr Asn Ala Pro Ser Gly Phe Ala Ser Thr Asn
            290                 295                 300

Trp Phe Asn Asn Asn Ala Pro Ser Phe Ser Ala Ile Glu Ala Ala Val
305                 310                 315                 320

Ile Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
                340                 345                 350

Gly His Arg Leu Asn Phe Arg Pro Ile Gly Gly Thr Leu Asn Thr Ser
            355                 360                 365

Thr His Gly Ala Thr Asn Thr Ser Ile Asn Pro Val Thr Leu Gln Phe
370                 375                 380

Thr Ser Arg Asp Val Tyr Arg Thr Glu Ser Tyr Ala Gly Ile Asn Ile
385                 390                 395                 400

Leu Leu Thr Thr Pro Val Asn Gly Val Pro Trp Ala Arg Phe Asn Trp
                405                 410                 415

Arg Asn Pro Leu Asn Ser Leu Arg Gly Ser Leu Leu Tyr Thr Ile Gly
                420                 425                 430

Tyr Thr Gly Val Gly Ile Gln Leu Phe Asp Ser Glu Thr Glu Leu Pro
            435                 440                 445

Pro Glu Thr Thr Glu Arg Pro Asn Tyr Glu Ser Tyr Ser His Arg Leu
450                 455                 460

Ser Asn Ile Arg Leu Ile Ser Gly Asn Thr Leu Arg Ala Pro Val Tyr
465                 470                 475                 480
```

```
Ser Trp Thr His Arg Ser Ala Asp Arg Thr Asn Thr Ile Ala Thr Asn
                485                 490                 495

Ile Ile Thr Gln Ile Pro Ala Val Lys Gly Asn Phe Leu Phe Asn Gly
            500                 505                 510

Ser Val Thr Ser Gly Pro Gly Phe Thr Gly Gly Asp Leu Val Arg Leu
        515                 520                 525

Asn Asn Ser Gly Asn Asn Ile Gln Asn Arg Gly Tyr Leu Glu Val Pro
    530                 535                 540

Ile Gln Phe Ile Ser Thr Ser Thr Arg Tyr Arg Val Arg Val Arg Tyr
545                 550                 555                 560

Ala Ser Val Thr Pro Ile Gln Leu Ser Val Asn Trp Gly Asn Ser Asn
                565                 570                 575

Ile Phe Ser Ser Ile Val Pro Ala Thr Ala Thr Ser Leu Asp Asn Leu
            580                 585                 590

Gln Ser Arg Asp Phe Gly Tyr Phe Glu Ser Thr Asn Ala Phe Thr Ser
        595                 600                 605

Ala Thr Gly Asn Val Val Gly Val Arg Asn Phe Ser Glu Asn Ala Gly
    610                 615                 620

Val Ile Ile Asp Arg Phe Glu Phe Ile Pro Val Thr Ala Thr Phe Glu
625                 630                 635                 640

Ala Glu Tyr Asp Leu Glu Arg Ala Gln Glu
                645                 650
```

<210> SEQ ID NO 10
<211> LENGTH: 1950
<212> TYPE: DNA
<213> ORGANISM: Artificial Sequence
<220> FEATURE:
<223> OTHER INFORMATION: coding sequence of Cry1B variant

<400> SEQUENCE: 10

```
atgccgagca atcgtaagaa tgaaaatgaa atcattaacg cagtgagcaa tcacagcgcg      60
cagatggatt tgagcccgga tgcgcgtatc gaggacagcc tgtgtgtcgc cgaggtaaac     120
aatattgatc cgttcgtcag cgcgagcacc gtgcaaaccg gcattaacat tgccggtcgt     180
atcctgggtg tcctgggcgt tccgtttgcg ggtcagctgg cgagctttta cagcttttg      240 gttggtgagt tgtggccgtc gggtcgtgac ccttgggaga ttttcatgga gcacgtcgag     300
caaattgtgc gccaacagat tacggagaat gcgcgcaaca ccgctctggc gcgtctgcaa     360
ggtctgggtg caagcttccg cgcttaccag cagtccctgg aagattggtt ggaaaaccgt     420
gatgatgcgc gcactcgctc cgtcctgtac acgcagtaca tcgcgctgga gctggacttc     480
ttgaacgcga tgccgctgtt tgcaatcaac aaccagcaag tgccgctgct gatggtctac     540
gcccaagccg cgaatctgca cttgctgctg ctgcgcgacg catctctgtt cggtagcgaa     600
tttggcctga ccagccagga gatccagcgc tactatgagc gtcaggccga gaaaacgcgt     660
gaatactccg actactgcgc tcgttggtac aacacgggtc tgaacaatct gcgtggcacc     720
aacgcggagt cctggctgcg ttacaaccag tttcgtcgcg atctgaccct gggtgttttg     780
gatttggttg cgctgtttcc gagctatgac acccgcatct atccgatcaa caccagcgcg     840
caactgactc gtgaaatcta tacggacccg attggccgca ctaatgcacc gtccggtttc     900
gcaagcacca actggttcaa taacaatgca ccgagcttca gcgcgatcga ggcggctgtc     960
atccgtccgc cgcacctgtt ggacttcccg gagcagctga ccatctactc tgcatctagc    1020
cgttggagca gcacgcagca catgaattac tgggttggcc atcgtctgaa cttccgcccg    1080
```

```
attggtggta cgctgaacac tagcacgcac ggtgccacta acacgagcat caacccggtg    1140
acgctgcaat tcaccagccg tgatgtttac cgtaccgagt cctacgccgg gatcaacatt    1200
ctgctgacca ccccggttaa cggcgtccct tgggctcgtt tcaattggcg taacccactg    1260
aatagcctgc gtggttcttt gctgtacacc attggttata ccggcgtcgg tattcaactg    1320
tttgactcgg aaactgagct gccaccggaa actaccgagc gtccgaacta cgaatcttat    1380
agccaccgtc tgtccaatat ccgtctgatc agcggcaaca ccctgcgtgc gccggtgtac    1440
agctggaccc accgtagcgc cgatcgcacg aacacgattg ccaccaacat tatcacccag    1500
atcccggcag tgaaaggcaa cttctgtttt aacggcagcg tgaccagcgg tccaggtttt    1560
accggcggtg acctggtgcg cctgaacaac agcggcaaca atatccaaaa ccgtggttat    1620
ctggaagtcc cgattcaatt catcagcacg agcacccgtt accgcgtccg tgttcgctac    1680
gcatccgtta cgccgatcca actgagcgtt aactggggca attccaacat tttcagcagc    1740
attgtccctg ctacggcgac ctctctggac aatttgcaga gccgtgactt cggctatttc    1800
gaaagcacca acgctttcac cagcgctacg ggcaatgtgg ttggtgttcg caatttcagc    1860
gagaatgcgg cgtcatcat tgaccgtttt gagtttatcc cggtgaccgc gaccttcgaa    1920
gcggagtacg atctggagcg tgcgcaggaa                                     1950
```

<210> SEQ ID NO 11
<211> LENGTH: 655
<212> TYPE: PRT
<213> ORGANISM: Artificial Sequence
<220> FEATURE:
<223> OTHER INFORMATION: Cry1B variant

<400> SEQUENCE: 11

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val

```
Thr Ser Gln Glu Ile Gln Arg Tyr Tyr Glu Arg Gln Ala Glu Lys Thr
    210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
            245                 250                 255
Arg Arg Asp Leu Thr Leu Gly Val Leu Asp Leu Val Ala Leu Phe Pro
                260                 265                 270
Ser Tyr Asp Thr Arg Ile Tyr Pro Ile Asn Thr Ser Ala Gln Leu Thr
            275                 280                 285
Arg Glu Ile Tyr Thr Asp Pro Ile Gly Arg Thr Asn Ala Pro Ser Gly
    290                 295                 300
Phe Ala Ser Thr Asn Trp Phe Asn Asn Asn Ala Pro Ser Phe Ser Ala
305                 310                 315                 320
Ile Glu Ala Ala Ile Phe Arg Pro Pro His Leu Leu Asp Phe Pro Glu
                325                 330                 335
Gln Leu Thr Ile Tyr Ser Ala Ser Ser Arg Trp Ser Ser Thr Gln His
            340                 345                 350
Met Asn Tyr Trp Val Gly His Arg Leu Asn Phe Arg Pro Ile Gly Gly
    355                 360                 365
Thr Leu Asn Thr Ser Thr His Gly Ala Thr Asn Thr Ser Ile Asn Pro
370                 375                 380
Val Thr Leu Gln Phe Thr Ser Arg Asp Val Tyr Arg Thr Glu Ser Tyr
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
            435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ile Gly Asn Thr Leu
465                 470                 475                 480
Arg Ala Pro Val Tyr Ser Trp Thr His Arg Ser Ala Asp Arg Thr Asn
            485                 490                 495
Thr Ile Ala Thr Asn Ile Ile Thr Gln Ile Pro Ala Val Lys Gly Asn
            500                 505                 510
Phe Leu Phe Asn Gly Ser Val Ile Ser Gly Pro Gly Phe Thr Gly Gly
    515                 520                 525
Asp Leu Val Arg Leu Asn Asn Ser Gly Asn Asn Ile Gln Asn Arg Gly
530                 535                 540
Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Gln Leu Ser Val Asn
                565                 570                 575
Trp Gly Asn Ser Asn Ile Phe Ser Arg Ile Val Pro Ala Thr Ala Tyr
            580                 585                 590
Ser Leu Asp Asn Leu Gln Ser Arg Asn Phe Gly Tyr Phe Glu Ser Thr
            595                 600                 605
Asn Ala Phe Thr Ser Ala Thr Gly Asn Val Val Gly Val Arg Asn Phe
    610                 615                 620
```

| Ser | Glu | Asn | Ala | Gly | Val | Ile | Ile | Asp | Arg | Phe | Glu | Phe | Ile | Pro | Val |
|---|---|---|---|---|---|---|---|---|---|---|---|---|---|---|---|
| 625 | | | | 630 | | | | | 635 | | | | | 640 | |

| Thr | Ala | Thr | Phe | Glu | Ala | Glu | Tyr | Asp | Leu | Glu | Arg | Ala | Gln | Glu |
|---|---|---|---|---|---|---|---|---|---|---|---|---|---|---|
| | | 645 | | | | | 650 | | | | | 655 | | |

<210> SEQ ID NO 12
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 12

| | | |
|---|---|---|
| atgccgagca atcgtaagaa tgaaaatgaa atcattaacg cactgtccat ccctgcagtg | 60 |
| agcaatcaca gcgcgcagat ggatttgagc ctggatgcgc gtatcgagga cagcctgtgt | 120 |
| attgccgagg caacaacat caatccgttg gtcagcgcga gcaccgtgca aaccggcatt | 180 |
| aacattgccg tcgtatcct gggtgtcctg ggcgttccgt ttgcgggtca gctggcgagc | 240 |
| ttttacagct ttatcgttgg tgagttgtgg ccgtcgggtc gtgaccctg ggagattttc | 300 |
| atggagcacg tcgagcaact ggtgcgccaa cagattacgg agaatgcgcg caacaccgct | 360 |
| ctggcgcgtc tgcaaggtct gggtgcaagc ttccgcgctt accagcagtc cctggaagat | 420 |
| tggttggaaa accgtgataa tgcgcgcact cgctccgtcc tgtacacgca gtacatcgcg | 480 |
| ctggagctgg acttcttgaa cgcgatgccg ctgtttgcaa tcaacaacca gcaagtgccg | 540 |
| ctgctgatgg tctacgccca agccgcgaat ctgcacttgc tgctgctgcg cgacgcatct | 600 |
| ctgttcggta gcgaatttgg cctgaccagc caggagatcc agcgctacta tgagcgtcag | 660 |
| gccgagaaaa cgcgtgaata ctccgactac tgcgctcgtt ggtacaacac gggtctgaac | 720 |
| aatctgcgtg gcaccaacgc ggagtcctgg ctgcgttaca accagttttcg tcgcgatctg | 780 |
| accctgggtg ttttggattt ggttgcgctg tttccgagct atgacacccg catctatccg | 840 |
| atcaacacca gcgcgcaact gactcgtgaa atctatacgg cccgattgg ccgcactaat | 900 |
| gcaccgtccg gtttcgcaag caccaactgg ttcaataaca atgcaccgag cttcagcgcg | 960 |
| atcgaggccg cgatctttcg tccgccgcac ctgttggact cccggagca gctgaccatc | 1020 |
| tactctgcat ctagccgttg gagcagcacg cagcacatga attactgggt tggccatcgt | 1080 |
| ctgaacttcc gcccgattgg tggtacgctg aacactagca cgcacggtgc cactaacacg | 1140 |
| agcatcaacc cggtgacgct gcaattcacc agccgtgatg tttaccgtac cgagtcctac | 1200 |
| gccggcatca acattctgct gaccaccccg gttaacggcg tcccttgggc tcgtttcaat | 1260 |
| tggcgtaacc cactgaatag cctgcgtggt tctttgctgt acaccattgg ttataccggc | 1320 |
| gtcggtacgc aactgtttga ctcggaaact gagctgccac cggaaactac cgagcgtccg | 1380 |
| aactacgaat cttatagcca ccgtctgtcc aatatccgtc tgatcatcgg caacaccctg | 1440 |
| cgtgcgccgg tgtacagctg gacccatcgt agcgccgatc gcacgaacac gattgccacc | 1500 |
| aacattatca cccagatccc ggcagtgaaa ggcaactttc tgtttaacgg cagcgtgatc | 1560 |
| agcggtccag gttttaccgg cggtgacctg gtgcgcctga caacagcgg caacaatatc | 1620 |
| caaaaccgtg gttatatcga agtcccgatt caattcatca gcacgagcac ccgttaccgc | 1680 |
| gtccgtgttc gctacgcatc cgttacgccg atccaactga gcgttaactg ggcaattcc | 1740 |
| aacattttca gccgcattgt ccctgctacg gcgtactctc tggacaattt gcagagccgt | 1800 |
| aacttcggct atttcgaaag caccaacgct ttcaccagcg ctacgggcaa tgtggttggt | 1860 |
| gttcgcaatt tcagcgagaa tgcgggcgtc atcattgacc gttttgagtt tatcccggtg | 1920 |

```
accgcgacct tcgaagcgga gtacgatctg gagcgtgcgc aggaa                    1965
```

<210> SEQ ID NO 13
<211> LENGTH: 655
<212> TYPE: PRT
<213> ORGANISM: Artificial Sequence
<220> FEATURE:
<223> OTHER INFORMATION: Cry1B variant

<400> SEQUENCE: 13

| Met | Pro | Ser | Asn | Arg | Lys | Asn | Glu | Asn | Glu | Ile | Ile | Asn | Ala | Leu | Ser |
|---|---|---|---|---|---|---|---|---|---|---|---|---|---|---|---|
| 1 | | | | 5 | | | | | 10 | | | | | 15 | |

| Ile | Pro | Ala | Val | Ser | Asn | His | Ser | Ala | Gln | Met | Asp | Leu | Ser | Leu | Asp |
|---|---|---|---|---|---|---|---|---|---|---|---|---|---|---|---|
| | | | 20 | | | | | 25 | | | | | 30 | | |

| Ala | Arg | Ile | Glu | Asp | Ser | Leu | Cys | Ile | Ala | Glu | Gly | Asn | Asn | Ile | Asn |
| | | 35 | | | | | 40 | | | | | 45 | | | |

| Pro | Leu | Val | Ser | Ala | Ser | Thr | Val | Gln | Thr | Gly | Ile | Asn | Ile | Ala | Gly |
| | 50 | | | | | 55 | | | | | 60 | | | | |

| Arg | Ile | Leu | Gly | Val | Leu | Gly | Val | Pro | Phe | Ala | Gly | Gln | Leu | Ala | Ser |
| 65 | | | | | 70 | | | | | 75 | | | | | 80 |

| Phe | Tyr | Ser | Phe | Ile | Val | Gly | Glu | Leu | Trp | Pro | Ser | Gly | Arg | Asp | Pro |
| | | | | 85 | | | | | 90 | | | | | 95 | |

| Trp | Glu | Ile | Phe | Met | Glu | His | Val | Glu | Gln | Leu | Val | Arg | Gln | Gln | Ile |
| | | | 100 | | | | | 105 | | | | | 110 | | |

| Thr | Glu | Asn | Ala | Arg | Asn | Thr | Ala | Leu | Ala | Arg | Leu | Gln | Gly | Leu | Gly |
| | | 115 | | | | | 120 | | | | | 125 | | | |

| Ala | Ser | Phe | Arg | Ala | Tyr | Gln | Gln | Ser | Leu | Glu | Asp | Trp | Leu | Glu | Asn |
| | 130 | | | | | 135 | | | | | 140 | | | | |

| Arg | Asp | Asn | Ala | Arg | Thr | Arg | Ser | Val | Leu | Tyr | Thr | Gln | Tyr | Ile | Ala |
| 145 | | | | | 150 | | | | | 155 | | | | | 160 |

| Leu | Glu | Leu | Asp | Phe | Leu | Asn | Ala | Met | Pro | Leu | Phe | Ala | Ile | Asn | Asn |
| | | | | 165 | | | | | 170 | | | | | 175 | |

| Gln | Gln | Val | Pro | Leu | Leu | Met | Val | Tyr | Ala | Gln | Ala | Ala | Asn | Leu | His |
| | | | 180 | | | | | 185 | | | | | 190 | | |

| Leu | Leu | Leu | Leu | Arg | Asp | Ala | Ser | Leu | Phe | Gly | Ser | Glu | Phe | Gly | Leu |
| | | 195 | | | | | 200 | | | | | 205 | | | |

| Thr | Ser | Gln | Glu | Ile | Gln | Arg | Tyr | Tyr | Glu | Arg | Gln | Ala | Glu | Lys | Thr |
| | 210 | | | | | 215 | | | | | 220 | | | | |

| Arg | Glu | Tyr | Ser | Asp | Tyr | Cys | Ala | Arg | Trp | Tyr | Asn | Thr | Gly | Leu | Asn |
| 225 | | | | | 230 | | | | | 235 | | | | | 240 |

| Asn | Leu | Arg | Gly | Thr | Asn | Ala | Glu | Ser | Trp | Leu | Arg | Tyr | Asn | Gln | Phe |
| | | | | 245 | | | | | 250 | | | | | 255 | |

| Arg | Arg | Asp | Leu | Thr | Leu | Gly | Val | Leu | Asp | Leu | Val | Ala | Leu | Phe | Pro |
| | | | 260 | | | | | 265 | | | | | 270 | | |

| Ser | Tyr | Asp | Thr | Arg | Ile | Tyr | Pro | Ile | Asn | Thr | Ser | Ala | Gln | Leu | Thr |
| | | 275 | | | | | 280 | | | | | 285 | | | |

| Arg | Glu | Ile | Tyr | Thr | Asp | Pro | Ile | Gly | Arg | Thr | Asn | Ala | Pro | Ser | Gly |
| | 290 | | | | | 295 | | | | | 300 | | | | |

| Phe | Ala | Ser | Thr | Asn | Trp | Phe | Asn | Asn | Asn | Ala | Pro | Ser | Phe | Ser | Ala |
| 305 | | | | | 310 | | | | | 315 | | | | | 320 |

| Ile | Glu | Ala | Ala | Ile | Phe | Arg | Pro | Pro | His | Leu | Leu | Asp | Phe | Pro | Glu |
| | | | | 325 | | | | | 330 | | | | | 335 | |

| Gln | Leu | Thr | Ile | Tyr | Ser | Ala | Ser | Ser | Arg | Trp | Ser | Ser | Thr | Gln | His |
| | | | 340 | | | | | 345 | | | | | 350 | | |

-continued

```
Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400
Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
        435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ile Gly Asn Thr Leu
465                 470                 475                 480
Arg Ala Pro Val Tyr Ser Trp Thr His Arg Ser Ala Asp Arg Thr Asn
                485                 490                 495
Thr Ile Ala Thr Asn Ile Ile Thr Gln Ile Pro Ala Val Lys Gly Asn
            500                 505                 510
Phe Leu Phe Asn Gly Ser Val Ile Ser Gly Pro Gly Phe Thr Gly Gly
        515                 520                 525
Asp Leu Val Arg Leu Asn Asn Ser Gly Asn Asn Ile Gln Asn Arg Gly
    530                 535                 540
Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Arg Leu Ser Val Asn
                565                 570                 575
Trp Gly Asn Ser Asn Ile Phe Ser Ser Ile Val Pro Ala Thr Ala Thr
            580                 585                 590
Ser Leu Asp Asn Leu Gln Ser Arg Asn Phe Gly Tyr Phe Glu Ser Arg
        595                 600                 605
Asn Ala Phe Thr Ser Ala Thr Gly Asn Val Val Gly Val Arg Asn Phe
    610                 615                 620
Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                645                 650                 655

<210> SEQ ID NO 14
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 14
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg gcaacaacat caatccgttg gtcagcgcga gcaccgtgca aaccggcatt     180
aacattgccg gtcgtatcct gggtgtcctg ggcgttccgt ttgcgggtca gctggcgagc     240
ttttacagct ttatcgttgg tgagttgtgg ccgtcgggtc gtgacccttg ggagattttc     300
atggagcacg tcgagcaact ggtgcgccaa cagattacgg agaatgcgcg caacaccgct     360
```

```
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccg cgatctttcg tccgccgcac ctgttggact ccccggagca gctgaccatc   1020
tactctgcat ctagccgttg gagcagcacg cagcacatga attactgggt tggccatcgt   1080
ctgaacttcc gcccgattgg tggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcgg caacaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga caacagcgg caacaatatc   1620
caaaaccgtg gttatatcga agtcccgatt caattcatca gcacgagcac ccgttaccgc   1680
gtccgtgttc gctacgcatc cgttacgccg atccgcctga cgttaactg gggcaattcc   1740
aacattttca gcagcattgt ccctgctacg gcgacctctc tggacaattt gcagagccgt   1800
aacttcggct atttcgaaag ccgcaacgct ttcaccagcg ctacgggcaa tgtggttggt   1860
gttcgcaatt tcagcgagaa tgcgggcgtc atcattgacc gttttgagtt tatcccggtg   1920
accgcgacct tcgaagcgga gtacgatctg gagcgtgcgc aggaa              1965
```

<210> SEQ ID NO 15
<211> LENGTH: 655
<212> TYPE: PRT
<213> ORGANISM: Artificial Sequence
<220> FEATURE:
<223> OTHER INFORMATION: Cry1B variant

<400> SEQUENCE: 15

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80
```

```
Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
            130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
    275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
            355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
```

```
                    500                 505                 510
Phe Leu Phe Asn Gly Ser Val Ile Ser Gly Pro Gly Phe Thr Gly Gly
            515                 520                 525

Asp Leu Val Arg Leu Asn Asn Ser Gly Asn Asn Ile Gln Asn Arg Gly
        530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 16
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 16
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg caacaacat caatccgttg tcagcgcga gcaccgtgca aaccggcatt       180
aacattgccg gtcgtatcct gggtgtcctg ggcgttccgt ttgcgggtca gctggcgagc     240
ttttacagct ttatcgttgg tgagttgtgg ccgtcgggtc gtgacccttg ggagattttc     300
atggagcacg tcgagcaact ggtgcgccaa cagattacg agaatgcgcg caacaccgct     360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca gccgcgaat ctgcacttgc tgctgctgcg cgacgcatct     600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggatt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccc gatctttcg tccgccgcac ctgttggact cccggagca gctgaccatc    1020 tactctgcat ctagccgttg gagcagcacg cagcacatga attactgggt tggccatcgt    1080
ctgaacttcc gcccgattgg tggtacgctg aacactagca cgcacggtgc cactaacacg    1140
agcatcaacc cggtgacgct gcaattcacc agccgtgatg tttaccgtac cgagtcctac    1200
```

-continued

```
gccggcatca acattctgct gaccaccccg gttaacgg

```
                225                 230                 235                 240
Asn Leu Arg Gly Thr Asn Ala Glu Ser Trp Leu Arg Tyr Asn Gln Phe
                    245                 250                 255
Arg Arg Asp Leu Thr Leu Gly Val Leu Asp Leu Val Ala Leu Phe Pro
                    260                 265                 270
Ser Tyr Asp Thr Arg Ile Tyr Pro Ile Asn Thr Ser Ala Gln Leu Thr
                    275                 280                 285
Arg Glu Ile Tyr Thr Asp Pro Ile Gly Arg Thr Asn Ala Pro Ser Gly
            290                 295                 300
Phe Ala Ser Thr Asn Trp Phe Asn Asn Asn Ala Pro Ser Phe Ser Ala
305                 310                 315                 320
Ile Glu Ala Ala Ile Phe Arg Pro Pro His Leu Leu Asp Phe Pro Glu
                        325                 330                 335
Gln Leu Thr Ile Tyr Ser Ala Ser Ser Arg Trp Ser Thr Gln His
                    340                 345                 350
Met Asn Tyr Trp Val Gly His Arg Leu Asn Phe Arg Pro Ile Gly Gly
                355                 360                 365
Thr Leu Asn Thr Ser Thr His Gly Ala Thr Asn Thr Ser Ile Asn Pro
        370                 375                 380
Val Thr Leu Gln Phe Thr Ser Arg Asp Val Tyr Arg Thr Glu Ser Tyr
385                 390                 395                 400
Ala Gly Ile Asn Ile Leu Leu Thr Thr Pro Val Asn Gly Val Pro Trp
                    405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
            435                 440                 445
Glu Thr Glu Leu Pro Pro Glu Thr Thr Glu Arg Pro Asn Tyr Glu Ser
        450                 455                 460
Tyr Ser His Arg Leu Ser Asn Ile Arg Leu Ile Ile Ser Gly Thr Leu
465                 470                 475                 480
Arg Ala Pro Val Tyr Ser Trp Thr His Arg Ser Ala Asp Arg Thr Asn
                    485                 490                 495
Thr Ile Ala Thr Asn Ile Ile Thr Gln Ile Pro Ala Val Lys Gly Asn
                500                 505                 510
Phe Leu Phe Asn Gly Ser Val Ile Ser Gly Pro Gly Phe Thr Gly Gly
            515                 520                 525
Asp Leu Val Arg Leu Asn Asn Ser Gly Asn Asn Ile Gln Asn Arg Gly
        530                 535                 540
Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Arg Leu Ser Val Asn
                    565                 570                 575
Trp Gly Asn Ser Asn Ile Phe Ser Ser Ile Val Pro Ala Thr Ala Thr
                580                 585                 590
Ser Leu Asp Asn Leu Gln Ser Arg Asn Phe Gly Tyr Phe Glu Ser Arg
            595                 600                 605
Asn Ala Phe Thr Ser Ala Thr Gly Asn Val Val Gly Val Arg Asn Phe
        610                 615                 620
Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                    645                 650                 655
```

<210> SEQ ID NO 18
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 18

| | | | | | |
|---|---|---|---|---|---|
| atgccgagca | atcgtaagaa | tgaaaatgaa | atcattaacg | cactgtccat | ccctgcagtg   60 |
| agcaatcaca | gcgcgcagat | ggatttgagc | ctggatgcgc | gtatcgagga | cagcctgtgt  120 |
| attgccgagg | caacaacat | caatccgttg | gtcagcgcga | gcaccgtgca | aaccggcatt  180 |
| aacattgccg | gtcgtatcct | gggtgtcctg | ggcgttccgt | ttgcgggtca | gctggcgagc  240 |
| ttttacagct | ttatcgttgg | tgagttgtgg | ccgtcgggtc | gtgacccttg | ggagattttc  300 |
| atggagcacg | tcgagcaact | ggtgcgccaa | gcgattacgc | tgaatgcgcg | caacaccgct  360 |
| ctggcgcgtc | tgcaaggtct | gggtgcaagc | ttccgcgctt | accagcagtc | cctggaagat  420 |
| tggttggaaa | accgtgataa | tgcgcgcact | cgctccgtcc | tgtacacgca | gtacatcgcg  480 |
| ctggagctgg | acttcttgaa | cgcgatgccg | ctgtttgcaa | tcaacaacca | gcaagtgccg  540 |
| ctgctgatgg | tctacgccca | agccgcgaat | ctgcacttgc | tgctgctgcg | cgacgcatct  600 |
| ctgttcggta | gcgaatttgg | cctgaccagc | caggagatcc | agcgctacta | tgagcgtcag  660 |
| gccgagaaaa | cgcgtgaata | ctccgactac | tgcgctcgtt | ggtacaacac | gggtctgaac  720 |
| aatctgcgtg | gcaccaacgc | ggagtcctgg | ctgcgttaca | accagtttcg | tcgcgatctg  780 |
| accctgggtg | ttttggattt | ggttgcgctg | tttccgagct | atgacacccg | catctatccg  840 |
| atcaacacca | gcgcgcaact | gactcgtgaa | atctatacgg | accccgattgg | ccgcactaat  900 |
| gcaccgtccg | gtttcgcaag | caccaactgg | ttcaataaca | atgcaccgag | cttcagcgcg  960 |
| atcgaggccg | cgatctttcg | tccgccgcac | ctgttggact | cccggagca | gctgaccatc 1020 |
| tactctgcat | ctagccgttg | gagcagcacg | cagcacatga | attactgggt | tggccatcgt 1080 |
| ctgaacttcc | gcccgattgg | tggtacgctg | aacactagca | cgcacggtgc | cactaacacg 1140 |
| agcatcaacc | cggtgacgct | gcaattcacc | agccgtgatg | tttaccgtac | cgagtcctac 1200 |
| gccggcatca | acattctgct | gaccaccccg | gttaacggcg | tcccttgggc | tcgtttcaat 1260 |
| tggcgtaacc | cactgaatag | cctgcgtggt | tctttgctgt | acaccattgg | ttataccggc 1320 |
| gtcggtacgc | aactgtttga | ctcggaaact | gagctgccac | cggaaactac | cgagcgtccg 1380 |
| aactacgaat | cttatagcca | ccgtctgtcc | aatatccgtc | tgatcatcag | cggcacccctg 1440 |
| cgtgcgccgg | tgtacagctg | gacccatcgt | agcgccgatc | gcacgaacac | gattgccacc 1500 |
| aacattatca | cccagatccc | ggcagtgaaa | ggcaactttc | tgtttaacgg | cagcgtgatc 1560 |
| agcggtccag | gtttaccgg | cggtgacctg | gtgcgcctga | caacagcgg | caacaatatc 1620 |
| caaaaccgtg | gttatatcga | agtcccgatt | caattcatca | gcacgagcac | ccgttaccgc 1680 |
| gtccgtgttc | gctacgcatc | cgttacgccg | atccgcctga | gcgttaactg | gggcaattcc 1740 |
| aacattttca | gcagcattgt | ccctgctacg | gcgaccctctc | tggacaattt | gcagagccgt 1800 |
| aacttcggct | atttcgaaag | ccgcaacgct | ttcaccagcg | ctacgggcaa | tgtggttggt 1860 |
| gttcgcaatt | tcagcgagaa | tgcgggcgtc | atcattgacc | gttttgagtt | tatcccggtg 1920 |
| accgcgacct | tcgaagcgga | gtacgatctg | gagcgtgcgc | aggaa       1965 |

<210> SEQ ID NO 19

<211> LENGTH: 655
<212> TYPE: PRT
<213> ORGANISM: Artificial Sequence
<220> FEATURE:
<223> OTHER INFORMATION: Cry1B variant

<400> SEQUENCE: 19

| | | | | | | | | | | | | | | | |
|---|---|---|---|---|---|---|---|---|---|---|---|---|---|---|

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
        420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
            485                 490                 495

Thr Ile Ala Thr Asn Ile Ile Thr Gln Ile Pro Ala Val Lys Gly Asn
        500                 505                 510

Phe Leu Phe Asn Gly Ser Val Ile Ser Gly Pro Gly Phe Thr Gly Gly
    515                 520                 525

Asp Leu Val Arg Leu Asn Asn Ser Gly Asn Asn Ile Gln Asn Arg Gly
530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
            565                 570                 575

Trp Gly Asn Ser Asn Ile Phe Ser Ser Ile Val Pro Ala Thr Ala Thr
        580                 585                 590

Ser Leu Asp Asn Leu Gln Ser Arg Asn Phe Gly Tyr Phe Glu Ser Arg
    595                 600                 605

Asn Ala Phe Thr Ser Ala Thr Gly Asn Val Val Gly Val Arg Asn Phe
610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
            645                 650                 655

<210> SEQ ID NO 20
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 20
atgccgagca atcgtaagaa tgaaaatgaa atcattaacg cactgtccat ccctgcagtg     60
agcaatcaca gcgcgcagat ggatttgagc ctggatgcgc gtatcgagga cagcctgtgt    120
attgccgagg caacaacat caatccgttg gtcagcgcga gcaccgtgca aaccggcatt    180
aacattgccg gtcgtatcct gggtgtcctg ggcgttccgt ttgcgggtca gctggcgagc    240
ttttacagct ttatcgttgg tgagttgtgg ccgtcgggtc gtgacccttg gagattttc    300 atggagcacg tcgagcaact ggtgcgccaa gcgattacgc tgaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540

```
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccg cgatctttcg tccgccgcac ctgttggact tcccggagca gctgaccatc   1020
tactctgcat ctagccgttg gagcagcacg cagcacatga attactgggt tggccatcgt   1080
ctgtatttcc gcccgattaa cggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcgg caacaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga acaacagcgg caacaatatc   1620
caaaaccgtg gttatatcga agtcccgatt caattcatca gcacgagcac ccgttaccgc   1680
gtccgtgttc gctacgcatc cgttacgccg atccgcctga gcgttaactg gggcaattcc   1740
aacattttca gcagcattgt ccctgctacg gcgacctctc tggacaattt gcagagccgt   1800
aacttcggct atttcgaaag ccgcaacgct ttcaccagcg ctacgggcaa tgtggttggt   1860
gttcgcaatt tcagcgagaa tgcgggcgtc atcattgacc gttttgagtt tatcccggtg   1920
accgcgacct tcgaagcgga gtacgatctg gagcgtgcgc aggaa                   1965
```

<210> SEQ ID NO 21
<211> LENGTH: 655
<212> TYPE: PRT
<213> ORGANISM: Artificial Sequence
<220> FEATURE:
<223> OTHER INFORMATION: Cry1B variant

<400> SEQUENCE: 21

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Ala Ile
            100                 105                 110
```

```
Thr Leu Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Tyr Phe Arg Pro Ile Gln Gly
            355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
                500                 505                 510

Phe Leu Phe Asn Gly Ser Val Ile Ser Gly Pro Gly Phe Thr Gly Gly
            515                 520                 525
```

```
Asp Leu Val Arg Leu Asn Asn Ser Gly Asn Asn Ile Gln Asn Arg Gly
        530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
            565                 570                 575

Trp Gly Asn Ser Asn Ile Phe Ser Ser Ile Val Pro Ala Thr Ala Thr
        580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
        610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 22
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 22
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg gcaacaacat caatccgttg gtcagcgcga gcaccgtgca aaccggcatt     180
aacattgccg tcgtatcctg ggtgtcctgg gcgttccgt ttgcgggtca gctggcgagc     240
ttttacagct ttatcgttgg tgagttgtgg ccgtcgggtc gtgacccttg ggagattttc     300
atggagcacg tcgagcaact ggtgcgccaa gcgattacgc tgaatgcgcg caacaccgct     360
ctggcgcgtc tgcaaggtct gggtgcaagc ttccgcgctt accagcagtc cctggaagat     420
tggttggaaa ccgtgataa tgcgcgcact cgctccgtcc tgtacacgca gtacatcgcg     480
ctggagctgg acttcttgaa cgcgatgccg ctgtttgcaa tcaacaacca gcaagtgccg     540
ctgctgatgg tctacgccca gccgcgaat ctgcacttgc tgctgctgcg cgacgcatct     600
ctgttcggta gcgaatttgg cctgaccagc caggagatcc agcgctacta tgagcgtcag     660
gccgagaaaa cgcgtgaata ctccgactac tgcgctcgtt ggtacaacac gggtctgaac     720
aatctgcgtg gcaccaacgc ggagtcctgg ctgcgttaca ccagtttcg tcgcgatctg     780 accctgggtg ttttggattt ggttgcgctg tttccgagct atgacacccg catctatccg     840
atcaacacca gcgcgcaact gactcgtgaa atctatacgg acccgattgg ccgcactaat     900
gcaccgtccg gtttcgcaag caccaactgg ttcaataaca atgcaccgag cttcagcgcg     960
atcgaggccg cgatctttcg tccgccgcac ctgttggact cccggagca gctgaccatc    1020 tactctgcat ctagccgttg gagcagcacg cagcacatga attactgggt tggccatcgt    1080
ctgtatttcc gcccgattca gggtacgctg aacactagca cgcacggtgc cactaacacg    1140
agcatcaacc cggtgacgct gcaattcacc agccgtgatg tttaccgtac cgagtcctac    1200
gccggcatca acattctgct gaccaccccg gttaacggcg tcccttgggc tcgtttcaat    1260
tggcgtaacc cactgaatag cctgcgtggt tctttgctgt acaccattgg ttataccggc    1320
gtcggtacgc aactgtttga ctcggaaact gagctgccac cggaaactac cgagcgtccg    1380
```
aactacgaat cttatagcca ccgtctgtcc aatatccgtc tgatcatcgg caacaccctg 1440
cgtgcgccgg tgtacagctg gacccatcgt agcgccgatc gcacgaacac gattgccacc 1500
aacattatca cccagatccc ggcagtgaaa ggcaactttc tgtttaacgg cagcgtgatc 1560
agcggtccag gttttaccgg cggtgacctg gtgcgcctga acaacagcgg caacaatatc 1620
caaaaccgtg gttatatcga agtcccgatt caattcatca gcacgagcac ccgttaccgc 1680
gtccgtgttc gctacgcatc cgttacgccg atccgcctga gcgttaactg gggcaattcc 1740
aacattttca gcagcattgt ccctgctacg gcgacctctc tggacaattt gcagagccgt 1800
aacttcggct atttcgaaag ccgcaacgct ttcaccagcg ctacgggcaa tgtggttggt 1860
gttcgcaatt tcagcgagaa tgcgggcgtc atcattgacc gttttgagtt tatcccggtg 1920
accgcgacct tcgaagcgga gtacgatctg gagcgtgcgc aggaa 1965

<210> SEQ ID NO 23
<211> LENGTH: 663
<212> TYPE: PRT
<213> ORGANISM: Artificial Sequence
<220> FEATURE:
<223> OTHER INFORMATION: Cry1B variant

<400> SEQUENCE: 23

Met Pro Ser Asn Arg Lys Asn Glu Asn Glu Ile Ile Asn Ala Val Ser
1 5 10 15

Asn His Ser Ala Gln Met Asp Leu Ser Leu Asp Ala Arg Ile Glu Asp
20 25 30

Ser Leu Cys Val Ala Glu Val Asn Asn Ile Asp Pro Phe Val Ser Ala
35 40 45

Ser Thr Val Gln Thr Gly Ile Ser Ile Ala Gly Arg Ile Leu Gly Val
50 55 60

Leu Gly Val Pro Phe Ala Gly Gln Leu Ala Ser Phe Tyr Ser Phe Leu
65 70 75 80

Val Gly Glu Leu Trp Pro Ser Gly Arg Asp Pro Trp Glu Ile Phe Met
85 90 95

Glu His Val Glu Gln Ile Val Arg Gln Gln Ile Thr Asp Ser Val Arg
100 105 110

Asp Thr Ala Ile Ala Arg Leu Glu Gly Leu Gly Arg Gly Tyr Arg Ser
115 120 125

Tyr Gln Gln Ala Leu Glu Thr Trp Leu Asp Asn Arg Asn Asp Ala Arg
130 135 140

Ser Arg Ser Ile Ile Arg Glu Arg Tyr Ile Ala Leu Glu Leu Asp Ile
145 150 155 160

Thr Thr Ala Ile Pro Leu Phe Ser Ile Arg Asn Gln Glu Val Pro Leu
165 170 175

Leu Met Val Tyr Ala Gln Ala Ala Asn Leu His Leu Leu Leu Leu Arg
180 185 190

Asp Ala Ser Leu Phe Gly Ser Glu Trp Gly Met Ser Ser Ser Asp Val
195 200 205

Asn Gln Tyr Tyr Gln Glu Gln Ile Arg Tyr Thr Glu Glu Tyr Ser Asn
210 215 220

His Cys Val Gln Trp Tyr Asn Thr Gly Leu Asn Asn Leu Arg Gly Thr
225 230 235 240

Asn Ala Glu Ser Trp Leu Arg Tyr Asn Gln Phe Arg Arg Asp Leu Thr
245 250 255

```
Leu Gly Val Leu Asp Leu Val Ala Leu Phe Pro Ser Tyr Asp Thr Arg
            260                 265                 270

Val Tyr Pro Met Asn Thr Ser Ala Gln Leu Thr Arg Glu Ile Tyr Thr
            275                 280                 285

Asp Pro Ile Gly Arg Thr Asn Ala Pro Ser Gly Phe Ala Ser Thr Asn
        290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                    325                 330                 335

Ser Ala Ser Ser Arg Trp Ser Ser Thr Gln His Met Asn Tyr Trp Val
                340                 345                 350

Gly His Arg Leu Asn Phe Arg Pro Ile Gly Gly Thr Leu Asn Thr Ser
                355                 360                 365

Thr Gln Gly Leu Thr Asn Asn Thr Ser Ile Asn Pro Val Thr Leu Gln
        370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
                420                 425                 430

Gln Pro Tyr Gln Gly Val Gly Ile Gln Leu Phe Asp Ser Glu Thr Glu
                435                 440                 445

Leu Pro Pro Glu Thr Thr Glu Arg Pro Asn Tyr Glu Ser Tyr Ser His
        450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
                500                 505                 510

Gly Gly Thr Ser Val Ile Thr Gly Pro Gly Phe Thr Gly Gly Asp Ile
            515                 520                 525

Leu Arg Arg Asn Thr Phe Gly Asp Phe Val Ser Leu Gln Val Asn Ile
        530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
            595                 600                 605

Asn Pro Phe Ser Phe Arg Ala Asn Pro Asp Ile Ile Gly Ile Ser Glu
        610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Arg Ala Gln Lys
            660
```

<210> SEQ ID NO 24
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 24

| | | | | | |
|---|---|---|---|---|---|
| atgccttcaa | ataggaaaaa | tgagaatgaa | attataaatg | ctgtatcgaa | tcattccgca | 60 |
| caaatggatc | tatcgctaga | tgctcgtatt | gaagatagct | tgtgtgtagc | cgaggtgaac | 120 |
| aatattgatc | catttgttag | cgcatcaaca | gtccaaacag | gtattagtat | agctggtaga | 180 |
| atattgggcg | tattaggtgt | gccgtttgct | ggacaactag | ctagttttta | tagttttctt | 240 |
| gttggggaat | tatggcctag | cggcagagat | ccatgggaaa | ttttatgga | acatgtcgag | 300 |
| caaattgtaa | gacaacaaat | aacggacagt | gttaggata | ccgctattgc | tcgtttagaa | 360 |
| ggtctaggaa | gagggtatag | atcttaccag | caggctcttg | aaacttggtt | agataaccga | 420 |
| aatgatgcaa | gatcaagaag | cattattcgt | gagagatata | ttgctttaga | acttgacatt | 480 |
| actactgcta | taccgctttt | cagcatacga | aatcaagagg | ttccattatt | aatggtatat | 540 |
| gctcaagctg | caaatttaca | cctattatta | ttgagagacg | catccctttt | tggtagtgaa | 600 |
| tgggggatgt | catcttccga | tgttaaccaa | tattaccaag | aacaaatcag | atatacagag | 660 |
| gaatattcta | accattgcgt | acaatggtat | aatacgggc | taaataactt | aagagggaca | 720 |
| aatgctgaaa | gttggttgcg | gtataatcaa | ttccgtagag | atctaacgtt | aggagtatta | 780 |
| gatctagtgg | cactattccc | aagctatgac | acgcgtgttt | atccaatgaa | tacgagtgct | 840 |
| cagttaacaa | gagaaattta | tacagatcca | attgggagaa | caaatgcacc | ttcaggattt | 900 |
| gcaagtacga | attggtttaa | taataatgca | ccatcgtttt | ctgccataga | ggctgccatt | 960 |
| ttcaggcctc | cgcatctact | tgattttcca | gaacaactta | caatttacag | tgcatcaagc | 1020 |
| cgttggagta | gcactcaaca | tatgaattat | tgggtgggac | ataggcttaa | cttccgccca | 1080 |
| ataggaggga | cattaaatac | ctcaacacaa | ggacttacta | ataatacttc | aattaatcct | 1140 |
| gtaacattac | agtttacgtc | tcgtgacgtt | tatagaacag | aatcaaatgc | agggacaaat | 1200 |
| atactattta | ctactcctgt | gaatggagta | ccttgggcta | gatttaattt | tataaaccct | 1260 |
| cagaatattt | atgaaagagg | cgccactacc | tacagtcaac | cgtatcaggg | agttgggatt | 1320 |
| caattatttg | attcagaaac | tgaattacca | ccagaaacaa | cagaacgacc | aaattatgaa | 1380 |
| tcatatagtc | atagattatc | tcatatagga | ctaatcatag | aaacacttt | gagagcacca | 1440 |
| gtctattctt | ggacgcatcg | tagtgcaact | cttacaaata | caattgatcc | agagagaatt | 1500 |
| aatcaaatac | ctttagtgaa | aggatttaga | gtttgggggg | gcacctctgt | cattacagga | 1560 |
| ccaggattta | caggagggga | tatccttcga | agaaatacct | ttggtgattt | tgtatctcta | 1620 |
| caagtcaata | ttaattcacc | aattacccaa | agataccgtt | taagatttcg | ttacgcttcc | 1680 |
| agtagggatg | cacgagttat | agtattaaca | ggagcggcat | ccacaggagt | gggaggccaa | 1740 |
| gttagtgtaa | atatgcctct | tcagaaaact | atggaaatag | gggagaactt | aacatctaga | 1800 |
| acatttagat | ataccgattt | tagtaatcct | ttttcattta | gagctaatcc | agatataatt | 1860 |
| gggataagtg | aacaacctct | atttggtgca | ggttctatta | gtagcggtga | actttatata | 1920 |
| gataaaattg | aaattattct | agcagatgca | acatttgaag | cagaatctga | tttagaaaga | 1980 |
| gcacaaaag | | | | | 1989 |

<210> SEQ ID NO 25

```
<211> LENGTH: 663
<212> TYPE: PRT
<213> ORGANISM: Artificial Sequence
<220> FEATURE:
<223> OTHER INFORMATION: Cry1B variant

<400> SEQUENCE: 25
```

| | | | | | | | | | | | | | | | |
|---|---|---|---|---|---|---|---|---|---|---|---|---|---|---|---|
|Met|Pro|Ser|Asn|Arg|

```
Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Gly Ala Arg Lys
            660
```

```
<210> SEQ ID NO 26
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 26
atgccttcaa ataggaaaaa tgagaatgaa attataaatg ctgtatcgaa tcattccgca     60
caaatggatc tatcgctaga tgctcgtatt gaagatagct tgtgtgtagc cgaggtgaac    120
aatattgatc catttgttag cgcatcaaca gtccaaacag gtattagtat agctggtaga    180
atattgggcg tattaggtgt gccgtttgct ggacaactag ctagttttta tagttttctt    240
gttggggaat tatggcctag cggcagagat ccatgggaaa tttttatgga acatgtcgag    300
caaattgtaa gacaacaaat aacggacagt gttagggata ccgctattgc tcgtttagaa    360
ggtctaggaa gagggtatag atcttaccag caggctcttg aaacttggtt agataaccga    420
```

```
aatgatgcaa gatcaagaag cattattcgt gagagatata ttgctttaga acttgacatt      480
actactgcta taccgctttt cagcatacga aatcaagagg ttccattatt aatggtatat      540
gctcaagctg caaatttaca cctattatta ttgagagacg catccctttt tggtagtgaa      600
tgggggatgt catcttccga tgttaaccaa tattaccaag aacaaatcag atatacagag      660
gaatattcta accattgcgt acaatggtat aatacagggc taaataactt aagagggaca      720
aatgctgaaa gttggttgcg gtataatcaa ttccgtagag atctaacgtt aggagtatta      780
gatctagtgg cactattccc aagctatgac actcgcactt atccaatcaa tacgagtgct      840
cagttaacaa gagaaattta tacagatcca attgggagaa caaatgcacc ttcaggattt      900
gcaagtacga attggtttaa taataatgca ccatcgtttt ctgccataga ggctgccatt      960
ttcaggcctc cgcatctact tgattttcca gaacaactta caatttacag tgcatcaagc     1020
cgttggagta gcactcaaca tatgaattat tgggtgggac ataggcttaa cttccgccca     1080
ataggaggga cattaaatac ctcaacacaa ggacttacta ataatacttc aattaatcct     1140
gtaacattac agtttacgtc tcgtgacgtt tatagaacag aatcaaatgc agggacaaat     1200
atactattta ctactcctgt gaatggagta ccttgggcta gatttaattt tataaaccct     1260
cagaatattt atgaaagagg cgccactacc tacagtcaac cgtatcaggg agttgggatt     1320
caattatttg attcagaaac tgaattacca ccagaaacaa cagaacgacc aaattatgaa     1380
tcatatagtc atagattatc tcatatagga ctaatcatag aaacacttt gagagcacca     1440 gtctattctt ggacgcatcg tagtgcaact cttacaaata caattgatcc agagagaatt     1500
aatcaaatac ctttagtgaa aggatttaga gtttgggggg gcacctctgt cattacagga     1560
ccaggattta caggagggga tatccttcga agaaatacct ttggtgattt tgtatctcta     1620
caagtcaata ttaattcacc aattacccaa agataccgtt taagatttcg ttacgcttcc     1680
agtagggatg cacgagttat agtattaaca ggagcggcat ccacaggagt gggaggccaa     1740
gttagtgtaa atatgcctct tcagaaaact atggaaatag gggagaactt aacatctaga     1800
acatttagat ataccgattt tagtaatcct tttcattta gagctaatcc agatataatt     1860
gggataagtg aacaacctct atttggtgca ggttctatta gtagcggtga actttatata     1920
gataaaattg aaattattct agcagatgca acatttgaag cagaatctga tttagaaggg     1980
gcgcggaag                                                             1989
```

<210> SEQ ID NO 27
<211> LENGTH: 663
<212> TYPE: PRT
<213> ORGANISM: Artificial Sequence
<220> FEATURE:
<223> OTHER INFORMATION: Cry1B variant

<400> SEQUENCE: 27

```
Met Pro Ser Asn Ar

```
Val Gly Glu Leu Trp Pro Ser Gly Arg Asp Pro Trp Glu Ile Phe Met
             85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
            115                 120                 125

Tyr Gln Gln Ala Leu Glu Thr Trp Leu Asp Asn Arg Asn Asp Ala Arg
            130                 135                 140

Ser Arg Ser Ile Ile Leu Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ala Ser Ser Asp Val
            195                 200                 205

Asn Gln Tyr Tyr Gln Glu Gln Ile Arg Tyr Thr Glu Glu Tyr Ser Asn
            210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Ile Tyr Thr
            275                 280                 285

Asp Pro Ile Gly Arg Thr Asn Ala Pro Ser Gly Phe Ala Ser Thr Asn
290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
            355                 360                 365

Thr Gln Gly Leu Thr Asn Asn Thr Ser Ile Asn Pro Val Thr Leu Gln
            370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
            435                 440                 445

Leu Pro Pro Glu Thr Thr Glu Arg Pro Asn Tyr Glu Ser Tyr Ser His
            450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
```

```
                500                 505                 510
Gly Gly Thr Ser Val Ile Thr Gly Pro Gly Phe Thr Gly Gly Asp Ile
            515                 520                 525

Leu Arg Arg Asn Thr Phe Gly Asp Phe Val Ser Leu Gln Val Asn Ile
530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
            595                 600                 605

Asn Pro Phe Ser Phe Arg Ala Asn Pro Asp Ile Ile Gly Ile Ser Glu
            610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Lys Ala Gln Lys
            660

<210> SEQ ID NO 28
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 28
atgccttcaa ataggaaaaa tgagaatgaa attataaatg ctgtatcgaa tcattccgca      60
caaatggatc tatcgctaga tgctcgtatt gaagatagct tgtgtgtagc cgaggtgaac     120
aatattgatc catttgttag cgcatcaaca gtccaaacgg gtattaacat agctggtaga     180
atactaggcg tattagggt gccgtttgct ggacaactag ctagttttta gagttttctt     240
gttggggaat tatggcctag cggcagagat ccatgggaaa tttttatgga acatgtcgag     300
caaattgtaa gacaacaaat aacggacagt gttagggata ccgctattgc tcgtttagaa     360
ggtctaggaa gagggtatag atcttaccag caggctcttg aaacttggtt agataaccga     420
aatgatgcaa gatcaagaag cattattctt gagcgctata ttgctttaga acttgacatt     480
actactgcta taccgctttt cagcatacga aatcaagagg ttccattatt gatggtatat     540
gctcaagctg caaatttaca cctattatta ttgagagacg catcccttt tggtagtgaa     600 tgggggatgg catcttccga tgttaaccaa tattaccaag aacaaatcag atatacagag     660
gaatattcta accattgcgt acaatggtat aatacagggc taaataactt aagagggaca     720
aatgctgaaa gttggttgcg gtataatcaa ttccgtagag acctaacgtt agggggtatta     780 gattagtag ccctattccc aagctatgat actcgcactt atccaatcaa tacgagtgct     840
cagttaacaa gagaaattta tacagatcca attgggagaa caaatgcacc ttcaggatt     900 gcaagtacga attggtttaa taataatgca ccatcgtttt ctgccataga ggctgccatt     960
ttcaggcctc cgcatctact tgattttcca gaacaactta caatttacag tgcatcaagc    1020
cgttggagta gcactcaaca tatgaattat tgggtgggac ataggcttaa cttccgccca    1080
ataggaggga cattaaatac ctcaacacaa ggacttacta taatacttc aattaatcct    1140
```

-continued

```
gtaacattac agtttacgtc tcgtgacgtt tatagaacag aatcaaatgc agggacaaat   1200
atactattta ctactcctgt gaatggagta ccttgggcta gatttaattt tataaaccct   1260
cagaatattt atgaaagagg cgccactacc tacagtcaac cgtatcaggg agttgggatt   1320
caattatttg attcagaaac tgaattacca ccagaaacaa cagaacgacc aaattatgaa   1380
tcatatagtc atagattatc tcatatagga ctaatcatag aaacactttt gagagcacca   1440
gtctattctt ggacgcatcg tagtgcaact cttacaaata caattgatcc agagagaatt   1500
aatcaaatac ctttagtgaa aggatttaga gtttgggggg gcacctctgt cattacagga   1560
ccaggattta caggagggga tatccttcga agaaatacct ttggtgattt tgtatctcta   1620
caagtcaata ttaattcacc aattacccaa agataccgtt taagatttcg ttacgcttcc   1680
agtagggatg cacgagttat agtattaaca ggagcggcat ccacaggagt ggggaggccaa   1740
gttagtgtaa atatgcctct tcagaaaact atggaaatag gggagaactt aacatctaga   1800
acatttagat ataccgattt tagtaatcct ttttcattta gagctaatcc agatataatt   1860
gggataagtg aacaacctct atttggtgca ggttctatta gtagcggtga actttatata   1920
gataaaattg aaattattct agcagatgca acatttgaag cagaatctga tttagagaaa   1980
gctcagaaa                                                           1989
```

<210> SEQ ID NO 29
<211> LENGTH: 663
<212> TYPE: PRT
<213> ORGANISM: Artificial Sequence
<220> FEATURE:
<223> OTHER INFORMATION: Cry1B variant

<400> SEQUENCE: 29

```
Met Pro Ser Asn Arg Lys Asn Glu Asn Glu Ile Ile Asn Ala Val Ser
  1               5                  10                  15

Asn His Ser Ala Gln Met Asp Leu Ser Leu Asp Ala Arg Ile Glu Asp
             20                  25                  30

Ser Leu Cys Val Ala Glu Val Asn Asn Ile Asp Pro Phe Val Ser Ala
         35                  40                  45

Ser Thr Val Gln Thr Gly Ile Ser Ile Ala Gly Arg Ile Leu Gly Val
     50                  55                  60

Leu Gly Val Pro Phe Ala Gly Gln Leu Ala Ser Phe Tyr Ser Phe Leu
 65                  70                  75                  80

Val Gly Glu Leu Trp Pro Ser Gly Arg Asp Pro Trp Glu Ile Phe Leu
                 85                  90                  95

Glu His Val Glu Gln Leu Ile Arg Gln Gln Val Thr Glu Asn Thr Arg
            100                 105                 110

Asn Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Leu Glu Arg Tyr Val Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ala Asp Val
        195                 200                 205
```

```
Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr Gln Gly Leu Thr Asn Asn Thr Ser Ile Asn Pro Val Thr Leu Gln
370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
610                 615                 620
```

-continued

```
Gln Pro Leu Phe Gly Ala Gly Ser Ile Ser Ser Gly Glu Leu Tyr Ile
625 630 635 640

Asp Lys Ile Glu Ile Ile Leu Ala Asp Ala Thr Phe Glu Ala Glu Ser
645 650 655

Asp Leu Glu Arg Ala Gln Lys
660

<210> SEQ ID NO 30
<211> LENGTH: 1989
<212> TYPE: DNA
<213> ORGANISM: Artificial Sequence
<220> FEATURE:
<223> OTHER INFORMATION: coding sequence of Cry1B variant
<400> SEQUENCE: 30
atgccttcaa ataggaaaaa tgagaatgaa attataaatg ctgtatcgaa tcattccgca 60
caaatggatc tatcgctaga tgctcgtatt gaagatagct tgtgtgtagc cgaggtgaac 120
aatattgatc catttgttag cgcatcaaca gtccaaacag gtattagtat agctggtaga 180
atattgggcg tattaggtgt gccgtttgct ggacaactag ctagtttttta tagttttctt 240
gttggggaat tatggcctag cggcagagat ccatgggaaa ttttcctgga acatgtcgaa 300
caacttataa gacaacaagt aacagaaaat actaggaata cggctattgc tcgattagaa 360
ggtctaggaa gaggctatag atcttaccag caggctcttg aaacttggtt agataaccga 420
aatgatgcaa gatcaagaag cattattctt gagcgctatg ttgctttaga acttgacatt 480
actactgcta taccgctttt cagcatacga aatcaagagg ttccattatt aatggtatat 540
gctcaagctg caaatttaca cctattatta ttgagagacg catccctttt tggtagtgaa 600
tgggggatgt catctgccga tgttaaccaa tattaccaag aacaaatcag atatacagag 660
gaatattcta accattgcgt acaatggtat aatacagggc taaataactt aagagggaca 720
aatgctgaaa gttggttgcg gtataatcaa ttccgtagag acctaacgtt aggggtatta 780
gatttagtag ccctattccc aagctatgac actcgcactt atccaatcaa tacgagtgct 840
cagttaacaa gagaaattta tacagatcca attgggagaa caaatgcacc ttcaggattt 900
gcaagtacga attggtttaa taataatgca ccatcgtttt ctgccataga ggctgccatt 960
ttcaggcctc cgcatctact tgattttcca gaacaactta caatttacag tgcatcaagc 1020
cgttggagta gcactcaaca tatgaattat tgggtgggac ataggcttaa cttccgccca 1080
ataggaggga cattaaatac ctcaacacaa ggacttacta ataatacttc aattaatcct 1140
gtaacattac agtttacgtc tcgtgacgtt tatagaacag aatcaaatgc agggacaaat 1200
atactattta ctactcctgt gaatggagta ccttgggcta gatttaattt tataaaccct 1260
cagaatattt atgaaagagg cgccactacc tacagtcaac cgtatcaggg agttgggatt 1320
caattatttg attcagaaac tgaattacca ccagaaacaa cagaacgacc aaattatgaa 1380
tcatatagtc atagattatc tcatatagga ctaatcatag gaaacacttt gagagcacca 1440
gtctattctt ggacgcatcg tagtgcaact cttacaaata caattgatcc agagagaatt 1500
aatcaaatac ctttagtgaa aggatttaga gtttgggggg gcacctctgt cattacagga 1560
ccaggattta caggaggga tatccttcga agaaatacct ttggtgattt tgtatctcta 1620
caagtcaata ttaattcacc aattacccaa agataccgtt taagatttcg ttacgcttcc 1680
agtagggatg cacgagttat agtattaaca ggagcggcat ccacaggagt gggaggccaa 1740
gttagtgtaa atatgcctct tcagaaaact atggaaatag gggagaactt aacatctaga 1800
```

-continued

```
acatttagat ataccgattt tagtaatcct ttttcattta gagctaatcc agatataatt    1860
gggataagtg aacaacctct atttggtgca ggttctatta gtagcggtga actttatata    1920
gataaaattg aaattattct agcagatgca acatttgaag cagaatctga tttagaaaga    1980
gcacaaaag                                                            1989

<210> SEQ ID NO 31
<211> LENGTH: 655
<212> TYPE: PRT
<213> ORGANISM: Artificial Sequence
<220> FEATURE:
<223> OTHER INFORMATION: Cry1B variant

<400> SEQUENCE: 31

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
                20                  25                  30

Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln His Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
```

```
                325                 330                 335
Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile His Gly
            355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Ser Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
            515                 520                 525

Asp Leu Val Arg Leu Asn Asn Ser Gly Asn Asn Ile Tyr Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
            595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 32
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 32
atgccctcca accgcaagaa cgagaacgag ataatcaacg ccctgtcgat cccagccgtc      60
tccaaccact ccgcgcagat ggacctctca ctggacgctc gcatcgagga ctcactctgc     120
atcgccgagg caacaacat caaccccgctc gtcagcgcct cgaccgtgca gactggcatc     180
aacatcgccg tcgcatact cggcgtcctc ggagtccat tcgcaggtca gctggcgagc     240
```

```
ttctacagct tcatcgtcgg cgagctctgg ccatcaggtc gcgatccctg ggagatcttc      300
atggagcacg tcgagcagct ggtcaggcag cacatcacgg agaacgctcg caacacggct      360
ctcgccagac tccaaggcct cggagccagc ttcagagcct accagcagtc cctcgaggac      420
tggctcgaga accgcgacaa cgcgaggacc cggagcgtcc tctacaccca gtacatcgcg      480
ctggagctcg acttcctgaa cgcgatgcca ctcttcgcca tcaacaacca gcaggtgccg      540
ctcctcatgg tctacgccca agctgccaac ctccacctcc tgctcctcag agacgctagc      600
ctgttcggca gcgagttcgg actcacgtcg caggagatcc agcgctacta cgagcgccag      660
gcggagaaga cccgggagta cagcgactac tgcgcacgct ggtacaacac cggcctgaac      720
aacctgcgcg gcacgaacgc tgagagctgg ctccgctaca accagttccg cagggacctc      780
acactcggag tcctcgacct cgtcgcgctg ttcccgagct acgacacgcg gatctacccg      840
atcaacacga gcgcgcagct cactcgcgag atctacacgg accccatcgg tcgcacgaac      900
gctccatccg gcttcgcctc caccaactgg ttcaacaaca acgcgccgtc gttcagcgcc      960
atcgaagctg caatcttccg cccacctcac ctgctggact cccagagca gctcaccatc     1020 tacagcgcct ccagccgctg gtccagcacg cagcacatga actactgggt cggccaccgc     1080
ctcaacttca ggcctatcca cggtaccctc aacacctcga cccacggcgc cacgaacacg     1140
tccatcaacc cggtgacgct ccagttcacg agcggacg tctaccgcac tgagagctac     1200
gctggcatca acatcctgct cacgacgcca gtgaacggcg tcccgtgggc acgcttcaac     1260
tggaggaacc ctctcaactc cctgcgcgga tcgctcctct acaccatcgg ctacaccgga     1320
gtcggtaccc agctcttcga cagcgagacc gagctcccac tgagaccacc gagaggccc     1380 aactacgaga gctactccca ccgcctgtcg aacatccgcc tcatcatctc caacacgctc     1440
agagctcccg tctactcctg gacgcacagg tcagctgacc ggacgaacac catcgcgacg     1500
aacatcatca cccagatccc ggccgtcaag ggcaacttcc tcttcaacgg ctccgtcatc     1560
tccggaccag gcttcaccgg aggagacctc gtccgcctca caactccgg caacaacatc     1620 tacaaccggg gctacatcga ggtgccgatc cagttcatct ccacgagcac tcggtaccgc     1680
gtcagagtgc gctacgcgag cgtcactccg atccgcctct ccgtcaactg gggcaactcg     1740
aacatcttca gctccatcgt cccagccacc gcgactagcc tcgacaacct gcagtcccgc     1800
aacttcggct acttcgagag ccgcaacgcc ttcacgagcg cgactggcaa cgtcgtcggc     1860
gtccgcaact tctccgagaa cgccggagtg atcatcgacc gcttcgagtt catccccgtg     1920
accgcgacct cgaggccga gtacgacctt gagagagctc aggaggcc                  1968
```

<210> SEQ ID NO 33
<211> LENGTH: 655
<212> TYPE: PRT
<213> ORGANISM: Artificial Sequence
<220> FEATURE:
<223> OTHER INFORMATION: Cry1B variant

<400> SEQUENCE: 33

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
```

```
            50                  55                  60
Arg Ile Leu Gly Val Leu Gly Val Pro Phe Ala Gly Gln Leu Ala Ser
 65                  70                  75                  80

Phe Tyr Ser Phe Ile Val Gly Glu Leu Trp Pro Ser Gly Arg Asp Pro
                 85                  90                  95

Trp Glu Ile Phe Met Glu His Val Glu Gln Leu Val Arg Gln His Ile
                100                 105                 110

Thr Glu Asn Ala Arg Asn Thr Ala Leu Ala Arg Leu Gln Gly Leu Gly
                115                 120                 125

Ala Ser Phe Arg Ala Tyr Gln Gln Ser Leu Glu Asp Trp Leu Glu Asn
            130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
            210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile His Gly
            355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ile Gly Asn Thr Leu
465                 470                 475                 480
```

-continued

```
Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Tyr Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Thr Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 34
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 34
atgccctcca accgcaagaa cgagaacgag ataatcaacg ccctgtcgat cccagccgtc     60
tccaaccact ccgcgcagat ggacctctca ctggacgctc gcatcgagga ctcactctgc    120
atcgccgagg gcaacaacat caacccgctc gtcagcgcct cgaccgtgca gactggcatc    180
aacatcgccg gtcgcatact cggcgtcctc ggagtcccat tcgcaggtca gctggcgagc    240
ttctacagct tcatcgtcgg cgagctctgg ccatcaggtc gcgatccctg ggagatcttc    300
atggagcacg tcgagcagct ggtcaggcag cacatcacgg agaacgctcg caacacggct    360
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca acgcgccgtc gttcagcgcc    960
atcgaagctg caatcttccg cccacctcac ctgctggact tcccagagca gctcaccatc   1020
tacagcgcct ccagccgctg gtccagcacg cagcacatga actactgggt cggccaccgc   1080
```

```
ctcaacttca ggcctatcca cggtaccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tcccgtgggc acgcttcaac   1260
tggaggaacc ctctcaactc cctgcgcgga tcgctcctct acaccatcgg ctacaccgga   1320
gtcggtaccc agctcttcga cagcgagacc gagctcccac ctgagaccac cgagaggccc   1380
aactacgaga gctactccca ccgcctgtcg aacatccgcc tcatcatcgg caacacgctc   1440
agagctcccg tctactcctg gacgcacagg tcagctgacc ggacgaacac catcgcgacg   1500
aacatcatca cccagatccc ggccgtcaag ggcaacttcc tcttcaacgg ctccgtcatc   1560
tccggaccag gcttcaccgg aggagacctc gtccgcctca caactccgg caacaacatc   1620 tacaaccggg gctacatcga ggtgccgatc cagttcatct ccacgagcac tcggtaccgc   1680
gtcagagtgc gctacgcgag cgtcactccg atccgcctct ccgtcaactg ggcaactcg   1740 aacatcttca gcaccatcgt cccagccacc gcgactagcc tcgacaacct gcagtcccgc   1800
aacttcggct acttcgagag ccgcaacgcc ttcacgagcg cgactggcaa cgtcgtcggc   1860
gtccgcaact tctccgagaa cgccggagtg atcatcgacc gcttcgagtt catccccgtg   1920
accgcgacct tcgaggccga gtacgacctt gagagagctc aggaggcc               1968
```

<210> SEQ ID NO 35
<211> LENGTH: 655
<212> TYPE: PRT
<213> ORGANISM: Artificial Sequence
<220> FEATURE:
<223> OTHER INFORMATION: Cry1B variant

<400> SEQUENCE: 35

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20

```
Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Thr Gln His
            340                 345                 350

Met Asn Tyr Trp Val Gly His Arg Leu Asn Phe Arg Pro Ile Gly Gly
    355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620
```

```
Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 36
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 36

| | | | | | |
|---|---|---|---|---|---|
| atgccctcca | accgcaagaa | cgagaacgag | ataatcaacg | ccctgtcgat | cccagccgtc | 60 |
| tccaaccact | ccgcgcagat | ggacctctca | ctggacgctc | gcatcgagga | ctcactctgc | 120 |
| atcgccgagg | gcaacaacat | caacccgctc | gtcagcgcct | cgaccgtgca | gactggcatc | 180 |
| aacatcgccg | tcgcatact | cggcgtcctc | ggagtcccat | cgcaggtca | gctggcgagc | 240 |
| ttctacagct | tcatcgtcgg | cgagctctgg | ccatcaggtc | gcgatccctg | ggagatcttc | 300 |
| atggagcacg | tcgagcagct | ggtcaggcag | atgatcacgc | tcaacgctcg | caacacggct | 360 |
| ctcgccagac | tccaaggcct | cggagccagc | ttcagagcct | accagcagtc | cctcgaggac | 420 |
| tggctcgaga | accgcgacaa | cgcgaggacc | cggagcgtcc | tctacaccca | gtacatcgcg | 480 |
| ctggagctcg | acttcctgaa | cgcgatgcca | ctcttcgcca | tcaacaacca | gcaggtgccg | 540 |
| ctcctcatgg | tctacgccca | agctgccaac | ctccacctcc | tgctcctcag | agacgctagc | 600 |
| ctgttcggca | gcgagttcgg | actcacgtcg | caggagatcc | agcgctacta | cgagcgccag | 660 |
| gcggagaaga | cccgggagta | cagcgactac | tgcgcacgct | ggtacaacac | cggcctgaac | 720 |
| aacctgcgcg | gcacgaacgc | tgagagctgg | ctccgctaca | accagttccg | cagggacctc | 780 |
| acactcggag | tcctcgacct | cgtcgcgctg | ttcccgagct | acgacacgcg | gatctacccg | 840 |
| atcaacacga | gcgcgcagct | cactcgcgag | atctacacgg | accccatcgg | tcgcacgaac | 900 |
| gctccatccg | gcttcgcctc | caccaactgg | ttcaacaaca | acgcgccgtc | gttcagcgcc | 960 |
| atcgaagctg | caatcttccg | cccacctcac | ctgctggact | cccagagca | gctcaccatc | 1020 |
| tacagcgcct | ccagccgctg | gtccagcacg | cagcacatga | actactgggt | cggccaccgc | 1080 |
| ctcaacttca | ggcctatcgg | cggtaccctc | aacacctcga | cccacggcgc | cacgaacacg | 1140 |
| tccatcaacc | cggtgacgct | ccagttcacg | agccgggacg | tctaccgcac | tgagagctac | 1200 |
| gctggcatca | acatcctgct | cacgacgcca | gtgaacggcg | tcccgtgggc | acgcttcaac | 1260 |
| tggaggaacc | ctctcaactc | cctgcgcgga | tcgctcctct | acaccatcgg | ctacaccgga | 1320 |
| gtcggtaccc | agctcttcga | cagcgagacc | gagctccac | ctgagaccac | cgagaggccc | 1380 |
| aactacgaga | gctactccca | ccgcctgtcg | aacatccgcc | tcatcatcgg | cggcacgctc | 1440 |
| agagctcccg | tctactcctg | gacgcacagg | tcagctgacc | ggacgaacac | catcgcgacg | 1500 |
| aacatcatca | cccagatccc | ggccgtcaag | ggcaacttcc | tcttcaacgg | ctccgtcatc | 1560 |
| tccggaccag | gcttcaccgg | aggagacctc | gtccgcctca | caactccgg | caacaacatc | 1620 |
| cagaaccggg | gctacatcga | ggtgccgatc | cagttcatct | ccacgagcac | tcggtaccgc | 1680 |
| gtcagagtgc | gctacgcgag | cgtcactccg | atccgcctct | ccgtcaactg | ggcaactcg | 1740 |
| aacatcttca | gctccatcgt | cccagccacc | gcgactagcc | tcgacaacct | gcagtcccgc | 1800 |
| aacttcggct | acttcgagag | ccgcaacgcc | ttcacgagcg | cgactggcaa | cgtcgtcggc | 1860 |
| gtccgcaact | tctccgagaa | cgccggagtg | atcatcgacc | gcttcgagtt | catccccgtg | 1920 |

```
accgcgacct tcgaggccga gtacgacctt gagagagctc aggaggcc        1968
```

<210> SEQ ID NO 37
<211> LENGTH: 655
<212> TYPE: PRT
<213> ORGANISM: Artificial Sequence
<220> FEATURE:
<223> OTHER INFORMATION: Cry1B variant

<400> SEQUENCE: 37

```
Met Pro Ser Asn Arg Lys Asn Glu Asn Glu Ile Ile Asn Ala Leu Ser
1               5                   10                  15

Met Asn Tyr Trp Val Gly His Arg Leu Asn Phe Arg Pro Ile Gly Gly
    355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 38
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 38
atgccctcca accgcaagaa cgagaacgag ataatcaacg ccctgtcgat cccagccgtc    60
tccaaccact ccgcgcagat ggacctctca ctggacgctc gcatcgagga ctcactctgc    120
atcgccgagg caacaacat caacccgctc gtcagcgcct cgaccgtgca gactggcatc    180
aacatcgccg tcgcatact cggcgtcctc ggagtcccat tcgcaggtca gctggcgagc    240
ttctacagct tcatcgtcgg cgagctctgg ccatcaggtc gcgatccctg ggagatcttc    300
atggagcacg tcgagcagct ggtcaggcag atgatcacga tgaacgctcg caacacggct    360

-continued

```
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca acgcgccgtc gttcagcgcc    960
atcgaagctg caatcttccg cccacctcac ctgctggact tcccagagca gctcaccatc   1020
tacagcgcct ccagccgctg gtccagcacg cagcacatga actactgggt cggccaccgc   1080
ctcaacttca ggcctatcgg cggtaccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tcccgtgggc acgcttcaac   1260
tggaggaacc ctctcaactc cctgcgcgga tcgctcctct acaccatcgg ctacaccgga   1320
gtcggtaccc agctcttcga cagcgagacc gagctcccac ctgagaccac cgagaggccc   1380
aactacgaga gctactccca ccgcctgtcg aacatccgcc tcatcatcgg cggcacgctc   1440
agagctcccg tctactcctg gacgcacagg tcagctgacc ggacgaacac catcgcgacg   1500
aacatcatca cccagatccc ggccgtcaag ggcaacttcc tcttcaacgg ctccgtcatc   1560
tccggaccag gcttcaccgg aggagacctc gtccgcctca acaactccgg caacaacatc   1620
cagaaccggg gctacatcga ggtgccgatc cagttcatct ccacgagcac tcggtaccgc   1680
gtcagagtgc gctacgcgag cgtcactccg atccgcctct ccgtcaactg gggcaactcg   1740
aacatcttca gctccatcgt cccagccacc gcgactagcc tcgacaacct gcagtcccgc   1800
aacttcggct acttcgagag ccgcaacgcc ttcacgagcg cgactggcaa cgtcgtcggc   1860
gtccgcaact tctccgagaa cgccggagtg atcatcgacc gcttcgagtt catccccgtg   1920
accgcgacct tcgaggccga gtacgacctt gagagagctc aggaggcc                1968
```

<210> SEQ ID NO 39
<211> LENGTH: 655
<212> TYPE: PRT
<213> ORGANISM: Artificial Sequence
<220> FEATURE:
<223> OTHER INFORMATION: Cry1B variant

<400> SEQUENCE: 39

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80
```

```
Phe Tyr Ser Phe Ile Val Gly Glu Leu Trp Pro Ser Gly Arg Asp Pro
                85                  90                  95
Trp Glu Ile Phe Met Glu His Val Glu Gln Leu Val Arg Gln Met Ile
            100                 105                 110
Thr His Asn Ala Arg Asn Thr Ala Leu Ala Arg Leu Gln Gly Leu Gly
            115                 120                 125
Ala Ser Phe Arg Ala Tyr Gln Gln Ser Leu Glu Asp Trp Leu Glu Asn
            130                 135                 140
Arg Asp Asn Ala Arg Thr Arg Ser Val Leu Tyr Thr Gln Tyr Ile Ala
145                 150                 155                 160
Leu Glu Leu Asp Phe Leu Asn Ala Met Pro Leu Phe Ala Ile Asn Asn
                165                 170                 175
Gln Gln Val Pro Leu Leu Met Val Tyr Ala Gln Ala Ala Asn Leu His
                180                 185                 190
Leu Leu Leu Leu Arg Asp Ala Ser Leu Phe Gly Ser Glu Phe Gly Leu
            195                 200                 205
Thr Ser Gln Glu Ile Gln Arg Tyr Tyr Glu Arg Gln Ala Glu Lys Thr
            210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
                260                 265                 270
Ser Tyr Asp Thr Arg Ile Tyr Pro Ile Asn Thr Ser Ala Gln Leu Thr
                275                 280                 285
Arg Glu Ile Tyr Thr Asp Pro Ile Gly Arg Thr Asn Ala Pro Ser Gly
            290                 295                 300
Phe Ala Ser Thr Asn Trp Phe Asn Asn Asn Ala Pro Ser Phe Ser Ala
305                 310                 315                 320
Ile Glu Ala Ala Ile Phe Arg Pro Pro His Leu Leu Asp Phe Pro Glu
                325                 330                 335
Gln Leu Thr Ile Tyr Ser Ala Ser Ser Arg Trp Ser Ser Thr Gln His
            340                 345                 350
Met Asn Tyr Trp Val Gly His Arg Leu Asn Phe Arg Pro Ile Gly Gly
            355                 360                 365
Thr Leu Asn Thr Ser Thr His Gly Ala Thr Asn Thr Ser Ile Asn Pro
            370                 375                 380
Val Thr Leu Gln Phe Thr Ser Arg Asp Val Tyr Arg Thr Glu Ser Tyr
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
            435                 440                 445
Glu Thr Glu Leu Pro Pro Glu Thr Thr Glu Arg Pro Asn Tyr Glu Ser
            450                 455                 460
Tyr Ser His Arg Leu Ser Asn Ile Arg Leu Ile Ile Gly Gly Thr Leu
465                 470                 475                 480
Arg Ala Pro Val Tyr Ser Trp Thr His Arg Ser Ala Asp Arg Thr Asn
                485                 490                 495
Thr Ile Ala Thr Asn Ile Ile Thr Gln Ile Pro Ala Val Lys Gly Asn
```

```
                500             505             510
Phe Leu Phe Asn Gly Ser Val Ile Ser Gly Pro Gly Phe Thr Gly Gly
            515                 520                 525

Asp Leu Val Arg Leu Asn Asn Ser Gly Asn Asn Ile Gln Asn Arg Gly
        530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 40
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 40
atgccctcca accgcaagaa cgagaacgag ataatcaacg ccctgtcgat cccagccgtc      60
tccaaccact ccgcgcagat ggacctctca ctggacgctc gcatcgagga ctcactctgc    120
atcgccgagg caacaacat caaccccgctc gtcagcgcct cgaccgtgca gactggcatc    180
aacatcgccg gtcgcatact cggcgtcctc ggagtcccat cgcaggtca gctggcgagc    240 ttctacagct tcatcgtcgg cgagctctgg ccatcaggtc gcgatccctg ggagatcttc    300
atggagcacg tcgagcagct ggtcaggcag atgatcacgc acaacgctcg caacacggct    360
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca acgcgccgtc gttcagcgcc    960
atcgaagctg caatcttccg cccacctcac ctgctggact tcccagagca gctcaccatc    1020
tacagcgcct ccagccgctg gtccagcacg cagcacatga actactgggt cggccaccgc    1080
ctcaacttca ggcctatcgg cggtaccctc aacacctcga cccacggcgc cacgaacacg    1140
tccatcaacc cggtgacgct ccagttcacg agccgggacg tctaccgcac tgagagctac    1200
```

```
gctggcatca acatcctgct cacgacgcca gtgaacggcg tcccgtgggc acgcttcaac    1260
tggaggaacc ctctcaactc cctgcgcgga tcgctcctct acaccatcgg ctacaccgga    1320
gtcggtaccc agctcttcga cagcgagacc gagctcccac ctgagaccac cgagaggccc    1380
aactacgaga gctactccca ccgcctgtcg aacatccgcc tcatcatcgg cggcacgctc    1440
agagctcccg tctactcctg gacgcacagg tcagctgacc ggacgaacac catcgcgacg    1500
aacatcatca cccagatccc ggccgtcaag ggcaacttcc tcttcaacgg ctccgtcatc    1560
tccggaccag gcttcaccgg aggagacctc gtccgcctca caactccgg caacaacatc     1620 cagaaccggg gctacatcga ggtgccgatc cagttcatct ccacgagcac tcggtaccgc    1680
gtcagagtgc gctacgcgag cgtcactccg atccgcctct ccgtcaactg gggcaactcg    1740
aacatcttca gctccatcgt cccagccacc gcgactagcc tcgacaacct gcagtcccgc    1800
aacttcggct acttcgagag ccgcaacgcc ttcacgagcg cgactggcaa cgtcgtcggc    1860
gtccgcaact tctccgagaa cgccggagtg atcatcgacc gcttcgagtt catccccgtg    1920
accgcgacct tcgaggccga gtacgacctt gagagagctc aggaggcc               1968
```

<210> SEQ ID NO 41
<211> LENGTH: 655
<212> TYPE: PRT
<213> ORGANISM: Artificial Sequence
<220> FEATURE:
<223> OTHER INFORMATION: Cry1B variant

<400> SEQUENCE: 41

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
                20

```
                225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
                260                 265                 270
Ser Tyr Asp Thr Arg Ile Tyr Pro Ile Asn Thr Ser Ala Gln Leu Thr
                275                 280                 285
Arg Glu Ile Tyr Thr Asp Pro Ile Gly Arg Thr Asn Ala Pro Ser Gly
                290                 295                 300
Phe Ala Ser Thr Asn Trp Phe Asn Asn Asn Ala Pro Ser Phe Ser Ala
305                 310                 315                 320
Ile Glu Ala Ala Ile Phe Arg Pro Pro His Leu Leu Asp Phe Pro Glu
                325                 330                 335
Gln Leu Thr Ile Tyr Ser Ala Ser Ser Arg Trp Ser Ser Thr Gln His
                340                 345                 350
Met Asn Tyr Trp Val Gly His Arg Leu Asn Phe Arg Pro Ile Gly Gly
                355                 360                 365
Thr Leu Asn Thr Ser Thr His Gly Ala Thr Asn Thr Ser Ile Asn Pro
                370                 375                 380
Val Thr Leu Gln Phe Thr Ser Arg Asp Val Tyr Arg Thr Glu Ser Tyr
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
                435                 440                 445
Glu Thr Glu Leu Pro Pro Glu Thr Thr Glu Arg Pro Asn Tyr Glu Ser
                450                 455                 460
Tyr Ser His Arg Leu Ser Asn Ile Arg Leu Ile Ile Gly Gly Thr Leu
465                 470                 475                 480
Arg Ala Pro Val Tyr Ser Trp Thr His Arg Ser Ala Asp Arg Thr Asn
                485                 490                 495
Thr Ile Ala Thr Asn Ile Ile Thr Gln Ile Pro Ala Val Lys Gly Asn
                500                 505                 510
Phe Leu Phe Asn Gly Ser Val Ile Ser Gly Pro Gly Phe Thr Gly Gly
                515                 520                 525
Asp Leu Val Arg Leu Asn Asn Ser Gly Asn Asn Ile Gln Asn Arg Gly
                530                 535                 540
Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Arg Leu Ser Val Asn
                565                 570                 575
Trp Gly Asn Ser Asn Ile Phe Ser Ser Ile Val Pro Ala Thr Ala Thr
                580                 585                 590
Ser Leu Asp Asn Leu Gln Ser Arg Asn Phe Gly Tyr Phe Glu Ser Arg
                595                 600                 605
Asn Ala Phe Thr Ser Ala Thr Gly Asn Val Val Gly Val Arg Asn Phe
                610                 615                 620
Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                645                 650                 655
```

<210> SEQ ID NO 42
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 42

| | | | | | |
|---|---|---|---|---|---|
| atgccctcca | accgcaagaa | cgagaacgag | ataatcaacg | ccctgtcgat | cccagccgtc | 60 |
| tccaaccact | ccgcgcagat | ggacctctca | ctggacgctc | gcatcgagga | ctcactctgc | 120 |
| atcgccgagg | gcaacaacat | caacccgctc | gtcagcgcct | cgaccgtgca | gactggcatc | 180 |
| aacatcgccg | gtcgcatact | cggcgtcctc | ggagtcccat | cgcaggtca | gctggcgagc | 240 |
| ttctacagct | tcatcgtcgg | cgagctctgg | ccatcaggtc | gcgatccctg | ggagatcttc | 300 |
| atggagcacg | tcgagcagct | ggtcaggcag | cacatcacga | tgaacgctcg | caacacggct | 360 |
| ctcgccagac | tccaaggcct | cggagccagc | ttcagagcct | accagcagtc | cctcgaggac | 420 |
| tggctcgaga | accgcgacaa | cgcgaggacc | cggagcgtcc | tctacaccca | gtacatcgcg | 480 |
| ctggagctcg | acttcctgaa | cgcgatgcca | ctcttcgcca | tcaacaacca | gcaggtgccg | 540 |
| ctcctcatgg | tctacgccca | agctgccaac | ctccacctcc | tgctcctcag | agacgctagc | 600 |
| ctgttcggca | gcgagttcgg | actcacgtcg | caggagatcc | agcgctacta | cgagcgccag | 660 |
| gcggagaaga | cccgggagta | cagcgactac | tgcgcacgct | ggtacaacac | cggcctgaac | 720 |
| aacctgcgcg | gcacgaacgc | tgagagctgg | ctccgctaca | accagttccg | cagggacctc | 780 |
| acactcggag | tcctcgacct | cgtcgcgctg | ttcccgagct | acgacacgcg | gatctacccg | 840 |
| atcaacacga | gcgcgcagct | cactcgcgag | atctacacgg | accccatcgg | tcgcacgaac | 900 |
| gctccatccg | gcttcgcctc | caccaactgg | ttcaacaaca | acgcgccgtc | gttcagcgcc | 960 |
| atcgaagctg | caatcttccg | cccacctcac | ctgctggact | tcccagagca | gctcaccatc | 1020 |
| tacagcgcct | ccagccgctg | gtccagcacg | cagcacatga | actactgggt | cggccaccgc | 1080 |
| ctcaacttca | ggcctatcgg | cggtaccctc | aacacctcga | cccacggcgc | cacgaacacg | 1140 |
| tccatcaacc | cggtgacgct | ccagttcacg | agccgggacg | tctaccgcac | tgagagctac | 1200 |
| gctggcatca | catcctgct | cacgacgcca | gtgaacggcg | tcccgtgggc | acgcttcaac | 1260 |
| tggaggaacc | ctctcaactc | cctgcgcgga | tcgctcctct | acaccatcgg | ctacaccgga | 1320 |
| gtcggtaccc | agctcttcga | cagcgagacc | gagctcccac | ctgagaccac | cgagaggccc | 1380 |
| aactacgaga | gctactccca | ccgcctgtcg | aacatccgcc | tcatcatcgg | cggcacgctc | 1440 |
| agagctcccg | tctactcctg | gacgcacagg | tcagctgacc | ggacgaacac | catcgcgacg | 1500 |
| aacatcatca | cccagatccc | ggccgtcaag | ggcaacttcc | tcttcaacgg | ctccgtcatc | 1560 |
| tccggaccag | gcttcaccgg | aggagacctc | gtccgcctca | caactccgg | caacaacatc | 1620 |
| cagaaccggg | gctacatcga | ggtgccgatc | cagttcatct | ccacgagcac | tcggtaccgc | 1680 |
| gtcagagtgc | gctacgcgag | cgtcactccg | atccgcctct | ccgtcaactg | ggcaactcg | 1740 |
| aacatcttca | gctccatcgt | cccagccacc | gcgactagcc | tcgacaacct | gcagtcccgc | 1800 |
| aacttcggct | acttcgagag | ccgcaacgcc | ttcacgagcg | cgactggcaa | cgtcgtcggc | 1860 |
| gtccgcaact | tctccgagaa | cgccggagtg | atcatcgacc | gcttcgagtt | catccccgtg | 1920 |
| accgcgacct | cgaggccga | gtacgacctt | gagagagctc | aggaggcc | | 1968 |

<210> SEQ ID NO 43

```
<211> LENGTH: 655
<212> TYPE: PRT
<213> ORGANISM: Artificial Sequence
<220> FEATURE:
<223> OTHER INFORMATION: Cry1B variant

<400> SEQUENCE: 43
```

| | | | | | | | | | | | | | | |
|---|---|---|---|---|---|---|---|---|---|---|---|---|---|---|
| Met | Pro | Ser | Asn | Arg | Lys | Asn | Gl

```
Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
        420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 44
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 44
atgccctcca accgcaagaa c

```
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca cgcgccgtc gttcagcgcc    960
atcgaagctg caatcttccg cccacctcac ctgctggact cccagagca gctcaccatc    1020
tacagcgcct ccagccgctg gtccagcacg cagcacatga actactgggt cggccaccgc    1080
ctcaacttca ggcctatcaa cggtaccctc aacacctcga cccacggcgc cacgaacacg    1140
tccatcaacc cggtgacgct ccagttcacg agccgggacg tctaccgcac tgagagctac    1200
gctggcatca acatcctgct cacgacgcca gtgaacggcg tcccgtgggc acgcttcaac    1260
tggaggaacc ctctcaactc cctgcgcgga tcgctcctct acaccatcgg ctacaccgga    1320
gtcggtaccc agctcttcga cagcgagacc gagctcccac ctgagaccac cgagaggccc    1380
aactacgaga gctactccca ccgcctgtcg aacatccgcc tcatcatcgg caacacgctc    1440
agagctcccg tctactcctg gacgcacagg tcagctgacc ggacgaacac catcgcgacg    1500
aacatcatca cccagatccc ggccgtcaag ggcaacttcc tcttcaacgg ctccgtcatc    1560
tccggaccag gcttcaccgg aggagacctc gtccgcctca caactccgg caacaacatc    1620
cagaaccggg gctacatcga ggtgccgatc cagttcatct ccacgagcac tcggtaccgc    1680
gtcagagtgc gctacgcgag cgtcactccg atccgcctct ccgtcaactg ggcaactcg    1740
aacatcttca gctccatcgt cccagccacc gcgactagcc tcgacaacct gcagtcccgc    1800
aacttcggct acttcgagag ccgcaacgcc ttcacgagcg cgactggcaa cgtcgtcggc    1860
gtccgcaact tctccgagaa cgccggagtg atcatcgacc gcttcgagtt catcccgtg    1920
accgcgacct cgaggccga gtacgacctt gagagagctc aggaggcc              1968
```

<210> SEQ ID NO 45
<211> LENGTH: 655
<212> TYPE: PRT
<213> ORGANISM: Artificial Sequence
<220> FEATURE:
<223> OTHER INFORMATION: Cry1B variant

<400> SEQUENCE: 45

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala

-continued

```
Thr Met Asn Ala Arg Asn Thr Ala Leu Ala Arg Leu Gln Gly Leu Gly
    115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Asn Phe Arg Pro Ile Asn Gly
            355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
                500                 505                 510

Phe Leu Phe Asn Gly Ser Val Ile Ser Gly Pro Gly Phe Thr Gly Gly
            515                 520                 525
```

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
            565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
            645                 650                 655

<210> SEQ ID NO 46
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 46

```
atgccctcca accgcaagaa cgagaacgag ataatcaacg ccctgtcgat cccagccgtc     60
tccaaccact ccgcgcagat ggacctctca ctggacgctc gcatcgagga ctcactctgc    120
atcgccgagg gcaacaacat caacccgctc gtcagcgcct cgaccgtgca gactggcatc    180
aacatcgccg tcgcatact cggcgtcctc ggagtcccat cgcaggtca gctggcgagc    240
ttctacagct tcatcgtcgg cgagctctgg ccatcaggtc gcgatccctg ggagatcttc    300
atggagcacg tcgagcagct ggtcaggcag cacatcacga tgaacgctcg caacacggct    360
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca cgcgccgtc gttcagcgcc    960
atcgaagctg caatcttccg cccacctcac ctgctggact cccagagca gctcaccatc   1020
tacagcgcct ccagccgctg gtccagcacg cagcacatga actactgggt cggccaccgc   1080
ctcaacttca ggcctatcaa cggtaccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tccgtgggc acgcttcaac   1260
tggaggaacc tctcaactc cctgcgcgga tcgctcctct acaccatcgg ctacaccgga   1320
gtcggtaccc agctcttcga cagcgagacc gagctcccac ctgagaccac cgagaggccc   1380
```

```
aactacgaga gctactccca ccgcctgtcg aacatccgcc tcatcatcgg caacacgctc    1440
agagctcccg tctactcctg gacgcacagg tcagctgacc ggacgaacac catcgcgacg    1500
aacatcatca cccagatccc ggccgtcaag ggcaacttcc tcttcaacgg ctccgtcatc    1560
tccggaccag gcttcaccgg aggagacctc gtccgcctca acaactccgg caacaacatc    1620
cagaaccggg gctacatcga ggtgccgatc cagttcatct ccacgagcac tcggtaccgc    1680
gtcagagtgc gctacgcgag cgtcactccg atccgcctct ccgtcaactg ggcaactcg     1740 aacatcttca gctccatcgt cccagccacc gcgactagcc tcgacaacct gcagtcccgc    1800
aacttcggct acttcgagag ccgcaacgcc ttcacgagcg cgactggcaa cgtcgtcggc    1860
gtccgcaact tctccgagaa cgccggagtg atcatcgacc gcttcgagtt catccccgtg    1920
accgcgacct tcgaggccga gtacgacctt gagagagctc aggaggcc                 1968
```

<210> SEQ ID NO 47  
<211> LENGTH: 655  
<212> TYPE: PRT  
<213> ORGANISM: Bacillus thuringiensis

<400> SEQUENCE: 47

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Leu Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270
```

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
530                 535                 540

Tyr Leu Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asp Phe Gly Tyr Phe Glu Ser Thr
        595                 600                 605

Asn Ala Phe Thr Ser Ala Thr Gly Asn Val Val Gly Val Arg Asn Phe
610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 48
<211> LENGTH: 1965
<212> TYPE: DNA
<213> ORGANISM: Bacillus thuringiensis

<400> SEQUENCE: 48

```
atgacttcaa ataggaaaaa tgagaatgaa attataaatg ctttatcgat tccagctgta     60
tcgaatcatt ccgcacaaat ggatctatca ccagatgctc gtattgagga ttctttgtgt    120
atagccgagg ggaataatat caatccactt gttagcgcat caacagtcca acgggtatt    180
aacattgctg gtagaatact aggcgtatta ggcgtaccgt ttgctggaca actagctagt    240
ttttatagtt ttattgtcgg tgaattatgg cctagcggca gagatccgtg gaaatctttt    300
ctagaacatg ttgaacaact tgtaagacaa caaataacag aaaatgctag gaatacggca    360
cttgctcgat tacaaggttt aggagcttcc tttagagcct atcaacaatc acttgaagac    420
tggctagaaa accgtgatga tgcaagaacg agaagtgttc tttataccca atatatagcc    480
ttagagcttg attttcttaa tgcgatgccg cttttcgcaa taaacaatca acaggttcca    540
ttattgatgg tatatgctca agctgcaaat ttacatctat tattattgag agatgcctct    600
cttttttggta gtgaatttgg gcttacatcg caggaaattc aacgttatta tgagcgccaa    660
gcggaaaaaa cgagagaata ttctgattat tgcgcaagat ggtataatac gggttttaaat   720
aatttgagag ggacaaatgc tgaaagttgg ttgcgatata atcaattccg tagagactta    780
acgctaggag tattagatct agtggcacta ttcccaagct atgacacgcg tatttatcca    840
ataaatacca gtgctcaatt aacaagagaa atttatacag atccaattgg gagaacaaat    900
gcaccttcag gatttgcaag tacgaattgg tttaataata tgcaccatc gttttctgcc     960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgtgacg tttatagaac agaatcatat   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacgaatac gattgctaca   1500
aatattatta ctcaaattcc tgcagtgaag ggaaactttc ttttaatgg ttctgtaatt    1560
tcaggaccag gatttactgg tggggactta gttagattaa ataatagtgg aaataatatt   1620
caaaatagag ctaccttgga ggttccgatt caattcatct ccacatctac cagatatcga   1680
gttcgtgtac gttatgcttc tgtaaccccg attcaactca gtgttaattg gggtaattca   1740
aacatttttt ccagcatagt accagctaca gctacgtcat tagataatct acaatcaagg   1800
gattttggtt attttgaaag taccaatgca tttacatctg caacaggtaa tgtagtaggt   1860
gttagaaatt ttagtgagaa tgcaggagtg ataatagaca gatttgaatt tatcccagtt   1920
actgcaacct tcgaagcaga atatgattta gaaagagcgc aagag                   1965
```

<210> SEQ ID NO 49
<211> LENGTH: 650
<212> TYPE: PRT
<213> ORGANISM: Bacillus thuringiensis

<400> SEQUENCE: 49

```
Met Pro Ser Asn Arg Lys Asn Glu Asn Glu Ile Ile Asn Ala Leu Ser
1               5                   10                  15
```

-continued

```
Ile Pro Ala Val Ser Asn His Ser Ala Gln Met Asp Leu Ser Pro Asp
                 20                  25                  30
Ala Arg Ile Glu Asp Ser Leu Cys Val Ala Glu Gly Asn Asn Ile Asp
             35                  40                  45
Pro Phe Val Ser Ala Ser Thr Val Gln Thr Gly Ile Ser Ile Ala Gly
 50                  55                  60
Arg Ile Leu Gly Val Leu Gly Val Pro Phe Ala Gly Gln Leu Ala Ser
 65                  70                  75                  80
Phe Tyr Ser Phe Leu Val Gly Glu Leu Trp Pro Ser Gly Arg Asp Pro
                 85                  90                  95
Trp Glu Ile Phe Met Glu His Val Glu Gln Ile Val Arg Gln Gln Ile
                100                 105                 110
Thr Asp Ser Val Arg Asp Thr Ala Ile Ala Arg Leu Glu Gly Leu Gly
                115                 120                 125
Arg Gly Tyr Arg Ser Tyr Gln Gln Ala Leu Glu Thr Trp Leu Asp Asn
            130                 135                 140
Arg Asn Asp Ala Arg Ser Arg Ser Ile Ile Arg Glu Arg Tyr Ile Ala
145                 150                 155                 160
Leu Glu Leu Asp Ile Thr Thr Ala Ile Pro Leu Phe Ser Ile Arg Asn
                165                 170                 175
Gln Glu Val Pro Leu Leu Met Val Tyr Ala Gln Ala Ala Asn Leu His
                180                 185                 190
Leu Leu Leu Leu Arg Asp Ala Ser Leu Phe Gly Ser Glu Trp Gly Met
            195                 200                 205
Ser Ser Ala Asp Val Asn Gln Tyr Tyr Gln Gln Ile Arg Tyr Thr
210                 215                 220
Glu Glu Tyr Ser Asn His Cys Val Gln Trp Tyr Asn Thr Gly Leu Asn
225                 230                 235                 240
Arg Leu Arg Gly Thr Thr Ala Glu Ser Trp Val Arg Tyr Asn Gln Phe
                245                 250                 255
Arg Arg Asp Leu Thr Leu Gly Val Leu Asp Leu Val Ala Leu Phe Pro
            260                 265                 270
Ser Tyr Asp Thr Arg Thr Tyr Pro Ile Pro Thr Thr Ala Gln Leu Thr
            275                 280                 285
Arg Glu Val Tyr Thr Asp Pro Asn Gly Val Val Ala Gly Pro Asn Asn
        290                 295                 300
Ser Trp Phe Arg Asn Gly Ala Ser Phe Ser Ala Ile Glu Asn Ala Ile
305                 310                 315                 320
Ile Arg Gln Pro His Leu Tyr Asp Phe Leu Thr Asn Leu Thr Ile Tyr
                325                 330                 335
Thr Arg Arg Ser Gln Val Gly Thr Thr Ile Met Asn Leu Trp Ala Gly
            340                 345                 350
His Arg Ile Thr Phe Asn Arg Ile Gln Gly Gly Ser Thr Ser Glu Met
        355                 360                 365
Val Tyr Gly Ala Ile Thr Asn Pro Val Ser Val Ser Asp Ile Pro Phe
370                 375                 380
Val Asn Arg Asp Val Tyr Arg Thr Val Ser Leu Ala Gly Gly Leu Gly
385                 390                 395                 400
Ser Leu Ser Gly Ile Arg Tyr Gly Leu Thr Arg Val Asp Phe Asp Met
                405                 410                 415
Ile Phe Arg Asn His Pro Asp Ile Val Thr Gly Leu Phe Tyr His Pro
            420                 425                 430
Gly His Ala Gly Ile Ala Thr Gln Val Lys Asp Ser Glu Thr Glu Leu
```

```
                435                 440                 445
Pro Pro Glu Thr Thr Glu Gln Pro Asn Tyr Arg Ala Phe Ser His Leu
    450                 455                 460

Leu Ser His Ile Ser Met Gly Pro Thr Thr Gln Asp Val Pro Pro Val
465                 470                 475                 480

Tyr Ser Trp Thr His Gln Ser Ala Asp Arg Thr Asn Thr Ile Asn Ser
                485                 490                 495

Asp Arg Ile Thr Gln Ile Pro Leu Val Lys Ala His Thr Leu Gln Ser
            500                 505                 510

Gly Thr Thr Val Val Lys Gly Pro Gly Phe Thr Gly Gly Asp Ile Leu
        515                 520                 525

Arg Arg Thr Ser Gly Gly Pro Phe Ala Phe Ser Asn Val Asn Leu Asp
    530                 535                 540

Phe Asn Leu Ser Gln Arg Tyr Arg Ala Arg Ile Arg Tyr Ala Ser Thr
545                 550                 555                 560

Thr Asn Leu Arg Ile Tyr Val Thr Val Ala Gly Glu Arg Ile Phe Ala
                565                 570                 575

Gly Gln Phe Asp Lys Thr Met Asp Ala Gly Ala Pro Leu Thr Phe Gln
            580                 585                 590

Ser Phe Ser Tyr Ala Thr Ile Asn Thr Ala Phe Thr Phe Pro Glu Arg
        595                 600                 605

Ser Ser Ser Leu Thr Val Gly Ala Asp Thr Phe Ser Ser Gly Asn Glu
    610                 615                 620

Val Tyr Val Asp Arg Phe Glu Leu Ile Pro Val Thr Ala Thr Phe Glu
625                 630                 635                 640

Ala Glu Ser Asp Leu Glu Arg Ala Arg Lys
                645                 650

<210> SEQ ID NO 50
<211> LENGTH: 1950
<212> TYPE: DNA
<213> ORGANISM: Bacillus thuringiensis

<400> SEQUENCE: 50
atgccttcaa ataggaaaaa tgagaatgaa attataaatg ctttatcgat tccagctgta      60
tcgaatcatt ccgcacaaat ggatctatca ccagatgctc gcattgagga tagcttgtgt     120
gtagccgagg gaacaatat tgatccattt gttagcgcat caacagtcca aacaggtatt      180
agtatagctg gtagaatatt aggcgtatta ggggtgccgt ttgccggaca actagctagt     240
ttttatagtt ttcttgttgg ggaattatgg cctagcggca gagatccatg gaaatttttt     300
atggaacatg tcgaacaaat tgtaagacaa caaataacgg acagtgttag ggataccgct     360
attgctcgtt tagaaggtct aggaagaggg tatagatctt accagcaggc tcttgaaact     420
tggttagata accgaaatga tgcaagatca agaagcatta ttcgtgagag atatattgct     480
ttagaacttg acattactac tgctataccg ctttttcagca tacgaaatca agaggttcca     540
ttattaatgg tatatgctca agctgcaaat ttacacctat tattattgag agacgcatcc     600 cttttttggta gtgaatgggg gatgtcatct gccgatgtta accaatatta ccaagaacaa     660
atcagatata cagaggaata ttctaaccat tgcgtacaat ggtataatac agggctaaat     720
agattaagag ggacaactgc cgaaagttgg gtacggtata tcaattccg tagagaccta      780 acattaggtg tattagattt agtggcacta ttcccaagct atgacactcg gacttatccc     840
attccaacta ccgcccaact tacaagagaa gtgtatacag atccaaacgg tgttgtagca     900
```

```
ggacccaata atagttggtt tagaaatgga gcttcgtttt ccgctataga aaacgcaatt    960
attcgacaac ctcacctata tgattttcta acgaacctta caatttacac gagaagaagt   1020
caagtaggca ctacaattat gaatttgtgg gcagggcata gaatcacgtt taatagaata   1080
caaggtggtt ctactagtga aatggtgtat ggggctatta ctaacccagt tagtgttagt   1140
gacataccat ttgtcaatcg ggatgtttac cgaactgtat cattagctgg tgggcttggc   1200
tctctgagtg gaatacgtta tggtttaact agagttgatt ttgatatgat atttcgtaac   1260
catcctgata tagtaactgg attattttat catccgggac acgcgggcat tgcaacccaa   1320
gtaaaagatt cagaaacaga attaccacct gaaacgacag aacagccaaa ttatagagca   1380
tttagtcatc tactaagtca tatttcaatg ggtccaacga ctcaagacgt acctccagta   1440
tattcttgga cacaccagag tgcagatcgt acgaatacaa tcaattcgga taggataaca   1500
caaataccat tggtaaaggc gcataccctc caatcgggta ccactgtagt aaaagggcca   1560
gggtttacag gaggggatat cctccgtcga acaagtggag gaccatttgc ttttagtaat   1620
gttaatctag attttaactt gtcacaaagg tatcgtgcta gaattcgtta tgcctctact   1680
actaacctaa gaatttacgt aacggttgca ggtgaacgaa tttttgctgg tcaatttgac   1740
aaaactatgg atgctggtgc cccattaaca ttccaatctt ttagttacgc aactattaat   1800
acagctttta cattcccaga aagatcgagc agcttgactg taggtgccga tacgtttagt   1860
tcaggtaatg aagtttatgt agatagattt gaattaatcc cagttactgc aaccttcgag   1920
gcagaatctg atttagaaag agcgcggaag                                    1950
```

```
<210> SEQ ID NO 51
<211> LENGTH: 3771
<212> TYPE: DNA
<213> ORGANISM: Bacillus thuringiensis

<400> SEQUENCE: 51
```

```
ttgacttcaa ataggaaaaa tgagaatgaa attataaatg ctttatcgat tccaacggta     60
tcgaatcctt ccacgcaaat gaatctatca ccagatgctc gtattgaaga tagcttgtgt    120
gtagccgagg tgaacaatat tgatccattt gttagcgcat caacagtcca aacgggtata    180
aacatagctg gtagaatatt gggcgtatta ggtgtgccgt ttgctggaca actagctagt    240
ttttatagtt ttcttgttgg tgaattatgg cctagtggca gagatccatg ggaaattttc    300
ctggaacatg tagaacaact tataagacaa caagtaacag aaaatactag gaatacggct    360
attgctcgat tagaaggtct aggaagaggc tatagatctt accagcaggc tcttgaaact    420
tggttagata accgaaatga tgcaagatca agaagcatta ttcttgagcg ctatgttgct    480
ttagaacttg acattactac tgctataccg cttttcagaa tacgaaatca agaggttcca    540
ttattaatgg tatatgctca agctgcaaat ttacacctat tattattgag ggacgcatcc    600
ctttttggta gtgaatgggg gacggcatct tccgatgtta accaatatta ccaagaacaa    660
atcagatata cagaggaata ttctaaccat tgcgtacaat ggtataatac ggggctaaat    720
aacttaagag ggacaaatgc tgaaagttgg gtacggtata atcaattccg cagagaccta    780
acattagggg tattagatct agtggcccta ttcccaagtt atgacactcg cacttatcca    840
atcaatacga gtgctcagtt aacaagagaa gtttatacag acgcaattgg gaccgtacat    900
ccgagtcaag cttttgcaag tacgacttgg tttaataata atgcaccatc gttttctgcc    960
atagaagctg ccgttatcag gcctccgcat ctacttgatt ttccagaaca acttacaatt   1020
tacagcacat taagtcgatg gagtaacact cagtttatga atatatgggc aggtcataga   1080
```

-continued

```
cttgaatccc gcccaatagc agggtcatta aatacctcta cacaaggatc taccaatact   1140
tctattaatc ctgtaacatt acagtttacg tctcgagaca tttataggac tgaatcattg   1200
gcagggctaa atatatttat aactcaacct gttaatgggg ttccttgggt tagatttaat   1260
tggagaaatc ccctgaattc tcttagaggt agccttctct atacgatagg gtatactgga   1320
gttgggacgc aattacaaga ttcagaaact gaattacccc cagaaacaac agaacgacca   1380
aattatgaat catatagtca tagattatct catataggac tcatttcatc atctcatgtg   1440
agagcattgg tatattcttg gacgcaccgt agtgcagatc gtacgaatac gattggacca   1500
aatagaatta ctcaaattcc tgcagtgaag ggaagatttc tttttaatgg ctctgtaatt   1560
tcaggaccag gatttactgg tggagacgta gttagattga ataggaataa tggtaatatt   1620
caaaatagag ggtatattga agttccaatt caattcacgt cgacatctac cagatatcga   1680
gttcgagtac gttatgcttc tgtaacctcg attgagctca atgttaattg gggcaattca   1740
tcaattttta cgaacacatt accagcaaca gctgcatcat tagataatct acaatcaggg   1800
gattttggtt atgttgaaat caacaatgct tttacatccg caacaggtaa tatagtaggt   1860
gttagaaatt ttagtgcaaa tgcagaggta ataatagaca gatttgaatt tatcccagtt   1920
actgcaacct tcgaggcaaa atatgattta gaaagagcac aaaaggcggt gaatgctctg   1980
tttacttcta caaatccaag aagattgaag acagatgtga cagattatca tattgaccaa   2040
gtgtccaatc tggtggtatg tttatcagat gaattttgct tggatgagaa gcgagaatta   2100
tttgagaaag tgaaatatgc gaagcgactc agtgatgaaa gaaacttact ccaagatcca   2160
aacttcacat tcatcaatgg gcaaccaagt tttgcatcca tcgatggaca atcaaacttc   2220
acctctatta atgagctatc taatcatgga tggtggggca gtgcgaatgt taccattcag   2280
gaagggaatg acgtatttaa agagaattac gtcacactac cgggtacttt taatgagtgt   2340
tatccaaatt atttatatca aaaaatagga gagtcagaat taaaggctta tacgcgctat   2400
caattaagag ggtatattga agatagtcaa gatctagaga tttatttaat tcgttacaat   2460
gcaaagcatg aaacattaaa tgttccaggt accgagtccc tatggccgct ttcagttgaa   2520
agcccaatcg gaaggtgcgg agaaccaaat cgatgcgcac cacattttgg atggaatcct   2580
gatctagatt gttcctgcag agatagagaa aaatgtgcgc atcattccca tcatttcact   2640
ttggatattg atgttggatg cacagacttg caagaggatc taggcgtgtg ggttgtattc   2700
aagattaaga cgcaggaagg ttatgcaaga ttaggaaatc tggaatttat cgaagagaaa   2760
ccattaattg gagaagcact gtctcgtgtg aagagagcgg aaaaaaaatg gagagacaaa   2820
agggaaaaac tacaagtgga aacaaaacga gtatatatag acgcaaaaga agctgtggat   2880
gctttattcg tagattctca atatgataga ttacaagcag atacaaacat cggtatgatt   2940
catgcggcag atagacttgt tcatcggatc cacgaggctt atcttccaga actacctttc   3000
attccaggaa taaatgtggt gattttgaa gaattagaaa accgtatttc tactgcattt   3060
tccttatatg atgcgagaaa tgtcattaaa aatggcgatt tcaataatgg attgacatgc   3120
tggaacgtga aagggcatgt agaggtacag cagctgaaca atcatcgttc ggtccttgtc   3180
atcccggaat gggaagcaga agtttcacaa aaggtgcgcg tctgtccagg tcgtggctat   3240
attcttcgtg tcacagcgta caaagaggga tatgggggaag gctgcgtaac tattcatgaa   3300
gtcgataata atacagacca attgaagttt agcaactgtg agaaaggaca agtatatcca   3360
ggtaatacga tagcatgtaa tgattataat aagaatcatg gtgcgaatgc atgtagttct   3420
```

-continued

```
cgtaatcgtg gatatgacga attctatgga aacaccccag ctgattattc tgcaaatcaa   3480
aaagaatacg gggtgcgta cacttcccac aatcatgcat atggcgaatc ttatgaaagt    3540
aattcgtcca taccagctga ttatgcgccg gtttatgaag aagaagcgta tacacatgga   3600
cgaagaggta attcttgtga atataacaga gggtatacac cattaccagc tggttatgtg   3660
acagcagagt tagaatactt cccagaaacg gatacagtat gggttgagat tggagaaacg   3720
gaaggaacat ttatcgtgga caatgtggaa ttactcctta tggaggaata g            3771
```

<210> SEQ ID NO 52
<211> LENGTH: 1256
<212> TYPE: PRT
<213> ORGANISM: Bacillus thuringiensis

<400> SEQUENCE: 52

```
Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Thr
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Val Tyr Thr Asp Ala Ile Gly Thr Val His Pro Ser Gln Ala
    290                 295                 300

Phe Ala Ser Thr Thr Trp Phe Asn Asn Asn Ala Pro Ser Phe Ser Ala
305                 310                 315                 320
```

-continued

```
Ile Glu Ala Ala Val Ile Arg Pro Pro His Leu Leu Asp Phe Pro Glu
                325                 330                 335

Gln Leu Thr Ile Tyr Ser Thr Leu Ser Arg Trp Ser Asn Thr Gln Phe
                340                 345                 350

Met Asn Ile Trp Ala Gly His Arg Leu Glu Ser Arg Pro Ile Ala Gly
                355                 360                 365

Ser Leu Asn Thr Ser Thr Gln Gly Ser Thr Asn Thr Ser Ile Asn Pro
            370                 375                 380

Val Thr Leu Gln Phe Thr Ser Arg Asp Ile Tyr Arg Thr Glu Ser Leu
385                 390                 395                 400

Ala Gly Leu Asn Ile Phe Ile Thr Gln Pro Val Asn Gly Val Pro Trp
                405                 410                 415

Val Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Gln Asp Ser
                435                 440                 445

Glu Thr Glu Leu Pro Pro Glu Thr Thr Glu Arg Pro Asn Tyr Glu Ser
            450                 455                 460

Tyr Ser His Arg Leu Ser His Ile Gly Leu Ile Ser Ser Ser His Val
465                 470                 475                 480

Arg Ala Leu Val Tyr Ser Trp Thr His Arg Ser Ala Asp Arg Thr Asn
                485                 490                 495

Thr Ile Gly Pro Asn Arg Ile Thr Gln Ile Pro Ala Val Lys Gly Arg
                500                 505                 510

Phe Leu Phe Asn Gly Ser Val Ile Ser Gly Pro Gly Phe Thr Gly Gly
                515                 520                 525

Asp Val Val Arg Leu Asn Arg Asn Asn Gly Asn Ile Gln Asn Arg Gly
            530                 535                 540

Tyr Ile Glu Val Pro Ile Gln Phe Thr Ser Thr Thr Arg Tyr Arg
545                 550                 555                 560

Val Arg Val Arg Tyr Ala Ser Val Thr Ser Ile Glu Leu Asn Val Asn
                565                 570                 575

Trp Gly Asn Ser Ser Ile Phe Thr Asn Thr Leu Pro Ala Thr Ala Ala
                580                 585                 590

Ser Leu Asp Asn Leu Gln Ser Gly Asp Phe Gly Tyr Val Glu Ile Asn
                595                 600                 605

Asn Ala Phe Thr Ser Ala Thr Gly Asn Ile Val Gly Val Arg Asn Phe
            610                 615                 620

Ser Ala Asn Ala Glu Val Ile Ile Asp Arg Phe Glu Phe Ile Pro Val
625                 630                 635                 640

Thr Ala Thr Phe Glu Ala Lys Tyr Asp Leu Glu Arg Ala Gln Lys Ala
                645                 650                 655

Val Asn Ala Leu Phe Thr Ser Thr Asn Pro Arg Arg Leu Lys Thr Asp
                660                 665                 670

Val Thr Asp Tyr His Ile Asp Gln Val Ser Asn Leu Val Cys Leu
                675                 680                 685

Ser Asp Glu Phe Cys Leu Asp Glu Lys Arg Glu Leu Phe Glu Lys Val
            690                 695                 700

Lys Tyr Ala Lys Arg Leu Ser Asp Glu Arg Asn Leu Leu Gln Asp Pro
705                 710                 715                 720

Asn Phe Thr Phe Ile Asn Gly Gln Pro Ser Phe Ala Ser Ile Asp Gly
                725                 730                 735
```

-continued

Gln Ser Asn Phe Thr Ser Ile Asn Glu Leu Ser Asn His Gly Trp Trp
            740                 745                 750

Gly Ser Ala Asn Val Thr Ile Gln Glu Gly Asn Asp Val Phe Lys Glu
            755                 760                 765

Asn Tyr Val Thr Leu Pro Gly Thr Phe Asn Glu Cys Tyr Pro Asn Tyr
            770                 775                 780

Leu Tyr Gln Lys Ile Gly Glu Ser Glu Leu Lys Ala Tyr Thr Arg Tyr
785                 790                 795                 800

Gln Leu Arg Gly Tyr Ile Glu Asp Ser Gln Asp Leu Glu Ile Tyr Leu
            805                 810                 815

Ile Arg Tyr Asn Ala Lys His Glu Thr Leu Asn Val Pro Gly Thr Glu
            820                 825                 830

Ser Leu Trp Pro Leu Ser Val Glu Ser Pro Ile Gly Arg Cys Gly Glu
            835                 840                 845

Pro Asn Arg Cys Ala Pro His Phe Gly Trp Asn Pro Asp Leu Asp Cys
            850                 855                 860

Ser Cys Arg Asp Arg Glu Lys Cys Ala His His Ser His His Phe Thr
865                 870                 875                 880

Leu Asp Ile Asp Val Gly Cys Thr Asp Leu Gln Glu Asp Leu Gly Val
            885                 890                 895

Trp Val Val Phe Lys Ile Lys Thr Gln Glu Gly Tyr Ala Arg Leu Gly
            900                 905                 910

Asn Leu Glu Phe Ile Glu Glu Lys Pro Leu Ile Gly Glu Ala Leu Ser
            915                 920                 925

Arg Val Lys Arg Ala Glu Lys Lys Trp Arg Asp Lys Arg Glu Lys Leu
            930                 935                 940

Gln Val Glu Thr Lys Arg Val Tyr Ile Asp Ala Lys Glu Ala Val Asp
945                 950                 955                 960

Ala Leu Phe Val Asp Ser Gln Tyr Asp Arg Leu Gln Ala Asp Thr Asn
            965                 970                 975

Ile Gly Met Ile His Ala Ala Asp Arg Leu Val His Arg Ile His Glu
            980                 985                 990

Ala Tyr Leu Pro Glu Leu Pro Phe Ile Pro Gly Ile Asn Val Val Ile
            995                 1000                1005

Phe Glu Glu Leu Glu Asn Arg Ile Ser Thr Ala Phe Ser Leu Tyr
            1010                1015                1020

Asp Ala Arg Asn Val Ile Lys Asn Gly Asp Phe Asn Asn Gly Leu
            1025                1030                1035

Thr Cys Trp Asn Val Lys Gly His Val Glu Val Gln Gln Leu Asn
            1040                1045                1050

Asn His Arg Ser Val Leu Val Ile Pro Glu Trp Glu Ala Glu Val
            1055                1060                1065

Ser Gln Lys Val Arg Val Cys Pro Gly Arg Gly Tyr Ile Leu Arg
            1070                1075                1080

Val Thr Ala Tyr Lys Glu Gly Tyr Gly Glu Gly Cys Val Thr Ile
            1085                1090                1095

His Glu Val Asp Asn Asn Thr Asp Gln Leu Lys Phe Ser Asn Cys
            1100                1105                1110

Glu Lys Gly Gln Val Tyr Pro Gly Asn Thr Ile Ala Cys Asn Asp
            1115                1120                1125

Tyr Asn Lys Asn His Gly Ala Asn Ala Cys Ser Ser Arg Asn Arg
            1130                1135                1140

Gly Tyr Asp Glu Phe Tyr Gly Asn Thr Pro Ala Asp Tyr Ser Ala

```
                    1145                1150                1155
Asn Gln Lys Glu Tyr Gly Gly Ala Tyr Thr Ser His Asn His Ala
        1160                1165                1170

Tyr Gly Glu Ser Tyr Glu Ser Asn Ser Ser Ile Pro Ala Asp Tyr
    1175                1180                1185

Ala Pro Val Tyr Glu Glu Glu Ala Tyr Thr His Gly Arg Arg Gly
    1190                1195                1200

Asn Ser Cys Glu Tyr Asn Arg Gly Tyr Thr Pro Leu Pro Ala Gly
    1205                1210                1215

Tyr Val Thr Ala Glu Leu Glu Tyr Phe Pro Glu Thr Asp Thr Val
    1220                1225                1230

Trp Val Glu Ile Gly Glu Thr Glu Gly Thr Phe Ile Val Asp Asn
    1235                1240                1245

Val Glu Leu Leu Leu Met Glu Glu
    1250                1255

<210> SEQ ID NO 53
<211> LENGTH: 3714
<212> TYPE: DNA
<213> ORGANISM: Bacillus thuringiensis

<400> SEQUENCE: 53
ttgaattcaa ataggaaaaa tgagaacgaa attatagatg cttcatttat tcccgcagta      60
tccaatgagt ctgttacaat ctctaaagaa tatgcacaaa caatcaatt acaaaacaat     120
agcattgagg atggtttgtg tatagccgaa ggggaatata ttgatccatt tgttagcgca     180
tcaacagtcc aaacggggat tagtatcgct ggtagaatat tgggtgtatt aggtgtgccg     240
tttgccggac aattagctag ttttttatagt tttattgttg gtgaattatg gcctaaaggc     300
agagaccaat gggaaatttt tatggaacat gtagaacaac ttgtaagaca acaaataaca     360
gcaaatgcta ggaatacggc ccttgctcga ttacaaggtt taggagattc ctttagagcc     420
tatcaacagt cacttgaaga ttggctagag aaccgtaatg atgcaagaac gagaagtgtt     480
ctttatactc aatatatagc cttagagctt gattttctaa atgcgatgcc gcttttcgca     540
ataagagagc aagaggttcc cttattaatg gtatacgctc aagctgcaaa cttgcaccta     600
ttattattga gagacgcctc cctttatggt cgtgaatttg gcttacctc ccaagaaatt     660
caacgttatt atgaacgcca agtagaaaga acgagggact attctgacca ttgcgtgcaa     720
tggtataata cgggtctaaa taacttaaga gggacaaatg ctgaaagttg ggtgcggtat     780
aatcaattcc gtagagacct aacattaggg gtattagatc tagtggcact attcccaagc     840
tatgacactc gcacttatcc aataaatacg agtgctcagt taacaaggga gtttataca     900
gacgcaattg gagcaacagg ggtaaatatg caagtatga attggtataa taataatgca     960
ccttcgtttt ccgctataga gactgcggtt atccgaagcc cgcatctact tgattttcta    1020
gaacaactta aaattttag cgcttcatca cgatggagta atactaggca tatgacttat    1080
tggcgggggc acacgattca atctcggcca ataagagggg cattaattac ctcgacacac    1140
ggaaatacca atacttctat taaccctgta acattccagt tcccgtcccg agacgtttat    1200
aggactgaat catatgcagg agtgcttcta tggggaattt accttgaacc tattcatggt    1260
gttcctactg ttagatttaa ttttaggaac cctcagaata cttttgaaag aggtactgct    1320
aactatagtc aaccctatga gtcacctggg cttcaattaa aagattcaga aactgaatta    1380
ccaccagaaa caacagaacg accaaattat gaatcatata gtcatagatt atctcacata    1440
```

```
gggatcattt tacaaactag gttgaatgta ccggtatatt cttggacgca tcgtagtgca    1500
gatcgtacaa atacaattgg accaaataga attactcaaa ttcctgcagt gaagggaaac    1560
cttcttttta atggttctgt aatttcagga ccaggattta ctggtgggga cttagttaga    1620
ttaaataata gtgaaataa tattcaaaat agaggctatc ttgaggttcc aattcaattc     1680
acatcgacat ctaccagata tcgagttcgt gtacgttatg cttctgtaac cccgattcac    1740
ctcagtgtta attggggtaa ttcaaacatt ttttccagca cagttccagc tacagctgcg    1800
tcattagata atctacaatc aagggatttt ggttattttg aaagtaccaa tgcatttaca    1860
tctgtaacag gtaatgtagt aggtgtaaga aatttagtg aaaatgccag agtgataata    1920
gacagatttg aatttattcc agttactgca accttcgaag cagaatacga tttagaaagg    1980
gcgcaagagg cggtgaatgc tctgtttact aatacgaatc caagaagatt gaaaacagat    2040
gtgacagatt atcatattga tcaagtatcc aatttagtgg cgtgtttatc ggatgaattc    2100
tgcttagatg aaaagagaga attacttgag aaagtgaaat atgcgaaacg actcagtgat    2160
gaaagaaact tactccaaga tccaaacttc acatccatca ataagcaacc agacttcata    2220
tctactaatg agcaatcgaa tttcacatct atccatgaac aatctgaaca tggatggtgg    2280
ggaagtgaga acattacaat ccaggaagga aatgacgtat taaagagaa ttacgtcaca     2340 ctaccaggta cttataatga gtgttatccg acgtatttat atcaaaaaat aggagagtcg    2400
gaattaaaag cttatactcg ctaccaatta agaggttata ttgaagatag tcaagattta    2460
gagatatatt tgattcgtta taatgcgaaa catgaaacat ggatgttcc aggtaccgag     2520 tccgtatggc cgctttcagt tgaaagccca atcagaaggt gcgagaaacc gaatcgatgc    2580
gcaccacatt ttgaatggaa tcctgatcta gattgttcct gcagagatgg agaaaaatgt    2640
gcgcatcatt cccatcattt ctctttggat attgatgttg gatgcataga cttgcatgag    2700
aacctaggcg tgtgggtggt attcaagatt aagacgcagg aaggtcatgc aagactaggg    2760
aacctggaat ttattgaaga gaaaccatta ttaggagaag cactgtctcg tgtgaagaga    2820
gcagagaaaa aatggagaga caaacgtgaa aaactacaat tggaaacaaa acgagtatat    2880
acagaggcaa aagaagctgt ggatgcttta tttgtagatt ctcaatatga tagattacaa    2940
gcggatacaa acattggcat gattcatgcg gcagataaac ttgttcatcg aattcgagag    3000
gcgtatcttt cagaattatc tgttatccca ggtgtaaatg cggaaatttt tgaagaatta    3060
gaaggtcgca ttatcactgc aatctcccta tacgatgcga gaaatgtcgt taaaaatggt    3120
gattttaata atggattagc atgctggaat gtaaaagggc atgtagatgt acaacagagc    3180
catcaccgtt ctgtccttgt tatcccagaa tgggaagcag aagtgtcaca agcagttcgc    3240
gtctgtccgg ggcgtggcta tatcctccgt gtcacagcgt acaaagaggg atatggagag    3300
ggttgtgtaa cgatccatga aatcgagaac aatacagacg aactaaaatt taaaaactgt    3360
gaagaagagg aagtgtatcc aacggataca ggaacgtgta atgattatac tgcacaccaa    3420
ggtacagcag catgtaattc ccgtaatgct ggatatgagg atgcatatga agttgatact    3480
acagcatctg ttaattacaa accgacttat gaagaagaaa cgtatacaga tgtacgaaga    3540
gataatcatt gtgaatatga cagagggtat gtgaattatc caccagtacc agctggttat    3600
atgacaaaag aattagaata cttcccagaa accgataagg tatggattga gattggagaa    3660
acggaaggga gtttattgt agacagcgtg gaattactcc ttatggagga atag          3714
```

<210> SEQ ID NO 54
<211> LENGTH: 1237

```
<212> TYPE: PRT
<213> ORGANISM: Bacillus thuringiensis

<400> SEQUENCE: 54

Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
            20                  25                  30

Gln Thr Asn Gln Leu Gln Asn Asn Ser Ile Glu Asp Gly Leu Cys Ile
        35                  40                  45

Ala Glu Gly Glu Tyr Ile Asp Pro Phe Val Ser Ala Ser Thr Val Gln
    50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
            100                 105                 110

Gln Leu Val Arg Gln Gln Ile Thr Ala Asn Ala Arg Asn Thr Ala Leu
        115                 120                 125

Ala Arg Leu Gln Gly Leu Gly Asp Ser Phe Arg Ala Tyr Gln Gln Ser
    130                 135                 140

Leu Glu Asp Trp Leu Glu Asn Arg Asn Asp Ala Arg Thr Arg Ser Val
145                 150                 155                 160

Leu Tyr Thr Gln Tyr Ile Ala Leu Glu Leu Asp Phe Leu Asn Ala Met
                165                 170                 175

Pro Leu Phe Ala Ile Arg Glu Gln Glu Val Pro Leu Leu Met Val Tyr
            180                 185                 190

Ala Gln Ala Ala Asn Leu His Leu Leu Leu Leu Arg Asp Ala Ser Leu
        195                 200                 205

Tyr Gly Arg Glu Phe Gly Leu Thr Ser Gln Glu Ile Gln Arg Tyr Tyr
    210                 215                 220

Glu Arg Gln Val Glu Arg Thr Arg Asp Tyr Ser Asp His Cys Val Gln
225                 230                 235                 240

Trp Tyr Asn Thr Gly Leu Asn Asn Leu Arg Gly Thr Asn Ala Glu Ser
                245                 250                 255

Trp Val Arg Tyr Asn Gln Phe Arg Arg Asp Leu Thr Leu Gly Val Leu
            260                 265                 270

Asp Leu Val Ala Leu Phe Pro Ser Tyr Asp Thr Arg Thr Tyr Pro Ile
        275                 280                 285

Asn Thr Ser Ala Gln Leu Thr Arg Glu Val Tyr Thr Asp Ala Ile Gly
    290                 295                 300

Ala Thr Gly Val Asn Met Ala Ser Met Asn Trp Tyr Asn Asn Asn Ala
305                 310                 315                 320

Pro Ser Phe Ser Ala Ile Glu Thr Ala Val Ile Arg Ser Pro His Leu
                325                 330                 335

Leu Asp Phe Leu Glu Gln Leu Lys Ile Phe Ser Ala Ser Ser Arg Trp
            340                 345                 350

Ser Asn Thr Arg His Met Thr Tyr Trp Arg Gly His Thr Ile Gln Ser
        355                 360                 365

Arg Pro Ile Arg Gly Ala Leu Ile Thr Ser His Gly Asn Thr Asn
    370                 375                 380

Thr Ser Ile Asn Pro Val Thr Phe Gln Phe Pro Ser Arg Asp Val Tyr
385                 390                 395                 400
```

-continued

```
Arg Thr Glu Ser Tyr Ala Gly Val Leu Leu Trp Gly Ile Tyr Leu Glu
            405                 410                 415
Pro Ile His Gly Val Pro Thr Val Arg Phe Asn Phe Arg Asn Pro Gln
            420                 425                 430
Asn Thr Phe Glu Arg Gly Thr Ala Asn Tyr Ser Gln Pro Tyr Glu Ser
            435                 440                 445
Pro Gly Leu Gln Leu Lys Asp Ser Glu Thr Glu Leu Pro Pro Glu Thr
450                 455                 460
Thr Glu Arg Pro Asn Tyr Glu Ser Tyr Ser His Arg Leu Ser His Ile
465                 470                 475                 480
Gly Ile Ile Leu Gln Thr Arg Leu Asn Val Pro Val Tyr Ser Trp Thr
            485                 490                 495
His Arg Ser Ala Asp Arg Thr Asn Thr Ile Gly Pro Asn Arg Ile Thr
            500                 505                 510
Gln Ile Pro Ala Val Lys Gly Asn Leu Leu Phe Asn Gly Ser Val Ile
            515                 520                 525
Ser Gly Pro Gly Phe Thr Gly Gly Asp Leu Val Arg Leu Asn Asn Ser
            530                 535                 540
Gly Asn Asn Ile Gln Asn Arg Gly Tyr Leu Glu Val Pro Ile Gln Phe
545                 550                 555                 560
Thr Ser Thr Ser Thr Arg Tyr Arg Val Arg Val Arg Tyr Ala Ser Val
            565                 570                 575
Thr Pro Ile His Leu Ser Val Asn Trp Gly Asn Ser Asn Ile Phe Ser
            580                 585                 590
Ser Thr Val Pro Ala Thr Ala Ala Ser Leu Asp Asn Leu Gln Ser Arg
            595                 600                 605
Asp Phe Gly Tyr Phe Glu Ser Thr Asn Ala Phe Thr Ser Val Thr Gly
            610                 615                 620
Asn Val Val Gly Val Arg Asn Phe Ser Glu Asn Ala Arg Val Ile Ile
625                 630                 635                 640
Asp Arg Phe Glu Phe Ile Pro Val Thr Ala Thr Phe Glu Ala Glu Tyr
            645                 650                 655
Asp Leu Glu Arg Ala Gln Glu Ala Val Asn Ala Leu Phe Thr Asn Thr
            660                 665                 670
Asn Pro Arg Arg Leu Lys Thr Asp Val Thr Asp Tyr His Ile Asp Gln
            675                 680                 685
Val Ser Asn Leu Val Ala Cys Leu Ser Asp Glu Phe Cys Leu Asp Glu
690                 695                 700
Lys Arg Glu Leu Leu Glu Lys Val Lys Tyr Ala Lys Arg Leu Ser Asp
705                 710                 715                 720
Glu Arg Asn Leu Leu Gln Asp Pro Asn Phe Thr Ser Ile Asn Lys Gln
            725                 730                 735
Pro Asp Phe Ile Ser Thr Asn Glu Gln Ser Asn Phe Thr Ser Ile His
            740                 745                 750
Glu Gln Ser Glu His Gly Trp Trp Gly Ser Glu Asn Ile Thr Ile Gln
            755                 760                 765
Glu Gly Asn Asp Val Phe Lys Glu Asn Tyr Val Thr Leu Pro Gly Thr
            770                 775                 780
Tyr Asn Glu Cys Tyr Pro Thr Tyr Leu Tyr Gln Lys Ile Gly Glu Ser
785                 790                 795                 800
Glu Leu Lys Ala Tyr Thr Arg Tyr Gln Leu Arg Gly Tyr Ile Glu Asp
            805                 810                 815
```

```
Ser Gln Asp Leu Glu Ile Tyr Leu Ile Arg Tyr Asn Ala Lys His Glu
                820                 825                 830

Thr Leu Asp Val Pro Gly Thr Glu Ser Val Trp Pro Leu Ser Val Glu
            835                 840                 845

Ser Pro Ile Arg Arg Cys Gly Glu Pro Asn Arg Cys Ala Pro His Phe
850                 855                 860

Glu Trp Asn Pro Asp Leu Asp Cys Ser Cys Arg Asp Gly Glu Lys Cys
865                 870                 875                 880

Ala His His Ser His His Phe Ser Leu Asp Ile Asp Val Gly Cys Ile
                885                 890                 895

Asp Leu His Glu Asn Leu Gly Val Trp Val Val Phe Lys Ile Lys Thr
                900                 905                 910

Gln Glu Gly His Ala Arg Leu Gly Asn Leu Glu Phe Ile Glu Glu Lys
                915                 920                 925

Pro Leu Leu Gly Glu Ala Leu Ser Arg Val Lys Arg Ala Glu Lys Lys
            930                 935                 940

Trp Arg Asp Lys Arg Glu Lys Leu Gln Leu Glu Thr Lys Arg Val Tyr
945                 950                 955                 960

Thr Glu Ala Lys Glu Ala Val Asp Ala Leu Phe Val Asp Ser Gln Tyr
                965                 970                 975

Asp Arg Leu Gln Ala Asp Thr Asn Ile Gly Met Ile His Ala Ala Asp
                980                 985                 990

Lys Leu Val His Arg Ile Arg Glu Ala Tyr Leu Ser Glu Leu Ser Val
                995                 1000                1005

Ile Pro Gly Val Asn Ala Glu Ile Phe Glu Glu Leu Glu Gly Arg
    1010                1015                1020

Ile Ile Thr Ala Ile Ser Leu Tyr Asp Ala Arg Asn Val Val Lys
    1025                1030                1035

Asn Gly Asp Phe Asn Asn Gly Leu Ala Cys Trp Asn Val Lys Gly
    1040                1045                1050

His Val Asp Val Gln Gln Ser His His Arg Ser Val Leu Val Ile
    1055                1060                1065

Pro Glu Trp Glu Ala Glu Val Ser Gln Ala Val Arg Val Cys Pro
    1070                1075                1080

Gly Arg Gly Tyr Ile Leu Arg Val Thr Ala Tyr Lys Glu Gly Tyr
    1085                1090                1095

Gly Glu Gly Cys Val Thr Ile His Glu Ile Glu Asn Asn Thr Asp
    1100                1105                1110

Glu Leu Lys Phe Lys Asn Cys Glu Glu Glu Glu Val Tyr Pro Thr
    1115                1120                1125

Asp Thr Gly Thr Cys Asn Asp Tyr Thr Ala His Gln Gly Thr Ala
    1130                1135                1140

Ala Cys Asn Ser Arg Asn Ala Gly Tyr Glu Asp Ala Tyr Glu Val
    1145                1150                1155

Asp Thr Thr Ala Ser Val Asn Tyr Lys Pro Thr Tyr Glu Glu Glu
    1160                1165                1170

Thr Tyr Thr Asp Val Arg Arg Asp Asn His Cys Glu Tyr Asp Arg
    1175                1180                1185

Gly Tyr Val Asn Tyr Pro Pro Val Pro Ala Gly Tyr Met Thr Lys
    1190                1195                1200

Glu Leu Glu Tyr Phe Pro Glu Thr Asp Lys Val Trp Ile Glu Ile
    1205                1210                1215

Gly Glu Thr Glu Gly Lys Phe Ile Val Asp Ser Val Glu Leu Leu
```

```
    1220                1225                1230

Leu Met  Glu Glu
    1235

<210> SEQ ID NO 55
<211> LENGTH: 650
<212> TYPE: PRT
<213> ORGANISM: Bacillus thuringiensis

<400> SEQUENCE: 55

Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350
```

```
Thr Ile Gln Ser Arg Pro Ile Gly Gly Leu Asn Thr Ser Thr His
            355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
        595                 600                 605

Gln Asp Ile Ile Arg Thr Ser Ile Gln Gly Leu Ser Gly Asn Gly Glu
    610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu
                645                 650

<210> SEQ ID NO 56
<211> LENGTH: 655
<212> TYPE: PRT
<213> ORGANISM: Bacillus thuringiensis

<400> SEQUENCE: 56

Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80
```

```
Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495
```

```
Thr Asn Thr Ile Gly Pro Asn Arg Ile Thr Gln Ile Pro Leu Val Lys
            500                 505                 510

Ala Leu Asn Leu His Ser Gly Val Thr Val Val Gly Pro Gly Phe
        515                 520                 525

Thr Gly Gly Asp Ile Leu Arg Arg Thr Asn Thr Gly Thr Phe Gly Asp
    530                 535                 540

Ile Arg Leu Asn Ile Asn Val Pro Leu Ser Gln Arg Tyr Arg Val Arg
545                 550                 555                 560

Ile Arg Tyr Ala Ser Thr Thr Asp Leu Gln Phe Phe Thr Arg Ile Asn
                565                 570                 575

Gly Thr Thr Val Asn Ile Gly Asn Phe Ser Arg Thr Met Asn Arg Gly
            580                 585                 590

Asp Asn Leu Glu Tyr Arg Ser Phe Arg Thr Ala Gly Phe Ser Thr Pro
        595                 600                 605

Phe Asn Phe Leu Asn Ala Gln Ser Thr Phe Thr Leu Gly Ala Gln Ser
    610                 615                 620

Phe Ser Asn Gln Glu Val Tyr Ile Asp Arg Val Glu Phe Val Pro Ala
625                 630                 635                 640

Glu Val Thr Phe Glu Ala Glu Tyr Asp Leu Glu Arg Ala Gln Lys
                645                 650                 655

<210> SEQ ID NO 57
<211> LENGTH: 655
<212> TYPE: PRT
<213> ORGANISM: Bacillus thuringiensis

<400> S

```
Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
        260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Leu Val Lys
            500                 505                 510

Ala Leu Asn Leu His Ser Gly Val Thr Val Val Gly Pro Gly Phe
        515                 520                 525

Thr Gly Gly Asp Ile Leu Arg Arg Thr Asn Thr Gly Thr Phe Gly Asp
    530                 535                 540

Ile Arg Leu Asn Ile Asn Val Pro Leu Ser Gln Arg Tyr Arg Val Arg
545                 550                 555                 560

Ile Arg Tyr Ala Ser Thr Thr Asp Leu Gln Phe Phe Thr Arg Ile Asn
                565                 570                 575

Gly Thr Thr Val Asn Ile Gly Asn Phe Ser Arg Thr Met Asn Arg Gly
            580                 585                 590

Asp Asn Leu Glu Tyr Arg Ser Phe Arg Thr Ala Gly Phe Ser Thr Pro
        595                 600                 605

Phe Asn Phe Leu Asn Ala Gln Ser Thr Phe Thr Leu Gly Ala Gln Ser
    610                 615                 620

Phe Ser Asn Gln Glu Val Tyr Ile Asp Arg Val Glu Phe Val Pro Ala
625                 630                 635                 640
```

```
Glu Val Thr Phe Glu Ala Glu Tyr Asp Leu Glu Arg Ala Gln Lys
                645                 650                 655
```

<210> SEQ ID NO 58
<211> LENGTH: 653
<212> TYPE: PRT
<213> ORGANISM: Bacillus thuringiensis

<400> SEQUENCE: 58

```
Met Thr Ser Asn Arg L

```
Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ser Phe
            500                 505                 510

Asn Leu Asn Ser Gly Thr Ser Val Val Ser Gly Pro Gly Phe Thr Gly
        515                 520                 525

Gly Asp Ile Ile Arg Thr Asn Val Asn Gly Ser Val Leu Ser Met Gly
    530                 535                 540

Leu Asn Phe Asn Asn Thr Ser Leu Gln Arg Tyr Arg Val Arg Val Arg
545                 550                 555                 560

Tyr Ala Ala Ser Gln Thr Met Val Leu Arg Val Thr Val Gly Gly Ser
                565                 570                 575

Thr Thr Phe Asp Gln Gly Phe Pro Ser Thr Met Ser Ala Asn Glu Ser
            580                 585                 590

Leu Thr Ser Gln Ser Phe Arg Phe Ala Glu Phe Pro Val Gly Ile Ser
        595                 600                 605

Ala Ser Gly Ser Gln Thr Ala Gly Ile Ser Ile Ser Asn Asn Ala Gly
    610                 615                 620

Arg Gln Thr Phe His Phe Asp Lys Ile Glu Phe Ile Pro Ile Thr Ala
625                 630                 635                 640

Thr Phe Glu Ala Glu Tyr Asp Leu Glu Arg Ala Gln Glu
                645                 650

<210> SEQ ID NO 59
<211> LENGTH: 654
<212> TYPE: PRT
<213> ORGANISM: Bacillus thuringiensis

<400> SEQUENCE: 59

Met Thr Ser Asn Arg Lys Asn Glu Asn Glu Ile Ile Asn Ala Leu Ser
1               5                   10                  15

Ile Pro Ala Val Ser Asn His Ser Thr Gln Met Asp Leu Ser Pro Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Gln
```

```
                         85                  90                  95
Trp Glu Ile Phe Leu Glu His Val Glu Gln Leu Ile Asn Gln Gln Ile
                    100                 105                 110

Thr Glu Asn Ala Arg Asn Thr Ala Leu Ala Arg Leu Gln Gly Leu Gly
                    115                 120                 125

Asp Ser Phe Arg Ala Tyr Gln Gln Ser Leu Glu Asp Trp Leu Glu Asn
                130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
                195                 200                 205

Thr Ser Gln Glu Ile Gln Arg Tyr Tyr Glu Arg Gln Val Glu Gln Thr
                210                 215                 220

Arg Asp Tyr Ser Asp Tyr Cys Val Glu Trp Tyr Asn Thr Gly Leu Asn
225                 230                 235                 240

Ser Leu Arg Gly Thr Asn Ala Ala Ser Trp Val Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Thr Tyr Pro Ile Asn Thr Ser Ala Gln Leu Thr
                275                 280                 285

Arg Glu Val Tyr Thr Asp Ala Ile Gly Ala Thr Gly Val Asn Met Ala
                290                 295                 300

Ser Met Asn Trp Tyr Asn Asn Ala Pro Ser Phe Ser Ala Ile Glu
305                 310                 315                 320

Thr Ala Val Ile Arg Ser Pro His Leu Leu Asp Phe Leu Glu Gln Leu
                325                 330                 335

Thr Ile Phe Ser Thr Ser Ser Arg Trp Ser Ala Thr Arg His Met Thr
                340                 345                 350

Tyr Trp Arg Gly His Thr Ile Gln Ser Arg Pro Ile Gly Gly Gly Leu
                355                 360                 365

Asn Thr Ser Thr His Gly Ser Thr Asn Thr Ser Ile Asn Pro Val Arg
                370                 375                 380

Leu Ser Phe Phe Ser Arg Asp Val Tyr Trp Thr Glu Ser Tyr Ala Gly
385                 390                 395                 400

Val Leu Leu Trp Gly Ile Tyr Leu Glu Pro Ile His Gly Val Pro Thr
                405                 410                 415

Val Arg Phe Asn Phe Arg Asn Pro Gln Asn Thr Phe Glu Arg Gly Thr
                420                 425                 430

Ala Asn Tyr Ser Gln Pro Tyr Glu Ser Pro Gly Leu Gln Leu Lys Asp
                435                 440                 445

Ser Glu Thr Glu Leu Pro Pro Glu Thr Thr Glu Arg Pro Asn Tyr Glu
                450                 455                 460

Ser Tyr Ser His Arg Leu Ser His Ile Gly Leu Ile Ser Gln Ser Arg
465                 470                 475                 480

Val His Val Pro Val Tyr Ser Trp Thr His Arg Ser Ala Asp Arg Thr
                485                 490                 495

Asn Thr Ile Ser Ser Asp Ser Ile Thr Gln Ile Pro Leu Val Lys Ser
                500                 505                 510
```

```
Phe Asn Leu Asn Ser Gly Thr Ser Val Val Ser Gly Pro Gly Phe Thr
            515                 520                 525

Gly Gly Asp Ile Ile Arg Thr Asn Val Asn Gly Ser Val Leu Ser Met
        530                 535                 540

Gly Leu Asn Phe Asn Asn Thr Ser Leu Gln Arg Tyr Arg Val Arg Val
545                 550                 555                 560

Arg Tyr Ala Ala Ser Gln Thr Met Val Leu Arg Val Thr Val Gly Gly
                565                 570                 575

Ser Thr Thr Phe Asp Gln Gly Phe Pro Ser Thr Met Ser Ala Asn Glu
            580                 585                 590

Ser Leu Thr Ser Gln Ser Phe Arg Phe Ala Glu Phe Pro Val Gly Ile
            595                 600                 605

Ser Ala Ser Gly Ser Gln Thr Ala Gly Ile Ser Ile Ser Asn Asn Ala
        610                 615                 620

Gly Arg Gln Thr Phe His Phe Asp Lys Ile Glu Phe Ile Pro Ile Thr
625                 630                 635                 640

Ala Thr Phe Glu Ala Glu Tyr Asp Leu Glu Arg Ala Gln Glu
                645                 650

<210> SEQ ID NO 60
<211> LENGTH: 661
<212> TYPE: PRT
<213> ORGANISM: Bacillus thuringiensis

<400> SEQUENCE: 60

Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
                20                  25                  30

Gln Thr Asn Gln Leu Gln Asn Asn Ser Ile Glu Asp Gly Leu Cys Ile
            35                  40                  45

Ala Glu Gly Glu Tyr Ile Asp Pro Phe Val Ser Ala Ser Thr Val Gln
        50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
                100                 105                 110

Gln Leu Val Arg Gln Gln Ile Thr Ala Asn Ala Arg Asn Thr Ala Leu
            115                 120                 125

Ala Arg Leu Gln Gly Leu Gly Asp Ser Phe Arg Ala Tyr Gln Gln Ser
        130                 135                 140

Leu Glu Asp Trp Leu Glu Asn Arg Asn Asp Ala Arg Thr Arg Ser Val
145                 150                 155                 160

Leu Tyr Thr Gln Tyr Ile Ala Leu Glu Leu Asp Phe Leu Asn Ala Met
                165                 170                 175

Pro Leu Phe Ala Ile Arg Glu Gln Glu Val Pro Leu Leu Met Val Tyr
            180                 185                 190

Ala Gln Ala Ala Asn Leu His Leu Leu Leu Leu Arg Asp Ala Ser Leu
        195                 200                 205

Tyr Gly Arg Glu Phe Gly Leu Thr Ser Gln Glu Ile Gln Arg Tyr Tyr
210                 215                 220

Glu Arg Gln Val Glu Arg Thr Arg Asp Tyr Ser Asp His Cys Val Gln
```

```
        225                 230                 235                 240
Trp Tyr Asn Thr Gly Leu Asn Asn Leu Arg Gly Thr Asn Ala Glu Ser
                    245                 250                 255
Trp Val Arg Tyr Asn Gln Phe Arg Arg Asp Leu Thr Leu Gly Val Leu
                    260                 265                 270
Asp Leu Val Ala Leu Phe Pro Ser Tyr Asp Thr Arg Thr Tyr Pro Ile
                    275                 280                 285
Asn Thr Ser Ala Gln Leu Thr Arg Glu Val Tyr Thr Asp Ala Ile Gly
                    290                 295                 300
Ala Thr Gly Val Asn Met Ala Ser Met Asn Trp Tyr Asn Asn Asn Ala
305                 310                 315                 320
Pro Ser Phe Ser Ala Ile Glu Thr Ala Val Ile Arg Ser Pro His Leu
                    325                 330                 335
Leu Asp Phe Leu Glu Gln Leu Lys Ile Phe Ser Ala Ser Ser Arg Trp
                    340                 345                 350
Ser Asn Thr Arg His Met Thr Tyr Trp Arg Gly His Thr Ile Gln Ser
                    355                 360                 365
Arg Pro Ile Arg Gly Ala Leu Ile Thr Ser Thr His Gly Asn Thr Asn
                    370                 375                 380
Thr Ser Ile Asn Pro Val Thr Phe Gln Phe Pro Ser Arg Asp Val Tyr
385                 390                 395                 400
Arg Thr Glu Ser Tyr Ala Gly Val Leu Leu Trp Gly Ile Tyr Leu Glu
                    405                 410                 415
Pro Ile His Gly Val Pro Thr Val Arg Phe Asn Phe Arg Asn Pro Gln
                    420                 425                 430
Asn Thr Phe Glu Arg Gly Thr Ala Asn Tyr Ser Gln Pro Tyr Glu Ser
                    435                 440                 445
Pro Gly Leu Gln Leu Lys Asp Ser Glu Thr Glu Leu Pro Pro Glu Thr
                    450                 455                 460
Thr Glu Arg Pro Asn Tyr Glu Ser Tyr Ser His Arg Leu Ser His Ile
465                 470                 475                 480
Gly Ile Ile Leu Gln Thr Arg Leu Asn Val Pro Val Tyr Ser Trp Thr
                    485                 490                 495
His Arg Ser Ala Asp Arg Thr Asn Thr Ile Ser Ser Asp Ser Ile Thr
                    500                 505                 510
Gln Ile Pro Leu Val Lys Ser Phe Asn Leu Asn Ser Gly Thr Ser Val
                    515                 520                 525
Val Ser Gly Pro Gly Phe Thr Gly Gly Asp Ile Ile Arg Thr Asn Val
                    530                 535                 540
Asn Gly Ser Val Leu Ser Met Gly Leu Asn Phe Asn Asn Thr Ser Leu
545                 550                 555                 560
Gln Arg Tyr Arg Val Arg Val Arg Tyr Ala Ala Ser Gln Thr Met Val
                    565                 570                 575
Leu Arg Val Thr Val Gly Gly Ser Thr Phe Asp Gln Gly Phe Pro
                    580                 585                 590
Ser Thr Met Ser Ala Asn Glu Ser Leu Thr Ser Gln Ser Phe Arg Phe
                    595                 600                 605
Ala Glu Phe Pro Val Gly Ile Ser Ala Ser Gly Ser Gln Thr Ala Gly
                    610                 615                 620
Ile Ser Ile Ser Asn Asn Ala Gly Arg Gln Thr Phe His Phe Asp Lys
625                 630                 635                 640
Ile Glu Phe Ile Pro Ile Thr Ala Thr Phe Glu Ala Glu Tyr Asp Leu
                    645                 650                 655
```

```
Glu Arg Ala Gln Glu
            660

<210> SEQ ID NO 61
<211> LENGTH: 643
<212> TYPE: PRT
<213> ORGANISM: Bacillus thuringiensis

<400> SEQUENCE: 61

Met Lys Asn Ser Ile Lys Leu Ser Glu Leu Trp Tyr Phe Asn Glu Arg
1               5                   10                  15

Lys Trp Arg Tyr Phe Met Glu Ile Val Asn Asn Gln Asn Gln Cys Val
            20                  25                  30

Pro Tyr Asn Cys Leu Asn Asn Pro Glu Ile Glu Ile Leu Glu Gly Gly
        35                  40                  45

Arg Ile Ser Val Gly Asn Thr Pro Ile Asp Ile Ser Leu Ser Leu Thr
    50                  55                  60

Gln Phe Leu Leu Ser Glu Phe Val Pro Gly Ala Gly Phe Val Leu Gly
65                  70                  75                  80

Leu Ile Asp Leu Ile Trp Gly Phe Val Gly Pro Ser Gln Trp Asp Ala
                85                  90                  95

Phe Leu Ala Gln Val Glu Gln Leu Ile Asn Gln Arg Ile Ala Glu Ala
            100                 105                 110

Val Arg Asn Thr Ala Ile Gln Glu Leu Glu Gly Met Ala Arg Val Tyr
        115                 120                 125

Arg Thr Tyr Ala Thr Ala Phe Ala Glu Trp Glu Lys Ala Pro Asp Asp
    130                 135                 140

Pro Glu Leu Arg Glu Ala Leu Arg Thr Gln Phe Thr Ala Thr Glu Thr
145                 150                 155                 160

Tyr Ile Ser Gly Arg Ile Ser Val Leu Lys Ile Gln Thr Phe Glu Val
                165                 170                 175

Gln Leu Leu Ser Val Phe Ala Gln Ala Ala Asn Leu His Leu Ser Leu
            180                 185                 190

Leu Arg Asp Val Val Phe Phe Gly Gln Arg Trp Gly Phe Ser Thr Thr
        195                 200                 205

Thr Val Asn Asn Tyr Tyr Asn Asp Leu Thr Glu Gly Ile Ser Thr Tyr
    210                 215                 220

Thr Asp Tyr Ala Val Arg Trp Tyr Asn Thr Gly Leu Glu Arg Val Trp
225                 230                 235                 240

Gly Pro Asp Ser Arg Asp Trp Val Arg Tyr Asn Gln Phe Arg Arg Glu
                245                 250                 255

Leu Thr Leu Thr Val Leu Asp Ile Val Ala Leu Phe Pro Asn Tyr Asp
            260                 265                 270

Ser Arg Arg Tyr Pro Ile Arg Thr Val Ser Gln Leu Thr Arg Glu Ile
        275                 280                 285

Tyr Thr Asn Pro Val Leu Glu Asn Phe Asp Gly Ser Phe Arg Gly Ser
    290                 295                 300

Ala Gln Gly Ile Glu Arg Ser Ile Arg Ser Pro His Leu Met Asp Ile
305                 310                 315                 320

Leu Asn Ser Ile Thr Ile Tyr Thr Asp Ala His Arg Gly Tyr Tyr Tyr
                325                 330                 335

Trp Ser Gly His Gln Ile Met Ala Ser Pro Val Gly Phe Ser Gly Pro
            340                 345                 350

Glu Phe Thr Phe Pro Leu Tyr Gly Thr Met Gly Asn Ala Ala Pro Gln
```

-continued

```
        355                 360                 365

Gln Arg Ile Val Ala Gln Leu Gly Gln Gly Val Tyr Arg Thr Leu Ser
    370                 375                 380

Ser Thr Phe Tyr Arg Arg Pro Phe Asn Ile Gly Ile Asn Asn Gln Gln
385                 390                 395                 400

Leu Ser Val Leu Asp Gly Thr Glu Phe Ala Tyr Gly Thr Ser Ser Asn
                405                 410                 415

Leu Pro Ser Ala Val Tyr Arg Lys Ser Gly Thr Val Asp Ser Leu Asp
            420                 425                 430

Glu Ile Pro Pro Gln Asn Asn Asn Val Pro Pro Arg Gln Gly Phe Ser
        435                 440                 445

His Arg Leu Ser His Val Ser Met Phe Arg Ser Gly Ser Ser Ser Ser
    450                 455                 460

Val Ser Ile Ile Arg Ala Pro Met Phe Ser Trp Ile His Arg Ser Ala
465                 470                 475                 480

Glu Phe Asn Asn Ile Ile Ala Ser Asp Ser Ile Thr Gln Ile Pro Ala
                485                 490                 495

Val Lys Gly Asn Phe Leu Phe Asn Gly Ser Val Ile Ser Gly Pro Gly
            500                 505                 510

Phe Thr Gly Gly Asp Leu Val Arg Leu Asn Ser Ser Gly Asn Asn Ile
        515                 520                 525

Gln Asn Arg Gly Tyr Ile Glu Val Pro Ile His Phe Pro Ser Thr Ser
    530                 535                 540

Thr Arg Tyr Arg Val Arg Val Arg Tyr Ala Ser Val Thr Pro Ile His
545                 550                 555                 560

Leu Asn Val Asn Trp Gly Asn Ser Ser Ile Phe Ser Asn Thr Val Pro
                565                 570                 575

Ala Thr Ala Thr Ser Leu Asp Asn Leu Gln Ser Ser Asp Phe Gly Tyr
            580                 585                 590

Phe Glu Ser Ala Asn Ala Phe Thr Ser Ser Leu Gly Asn Ile Val Gly
        595                 600                 605

Val Arg Asn Phe Ser Gly Thr Ala Gly Val Ile Ile Asp Arg Phe Glu
    610                 615                 620

Phe Ile Pro Val Thr Ala Thr Leu Glu Ala Glu Tyr Asn Leu Glu Arg
625                 630                 635                 640

Ala Gln Lys
```

That which is claimed:

1. A variant Cry1B polypeptide, wherein the variant Cry1B polypeptide comprises an amino acid sequence having at least 98% sequence identity to SEQ ID NO: 29, wherein the variant Cry1B polypeptide comprises conserved amino acid residues Serine (S) at position 168, a Glutamine (Q) at position 172, a Threonine (T) at position 490, a Leucine (L) at position 491, an Aspartic acid (D) at position 496, a Glutamic acid (E) at position 498, and an Asparagine (N) at position 501.

2. The variant Cry1B polypeptide of claim 1, wherein the variant Cry1B polypeptide comprises an amino acid sequence having at least 99% sequence identity to SEQ ID NO: 29.

3. A composition comprising the variant Cry1B polypeptide of claim 1.

4. The composition of claim 3, wherein the composition comprises from 1% to 99% by weight of the variant Cry1B polypeptide.

* * * * *